US009676828B2

(12) United States Patent
De Villiers et al.

(10) Patent No.: US 9,676,828 B2
(45) Date of Patent: Jun. 13, 2017

(54) REARRANGED TT VIRUS MOLECULES FOR USE IN DIAGNOSIS, PREVENTION AND TREATMENT OF CANCER AND AUTOIMMUNITY

(71) Applicant: Deutsches Krebsforschungszentrum, Heidelberg (DE)

(72) Inventors: Ethel-Michele De Villiers, Waldmichelbach (DE); Harald Zur Hausen, Waldmichelbach (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 83 days.

(21) Appl. No.: 13/719,835

(22) Filed: Dec. 19, 2012

(65) Prior Publication Data

US 2013/0259869 A1 Oct. 3, 2013
US 2017/0066802 A9 Mar. 9, 2017

Related U.S. Application Data

(63) Continuation-in-part of application No. PCT/EP2011/003119, filed on Jun. 24, 2011, which is a continuation-in-part of application No. 12/821,634, filed on Jun. 23, 2010, now abandoned.

(30) Foreign Application Priority Data

Jun. 23, 2010 (EP) .................................... 10006541
Nov. 23, 2010 (EP) .................................... 10014907

(51) Int. Cl.
| | |
|---|---|
| C07K 14/01 | (2006.01) |
| C12N 7/00 | (2006.01) |
| C07K 16/08 | (2006.01) |
| G01N 33/569 | (2006.01) |
| C12Q 1/70 | (2006.01) |
| C12N 15/113 | (2010.01) |
| C12Q 1/68 | (2006.01) |
| C07K 14/005 | (2006.01) |

(52) U.S. Cl.
CPC ............ *C07K 14/01* (2013.01); *C07K 14/005* (2013.01); *C07K 16/081* (2013.01); *C12N 7/00* (2013.01); *C12N 15/1131* (2013.01); *C12Q 1/6883* (2013.01); *C12Q 1/6886* (2013.01); *C12Q 1/701* (2013.01); *G01N 33/56983* (2013.01); *C12N 2750/00021* (2013.01); *C12N 2750/00022* (2013.01); *G01N 2800/50* (2013.01)

(58) Field of Classification Search
None
See application file for complete search history.

(56) References Cited

FOREIGN PATENT DOCUMENTS

| WO | WO 00/28039 | 5/2000 |
|---|---|---|
| WO | WO 01/42299 | 6/2001 |
| WO | WO 00/46407 | 8/2002 |
| WO | WO 03/023027 | 3/2003 |
| WO | WO 2007/130519 | 11/2007 |
| WO | WO 2008/138619 | 11/2008 |

OTHER PUBLICATIONS

Leppik et al. In Vivo and In Vitro Intragenomic Rearrangement of TT Viruses. Journal of Virology. Sep. 2007, 81: 9346-9356.*
GenBank: AJ620222.1. Torque teno virus, isolate tth25, complete genome. Feb. 3, 2009. http://www.ncbi.nlm.nih.gov/nuccore/aj620222.*
Kamada et al. Transcriptional regulation of TT virus: promoter and enhancer regions in the 1.2-kb noncoding region. Virology. Apr. 10, 2004;321(2):341-8.*
Yu et al. TT virus: preferential distribution in CD19(+) peripheral blood mononuclear cells and lack of viral integration. J Med Virol. Feb. 2002;66(2):276-84.*
Koidl et al.Detection of transfusion transmitted virus DNA by real-time PCR. Journal of Clinical Virology 29 (2004) 277-281.*
E.M. De Villiers, et al., Intragenomic Rearrangement in TT Viruses: A Possible Role in the Pathogenesis of Disease, Current Topics in Microbiology and Immunology (2009) vol. 331, p. 91-107.
Ilijas Jelcic, et al., Isolation of Multiple TT Virus Genotypes From Spleen Biopsy Tissue From a Hodgkin's Disease Patient: Genome Reorganization and Diversity in the Hypervariable Region; Journal of Virology (2004) vol. 78, No. 14, p. 7498-7507.
Laura Kakkola, et al., Construction and Biological Activity of a Full-Length Molecular Clone of Human Torque Teno Virus (TTV) Genotype 6, FEBS Journal (2007) vol. 274, p. 4719-4730.
Y.H. Peng, et al. Analysis of the Entire Genomes of Thirteen TT Virus Variants Classifiable Into the Fourth and Fifth Genetic Groups, Isolated From Viremic Infants, Archives of Virology (2002) vol. 147, p. 21-41.
Mireia Sospedra, et al., Recognition of Conserved Amino Acids Motifs of Common Viruses and Its Role in Autoimmunity, PLoS Pathog. (2005) vol. 1, Issue 4, e41, p. 0335-0348.

* cited by examiner

*Primary Examiner* — Nick Zou
(74) *Attorney, Agent, or Firm* — Vedder Price P.C.; Thomas J. Kowalski; Deborah L. Lu

(57) ABSTRACT

The present invention relates to rearranged molecules of (a) a specific TT virus sequence and (b) a nucleotide sequence encoding a polypeptide showing homology to mammalian proteins associated with cancer and autoimmune diseases that are capable of replicating autonomously for use in diagnosis, prevention and treatment of diseases like cancer and autoimmunity.

4 Claims, 59 Drawing Sheets

FIG. 6
zyb2  CGGGTGCCGA AGGTGAGTTT ACACACCGCA GTCAAGGGGC AATTCGGGCT CGGGACTGGC CGGGCCATGG G
zyb9  CGGGTGCCGA AGGTGAGTTT ACACACCGCA GTCAAGGGGC AATTCGGGCT CGGGACTGGC CGGGCTATGG G
zkb5  CGGGTGCCGT AGGTGAGTTT ACACACCGCA GTCAAGGGGC AATTCGGGCT CGGGACTGGC CGGGCTATGG G
zkb69 CGGGTGCCGG AGGTGAGTTT ACACACCGCA GTCAAGGGGC AATTCGGGCT CGGGACTGGC CGGGCTATGG G
                                                                

FIG. 8A

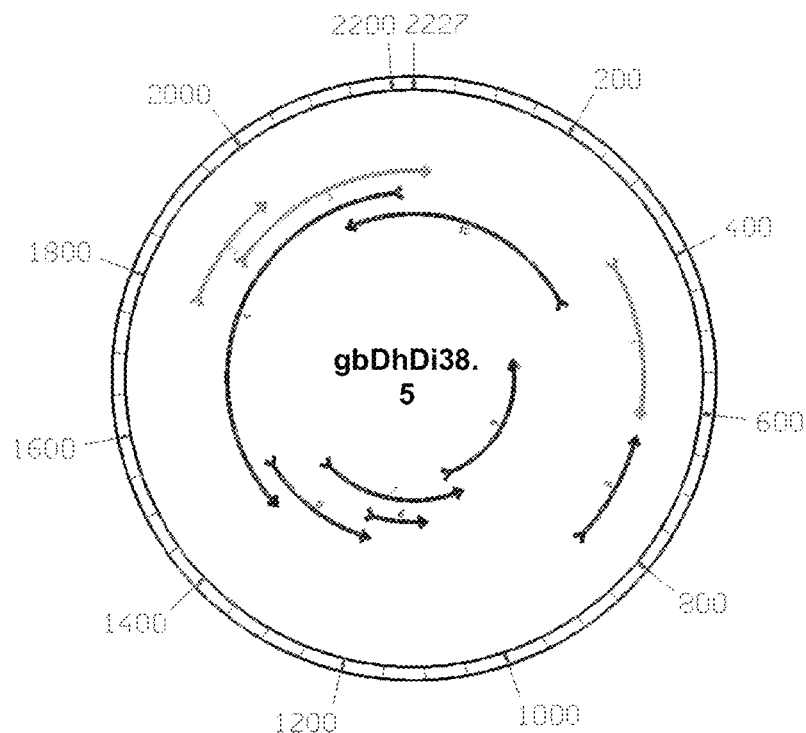

FIG. 8B gb38.5
gbDhDi38.5

WV13038 Klon6
 long-pcr according to Templiphi
primer:t3pb1+2    ann.:65°C
Length: 2227

```
  1  CAATTCGTGC ACGGGACTAC AAGGAAAGGG GTTGACCCCC ACCCTCCCCC

51  GCCATGCCCA GGAGGGTGCA GACACAACTG GGAAGGTGCT AGAGACCCCG

101  GGGGGAGGCT GGGCCAGCAC CAGGCATTGG GGGCAGGTT CCCGTCTCTA

151  CACCCCAGCC CCAGGCGGAC AGCGCGTGCC CCTCCCGCTG CCCCACCTGT

201  CACCCACCTG CTGGCCCCGG GCTGTCTCTG CTCCTGGCTC CCCTCCCAGC

251  TGCGTCCCCA GCTGCCTCTC CAGGGAGGAG TGACAGCTGG CCTGTGCCAC

301  ACCCTCGAGC CCCCCCGGAC TACCCCCTCC CTGGGGCAGG ACCCCTGCCT
```

FIG. 8C

```
 351  GTGGCACAAC CAAGGGGCCT GCTGATGGGG GCTCATGTGA GCAGTGCCCC
 401  AGCTGTGGGT GTGGGTGCTG CCAGCTGCCA CCGCCTTTGC CCTGGTTTCC
 451  CAGATAGACC CCGACCCACA CTCCGAAGCT GTATCATGAA CGCTGTGGTG
 501  GGCGGCTGGT GGGGAGCGGG GTTGCCGTCC CACTACCCTC TGGAAGCCTC
 551  AGCCATGAAG GGCCCCTGTG GCACCTTTT CCCGGCACAC GGTGCTGTGT
 601  TTCTCCACTC TTGGGCTCTG CAGTGACTTG AGGGGTCAAG TCTATGATCC
 651  CACGGGAGGC TGGGCTAATG AGGGGACCAG AGACCTCAGT GCTGTGCAGG
 701  GAGTCCTGAA CCACCCTGGT GGAAGGCCCA GCCCAACTCC CCAGTCCTCC
 751  CGCCAGCTCC CTGTGGTGTC CAGGAGACCT GTGGTCAGGC CTGGAGGAGA
 801  AGCTCCTCCT CCCCTCGACA TCCTCCCTGC AGCCCTTGCT CTTCACCAGA
 851  GCCTCCTGAC TCCCCAGGAC CCCAGAGAGG ACTGACCCTC TCCAGCCGAC
 901  CTCTGGGCTC AGGACAGCTG GGCGGGGCAG CCACAGGAGC TGCCTGTAGG
 951  GAGCAGAGTC AGGACGGGGA CCGAGCCGGA CACCCATTCT GGAAGTGTCT
1001  GCACTTCCAG GCAGGGGAAG GACGGCAGTG GGTAGCTGGG AGTGCTGGGC
1051  CGAAGATGGG CATTGTCAGG CCCTCAGTGG GGACTGGGAG GTAGAGGTGG
1101  GGAGGTCTGT GGAGGAAGGA GAAGAAGGGC CAGTGTCCCG AGTTGGGGGT
1151  GGTTGGCAGT GGACGAGGCC GACAGGAACA GACCTGAGCT TGGGGAGCTC
1201  CACTCAGAAC GAGGCATCCT TCAGGGTTCT GTGCATACTG GTGTCCCTGG
1251  CTGGGGGCCG GGCCCCGAAG TGGAGCCTGG GACTGTGAGG GTGGGGGGGG
1301  TGTGCTGGGG TGGGAGGTGG ATGGAGCCCC CCTCCACCG CCTGGCCGCT
1351  TGGGCTGAAC CTTGGACTTC GGAGCCGGAA CAGACATAGG AAATGGCCTA
1401  ACTGCATTTG CGCAGGAACA CCAAATCCCT CGCAGCTGCA CGGGGCTGAG
1451  CCAGGGCCAC GGGCGGGGTC GGCCATCCCA GAGTCCTGAC AGCTCCGTGG
1501  TGTATGCCAA GGGGCCTGGG CCGCTGACCG AGGGGCGCCT TCCCAGGCC
1551  AGAGGCCCCC ACCCCACCCC AGGAGAGCTG CCCCCCTTTC AGTTCCCAGA
1601  ACGGAGCCCG GCTGTGGAAT AGTGATGCGG TGAGGTCATG GGGAGGGGGC
1651  CCGCATGACT CATATCCTGG GGTAGGGGAA AGGGAGGAGA CGGAGAAGGG
1701  GCCCAGAGGC CTCCACGTCC TCAGCTCTGC TGGGTCAGAG GCCAGGGGCT
1751  GGCGGGGCTT CTCCCCAGCA CTGGGTTTTA GGGGAGACAC CAGGAGATGC
```

FIG. 8D

```
1801  TTACTCTGCA  TCCCCACTCT  GTCCCCCAGG  CCCCTAGCCA  GGGAGAGCTC
1851  AGTCAGAGTG  ATCCTCCAGG  GGCCCAGCTC  TGCATGGATG  ATGTTCCCAG
1901  AGTACACACC  TGGGCCTCGT  GCCAGGGCCG  GCACCGCCGT  TGTCAGGGCT
1951  ATGGCAAGGC  AAACAGTCAA  TGTTTGCCTC  ACTAAAGTGA  GGCTGCAGCA
2001  CCCTGAAGGG  ATCCCTGGAG  GGGGACGTGG  TCCCCTTGTT  CCCAAGCTTG
2051  TCTGCACATG  CACGTGGATG  TCAAGGGTTC  CCGTGTGTGA  GCACATGCAT
2101  ATTTGTATGT  GCATGGGGTG  CGGGCATGTG  TGCCTGTGTG  GCCGGAGCGT
2151  GGGCTCGTGG  AGAATGTGTG  TGAGTTGGGT  GTGCACCTGC  ATGTGCCCCA
2201  GGCCTAGGGA  GTCCCGTGCC  CGAATTG
``` gb40.27
gbDfDg40.27.seq (cellular sequence from gb40 plus further ms-brain)
 Length: 883
long-pcr according to Templiphi
  primer: hel 1 + hel 2  ann 68 C (nested)
  vector: pcr2.1 invitrogen

1  CGGGACTGGC CGGGCTATGC CCAGACACA CTCACGTAGG GGTGTCCGGC

51  CTGGCAGCCC AGGACCATGG TCTGCAGGGT TTCCTCTCGG CCATTCAGGA

101  CAACCCTAGT CTCCAGGGAA TAGCGCTGGT GTCGCCTATC AGCCGTGAAG

FIG. 8G

```
151  GTCTCCTGCA GGAGGAGGCT CTGCGGGATG GGCAGGTGCA ATGGGTGCCT
201  GGTGTGCAGA GGGAAAAACA GGCCAAAGCC ATTAAAGCAG CTGGCAGTGC
251  CAGGGGACAA TTGTGCCCCA CGGTCTCAGC CTGGGCCTGT CACGAGCTTG
301  CAGAGTTAAG ACTCTGCCAC AGAGAAGAGA ACATCAGGAC ACCTGGCAGC
351  CCTATGCTTT ACAATGTGGC ATCCAGAACC CTTCACCACC TCACTGTGCC
401  AGAGAAGTGG GCATGGCTGG GGTCCCCGTC GCCATTTGAC AGCAAAGACC
451  CAAGAGGATA GATGACACAC AGCATCTGGT GTCACACAGA CTGGGATTAG
501  AATCCAGGCA CGGTCTTTCA CTAGCTGTGT GACCTTGGGA AAAGGACTTG
551  ACTGTTCTGT GCCTCAGTTT CCCCATCTGT AAAACGGAGG CTAAAATAAT
601  ACTGATCGGA CACAGTGGTC AGGGTTAGAG ATAACATACA TGAAACGACC
651  ACAAGCTCCC CAAGGGCAAA GGTTTCTGAC ATTCCGGTTC TCTGCCATTT
701  TCCATGTGCC CAGAAGAGCA CTTGGTCCAT AGTATGTGCT CAATGAATGT
751  AAATGGGATA AAAACACGAA CGAACACTCT GCCAACGATG CTGCTGTTCC
801  TTTGTCATCA CTGCTTCTGT TTAGGCTGTA GCTGACTTAT CTAAGGCCAT
851  ACAGCTGCTC AATGCATAGC CCGGCCAGTC CCG
```

FIG. 8H

FIG. 8I gb43.30
gbDhDi43.30.seq (cellular sequence from gb43 plus further ms-brain)
Length: 291
long-pcr nach Temp.
primer: t3pb 1+2 ann.65%
Vektor: pCR2.1, Invitrogen

```
  1  CCCCTTGACT TCGGTGTGTA AACTTGTGGT ATAGAACATG ATGTTTTAAG

51  ATACATGTAC ATTGTGGAAT GGCTTGATCA TGCTAATTAA CATATGAATT

101  ACCTCACTTA GCTATCTTTT TTATGGTGAA AGCACTTAAA ATCTACCCTC

151  AGCAGTTTTC AAGTACACAA TACATTTCTA TTAACTATAG TCACCATGTT

201  GTACAATAAA TCTCTTGAAT TTATTCCTCC TGCCTAACTG ACATTTTGTA

251  TCCTTTGACT GATCTCTCTC CCAGTCCCG TGCCCGAATT G
```

*Bold - primer sequence*
*Italic - continuation of cellular sequence*

FIG. 8J

BLASTN2 of: /home/vir088/ttbrain/gbDhDi43.30.seq   from: 1 to: 291  June 9, 2010 12:21
compared to database: nrnuc   ..

>>>>nrnuc:GI_225543527 Gi|225543527|ref|NG_011635.1| Homo sapiens myosin IIIA (MYO3A), RefSeqGene on chromosome 10. 0/0
        Length = 285464

Score =  525 bits (265), Expect = e-146
 Identities = 268/269 (99%)
 Strand = Plus / Plus

CCCTTGACTTCG
Query: 14      gtgtgtaaacttgtggtatagaacatgatgttttaagatacatgtacattgtggaatggc 73
                   |||| ||||||||||||||||||||||||||||||||||||||||||||||||||||||
Sbjct: 276074  gtgtataaacttgtggtatagaacatgatgttttaagatacatgtacattgtggaatggc 276133
 *TAATTGACAAAAC*

Query: 74      ttgatcatgctaattaacatatgaattacctcacttagctatctttttatggtgaaagc 133
               ||||||||||||||||||||||||||||||||||||||||||||||||||||||||||||
Sbjct: 276134  ttgatcatgctaattaacatatgaattacctcacttagctatctttttatggtgaaagc 276193

Query: 134     acttaaaatctaccctcagcagttttcaagtacacaatacatttctattaactatagtca 193
               ||||||||||||||||||||||||||||||||||||||||||||||||||||||||||||
Sbjct: 276194  acttaaaatctaccctcagcagttttcaagtacacaatacatttctattaactatagtca 276253

Query: 194     ccatgttgtacaataaatctcttgaatttattcctcctgcctaactgacattttgtatcc 253
               ||||||||||||||||||||||||||||||||||||||||||||||||||||||||||||
Sbjct: 276254  ccatgttgtacaataaatctcttgaatttattcctcctgcctaactgacattttgtatcc 276313

Query: 254     tttgactgatctctctcccagtcccgtg 282      CCCGAATTG
               |||||||||||||||||||||||||||
Sbjct: 276314  tttgactgatctctctcccagtcccgtg 276342  *ACCAGTGCCCT*

>>>>nrnuc:GI_14018255 Gi|14018255|emb|AL162503.12| Human DNA sequence
           from clone RP11-420F12 on chromosome 10 Contains the GAD2
           gene for glutamate decarboxylase 2 (pancreatic islets and
           brain 65kDa), the 3' end of the MYO3A gene for myosin IIIA
           and two CpG islands, . . . 0/0
        Length = 175594

Score =  525 bits (265), Expect = e-146
 Identities = 268/269 (99%)
 Strand = Plus / Plus Query: 14     gtgtgtaaacttgtggtatagaacatgatgttttaagatacatgtacattgtggaatggc 73
                  |||| |||||||||||||||||||||||||||||||||||||||||||||||||||||
Sbjct: 35112 gtgtataaacttgtggtatagaacatgatgttttaagatacatgtacattgtggaatggc 35171

FIG. 8K

```
Query:    74 ttgatcatgctaattaacatatgaattacctcacttagctatcttttttatggtgaaagc 133
             ||||||||||||||||||||||||||||||||||||||||||||||||||||||||||||
Sbjct: 35172 ttgatcatgctaattaacatatgaattacctcacttagctatcttttttatggtgaaagc 35231

Query:   134 acttaaaatctaccctcagcagttttcaagtacacaatacatttctattaactatagtca 193
             ||||||||||||||||||||||||||||||||||||||||||||||||||||||||||||
Sbjct: 35232 acttaaaatctaccctcagcagttttcaagtacacaatacatttctattaactatagtca 35291

Query:   194 ccatgttgtacaataaatctcttgaatttattcctcctgcctaactgacattttgtatcc 253
             ||||||||||||||||||||||||||||||||||||||||||||||||||||||||||||
Sbjct: 35292 ccatgttgtacaataaatctcttgaatttattcctcctgcctaactgacattttgtatcc 35351

Query:   254 tttgactgatctctctccccagtcccgtg 282
             |||||||||||||||||||||||||||||
Sbjct: 35352 tttgactgatctctctccccagtcccgtg 35380
```

Open reading frame: 49aa

(Peptide) FASTA of: gbDhDi43.30rev.49.pep  from: 1 to: 49  June 9, 2010

REFORMAT of: gbDhDi43.30rev.49.pep  check: 3689  from: 1 to: 49  June 9,

TO: SwissProtPlus:* Sequences: 11,223,768  Symbols: 3,635,054,084  Word Size: 2

```
SPTREMBL:Q9WB12_9VIRU      Begin: 19   End: 60
! Q9wb12 SubName: Full=ORF2; Flags: F...    84    109    108    181.5    0.3
SPTREMBL:Q9WB09_9VIRU      Begin: 19   End: 54
! Q9wb09 SubName: Full=ORF2; Flags: F...    91     91    104    176.0    0.61
SPTREMBL:Q9WB02_9VIRU      Begin: 19   End: 59
! Q9wb02 SubName: Full=ORF2; Flags: F...    82     82    100    168.8    1.5
SPTREMBL:Q9WSW4_9VIRU      Begin: 32   End: 73
! Q9wsw4 SubName: Full=ORF2; Flags: F...    82     82     97    162.5    3.4
SPTREMBL:Q9WAY4_9VIRU      Begin: 19   End: 54
! Q9way4 SubName: Full=ORF2; Flags: F...    84     84     94    160.8    4.2
SPTREMBL:Q9WB10_9VIRU      Begin: 19   End: 54
! Q9wb10 SubName: Full=ORF2; Flags: F...    84     84     94    160.1    4.6
SPTREMBL:Q9WAZ2_9VIRU      Begin: 19   End: 54
! Q9waz2 SubName: Full=ORF2; Flags: F...    84     84     94    160.1    4.6
SPTREMBL:O70807_9VIRU      Begin: 23   End: 58
! O70807 SubName: Full=Putative uncha...    84     84     94    158.2    5.9
\\End of List gbDhDi43.30rev.49.pep
SPTREMBL:Q9WB12_9VIRU ID   Q9WB12_9VIRU            Unreviewed;       150 AA.
AC   Q9WB12;
DT   01-NOV-1999, integrated into UniProtKB/TrEMBL.
DT   01-NOV-1999, sequence version 1.
DT   09-FEB-2010, entry version 20.
```

FIG. 8L

```
DE   SubName: Full=ORF2; . . .

SCORES   Initl: 84    Initn: 109   Opt: 108    z-score: 181.5 E(): 0.3
>>SPTREMBL:Q9WB12_9VIRU                                    (150 aa)
 initn: 109 initl:  84 opt: 108 Z-score: 181.5 expect():  0.3
Smith-Waterman score: 108;    53.5% identity in 43 aa overlap
 (6-46:19-60)

10        20        30        40
gbDhDi43.30r       MFYTTSLHTEVKGQFGHGTGERDQSKDTKCQ--LGRRNKFKRFIVQH
                        ::::  ::::::  :::  :  ::: :  :   : :  ::  :  :
Q9WB12_9VIRU   AQTQRRVIPASRGRVPEVSLHTXVKGQFGLGTG-RAMGKALKKDMFLGKLYKKKRALSLH
                       10        20        30        40        50 gbDhDi43.30r   GDYS
               :
Q9WB12_9VIRU   GLRTPEAKPPAMSWRPPVHNPNRIERNLWEAFFRIHASSCGCGHLVGHLTVLARRYGAPP
                       60        70        80        90       100       110

ID   Q9WB12_9VIRU             Unreviewed;      150 AA.
AC   Q9WB12;
DT   01-NOV-1999, integrated into UniProtKB/TrEMBL.
DT   01-NOV-1999, sequence version 1.
DT   09-FEB-2010, entry version 20.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024379; BAA77446.1; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER       1       1
FT   NON_TER     150     150
SQ   SEQUENCE   150 AA;  16415 MW;  A4A7DF15855FC40D CRC64;
     AQTQRRVIPA SRGRVPEVSL HTXVKGQFGL GTGRAMGKAL KKDMFLGKLY KKKRALSLHG
     LRTPEAKPPA MSWRPPVHNP NRIERNLWEA FFRIHASSCG CGHLVGHLTV LARRYGAPPR
     PPAPGAPRPA LKRQLALPAP PADPQQANPT
```

FIG. 9A hodl1 hodL.VvWw.1.seq  Length: 639
Hodgkin L1236+TPA
PCR Primer: hif1+Lr1 GCI 59°C
Vektor pGEM T-Easy

```
  1  CCCCTTGACT GCGGTGTGTA AAGCGCCCCA GCCTGTGCCT GCACAGTGCC

51  TGTGTGGTGT GAACCCATGA CCAGGCCTCT GGAGGGAAGG AAGGTTAGGC

101  TTAGTGGACA CCAGCTTTCC TAAGGTGGGT CTTAGACCAA CTCATTAAAA

151  TGGCAGGATG GGCTTTTGTG CTGTATTTCT TGGGATTTTC AAGATGCCCC

201  ACACAGCAGA AGGGATGTGC ATTTTTTTCT CTGCCCTGAG TTGTTTGATA

251  AAAATCAGTG ACCTCGTTCT CCACTTAGAA CTCCCCTGAA CTGCACTCGG

301  TGTCTAGGAC TGTTGGGGAA GGAAGTGAAG AGCCAGCATG TAGTCTCCTC

351  TGGACTCTTA CAGGATCTGT CCACCTCTGG GCTCTTTATG TAGGGGAAGG

401  TGTGAGCTCC TGGGAGTACT CCTGATAGAG GACTGTTTCC CTGAAAACCT

451  CAGCAGTGTT TGAGGCCCTA GCAGGGGGAA CCCAGACCCC GCCTGCCAAA

501  GCCCCTAATC CCTCAGGGCT ATTATCAGCA GCCTAAGCGC CTTAGGGTGG

551  CCAGAGTCCA GCCCAGCAAG CAGCAAAGTC AGCAGCCTCC TCGCCCTATC

601  CTCTCCATGC CCCGGGGCAC TCCAGTCCCG ACCGAATTG
```

Primers in bold
Continuation of cellular sequence in italics

BLASTN2 of: /home/vir088/ttmixture/hodL.VvWw.1.seq  from: 1 to: 639
compared to database: nrnuc     ..
Database: nrnuc

```
>>>nrnuc:GI_18121492  Gi|18121492|emb|AL513485.10| Human DNA sequ...    690    0.0
>>>nrnuc:GI_149944898 Gi|149944898|gb|AC198797.3| MACACA MULATTA...     509    e-141
>>>nrnuc:GI_55416061  Gi|55416061|gb|AC121551.11| Mus musculus ch...     84    1e-12
>>>nrnuc:GI_241752248 Gi|241752248|ref|XM_002400984.1| Ixodes sc...      46    0.26
>>>nrnuc:GI_291191454 Gi|291191454|gb|GU722348.1| Torque teno vi...      44    1.0
>>>nrnuc:GI_291191453 Gi|291191453|gb|GU722347.1| Torque teno vi...      44    1.0
>>>nrnuc:GI_291191452 Gi|291191452|gb|GU722346.1| Torque teno vi...      44    1.0
>>>nrnuc:GI_217416834 Gi|217416834|gb|FJ426280.1| Torque teno vi...      44    1.0

>>>nrnuc:GI_18121492  Gi|18121492|emb|AL513485.10| Human DNA sequence
         from clone RP11-48O20 on chromosome 1 Contains the TAGLN2
         gene for transgelin 2, the IGSF9 gene for immunoglobulin
         superfamily member 9, the SLAMF9 gene for SLAM family
         member 9, a novel gene and . . . 0/0
       Length = 80398
```

FIG. 9B

```
Score =  690 bits (348), Expect = 0.0
Identities = 348/348 (100%)
Strand = Plus / Plus Query: 282    tccoctgaactgcactcggtgtctaggactgttggggaaggaagtgaagagccagcatgt 341
              ||||||||||||||||||||||||||||||||||||||||||||||||||||||||||||
Sbjct: 26212  tccoctgaactgcactcggtgtctaggactgttggggaaggaagtgaagagccagcatgt 26271

Query: 342    agtctcctctggactcttacaggatctgtccacctctgggctctttatgtaggggaaggt 401
              ||||||||||||||||||||||||||||||||||||||||||||||||||||||||||||
Sbjct: 26272  agtctcctctggactcttacaggatctgtccacctctgggctctttatgtaggggaaggt 26331

Query: 402    gtgagctcctgggagtactcctgatagaggactgtttccctgaaaacctcagcagtgttt 461
              ||||||||||||||||||||||||||||||||||||||||||||||||||||||||||||
Sbjct: 26332  gtgagctcctgggagtactcctgatagaggactgtttccctgaaaacctcagcagtgttt 26391

Query: 462    gaggccctagcaggggggaacccagaccccgcctgccaaagcccctaatccctcaggcta 521
              ||||||||||||||||||||||||||||||||||||||||||||||||||||||||||||
Sbjct: 26392  gaggccctagcaggggggaacccagaccccgcctgccaaagcccctaatccctcaggcta 26451

Query: 522    ttatcagcagcctaagcgccttagggtggccagagtccagcccagcaagcagcaaagtca 581
              ||||||||||||||||||||||||||||||||||||||||||||||||||||||||||||
Sbjct: 26452  ttatcagcagcctaagcgccttagggtggccagagtccagcccagcaagcagcaaagtca 26511

Query: 582    gcagcctcctcgccctatcctctccatgccccggggcact ccagtccc 629    GACCGAATTG
              |||||||||||||||||||||||||||||||||||||||||||||||||
Sbjct: 26512  gcagcctcctcgccctatcctctccatgccccggggcactccagtccc 26559    AGCTGGCTGATC Score =  505 bits (255), Expect = e-140
Identities = 272/280 (97%)
Strand = Plus / Minus CCCCTTGA
Query: 9      ctgcggtgtgtaaa gcgccccagcctgtgcctgcacagtgcctgtgtggtgtgaacccat 68
              ||||  ||||||||||||||||||||||||||||||||||||||||||||||||||||||
Sbjct: 29128  ctgctgtgtgtaaagcgccccagcctgtgcctgcacagtgcctgtgtggtgtgaacccat 29069
              TTCAGTTAG Query: 69     gaccaggcctctggagggaaggaaggttaggcttagtggacaccagctttcctaaggtgg 128
              ||||||||||||||||||||||||||||||||||||||||||||||||||||||||||||
Sbjct: 29068  gaccaggcctctggagggaaggaaggttaggcttagtggacaccagctttcctaaggtgg 29009

Query: 129    gtcttagaccaactcattaaaatggcaggatgggcttttgtgctgtatttcttgggattt 188
              ||||||||||||||||||||||||||||||||||||||||||||||||||||||||||||
Sbjct: 29008  gtcttagaccaactcattaaaatggcaggatgggcttttgtgctgtatttcttgggattt 28949

Query: 189    tcaagatgccccacacagcagaagggatgtgcannnnnnnnctctgccctgagttgtttga 248
              ||||||||||||||||||||||||||||||||||||        ||||||||||||||||
Sbjct: 28948  tcaagatgccccacacagcagaagggatgtgcatttttttctctgccctgagttgtttga 28889
```

FIG. 9C

```
Query:    249  taaaaatcagtgacctcgttctccacttagaactccnctg  288
               ||||||||||||||||||||||||||||||||||||||||
Sbjct:  28888  taaaaatcagtgacctcgttctccacttagaactccnctg  28849
```

FIG. 9D hoht33
hoHT.vAf.33a.seq Length: 3387
Lymphom HSB+TPA, Templiphi-RCA
PCR-Primer HLF1+Hr4 60°C
Vector pCR2.1

```
   1  AATTCGGTCG GGACTGGCAG AGTGACGCTC AGGTCAGCCT GACAGCAGGG
  51  TGATTGAAGG GGCCAGATAC CCCAGCAGGG CCTGAGGCCA GAACACAGCA
 101  TAGGCTGGCT CTGATGGGTG GAGGAGGTGG CCAGGCATCA TCTGGAGCTT
 151  GGAGTTGAGA ACATCTGTGA CTCCTCCTTC AGGAGGGTGC TCTAGGAGTT
 201  GAGAGCATCC TAGGTAGGAC CATACATCTA CCCCCATCCT AGTTCCCTCC
 251  AGCCTCTCTT TTCAGCTCCA GGTCTACCTT AAGGGACCTA GGACACCTGG
 301  GCTGGGGCAT AACAGGACTT GGTTTTATGT AAAGGAGCTG GGAAGAGACT
 351  GAGATAACAG AGGGCTGCAA GGAGAGAGAC AGAGAGAGAA GAACCTGCCA
 401  GAAGAAGCTC CTCAGCAATC CACTAAGCCC TGATCTTTGC CTCACTGCCT
 451  GTCCCTTCCC ATCCGCTCTT CTGCTCTCTC AATCTCTGCC TTCAAGAAAT
 501  TTGGTGCATA TTGGAATAGG GAGGAATAGA AGCACCCTGG GTGGAGCTCT
 551  GGGCTTGGCT GTGCACGAGC TTTCAGTGGG TGGTTTGCTG GTCTCCAAAG
 601  ATGACCCTCC ATTAGTCATG CTTCTCGGTG TTTGTCCTCA GGTAGTCTCA
 651  TCCCATCTTG AGTCTGGGCT TGCCCTGTGA CTCACTTTAA CCACAAGAAT
 701  GTGGCAGAAA GGATGTTGTG CCAGTTCTAG AACTAAGCCT TCAGAAAGCC
 751  TAGCACCTTC TGCTTTTAGG AGCACTGAGC CCCATGTTA GAAGTCCACT
 801  TTTATACTCT GCTCTGGAGA CTAGCAGAAT TAGAAATGCA CTGCTGAATG
 851  CTGCTCGAGA GACTAATGGA GAGGCCATGT GAATAAGGAG GCCTGAAACT
 901  ACATGGAGAT AGAGGGCCAG CCACCCCAGC ACCACGGCTC AGCTGTGCCT
 951  CCCAGCCATC TCTGCCAGTC CTCCAGGGCT ATGAGTGAAC CATCTTGGAT
1001  GTTCTAGCTC GGTGGAGCCC CCAGGTGATT GCAGCCTCAG CCACCATCTG
1051  ACTGTAGCTG CATGAGAGGC CCCCAGTGGG ACCAGCAGGA CTGCCAAGCT
1101  GAGCCCTGCC CACCCACAGA ACTGTGAGAA ATAAAAAAAT GGTTGTTTCC
1151  TTAAGCCATT AAGTTTTGGA ATGATTTGTT ACTCACAATT GATAACTGAT
1201  ACAGTCTGTC TTTAGGGAAA ACAAGGGATA ACTCTGGGCT CCAGGTGTCT
1251  TCTATAGGAT GAATGGGACT TGGTTGCTGA CAAGCTGACA AGTTTGAGCA
1301  TGAAACTCTT TTTTTTTTT GGAGAAGGAA TTTTGCTCTT GTTATCCAGG
1351  CTGGAATACA GTGGTGCGAT CTCGGCCCAA GGCAACCTCT GCCTCCTGGG
1401  TTCAAGCAAT TCTCCTGCCT CAGCCTCCTG AGTAGCTGGG ATTACAGGCA
```

FIG. 9E

```
1451  CCCACCACTA CACCTGGCTC TTTTTTTTTT TTGTATTTTT AGTAGAGACA
1501  GGTTTTCATT ATGTTGGCCT GGTCAGGTTT TGAACTCCTG ACCTCAGGTG
1551  ATCCACCTGC CTTGGCCTCC TAAAATGCTG GGATTACAGG TGTGAGCCAC
1601  CGTGCCTGGC CTGAGCATGA AACTTTTATG CTCAAACATT AAAGTGTAAA
1651  CACTCACCAG CTCAGCTGAA TAAGAACTTC TGGGGGCAAG GCCCAGGAAT
1701  CTACAGTTTA GTAAGTGCCC CCACCACTGG ACCCTGGGAA AGTGGACTGC
1751  ATTTTGAAAA ACTCTAGATC AGTTGATACC CAGGAGTCCT CATAACACTA
1801  AGTTGTAATA CCTCAGTGTG AATTAGTCTG ATGCAGCTCT TCTTAGAGGT
1851  CATTGACAGA GGGCAAGACA TTTCCAAAAG GAAGGAATAG CCAATATGGA
1901  ATGACAGGTG GATTGGATGA CCCTCTATTA TTTAGTTTCA ACCTGCCCTT
1951  CCTGCCTTCC CTCCCACAAA TTCCCTTTCA GATCCTCCGT CCTAATCCTC
2001  TTCGATAGTT CATTGTTCTT CTGCAGACAG AGCAGCGAAG TGTTATCTGT
2051  TGTACCCACT ATGACTAGTT GATGGTGCAT GGCTTCCATG GAGCAGTGCT
2101  GTGATCCATT AGTCATGGAG CAGTGCTGTG ATCCATTGTC ATGTCTGCCA
2151  TGAACACTGG AAGGGGCAGT GGTAATGACA GCCTCTTACA TTTGCCAACT
2201  CTGCCCAACA TTCTTCCCAG TGTTGGGAAA GCCTTTGCTT ATTCCATTCC
2251  TTCTTGGAAA GCTTTGTTCC TCCATTTCAC ATTTTTAATT TTTCTCATTT
2301  TTATGGTGCA CCATGGATAC CACCTGTCCA TATAGCTGGC TTCTGATTTT
2351  TCCAGATGAA AGTAATCCTT CCTCTCCTAA CCTCCCATGA CACCTAACCT
2401  GGCACTCATT TACGGTGTTC AGCTCCTTCT CCTGTACGTT CTCATTGTTC
2451  TCCTCTCATC TTCTCCCCAG GAATGGATTC CCCGCCAAGG GAGGTACCAG
2501  GTCAGTTTCT TCTTTGTGCA ACAGGGTGTC CCTGATGAGC ACAAACCTGG
2551  AACAAGTGTT TGTAGGGCTG GTGGGCATCT GGTTCCTCTG GGTGTTGTGT
2601  AGCCTGAGCC GGGGGGCAAA TGGGTGTTTG TTTTTCTGAA GAAGGCAGGC
2651  GTTCTGTGGC AGATGTGGGT GGAGGGGGTT GGGGAGTAGT ATCATGGAGA
2701  GGCTGGGATC CTATCTATCT CCTTCCCCTG CTTGAAGGGC AACTTGGGAG
2751  AAGCTCAAGA GGGAGGAGTT GACTGCAGAA GCTGGGATAC CTGCATAACT
2801  CTCAGGTTCA AGCATCACTG CTTTAGGGCC CTGGGGGCCT ATGTGTGAGT
2851  CAAGAAAGGG AGATAGAGAG AGAAGAGAGA GAGAGGAGAG AGAGAGAGAG
2901  AGAGAGAAGA CAGAGGAGAG AGAGAGAGAA GAAAGAGGAG AGAGAGAGAA
2951  GAGAGAGCAG AGAGAGAGAG CATGCTGTCA GTGAGGTGGC CCTAAGCCCT
3001  CTTGGAAATA ACTTGGAGGC ACTGTGGGGT GGCTCTGAGG TGCTGAGGTA
3051  TACCTGTAGT GGGGCTAGGA CCTTTCCAAC CTGGGTCTGA AGGTTGAGGC
3101  AACCTTGGGT GTACCTGCTG GTGAGCTGAG AGCCCTGGGG ACCTTTGGCA
3151  GACATTCCCA CCCCTGCAGC CTGGAGGGTT TGCATGCAGT GAGGCTGTCC
3201  TGCTCATCAC TACGTCCTCT GGGACAGCAC ATTGCCTGTG CTGAACAGGC
3251  ATTCAGTTGC GATTTGTGGA ATCAGTGTTG GTGAGGAGGG CAAGTGGCAA
3301  CAGAAATGGG GGTGTGCTCC CCCCAGTTCC TCAGCTACAA TCTCCATGAC
```

FIG. 9F

3351 CTTCTACACT GCCCTGGGCC CAGTCCCGAC CGAATTG

FIG. 9G hoht22
hoHT.vAf.22a.seq Length: 1790
Lymphom HSB+TPA, Templiphi-RCA
PCR-Primer HLF1+Hr4 60°C
Vector pCR2.1

```
   1 CAATTCGGTC GGGACTGGGG AGCTGTGAGA AAGAGAAGAG AAGGTCAGAT
  51 CAGGAACATT ACACAGAAGT CGGCAAAACT GGAACGAGGA GGGAAAGAAA
 101 TGAGCGAGTC TGACACTCAG TCCATCCTAG TTCCTATCAC ACAGGGAGGG
 151 ACATTGCCAT GCACATCCCC ACAGAGATGC ACCGTGTAAG GGGTCGAGGC
 201 AGATCCTGTC CACTATTGCC AGCTCTGAGG TGATCAAATT GTGTCTGCCC
 251 AGGGTAACCC GGTTGACCTA AACCAACCCA CTCCCTTGCA CATCTTAGGT
 301 GTTCCTGAGT CAGCAAGGCT GAGGAAGCCA CTCCAGCCAA AATCCCTTGT
 351 GCGATCTTCA AGCCCCAATC ACAGGCAATG ACAAGGCCAT GTCTGGCTGG
 401 CCTCATGGGG ACTGCCCTCC CCTCACCAGA CCTAGAACAC AGGCAATGCT
 451 CAGCAGCGTT CTGAGAAGAG CTGAGGTCAA GAACTCCAAC CCACGCAAC
 501 CCAGACCTGA TACAAACAGA CACCCATTTG CACTCCTAAC CCTTGAGCCT
 551 CTATTTCCAG ACCTCCTCAC TGGGTCTCAG CTGAGAACCC ACTTTTAGCC
 601 AAGCATCTTT AGTTCAGAGT TCCTCGCAGT GAGGGGATCC CTCCCCTGCC
 651 TTGCTGTCTG TGCTGCATCC ATTATACCCT CACACGGTGC TACTCAGCAG
 701 GGGAGAAATG GAGCCCTGGG GAGCCGGCAC TTTTCTCTTC TGCCTCTTCC
 751 TTGCCTTGCC TCAGGAAGGG GAAAAACTCT GGGTTGTTTT AGTTTGATCC
 801 CCTGTCCTAA GTGACCACAG GAACACTAGG CAGTGAGTAC ATATGGATTC
 851 TTAGCAGAGA GCTGACAAGT CTTCAGAAAC ATAGAAAACA TAGAAGCTTT
 901 GAGTGAGGAG ATCAGAATGT AATTAGGAGT TTCTTTTGGA GCAAACCCCA
 951 CCCCAAGAGA GTGAGCCCAA GTTCTTGAAG GCCCACCTGA GCAGATGACA
1001 CCAGCGTCTT CACTATGGCC ACAGTTGTGG GTGAGCCAGC CATTGTGGGG
1051 GCAGCTCCAC AGGTAGGACT CGTGTCCTGA GCAGCGCACA TCATCCAGGA
1101 CAATGGGTCC TGAGCCCTGG CCAAACTGGG CATTTCCTGG GGCTGACATG
1151 GCCCAGCCAC AGCCCGGCTG CCTGCAGACC ACATTGGCAT CATTGGTGTC
1201 CCAGTAGTCA TCACACACGG TGCCCCAGGA GCCTCGGTAT AGGACCTCCA
1251 CTCGGCCTCG ACACCTGTCG CCTCCATTCA CCAGCCTCAG GGCCAAACTG
1301 GATTCAGATC CTACAGGGGA ACACAAGAAC CTTTCATCCA TCCCTATCAT
1351 GAGGTCAAGA ATCTAAGGTA AGTTCCACAC TCAGGGTACT TCCTAATGAA
1401 CTAAGTCACC TAGGCAGGCA GTCACCTTTG CATATGACTA CAGACTAGGC
1451 TTCATCACCG TGAAAGTAGC ACTGATAACC TACTCTGCCC AGGTCTATGG
```

FIG. 9H

```
1501  GTGCTCAACT TTTGGGGAAG CACCTGTGAC CCCAGTGGAT GTGATGGGAA

1551  TGGATGCCCC ACTCCCCAGT TGGGTACACA GAGGATGGAG CTGCTCAGCT

1601  CCAGATGGCA GGCCCAGACC CCTCCCTTAT TCAGGAGCAT GGTCCTATCT

1651  GGGATCTGAC TGGCAGAGTA CCAGAGATGG CAGGGATGAG GTCCCCATAG

1701  GATTAGGGAG ACCCCCAGGG CTTGTTCTGA GCCCATAGAT AAGGATCTTT

1751  TCTGACCACT TGGAACAGGA TCCCAGTCCC GACCGAATTG
```

FIG. 10

DhDi:
t3pb-1.prime  Length: 18  long-pcr primer forward
    1  caattcgggc acgggact t3pb-2.prime  Length: 24  long-pcr primer reverse
    1  ccccttgact tcggtgtgta aact cd:
tth4prime1.seq  Length: 28 long pcr primer forward back-to-back with prime2
    1  CAGCGAGAAC GCCACGGAGG GAGATCCT tth4prime2.seq  Length: 28 long pcr primer reverse back to back with prime1
    1  CGGACGGGCG TGGAAAACTC AGCCATTC

DfDg:
hel32-1.prime  Length: 18  long-pcr primer forward
    1  cgggactggc cgggctat hel32-2.prime  Length: 19  long-pcr primer reverse
    1  agcccgaatt gcccctga

FIG. 11A ttgb33.35
gbDhDi33.35.seq (complete genome from ms-biopsy)
long-pcr, Templiphi
 primer: T3PB 1 + T3PB 2   ann.:65 C
 vector:TA-cloning  pCR2.1  invitrogen Length: 3725
```
    1 ATTTTGTGCA GCCCGCCAAT TTCTGTTCAA ACAGACCAAT CAGGACCTTC
   51 TACGTGCACT TCCTGGGGCG TGTCTACGAG GTCTATATAA GCAACAGCGG
  101 TGACGAATGG TAGAGTTTTT CTTCGCCCGT CCGCGGCGAG AGCGCGAGCG
  151 AAGCGAGCGA TCGAGCGTCC CGTGGGCGGG TGCCGTAGGT GAGTTTACAC
  201 ACCGAAGTCA AGGGGCAATT CGGGCACGGG ACTGGCCGGG CTATGGGCAA
  251 GGCTCTTAAA AAATTCCCCC GCTCTGCTCT CCGGCAGGAC ACAAAGTCAT
  301 GCCGTGGAGA CCGCCGGTCC ATAACGTGCC AGGTAGAGAG AATCAATGGT
  351 TTGCAGCGTT CTTTCACGGT CATGCTGCTT TCTGCGGGTG TGGTGACCCT
  401 GTTGGGCATC TTAACGGCAT TGCTCCTCGC TTTCCTAACG CCGGTCCACC
  451 GAGACCACCT CCAGGGCTAG ACCAGCTTAA TCCCGAGGGC CCGGCAGGTC
  501 CCGGAGGGCC CCCCGCCATC TTGCCAGCTC TGCCGGCCCC GGCAGACCCT
  551 GAACCGGCAC CACGGCGTGG TGGTGGGGCA GATGGAGGCG CCGCCGCTGG
  601 GGCCGCCGCC GACGCAGACC ATACCGGGTA CGAAGAAGGA GACCTAGAAG
  651 ATCTTTTCGC CGCCGCGGCC GAGGACGATA TGTGAGTAGG CGGAGGCGCC
  701 GCCGCTACTA CAGGCGCAGA CTGAGACGGG GCAGACGCAG AGGGCGACGA
  751 AAGAGACACA GACAGACTCT AGTAGTGAGG CAGTGGCAAC CTGACGTTGT
  801 TAAAAAGTGT AAAATAACAG GATGGATGCC TCTTATAATC TGTGGCTCTG
  851 GAAGCACACA GATGAACTTT ATAACTCACA TGGACGATAC TCCCCCTATG
  901 GGATACACCT ACGGGGGCAA CTTTGTAAAT GTAACTTTCA GTCTAGAGGC
  951 CATCTATGAA CAATTCCTGT ACCACAGAAA CAGGTGGTCC AGGTCTAACC
 1001 ATGACTTAGA CCTGGCCAGA TACCAAGGAA CCACTCTAAA ACTTTACAGA
 1051 CACCAAACCG TGGACTATAT AGTTAGCTAC AACAGAACAG GCCCCTTTAC
 1101 TATAAGTGAA ATGACTTACA TGAGCACACA CCCGGCTCTC ATGCTACTAC
 1151 AAAAACATAG AATAGTTGTA CCCAGCTTCA GAACCAAGCC AAAAGGCAAA
 1201 AGAGCCATAA AAATTAGAAT AAGGGCCCCA AAACTAATGC TCACCAAGTG
 1251 GTACTTTACA AAAGACATTT GCTCCATGGG CCTCTTTCAA CTAATGGCAA
 1301 CAGCTGCAGA ACTTACAAAC CCATGGCTCA GAGACACCAC AAAAAGCCCA
 1351 GTAATTGGCT TCAGAGTCTT AAAAAACAGC TTATACACAT GCCTTTCCAA
 1401 CTTAAAAGAC CAAGCAATAC AAGGTGAAAG AAAGACTGTA CAAAATAGAT
```

FIG. 11B

```
1451  TACACCCAGA AAACCTACAT GGCACAGGAC CTAATGCTAA AGGCTGGGAA
1501  TACACATACA CAAAACTAAT GGCATCTACA TACTACTCAG CCAACAGAAA
1551  CAGCACCTAC AACTGGCAAA ACTATCAAAC TAACTATGCA AACACATATA
1601  CAAAATTTAA AGAAAAAAGA ACAGCAAACT TAAACTTAAT TAAAGCAGAA
1651  TACCTATATC ATTACCCTAA CAATGTCACA CAATCTGACT TTATATTAGA
1701  CTACACACTA ACACCCGACT GGGGCATATA CAGCCCCTAC TACCTAACAC
1751  CCACCAGAAT TAGCCTAGAC TGGGACACAC CATGGACATA TGTAAGATAC
1801  AACCCACTAT CAGACAAAGG CATAGGTAAC AGAATATATG CACAGTGGTG
1851  CTCAGAAAAA TCTAGTAAAT TAGACACCAC AAAGAGCAAG TGCATACTAA
1901  GAGACTTCCC ACTGTGGGCC ATGGCCTATG GCTACTGTGA CTGGGTGGTG
1951  AAGTGCACAG GAGTGTCCAG TGCTTGGACA GACATGAGAA TAGCCATTAT
2001  ATGTCCCTAC ACAGAACCAG CACTTATAGG GTCAACAGAA GACGTAGGCT
2051  TCATTCCAGT AAGTGACACC TTTTGCAACG GAGACATGCC GTTTCTTGCA
2101  CCATACATAC CTATTACATG GTGGATTAAG TGGTACCCCA TGATTACACA
2151  CCAAAAGGAA GTTCTTGAGG CAATAGTTAA CTGTGGACCG TTTGTACCCC
2201  GAGACCAAAC TTCCCCAGCT TGGGAATAAC CATGGGTTAC AAAATGGATT
2251  GGAAATGGGG CGGCTCTCCC CTGCCTTCAC AGGCAATCGA CGACCCCTGC
2301  CAGAAGTCCA CCCACGAACT TCCCGACCCC GATAGACACC CTCGCATGTT
2351  ACAAGTCTCT GACCCGACAA AGCTCGGACC GAAGACAGTT TTTCACAAAT
2401  GGGACTGGAG ACGTGGGATG CTTAGCAAAA GAAGTATTAA AAGAGTCCAA
2451  GAAGACTCAA CAGACGATGA ATATGTTGCA GGACCCTTAC CAAGAAAAAG
2501  AAACAAGTTC GATACTCGAG TCCAAGGCCC TCCAACCCCA GAAAAAGAAA
2551  GTTACACTTT ACTCCAAGCC CTCCAAGAGT CGGGGCAAGA GAGCAGCTCA
2601  GAGGACCAAG AACAAGCACC CCAAGAAAAA GAGGACCAGA AGGAAGCGCT
2651  CATGGAGCAG CTCCAGCTCC AGAAACACCA CCAGCGAGTC CTCAAGCGAG
2701  GCCTCAAACT CCTCCTCGGA GACGTGCTCC GACTCCGGAG AGGAGTCCAC
2751  TGGGACCCCC TCCTGTCCTA ATTCAAGGTC CCAGTATCCC AGACCTGCTT
2801  TTCCCTAACA CACAAAAAAA AAAACGATTT TCCAACTACG ACTGGGTGTG
2851  CGAGTACGAG CTGGCCAAAT GGATGGATCG GCCCTTGCGG CACTACCCAT
2901  CAGACCCCCC TCACTACCCC TGGCTACCAA AAAAGCCTCC TACCCCTCCT
2951  ACATGTAGAG TAAGTTTCAA ATTAAAGCTC AATGACTAAA ATTCAAGGCC
3001  GTGGGTGTTT CACTTCATCG GTGTCTACCT CTAAAAGTCA CTAAGCACTC
3051  CGAGCGTAAG CGAGGAGTGC GACCCCCCTG CCCGGTAGCA ACTTCCTCGG
3101  GGTCCGGCGC TACGCCTTCG GCTGCGCCGG GCGCCTCGGA CCCCCCCTCG
3151  ACCCGAATCG CTCGCGCGAT TCGGACCTGC GGCCTCGGGG GGGTCGGGGG
3201  CTTTACTAAA CAGACTCTGA GGTGCCGTTG GACACTGAGG GGGTGAACAG
3251  CAACGAAAGT GAGTGGGGCC AAACTTCGCC ATAAGGCCTT TAACTTTGGG
```

FIG. 11C

```
3301  TCGCTTGTCA GCAGCTTCCG GGTCCGCCTG GAGGCCGCCA TTTTACATTC
3351  GGCCGCCATT TTAGGCCCTC GCGGGCCTCC ATAGTCGCAC ATCAGTGACG
3401  TCACGGCAGC CATCTTGGCT GTGACGTCAA CGTCACGTGG GGAGGACGGC
3451  GTGTAACCCG GAAGTCATCC TCATCACGCG ACCTGACGTC ACGGCCGCCA
3501  TTTTGTGCTG TCCGCCATCT TGTGACTTCC TTCCGCTTTT TGTAAAAAAA
3551  AGAGGAAGTG TGACGTAGCG GCGGGGGGGn nnnnnnnnnn nnnnnnnCGC
3601  CACCAGGGGG CGCTACGCGC CCCCCCCCGC GCATGTGCGG GTCCCCCCCC
3651  TCGGGGGGGG CTCCGCCCCC CCGGCCCCCC CCGGGCTAA ATACACCGCG
3701  CATGCGCGGC CACGCCCCCG CCGCC
```

FIG. 11D zpr4.20
zpr4.20.seq (subviral molecule, ttgb33.35)
 293TT +4 (gbDhDi33.35) PCR
Tr9.7 A/9nested B5 in pCR2.1, Nova Blue zpr4.B5.20.seq  Length: 719

```
  1  CAATTCGGGC ACGGGACTGG CCGGGCTATG GGCAAGGCTC TTAAAAAATT
 51  CCCCCGCTCT GCTCTCCGGC AGGACACAAA GTCATGCCGT GGAGACCGCC
101  GGTCCATAAC GTGCCAGGTA GAGAGAATCA ATGGTTTGCA GCGTTCTTTC
151  ACGGTCATGC TGCTTTCTGC GGGTGTGGTG ACCCTGTTGG GCATCTTAAC
201  GGCATTGCTC CTCGCTTTCC TAACGCCGGT CCACCGAGAC CACCTCCAGG
251  GCTAGACCAG CTTAATCCCG AGGGCCCGGC AGGTCCCGGA GGGCCCCCCG
301  CCATCTTGCC AGCTCTGCCG GCCCCGGCAG ACCCTGAACC GGCACCACGG
351  CGTGGTGGTG GGGCAGATGG AGGCGCCGCC GCTGGGGCCG CCGCCGACGC
401  AGACCATACC GGGTACGAAG AAGGAGACCT CGGGGGGGGC TCCGCCCCCC
451  CGGCCCCCCC CCGGGCTAAA TACACCGCGC ATGCGCGGCC ACGCCCCCGC
501  CGCCATTTTG TGCAGCCCGC CAATTCTGT CAAACAGAC CAATCAGGAC
551  CTTCTACGTG CACTTCCTGG GGCGTGTCTA CGAGGTCTAT ATAAGCAACA
601  GCGGTGACGA ATGGTAGAGT TTTCTTCGC CCGTCCGCGG CGAGAGCGCG
651  AGCGAAGCGA GCGATCGAGC GTCCCGTGGG CGGGTGCCGT AGGTGAGTTT
701  ACACACCGAA GTCAAGGGG
```

FIG. 12A

```
tth25 (complete genome)
length 3758

1 AAGTACGTCA CTAACCACGT GACTCCCGCA GGCCAACCAG AGTCTACGTC
  51 GTGCACTTCC TGGGCATGGT CTACATCATA ATATAAGAAC GTGCACTTCC
 101 GAATGGCTGA GTTTTCCACG CCCGTCCGCA GCGAGAACGC CACGGAGGGA
 151 GATCCTCGCG TCCCGAGGGC GGGTGCCGGA GGTGAGTTTA CACACCGCAG
 201 TCAAGGGGCA ATTCGGGCTC GGGACTGGCC GGGCCCCGGG CAAGGCTCTT
 251 AAAAAATGCG TTTTCGCAGG GTTGCCCAGA AAAGGAAAGT GCTTTTGCAA
 301 ACTGTGCCAG CTGCAAAGAA GGCTAGGCGG CTTCTAGGTA TGTGGCAGCC
 351 CCCCACGCAC AATGTCCCGG GCATCGAGAG AAACTGGTAC GAGAGCTGTT
 401 TTAGATCCCA CGCTGCTGTT TGTGGCTGTG GCGATTTTGT TGGCCATCTT
 451 AATCATCTGG CAACTACTCT GGGTCGTCCT CCGCGTCCTG GGCCCCCAGG
 501 CGGACCCCGC ACGCCGCAAA TAAGAAACCT GCCAGCGCTC CCGGCGCCCC
 551 AGGGCGAGCC CGGTGACAGA GCGCCATGGC ATGGGGCTTC TGGGGCCGAC
 601 GCCGCCGGTG GAGACGATGG AGAGCGCGGC GCAGACGGTG GAGACCCCGC
 651 AGACGTAGGA GACGACGCCC TACTCGCCGC TTTCGAGCTC GTCGAAGAGT
 701 AAGGAGGCGC GGGGGGAGGT GGCGCAGACG CTACAGAAAA TGGCGACGGG
 751 GCAGACGCAG ACGGACTCAT AGAAAAAAGA TAGTCATAAA ACAGTGGCAA
 801 CCAAACTTTA TAAGACGCTG CTACGTCATA GGGTACTTAC CACTTATATT
 851 CTGCGGCGAA AATACAACCG CCCAGAACTT TGCCACTCAC TCGGACGACA
 901 TGATAAGCAA AGGACCGTAC GGGGGGGGCA TGACTACCAC CAAATTCACT
 951 CTGAGAATAC TGTACGACGA GTTACCAGG TTTATGAACT TTTGGACTGT
1001 CAGTAACGAA GACCTAGACC TGTGTAGATA CGTGGGCTGC AAACTAATAT
1051 TTTTTAAACA CCCCACGGTG GACTTTATAG TACAGATAAA CACTCAGCCT
1101 CCTTTCTTAG ACACGCACCT CACGGCGGCC AGCATACACC CGGGCATCAT
1151 GATGCTCAGC AAGAGACACA TACTAATACC CTCTCTAAAG ACCCGGCCCA
1201 GCAGAAAACA CAGGGTGGTC GTCAGGGTGG GCGCCCCAAG ACTTTTTCAG
1251 GACAAGTGGT ACCCCCAGTC AGACCTGTGT GACACAGTTC TGCTTTCCAT
1301 ATTTGCAACC GCCTGCGACT TGCAATATCC GTTCGGCTCA CCACTAACTG
1351 ACAACCCTTG CGTCAACTTC CAGATCCTGG GGCCCCAGTA CAAAAAACAC
1401 CTTAGTATTA GCTCCACTAT GGATCAAACT AACGAAAACC ATTATAAAGA
1451 AAACTTATTT AACAAAACTG AACTATACAA CACCTTTCAA ACCATAGCTC
1501 AGCTTAAAGA GACAGGACAC ATTTCAGGCA TTAGTCCTAC TTGGAATGAA
1551 GTCCAGAATT CAACAACACT TACTAAAGGA GGTGACAATG CCACTCAGAG
1601 TAGAGACACT TGGTATAAAG GAAATACATA CAACGAGAAG ATATGCGAGT
1651 TAGCACAAAT AACCAGAAAC AGATTTAAAA ATGCAACCAA AGGAGCACTA
```

FIG. 12B

```
1701  CCAAACTACC CCACAATAAT GTCCACAGAC CTATATGAAT ACCACTCAGG
1751  CATACACTCC AGCATATATC TATCAGCTGG CAGGAGCTAC TTTGAAACCA
1801  CCGGGGCCTA CTCTGACATT ATATACAACC CTTTCACAGA CAAAGGCACA
1851  GCCAACATAA TCTGGATAGA CTACCTCACA AAAGAAGACA CCATTTTTGT
1901  GAAAAACAAA AGCAAATGCG AGATAATGGA CATGCCCCTG TGGGCGGCCT
1951  GCACAGGATA CACAGAGTTT TGTGCAAAGT ATACAGGCGA CTCTGCCATT
2001  ATCTACAATG CAAGAATACT CATAAGATGC CCATACACTG AGCCCATGTT
2051  AATAGACCAC TCAGACCCAA ACAAAAGCTT CGTTCCCTAC TCATTTAACT
2101  TTGGCAACGG AAAGATGCCC GGAGGCAGCT CCAACGTGCC CATAAGAATG
2151  AGAGCCAAGT GGTACGTGAA CATATTCCAC CAAAAAGAAG TATTAGAGAG
2201  CATAGTACAG TCCGGACCGT TTGGGTACAA GGGCGACATA AGATCAGCTG
2251  TACTAGCCAT GAAATACAGA TTTCACTGGA AGTGGGGCGG AAACCCTATA
2301  TCCAAACAGG TCGTCAGGAA TCCCTGCTCC AACTCCAGCT CCTCCGCGGC
2351  CCATAGAGGA CCTCGCAGCG TACAAGCGGT TGACCCGAAA TACAATACCC
2401  CAGAGGTCAC GTGGCACTCG TGGGACATTA GACGAGGACT CTTTGGCAAA
2451  GCAGGTATTA AAAGAATGCA ACAGGAATCA GATGCTCTTT ACATTCCTCC
2501  AGGACCAATC AAGAGACCTC GCAGGGACAC CAACGCCCAA GACCCAGAAG
2551  AGCAAAACGA AAGCTCAGGT TTCAGAGTCC AGCAGCGACT CCCGTGGGTC
2601  CACTCCAGCC AAGAGACGCA AAGCTCCCAA GAAGAGACGG AGGCGCAGGG
2651  GTCGGTACAA GACCAACTAC TCCTCCAGCT CCGAGAGCAG CGAGTTCTCC
2701  GACTCCAGCT CCAGCAACTC GCAACCCAAG TCCTCAAAGT CCAAGCAGGG
2751  CACAGCCTAC ACCCCTATT ATCTTCCCAA GCATAAACAA AGCCTTTATG
2801  TTTGAGCCCC AGGGTCCTAA ACCCATACAG GGGTACAACG ACTGGCTAGA
2851  AGAGTACACT GCTTGCAAAT CTGGGACAG ACCCCCCAGA AAGCTACACA
2901  CAGACATACC CTTCTACCCC TGGGCACCAA AACCCCAACA GCAAGTCAGG
2951  GTGTCCTTTA AACTCAACTT TCAATAAAAA TTCTAGGCCG TGGGAGTTTC
3001  ACTTGTCGGT GTCTGCTTCT TAAGGTCGCC AAGCACTCCG AGCGCCAGCG
3051  AGGAGTGCGA CCCCCCCTCC GGTAGCAACG CCTTCGGAGC CGCGCGCTAC
3101  GCCTTCGGCT GCGCGCGGCA CCTCAGACCC CCCTCCACC CGAAACGCTT
3151  GCGCGTTTCG GACCTTCGGC GTCGGGGGG TCGGGAGCTT TATTAAACAG
3201  ACTCCGAGTT GCCATTGGAC ACTGGAGCTG TGAATCAGTA ACGAAAGTGA
3251  GTGGGGCCAG ACTTCGCCAT AGGGCCTTTA TCTTCTCGCC ATTGGATAGT
3301  GTCCGGGGTC GCCGTAGGCT TCGGCCTCGT TTTTAGGCCT TCCGGACTAC
3351  AAAAATGGCG GTTTAGTGA CGTCACGGCC GCCATTTTAA GTAAGGCGGA
3401  AGCAGCTCCA CTTTCTCACA AAATGGCGGC GGAGCACTTC CGGCTTGCCC
3451  AAAATGGCGG GCAAGCTCTT CCGGGTAAAG GGTCAGCAGC TACGTCACAA
3501  GTCACCTGAC TGGGGAGGGG TCACAACCCG GAAGCCCTCC TCAGTCACGT
```

FIG. 12C

```
3551 GGCTGTTCAC GTGGTTGCTA CGTCATCGGC GCCATCTTGT GTCGCAAAAT
3601 GGCGGACAAC TTCCGCTTTT TTAAAAAAG GCGCGAAAAA ACGGCGGCGG
3651 CGGCGCGCGC GCTGTGCGCG CGCGCCGGGG GGGCGCCAGC GCCCCCCCCC
3701 CCGCGCATGC GCGGGTCCCC CCCCCGCGG GGGGCTCCGC CCCCCGGCCC
3751 CCCCCCCG
```

FIG. 12D zpr9.6
zpr9.B1.6.seq (subviral molecule, tth25)
 293TT+9(tth25smfr3)PCR
Tr11.8 C/6
In pCR2.1,ONEShot Topo10F' zpr9.B1.6.seq  Length: 621

```
  1 CCGCAGCGAG AACGCCACGG AGGGAGATCC TCGCGTCCCG AGGGCGGGTG
 51 CCGGAGGTGA GTTTACACAC CGCAGTCAAG GGGCAATTCG GGCTCGGGAC
101 TGGCCGGGCC CCGGGCAAGG CTCTTAAAAA ATGCGTTTTC GCAGGGTTGC
151 CCAGAAAAGG AAAGTGCTTT TGCAAACTGT GCCAGCTGCA AAGAAGGCTA
201 GGCGGCTTCT AGGTATGTGG CAGCCCCCCA CGCACAATGT CCCGGGCATC
251 GAGAGAAACT GGTACGAGAG CTGTTTTAGA TCCCACGCTG CTGTTTGTGG
301 CTGTGGCGAT TTTGTTGGCC ATCTTAATCA TCTGGCAACT ACTCTGGGTC
351 GTCCTCCGCG TCCTGGGCCC CCAGGCGGAC CCCGCACGCC GCAAATAAGA
401 AACCTGCCAG CGCTCCCGGC GCCCCAGGGC GAGCCCGGTG ACAGAGCGCC
451 ATGGCATGGG GCTTCTGGGG CCGACGCCGC CGGTGGAGAC GATGGAGAGC
501 GCGGCGCAGA CGGTGGAGAC CCCGCAGGCC AACCAGAGTC TACGTCGTGC
551 ACTTCCTGGG CATGGTCTAC ATCATAATAT AAGAACGTGC ACTTCCGAAT
601 GGCTGAGTTT TCCACGCCCG T
```

FIG. 13A ttrh215
rheu.cd.215.seq
Genomiphi tth4-primer
ann.78°+ additional taq polymerase(progr.tth4*78)
 vector:TA-cloning pcr2.1 invitrogen rheu.cd.215rp.seq   Length: 3758

```
   1   AAAGTACGTC ACTAACCACG TGACTCCCAC AGGCCAACCA CAGTCTACGT
  51   CGTGCATTTC CTGGGCATGG TCTACATCAT AATATAAGAA GGCGCACTTC
 101   CGAATGGCTG AGTTTTCCAC GCCCGTCCGC AGCGAGAACG CCACGGAGGG
 151   AGATCCTCGC GTCCCGAGGG CGGGTGCCGG AGGTGAGTTT ACACACCGCA
 201   GTCAAGGGGC AATTCGGGCT CGGGACTGGC CGGGCCCTGG GCAAGGCTCT
 251   TAAAAAATGC GCTTTCGCAG GGTTGCGGAG AAAAGGAAAG TGCTTCTGCA
 301   AACTCTGCGA GCTGCAAAGC AGGCTAGGCG GCTTCTAGGT ATGTGGCAGC
 351   CCCCCGCGCA CAATGTCCCC GGCATCGAGA GAAACTGGTA CGAGAGCTGC
 401   TTCAGGTCTC ACGCTGCTGT TTGTGGCTGT GGCGACTTTG TTGGCCATAT
 451   TAATCATTTG GCAACTACTC TGGGTCGTCC TCCGCGTCCT GGGCCCCCAG
 501   GCGGACCCCG CACGCCGCAA ATAAGAAACC TGCCAGCGCT CCCGGCGCCC
 551   CAGGGCGAGC CCGGTGACAG AGCGCCATGG CGTGGGGTTT CTGGGGCCGA
 601   CGCCGCCGGT GGAGACGGTG GAGAGCGCGG CGCAGACGGT GGAGACCCCG
 651   GAGACGTAGG AGACGACGCC CTGCTCGCCG CTTTCGAGCT CGTCGAAGAG
 701   TAAGGAGACG CGGGGGGAGG TGGCGCAGAC GCTACAGAAA ATGGCGACGG
 751   GGCAGACGCA GACGGACTCA CAGAAAAAAG ATAATTATAA AACAGTGGCA
 801   ACCAAACTTT ATTAGACGCT GCTACATAAT AGGATGCCTA CCTCTCGTTT
 851   TCTGTGGCGA AAATACAACC GCCCAGAACT ATGCCACTCA CTCAGACGAT
 901   ATGATAAGCA AAGGACCGTA CGGGGGGGGC ATGACTACCA CGAAATTCAC
 951   TCTGAGAATA CTGTACGACG AGTTTACCAG GTTTATGAAC TTTTGGACTG
1001   TCAGTAACGA AGACCTAGAC CTGTGTAGAT ACGTGGGCTG CAAACTGATA
1051   TTTTTTAAAC ACCCCACGGT GGACTTTATG GTACAGATAA ACACTCAGCC
1101   TCCTTTCTTA GACACAAGCC TCACCGCGGC CAGCATACAC CCGGGCATCA
1151   TGATGCTCAG CAAGAGACGC ATATTAATAC CCTCTCTAAA GACCCGGCCG
1201   AGCAGAAAAC ACAGGGTGGT CGTCAGGGTG GGCGCCCCAA GACTTTTTCA
1251   GGACAAGTGG TACCCCAGT CAGACCTATG TGACACAGTT CTGCTTTCCA
1301   TATTTGCAAC CGCCCGCGAC TTGCAATATC CGTTCGGCTC ACCACTAACT
1351   GACAACCCTT GCGTCAACTT CCAGATCCTG GGGCCCCAGT ACAAAAAACA
1401   CCTTAGTATT AGCTCCACTA TGGATGATAC TAACAAACAG CACTATAACA
1451   GCAACTTATT TAATAAAACT GCACTATACA ACACCTTTCA AACCATAGCC
```

FIG. 13B

```
1501  CGGCTTAAAG AGACAGGACA AACTGCAAAC ATTAGTCCAA GTTGGAGTGA
1551  AGTACAAAAC ACAAAACTAC TAGATCACAC AGGTGCTAAT GCAACTGCCA
1601  GCAGAGACAC TTGGTACAAG GGAAACACAT ACAATGACTA CATACAACAG
1651  TTAGCAGAGA AAACAAGAGA AAGGTTTAAA AAAGCAACAA TGTCAGCACT
1701  ACCAAACTAC CCCACAATAA TGTCCACAGA CTTATACGAA TACCACTCAG
1751  GCATATACTC CAGCATATTT CTATCAGCTG GCAGGAGCTA CTTTGAAACC
1801  ACTGGGGCCT ACTCTGACAT TATATACAAC CCTTTGACAG ACAAAGGCAC
1851  AGGCAACATA ATCTGGATAG ACTACCTTAC AAAAGACGAC ACAATCTTTG
1901  TAAAAAACAA AAGCAAATGT GAGATAATGG ACATGCCCCT GTGGGCGGCC
1951  GGCACAGGAT ACACAGAGTT TTGTGCAAAG TACACAGGAG ACTCTGCCAT
2001  TATTTACAAT GCCAGAATAC TCATAAGATG CCCATACACT GAACCCATGC
2051  TAATAGACCA CTCAGACCCA AACAAAGGCT TTGTACCGTA CTCATTTAAC
2101  TTTGGCAACG GAAAGATGCC GGGAGGCAGC TCCAACGTGC CCATAAGAAT
2151  GAGAGCCAAG TGGTACGTAA ACATATTCCA CCAAAAAGAA GTATTGGAGA
2201  GCATAGTACA GTCCGGACCG TTCGGGTACA GGGGCGACAT AAAATCAGCT
2251  GTACTGTCCA TGAAATACAG ATTTCACTGG AAATGGGGCG GAAACCCTAT
2301  ATCCAAACAG GTCGTCAGGA ATCCCTGCTC CAACTCCAGC ACCTCCGCGG
2351  CCCATAGAGG ACCTCGCAGC GTACAAGCGG TTGACCCGAA ATACAATACC
2401  CCAGAAGTCA CTTGGCACTC GTGGGACATC AGACGAGGAC TCTTTGGCAA
2451  AGCAGGTATT AAAAGAATGC AACAAGAATC AGATGCTCTT TACGTTCCTG
2501  CAGGACCACT CAAGAGGCCT CGCAGAGACA CCAACGCCCA AGACCCGGAA
2551  AAGCAAAACG AAAGCTCACG TTTCGGAGTC CAGCAGCGAC TCCCGTGGGT
2601  CCACTCCAGC CAAGAGACGC AAAGCTCCGA GAAGAGACG CAGGCGCAGG
2651  GGTCGGTACA AGACCAACTA CTCCTCCAGC TCCGAGAGCA GCGAGTACTC
2701  CGACTCCAGC TCCAACAACT CGCACCCCAA GTCCTCAAAG TTCAAGCAGG
2751  ACACAGCCTA CACCCCCTAT TATCCTCCCA AGCATAAACA AAGCCTATAT
2801  GTTTGAACCC CAGGGTCCTA AACCCATACA GGGGTACAAC GATTGGCTAG
2851  AGGAGTACAC TAGTTGCAAG TTCCGGGACA GACCCCCGAG AATGCTACAC
2901  ACAGACTTAC CCTTTTACCC CTGGGCACCA AAACCCCAAG ACCAAGTCAG
2951  GGTAACCTTT AAAACTCAACT TTCAATAAAA ATTCTAGGCC GTGGGACTTT
3001  CACTTGTCGG TGTCTGCTTC TTAAGGTCGC CAAGCACTCC GAGCGTCAGC
3051  GAGGAGTGCG ACCCCCCCCC TCGGTAGCAA CGCCTTCGGA GCCGCGCGCT
3101  ACGCCTTCGG CTGCGCGCGG CACCTCAGAC CCCCCCTCCA CCCGAAACGC
3151  TTGCGCGTTT CGGACCTTCG GCGTCGGGGG GGTCGGGAGC TTTATTAAAC
3201  AGACTCCGAG TTGCCATTGG ACACTGGAGC TGTGAATCAG TAACGAAAGT
3251  GAGTGGGGCC AGACTTCGCC ATAGGGCCTT TATCTTCTCG CCATTGGATA
3301  GTGTCCGGGG TTGCCGTAGG CTTCGGCCTC GTTTTTAGGC CTTCCGGACT
```

FIG. 13C

```
3351  ACAAAAATGG CGGATTTTGT GACGTCACGG CCGCCATTTT AAGTAAGGCG
3401  GAAGCAGCTC CACCCTCTCA CATAATGGCG GCGGAGCACT CCCGGCTTGC
3451  CCAAAATGGC GGGCAAGCTC TTCCGGGTCA AAGGTTGGCA GCTACGTCAC
3501  AAGTCACCTG ACTGGGGAGG AGTTACATCC CGGAAGTTCT CCTCGGTCAC
3551  GTGACTGTAC ACGTGACTGC TACGTCATTG ACGCCATCTT GTGTCACAAA
3601  ATGGCGGTGC ACTTCCGCTT TTTTGAAAAA AGGCGCGAAA AAACGGCGGC
3651  GGCGGCGCGC GCGCTGCGCG CGCGCGCCGG GGGGGCGCCA GCGCCCCCCC
3701  CCCCGCGCAT GCACGGGTCC CCCCCCCCAC GGGGGGCTCC GCCCCCCGGC
3751  CCCCCCCC
```

FIG. 13D zpr12.24
zpr12.24.seq (subviral molecule, ttrh215)
Length: 642

```
  1  CAGCGAGAAC GCCACGGAGG GAGATCCTCG CGTCCCGAGG GCGGGTGCCG
 51  GAGGTGAGTT TACACACCGC AGTCAAGGGG CAATTCGGGC TCGGGACTGG
101  CCGGGCCCCG GGCAAGGCTC TTAAAAAATG CGCTTTCGCA GGGTTGCTGA
151  GAAAAGGAAA GTGCTTCTGC AAACTGTGCG AGCTACACAG AAGACTAGGC
201  GGCTTCTAAG CCGCCCACAG GGGCATGTCT ACATGCTTCC GCAGCGAGAA
251  CGCCACGGAG GGAGATCCTC GCGTCCCGAG GCGGGTGCC GGAGGTGAGT
301  TTACACACCG CAGTCAAAGG GCAATTCGGG CTCGGGACTG GCCGGGCCCC
351  GGGCAAGGCT CTTAAAAAAT GCGCTTTCGC GGGGTTGCTG AGAAAAGGAA
401  AGTGCTTCTG CAAACTGTGC GAGCTACACA GAAGACTAGG CGGCTTCTAG
451  GTATGTGGCA GCCCCCCGTG CACAATGTCC CCGGCATCTT ATTAGTACTC
501  TGGCGTTGTA GATAATGGCA GAGTCTCCAG TGTACTTTGC ACAGAACTCT
551  GTGTATCCTG TGCAGGCCGC CCACAGGGGC ATGTCTACAT CATAATATAA
601  TAAGGCGCAC TTCCGAATGG CTGAGTTTTC CACGCCCGTC CG
```

FIG. 14A

*Open reading frames of 71 nt (HCR):*

```
zyb2.1.pep    RVPKVSLHTA VKGQFGLGTG RAM
zyb9.1.pep    RVPKVSLHTA VKGQFGLGTG RAM
zkb69.1.pep   RVPEVSLHTA VKGQFGLGTG RAM zyb2.3.pep    GAEGEFTHRS QGAIRARDWP GHG
zyb9.3.pep    GAEGEFTHRS QGAIRARDWP GYG
zkb5.3.pep    GAVGEFTHRS QGAIRARDWP GYG
zkb69.3.pep   GAGGEFTHRS QGAIRARDWP GYG
``` zyb2.1.pep
nucleotide 1-71
Length: 23aa

RVPKVSLHTA VKGQFGLGTG RAM

BlastP2 of: zyb2.1.pep
compared to database: uniprot ..

```
>>>sptrembl:Q9WSW0_9VIRU  Q9wsw0  SubName: Full=ORF2; Flags: Fragm...    49    1e-04
>>>sptrembl:Q9WB09_9VIRU  Q9wb09  SubName: Full=ORF2; Flags: Fragm...    48    4e-04
>>>sptrembl:Q9WSW2_9VIRU  Q9wsw2  SubName: Full=ORF2; Flags: Fragm...    48    4e-04
>>>sptrembl:Q9WSX0_9VIRU  Q9wsx0  SubName: Full=ORF2; Flags: Fragm...    47    4e-04
>>>sptrembl:Q9WB10_9VIRU  Q9wb10  SubName: Full=ORF2; Flags: Fragm...    47    5e-04
>>>sptrembl:Q9WAZ2_9VIRU  Q9waz2  SubName: Full=ORF2; Flags: Fragm...    47    5e-04
>>>sptrembl:O70807_9VIRU  O70807  SubName: Full=Putative uncharact...    47    6e-04
>>>sptrembl:Q9WAY4_9VIRU  Q9way4  SubName: Full=ORF2; Flags: Fragm...    47    7e-04
>>>sptrembl:Q9WB02_9VIRU  Q9wb02  SubName: Full=ORF2; Flags: Fragm...    47    8e-04
>>>sptrembl:Q9WSW4_9VIRU  Q9wsw4  SubName: Full=ORF2; Flags: Fragm...    46    0.001
>>>sptrembl:Q9WB12_9VIRU  Q9wb12  SubName: Full=ORF2; Flags: Fragm...    46    0.001
>>>sptrembl:Q9WSW6_9VIRU  Q9wsw6  SubName: Full=ORF2; Flags: Fragm...    45    0.002
>>>sptrembl:B3FWR6_9VIRU  B3fwr6  SubName: Full=ORF2; Flags: Fragm...    36    0.94

>>>>sptrembl:Q9WSW0_9VIRU Q9wsw0 SubName: Full=ORF2; Flags:
         Fragment;. 2/2010
         Length = 204
 Score = 49.3 bits (116), Expect = 1e-04,  Method: Compositional matrix adjust.
 Identities = 23/23 (100%), Positives = 23/23 (100%)
Query:  1 RVPKVSLHTAVKGQFGLGTGRAM 23
          RVPKVSLHTAVKGQFGLGTGRAM
Sbjct: 27 RVPKVSLHTAVKGQFGLGTGRAM 49

>>>>sptrembl:Q9WB09_9VIRU Q9wb09 SubName: Full=ORF2; Flags:
         Fragment;. 2/2010
         Length = 138
 Score = 47.8 bits (112), Expect = 4e-04,  Method: Compositional matrix adjust.
 Identities = 22/23 (95%), Positives = 22/23 (95%)
Query:  1 RVPKVSLHTAVKGQFGLGTGRAM 23
          RVPKVSLHT VKGQFGLGTGRAM
Sbjct: 14 RVPKVSLHTEVKGQFGLGTGRAM 36

ID  Q9WSW0_9VIRU          Unreviewed;       204 AA.
```

FIG. 14B

```
AC   Q9WSW0;
DT   01-NOV-1999, integrated into UniProtKB/TrEMBL.
DT   01-NOV-1999, sequence version 1.
DT   09-FEB-2010, entry version 23.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   STRAIN=KC205/1-12G; TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024383; BAA77450.2; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER       1     1
SQ   SEQUENCE   204 AA;  21953 MW;  6352C96D2AC0DF21 CRC64;
     CTSEWLSFPR PSAAAXPRRV IPASRWRVPK VSLHTAVKGQ FGLGTGRAMG KALKVFILKM
     HFSRISRSKR KVLLPALPAP PPPRQLLMWQ PPIQNGTQLD RHWFESVWRS HAAYCGCGDC
     VGHLQHLAAN LGRPPHPQPP REQHPPQIRG LPALPAPPSN RNSWPGTGGD AAGEQAGGSR
     GAGDGGDGEL ADDDLXDAAA LVEE ID   Q9WB09_9VIRU            Unreviewed;       138 AA.
AC   Q9WB09;
DT   01-NOV-1999, integrated into UniProtKB/TrEMBL.
DT   01-NOV-1999, sequence version 1.
DT   09-FEB-2010, entry version 22.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024376; BAA77443.1; -; Genomic_DNA.
```

FIG. 14C

```
DR    InterPro; IPR004118; Gyrovir_VP2/TT_ORF2.
DR    Pfam; PF02957; TT_ORF2; 1.
PE    4: Predicted;
FT    NON_TER       1       1
FT    NON_TER     138     138
SQ    SEQUENCE   138 AA;   15494 MW;   2DF27B3A4F0CA641 CRC64;
      AVKPRREISA SRGRVPKVSL HTEVKGQFGL GTGRAMGKAL KKSMFIGRHY RKKRALSLCA
      VRTTKKACKL LIVMWTPPRN DQQYLNWQWY SSVLSSHAAM CGCPDAIAHL SHLAFVFRAP
      QNFPPPGPQR NLPLRRLP
``` zyb2.3.pep
nucleotide 3-71
Length: 23aa

GAEGEFTHRS QGAIRARDWP GHG

BlastP2 of: zyb2.3.pep    from: 1 to: 23
compared to database: uniprot

```
>>>sptrembl:Q98Y39_9VIRU   Q98y39 SubName: Full=ORF2;. 2/2010              50    7e-05
>>>sptrembl:Q9WAY7_9VIRU   Q9way7 SubName: Full=ORF2; Flags: Fragm...      50    7e-05
>>>sptrembl:Q786D4_9VIRU   Q786d4 SubName: Full=ORF2;. 2/2010              50    9e-05
>>>sptrembl:O70738_9VIRU   O70738 SubName: Full=ORF2, ORF1 genes;....      50    9e-05
>>>sptrembl:Q9JG33_9VIRU   Q9jg33 SubName: Full=Putative uncharact...      50    9e-05
>>>sptrembl:O90363_9VIRU   O90363 SubName: Full=ORF2 protein;. 2/2010      50    9e-05
>>>sptrembl:Q9WFY6_9VIRU   Q9wfy6 SubName: Full=ORF2;. 2/2010              50    1e-04
>>>sptrembl:Q9JGT0_9VIRU   Q9jgt0 SubName: Full=PORF2a;. 12/2009           50    1e-04
>>>sptrembl:Q9YKL2_9VIRU   Q9ykl2 SubName: Full=ORF2 protein;. 2/2010      50    1e-04
>>>sptrembl:Q9JGS7_9VIRU   Q9jgs7 SubName: Full=PORF2a;. 12/2009           49    1e-04
>>>sptrembl:Q9DYC0_9VIRU   Q9dyc0 SubName: Full=Putative uncharact...      49    1e-04
>>>sptrembl:Q9W7S4_9VIRU   Q9w7s4 SubName: Full=Putative uncharact...      49    2e-04
>>>sptrembl:Q77S01_9VIRU   Q77s01 SubName: Full=Putative uncharact...      49    2e-04
>>>sptrembl:Q9JGT3_9VIRU   Q9jgt3 SubName: Full=PORF2a;. 12/2009           46    0.001
>>>sptrembl:Q9JGS4_9VIRU   Q9jgs4 SubName: Full=PORF2a;. 12/2009           46    0.001
>>>sptrembl:Q9YR02_9VIRU   Q9yr02 SubName: Full=Putative uncharact...      45    0.003
>>>sptrembl:B2YFW4_9VIRU   B2yfw4 SubName: Full=ORF2; Flags: Fragm...      34    3.7

>>>>sptrembl:Q98Y39_9VIRU   Q98y39 SubName: Full=ORF2;. 2/2010
         Length = 202
 Score = 50.1 bits (118),  Expect = 7e-05,   Method: Compositional matrix adjust.
 Identities = 22/23 (95%), Positives = 23/23 (100%)
Query:  1  GAEGEFTHRSQGAIRARDWPGHG 23
           GAEGEFTHRSQGAIRARDWPG+G
Sbjct: 24  GAEGEFTHRSQGAIRARDWPGYG 46
```

Q98Y39_9VIRU              Unreviewed;        202 AA.
AC    Q98Y39;
DT    01-JUN-2001, integrated into UniProtKB/TrEMBL.
DT    01-JUN-2001, sequence version 1.
DT    09-FEB-2010, entry version 17.
DE    SubName: Full=ORF2;
OS    Torque teno virus.
OC    Viruses; ssDNA viruses; Anelloviridae; unclassified Anelloviridae.
OX    NCBI_TaxID=68887;
RN    [1]
RP    NUCLEOTIDE SEQUENCE.
RC    STRAIN=TWH;
RA    He H.-T., Luo K.-X., Xiao H., Liu D.-X.;

FIG. 14D

```
RT   "Complete circular genome of TT virus isolated from feces of a
RT   hepatitis patient.";
RL   Submitted (FEB-2001) to the EMBL/GenBank/DDBJ databases.
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AF351132; AAK29446.1; -; Genomic_DNA.
DR   InterPro; IPR004118; Gyrovir_VP2/TT_ORF2.
DR   InterPro; IPR013267; TTV_ORF2a.
DR   Pfam; PF02957; TT_ORF2; 1.
DR   Pfam; PF08197; TT_ORF2a; 1.
PE   4: Predicted;
SQ   SEQUENCE   202 AA;  21437 MW;  105B9ED104956EDE CRC64;
     MAEFSTPVRS GEATEGDHRV PRAGAEGEFT HRSQGAIRAR DWPGYGQGSE KSMFIGRHYR
     KKRALSLCAV RTTKKACKLL IVMWTPPRND QQYLNWQWYS SVLSSHASMC GCPDAVAHLI
     NLASVLRAFQ NPPPPGPQRN LPLRRLPALP AAPEAPGDRA PWPMAGGAEG ENGGAGGDAD
     HGGAAGGPED ANLLDAVAAA ET
//
``` zyb9.1.pep
nucleotide 1-71
Length: 23aa

RVPKVSLHTA VKGQFGLGTG RAM

BlastP2 of: zyb9.1.pep    from: 1 to: 23
compared to database: uniprot  ..

```
>>>sptrembl:Q9WSW0_9VIRU  Q9wsw0  SubName: Full=ORF2; Flags: Fragm...   49   1e-04
>>>sptrembl:Q9WB09_9VIRU  Q9wb09  SubName: Full=ORF2; Flags: Fragm...   48   4e-04
>>>sptrembl:Q9WSW2_9VIRU  Q9wsw2  SubName: Full=ORF2; Flags: Fragm...   48   4e-04
>>>sptrembl:Q9WSX0_9VIRU  Q9wsx0  SubName: Full=ORF2; Flags: Fragm...   47   4e-04
>>>sptrembl:Q9WB10_9VIRU  Q9wb10  SubName: Full=ORF2; Flags: Fragm...   47   5e-04
>>>sptrembl:Q9WAZ2_9VIRU  Q9waz2  SubName: Full=ORF2; Flags: Fragm...   47   5e-04
>>>sptrembl:O70807_9VIRU  O70807  SubName: Full=Putative uncharact...   47   6e-04
>>>sptrembl:Q9WAY4_9VIRU  Q9way4  SubName: Full=ORF2; Flags: Fragm...   47   7e-04
>>>sptrembl:Q9WB02_9VIRU  Q9wb02  SubName: Full=ORF2; Flags: Fragm...   47   8e-04
>>>sptrembl:Q9WSW4_9VIRU  Q9wsw4  SubName: Full=ORF2; Flags: Fragm...   46   0.001
>>>sptrembl:Q9WB12_9VIRU  Q9wb12  SubName: Full=ORF2; Flags: Fragm...   46   0.001
>>>sptrembl:Q9WSW6_9VIRU  Q9wsw6  SubName: Full=ORF2; Flags: Fragm...   45   0.002
>>>sptrembl:B3FWR6_9VIRU  B3fwr6  SubName: Full=ORF2; Flags: Fragm...   36   0.94

>>>>sptrembl:Q9WSW0_9VIRU  Q9wsw0  SubName: Full=ORF2; Flags:
         Fragment;. 2/2010
         Length = 204
 Score = 49.3 bits (116),  Expect = 1e-04,   Method: Compositional matrix adjust.
 Identities = 23/23 (100%), Positives = 23/23 (100%)
Query: 1   RVPKVSLHTAVKGQFGLGTGRAM 23
           RVPKVSLHTAVKGQFGLGTGRAM
Sbjct: 27  RVPKVSLHTAVKGQFGLGTGRAM 49

>>>>sptrembl:Q9WB09_9VIRU  Q9wb09  SubName: Full=ORF2; Flags:
         Fragment;. 2/2010
         Length = 138
 Score = 47.8 bits (112),  Expect = 4e-04,   Method: Compositional matrix adjust.
```

FIG. 14E

```
Identities = 22/23 (95%), Positives = 22/23 (95%)
Query: 1   RVPKVSLHTAVKGQFGLGTGRAM 23
           RVPKVSLHT VKGQFGLGTGRAM
Sbjct: 14  RVPKVSLHTEVKGQFGLGTGRAM 36

Q9WSW0_9VIRU              Unreviewed;       204 AA.
AC   Q9WSW0;
DT   01-NOV-1999, integrated into UniProtKB/TrEMBL.
DT   01-NOV-1999, sequence version 1.
DT   09-FEB-2010, entry version 23.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   STRAIN=KC205/1-12G; TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024383; BAA77450.2; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER       1      1
SQ   SEQUENCE   204 AA;  21953 MW;  6352C96D2AC0DF21 CRC64;
     CTSEWLSFPR PSAAAXPRRV IPASRWRVPK VSLHTAVKGQ FGLGTGRAMG KALKVFILKM
     HFSRISRSKR KVLLPALPAP PPPRQLLMWQ PPIQNGTQLD RHWFESVWRS HAAYCGCGDC
     VGHLQHLAAN LGRPPHPQPF REQHPPQIRG LPALPAPPSN RNSWPGTGGD AAGEQAGGSR
     GAGDGGDGEL ADDDLXDAAA LVEE Q9WB09_9VIRU              Unreviewed;       138 AA.
AC   Q9WB09;
DT   01-NOV-1999, integrated into UniProtKB/TrEMBL.
DT   01-NOV-1999, sequence version 1.
DT   09-FEB-2010, entry version 22.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
```

FIG. 14F

```
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024376; BAA77443.1; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER      1      1
FT   NON_TER    138    138
SQ   SEQUENCE   138 AA;  15494 MW;  2DF27B3A4F0CA641 CRC64;
     AVKPRREISA SRGRVPKVSL HTEVKGQFGL GTGRAMGKAL KKSMFIGRHY RKKRALSLCA
     VRTTKKACKL LIVMWTPPRN DQQYLNWQWY SSVLSSHAAM CGCPDAIAHL SHLAFVFRAP
     QNPPPPGPQR NLPLRRLP
``` zyb9.3.pep
nucleotide 3-71
Length: 23aa

GAEGEFTHRS QGAIRARDWP GYG

BlastP2 of: zyb9.3.pep   from: 1 to: 23
compared to database: uniprot

```
>>>sptrembl:Q9WAY7_9VIRU  Q9way7  SubName: Full=ORF2; Flags: Fragm...    52   2e-05
>>>sptrembl:Q98Y39_9VIRU  Q98y39  SubName: Full=ORF2;. 2/2010            52   2e-05
>>>sptrembl:Q9WFY6_9VIRU  Q9wfy6  SubName: Full=ORF2;. 2/2010            52   3e-05
>>>sptrembl:Q9JGT0_9VIRU  Q9jgt0  SubName: Full=PORF2a;. 12/2009         52   3e-05
>>>sptrembl:Q786D4_9VIRU  Q786d4  SubName: Full=ORF2;. 2/2010            52   3e-05
>>>sptrembl:O70738_9VIRU  O70738  SubName: Full=ORF2, ORF1 genes;....    52   3e-05
>>>sptrembl:Q9JG33_9VIRU  Q9jg33  SubName: Full=Putative uncharact...    52   3e-05
>>>sptrembl:O90363_9VIRU  O90363  SubName: Full=ORF2 protein;. 2/2010    52   3e-05
>>>sptrembl:Q9YKL2_9VIRU  Q9ykl2  SubName: Full=ORF2 protein;. 2/2010    51   3e-05
>>>sptrembl:Q9JGS7_9VIRU  Q9jgs7  SubName: Full=PORF2a;. 12/2009         51   3e-05
>>>sptrembl:Q9DYC0_9VIRU  Q9dyc0  SubName: Full=Putative uncharact...    51   4e-05
>>>sptrembl:Q9W7S4_9VIRU  Q9w7s4  SubName: Full=Putative uncharact...    50   5e-05
>>>sptrembl:Q77S01_9VIRU  Q77s01  SubName: Full=Putative uncharact...    50   5e-05
>>>sptrembl:Q9JGS4_9VIRU  Q9jgs4  SubName: Full=PORF2a;. 12/2009         48   3e-04
>>>sptrembl:Q9JGT3_9VIRU  Q9jgt3  SubName: Full=PORF2a;. 12/2009         48   3e-04
>>>sptrembl:Q9YR02_9VIRU  Q9yr02  SubName: Full=Putative uncharact...    47   7e-04
>>>sptrembl:B2YFW4_9VIRU  B2yfw4  SubName: Full=ORF2; Flags: Fragm...    35   3.2

>>>>sptrembl:Q9WAY7_9VIRU  Q9way7  SubName: Full=ORF2; Flags:
           Fragment;. 2/2010
           Length = 138
 Score = 52.0 bits (123), Expect = 2e-05, Method: Compositional matrix adjust.
 Identities = 23/23 (100%), Positives = 23/23 (100%)
Query: 1  GAEGEFTHRSQGAIRARDWPGYG 23
          GAEGEFTHRSQGAIRARDWPGYG
Sbjct: 15 GAEGEFTHRSQGAIRARDWPGYG 37
```

FIG. 14G

```
Q9WAY7_9VIRU            Unreviewed;       138 AA.
AC   Q9WAY7;
DT   01-NOV-1999, integrated into UniProtKB/TrEMBL.
DT   01-NOV-1999, sequence version 1.
DT   09-FEB-2010, entry version 23.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024348; BAA77415.1; -; Genomic_DNA.
DR   InterPro; IPR004118; Gyrovir_VP2/TT_ORF2.
DR   InterPro; IPR013267; TTV_ORF2a.
DR   Pfam; PF02957; TT_ORF2; 1.
DR   Pfam; PF08197; TT_ORF2a; 1.
PE   4: Predicted;
FT   NON_TER        1       1
FT   NON_TER      138     138
SQ   SEQUENCE   138 AA;  15416 MW;  93F7D9685085141D CRC64;
     SGEATEGDLR VPRAGAEGEF THRSQGAIRA RDWPGYGQGS EKSMFIGRHY RKKRALSLCA
     VRTTKKACKL LIVMWTPPRN DQQYLNWQWY SSVLSSHAAM CGCPDAVAHF NHLAAVLRAP
     QNPPPPGPQR NLPLRPLP
``` zkb5.3.pep
nucleotide 3-71
Length: 23aa

GAVGEFTHRS QGAIRARDWP GYG

BlastP2 of: zkb5.3.pep
compared to database: uniprot ..

```
>>>sptrembl:Q98Y39_9VIRU  Q98y39 SubName: Full=ORF2;. 2/2010           49   1e-04
>>>sptrembl:Q9WAY7_9VIRU  Q9way7 SubName: Full=ORF2; Flags: Fragm...   49   1e-04
>>>sptrembl:Q9JGT0_9VIRU  Q9jgt0 SubName: Full=PORF2a;. 12/2009        49   1e-04
>>>sptrembl:O90363_9VIRU  O90363 SubName: Full=ORF2 protein;. 2/2010   49   1e-04
>>>sptrembl:Q9JG33_9VIRU  Q9jg33 SubName: Full=Putative uncharact...   49   1e-04
>>>sptrembl:Q786D4_9VIRU  Q786d4 SubName: Full=ORF2;. 2/2010           49   1e-04
>>>sptrembl:O70738_9VIRU  O70738 SubName: Full=ORF2, ORF1 genes;...    49   1e-04
>>>sptrembl:Q9YKL2_9VIRU  Q9ykl2 SubName: Full=ORF2 protein;. 2/2010   49   1e-04
>>>sptrembl:Q9WFY6_9VIRU  Q9wfy6 SubName: Full=ORF2;. 2/2010           49   1e-04
```

FIG. 14H

```
>>>sptrembl:Q9JGS7_9VIRU  Q9jgs7 SubName: Full=PORF2a;. 12/2009      49    2e-04
>>>sptrembl:Q9DYC0_9VIRU  Q9dyc0 SubName: Full=Putative uncharact... 49    2e-04
>>>sptrembl:Q9W7S4_9VIRU  Q9w7s4 SubName: Full=Putative uncharact... 49    2e-04
>>>sptrembl:Q77S01_9VIRU  Q77s01 SubName: Full=Putative uncharact... 49    2e-04
>>>sptrembl:Q9JGS4_9VIRU  Q9jgs4 SubName: Full=PORF2a;. 12/2009      48    3e-04
>>>sptrembl:Q9JGT3_9VIRU  Q9jgt3 SubName: Full=PORF2a;. 12/2009      48    3e-04
>>>sptrembl:Q9YR02_9VIRU  Q9yr02 SubName: Full=Putative uncharact... 47    7e-04

>>>>sptrembl:Q98Y39_9VIRU Q98y39 SubName: Full=ORF2;. 2/2010
          Length = 202
 Score = 49.3 bits (116), Expect = 1e-04,  Method: Compositional matrix adjust.
 Identities = 22/23 (95%), Positives = 22/23 (95%)
Query: 1  GAVGEFTHRSQGAIRARDWPGYG 23
          GA GEFTHRSQGAIRARDWPGYG
Sbjct: 24 GAEGEFTHRSQGAIRARDWPGYG 46

Q98Y39_9VIRU              Unreviewed;         202 AA.
AC   Q98Y39;
DT   01-JUN-2001, integrated into UniProtKB/TrEMBL.
DT   01-JUN-2001, sequence version 1.
DT   09-FEB-2010, entry version 17.
DE   SubName: Full=ORF2;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   STRAIN=TWH;
RA   He H.-T., Luo K.-X., Xiao H., Liu D.-X.;
RT   "Complete circular genome of TT virus isolated from feces of a
RT   hepatitis patient.";
RL   Submitted (FEB-2001) to the EMBL/GenBank/DDBJ databases.
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AF351132; AAK29446.1; -; Genomic_DNA.
DR   InterPro; IPR004118; Gyrovir_VP2/TT_ORF2.
DR   InterPro; IPR013267; TTV_ORF2a.
DR   Pfam; PF02957; TT_ORF2; 1.
DR   Pfam; PF08197; TT_ORF2a; 1.
PE   4: Predicted;
SQ   SEQUENCE   202 AA;  21437 MW;  105B9ED104956EDE CRC64;
     MAEFSTPVRS GEATEGDHRV PRAGAEGEFT HRSQGAIRAR DWPGYGQGSE KSMFIGRHYR
     KKRALSLCAV RTTKKACKLL IVMWTPPRND QQYLNWQWYS SVLSSHASMC GCPDAVAHLI
     NLASVLRAPQ NPPPPGPQRN LPLRRLPALP AAPEAPGDRA PWPMAGGAEG ENGGAGGDAD
     HGGAAGGPED ANLLDAVAAA ET
//
``` zkb69.1.pep
nucleotide 1-71
Length: 23aa

FIG. 14I

```
RVPEVSLHTA VKGQFGLGTG RAM

BlastP2 of:  zkb69.1.pep   from: 1 to: 23
compared to database: uniprot
>>>sptrembl:Q9WAZ2_9VIRU  Q9waz2 SubName: Full=ORF2; Flags: Fragm...    49   1e-04
>>>sptrembl:Q9WB10_9VIRU  Q9wb10 SubName: Full=ORF2; Flags: Fragm...    49   1e-04
>>>sptrembl:O70807_9VIRU  O70807 SubName: Full=Putative uncharact...    49   2e-04
>>>sptrembl:Q9WAY4_9VIRU  Q9way4 SubName: Full=ORF2; Flags: Fragm...    49   2e-04
>>>sptrembl:Q9WSW0_9VIRU  Q9wsw0 SubName: Full=ORF2; Flags: Fragm...    48   3e-04
>>>sptrembl:Q9WB12_9VIRU  Q9wb12 SubName: Full=ORF2; Flags: Fragm...    48   4e-04
>>>sptrembl:Q9WSW2_9VIRU  Q9wsw2 SubName: Full=ORF2; Flags: Fragm...    48   4e-04
>>>sptrembl:Q9WSW4_9VIRU  Q9wsw4 SubName: Full=ORF2; Flags: Fragm...    47   7e-04
>>>sptrembl:Q9WB09_9VIRU  Q9wb09 SubName: Full=ORF2; Flags: Fragm...    47   9e-04
>>>sptrembl:Q9WSX0_9VIRU  Q9wsx0 SubName: Full=ORF2; Flags: Fragm...    46   0.001
>>>sptrembl:Q9WB02_9VIRU  Q9wb02 SubName: Full=ORF2; Flags: Fragm...    45   0.002
>>>sptrembl:Q9WSW6_9VIRU  Q9wsw6 SubName: Full=ORF2; Flags: Fragm...    45   0.002
>>>sptrembl:B3FWR6_9VIRU  B3fwr6 SubName: Full=ORF2; Flags: Fragm...    38   0.34

>>>>sptrembl:Q9WAZ2_9VIRU  Q9waz2 SubName: Full=ORF2; Flags:
         Fragment;. 2/2010
         Length = 152
 Score = 49.3 bits (116), Expect = 1e-04,  Method: Compositional matrix adjust.
 Identities = 23/23 (100%), Positives = 23/23 (100%)
Query: 1  RVPEVSLHTAVKGQFGLGTGRAM 23
          RVPEVSLHTAVKGQFGLGTGRAM
Sbjct: 14 RVPEVSLHTAVKGQFGLGTGRAM 36

Q9WAZ2_9VIRU            Unreviewed;       152 AA.
AC   Q9WAZ2;
DT   01-NOV-1999, integrated into UniProtKB/TrEMBL.
DT   01-NOV-1999, sequence version 1.
DT   09-FEB-2010, entry version 23.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024353; BAA77420.1; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER     1       1
FT   NON_TER    152     152
SQ   SEQUENCE    152 AA;  16658 MW;  1DEC53175C043A17 CRC64;
```

FIG. 14J

```
ARTPRRGVRA SRGRVPEVSL HTAVKGQFGL GTGRAMGKAL KKAMFLGRIY RKKRRLPLSP
LHSPPKARKL LRGMWRPPTQ NVSGQERSWY DSVFYSHAAF CGCGDCVGHL SYLATHLGRP
PSAQPPPQLQ PPVIRRLPAL PAPPNPSGDR AA
``` zkb69.3.pep
nucleotide 3-71
Length: 23

GAGGEFTHRS QGAIRARDWP GYG

```
BlastP2 of: zkb69.3.pep    from: 1 to: 23
compared to database: uniprot    ..
>>>sptrembl:Q9JGT3_9VIRU  Q9jgt3  SubName: Full=PORF2a;. 12/2009          50    5e-05
>>>sptrembl:Q9JGS4_9VIRU  Q9jgs4  SubName: Full=PORF2a;. 12/2009          50    5e-05
>>>sptrembl:Q98Y39_9VIRU  Q98y39  SubName: Full=ORF2;. 2/2010             49    1e-04
>>>sptrembl:Q9WAY7_9VIRU  Q9way7  SubName: Full=ORF2; Flags: Fragm...     49    1e-04
>>>sptrembl:Q9YR02_9VIRU  Q9yr02  SubName: Full=Putative uncharact...     49    1e-04
>>>sptrembl:Q786D4_9VIRU  Q786d4  SubName: Full=ORF2;. 2/2010             49    1e-04
>>>sptrembl:O70738_9VIRU  O70738  SubName: Full=ORF2, CRF1 genes;...      49    1e-04
>>>sptrembl:Q9JG33_9VIRU  Q9jg33  SubName: Full=Putative uncharact...     49    2e-04
>>>sptrembl:O90363_9VIRU  O90363  SubName: Full=ORF2 protein;. 2/2010     49    2e-04
>>>sptrembl:Q9JGT0_9VIRU  Q9jgt0  SubName: Full=PORF2a;. 12/2009          49    2e-04
>>>sptrembl:Q9YKL2_9VIRU  Q9ykl2  SubName: Full=ORF2 protein;. 2/2010     49    2e-04
>>>sptrembl:Q9WFY6_9VIRU  Q9wfy6  SubName: Full=ORF2;. 2/2010             49    2e-04
>>>sptrembl:Q9JGS7_9VIRU  Q9jgs7  SubName: Full=PORF2a;. 12/2009          48    3e-04
>>>sptrembl:Q9DYC0_9VIRU  Q9dyc0  SubName: Full=Putative uncharact...     48    3e-04
>>>sptrembl:Q9W7S4_9VIRU  Q9w7s4  SubName: Full=Putative uncharact...     48    3e-04
>>>sptrembl:Q77S01_9VIRU  Q77s01  SubName: Full=Putative uncharact...     48    3e-04
>>>sptrembl:B3FWR5_9VIRU  B3fwr5  SubName: Full=ORF2; Flags: Fragm...     34    5.2
>>>sptrembl:B6SFP1_9VIRU  B6sfp1  SubName: Full=ORF2; Flags: Fragm...     34    5.6

>>>>sptrembl:Q9JGT3_9VIRU  Q9jgt3  SubName: Full=PORF2a;. 12/2009
         Length = 49
 Score = 50.4 bits (119), Expect = 5e-05,  Method: Compositional matrix adjust.
 Identities = 23/23 (100%), Positives = 23/23 (100%)
Query: 1   GAGGEFTHRSQGAIRARDWPGYG 23
           GAGGEFTHRSQGAIRARDWPGYG
Sbjct: 24  GAGGEFTHRSQGAIRARDWPGYG 46

Q9JGT3_9VIRU              Unreviewed;         49 AA.
AC   Q9JGT3;
DT   01-OCT-2000, integrated into UniProtKB/TrEMBL.
DT   01-OCT-2000, sequence version 1.
DT   15-DEC-2009, entry version 17.
DE   SubName: Full=PORF2a;
GN   Name=ORF2a;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RX   MEDLINE=20417334; PubMed=10963344; DOI=10.1007/s007050070097;
RA   Tanaka Y., Orito E., Ohno T., Nakano T., Hayashi K., Kato T.,
RA   Mukaide M., Iida S., Mizokami M.;
RT   "Identification of a novel 23kDa protein encoded by putative open
RT   reading frame 2 of TT virus (TTV) genotype 1 different from the other
RT   genotypes.";
```

FIG. 14K

```
RL   Arch. Virol. 145:1385-1398(2000).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB030486; BAA90401.1; -; Genomic_DNA.
DR   InterPro; IPR013267; TTV_ORF2a.
DR   Pfam; PF08197; TT_ORF2a; 1.
PE   4: Predicted;
SQ   SEQUENCE   49 AA;  5118 MW;  596E44680A5D863A CRC64;
     MAEFSTPVRS EGATEGIPNV PRAGAGGEFT HRSQGAIRAR DWPGYGQGS
```

FIG. 16A
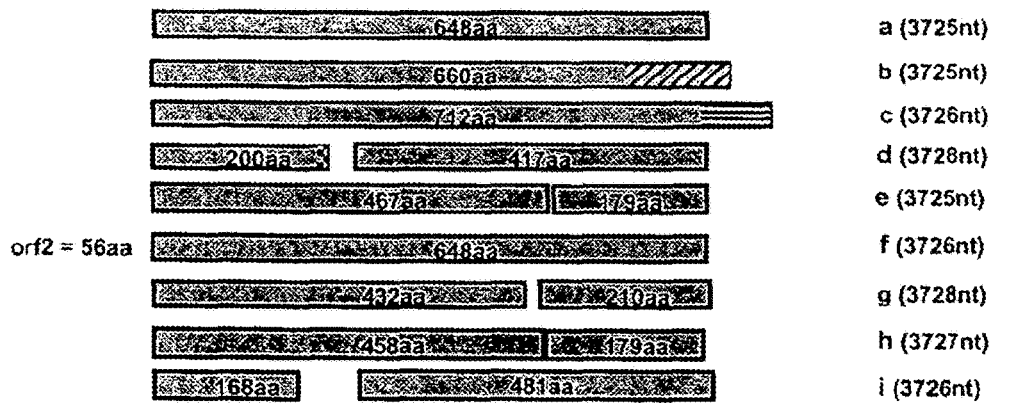
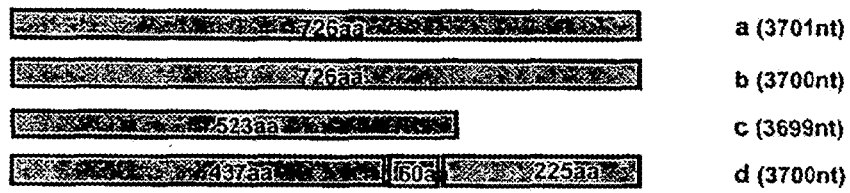
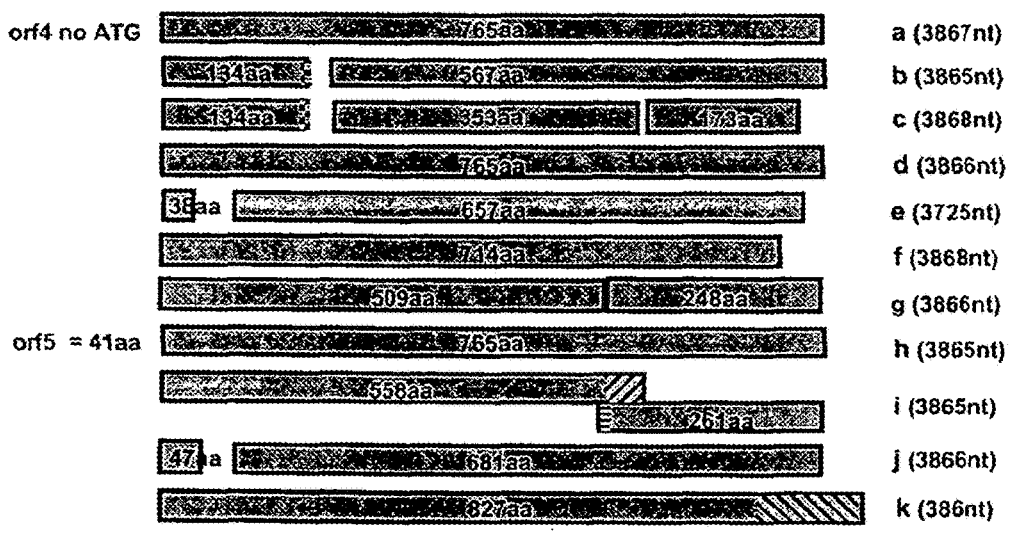

FIG. 16B
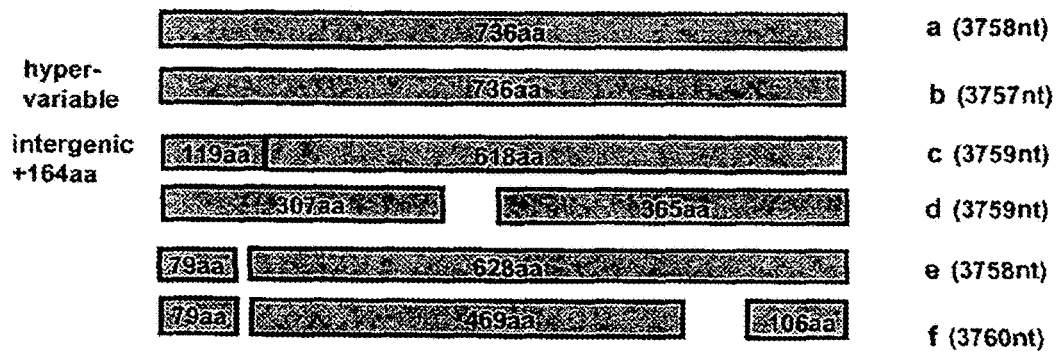

FIGS. 20A-D

REARRANGED TT VIRUS MOLECULES FOR USE IN DIAGNOSIS, PREVENTION AND TREATMENT OF CANCER AND AUTOIMMUNITY

This application is a continuation-in-part application of international patent application Serial No. PCT/EP2011/003119 filed 24 Jun. 2011, which published as PCT Publication No. WO 2011/160848 on 29 Dec. 2011, which claims priority to U.S. patent application Ser. No. 12/821,634 filed 23 Jun. 2010 and Ser. No. 12/952,300 filed 23 Nov. 2010 and European patent application Serial Nos. EP 10006541 filed 23 Jun. 2010 and EP 10014907 filed 23 Nov. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to rearranged molecules of (a) a specific TT virus sequence and (b) a nucleotide sequence encoding a polypeptide showing homology to mammalian proteins associated with cancer or an autoimmune disease that are capable of replicating autonomously for use in diagnosis, prevention and treatment of diseases like cancer or autoimmunity.

BACKGROUND OF THE INVENTION

The family Anelloviridae includes Torque teno viruses (TTV), TT-midiviruses (TTMDV) and TT-miniviruses (TTMV), the majority originating from samples of human origin (Nishizawa et al., 1997; Takahashi et al., 2000; Ninomiya et al., 2007; Okamoto, 2009; Biagini and de Micco, 2010). The plurality of this family of ssDNA viruses is reflected not only in DNA sequence, but also in genome size and organization.

Multiple attempts have been made to find a suitable in vitro system for the replication and propagation of TT viruses. Replicative forms of its DNA have been demonstrated in bone marrow cells and in the liver (Kanda et al., 1999; Okamoto et al., 2000a, c, d). Peripheral blood acts as reservoir for TT viruses (Okamoto et al., 2000b) and replication in vivo seems to occur preferably in activated mononuclear cells (Maggi et al., 2001b; Mariscal et al., 2002; Maggi et al., 2010). Although in vitro transcription has been investigated in a variety of cell lines (Kamahora et al., 2000; Kamada et al., 2004; Kakkola et al., 2007; 2009; Qiu et al., 2005; Müller et al., 2008), long term replication leading to virus production has been difficult to achieve (Leppik et al., 2007).

The presence of a variety of intragenomic rearranged TT subviral molecules in sera samples and the in vitro transcription of a subviral molecule constituting only 10% of the complete genome, initiated the discussion whether TT viruses may share similarities to the plantvirus family Geminiviridae (Leppik et al., 2007; de Villiers et al., 2009). Both mono- and bipartite Geminiviruses associate with single-stranded DNA satellites to form disease-inducing complexes (Saunders et al., 2000; Stanley, 2004; Nawaz-ul-Rehman and Fauquet, 2009; Jeske 2009; Paprotka et al., 2010; Patil et al., 2010).

Infections occur within the first days of life with close to 100% of infants being infected at one year of age. The primary route of infection however still remains unclear (Kazi et al., 2000; Peng et al., 2002; Ninomiya et al., 2008). The ubiquitous nature of TTV infections has hampered efforts to associate it with the pathogenesis of disease (Jelcic et al., 2004; Leppik et al., 2007; de Villiers et al., 2009; Okamoto, 2009). A possible etiological association with diseases of the liver (reviewed in Okamoto, 2009), respiratory tract (Biagini et al., 2003; Maggi et al., 2003a,b; Pifferi et al., 2005), hematopoietic malignancies (Jelcic et al., 2004; Leppik et al., 2007; de Villiers et al., 2002; 2009; Shiramizu et al., 2002; Garbuglia et al., 2003; zur Hausen and de Villiers, 2005) and auto-immune diseases (Sospedra et al., 2005; Maggi et al., 2001a; 2007; de Villiers et al., 2009) have been reported. During the past years, additional data has been compiled indicative of an association of TT virus infection with human malignant tumors. A high rate of TT virus load has been noted in a spleen biopsy of a patient with Hodgkin's lymphoma (24 individual TTV genotypes). Similarly, other reports describe a higher rate of TTV prevalence in colorectal and esophageal cancer and in hematopoietic malignancies in comparison to non-tumorous tissue from the same or other patients. Yet, the ubiquity of these infections rendered an interpretation of these results rather difficult and did not permit a linkage of these observations with tumor development.

Citation or identification of any document in this application is not an admission that such document is available as prior art to the present invention.

SUMMARY OF THE INVENTION

Thus, the technical problem underlying the present invention is to identify specific TTV sequences that might be clearly associated with diseases like cancer or autoimmune diseases and, thus, to provide means for diagnosis and therapy.

The solution to said technical problem is achieved by providing the embodiments characterized in the claims. During the experiments resulting in the present invention more than 200 genomes of TT viruses have been isolated. The isolates grouping in the genus Alphatorquevirus (ca 3.8 kb in size) share very low DNA sequence homology and differ in their genome organization. A short stretch (71 bp) of the intergenic region is highly conserved among all human TTV isolates (Peng et al., 2002) and is widely used to demonstrate TT virus infection. Samples from a broad spectrum of diseases were analysed for the presence of torque teno virus DNA by applying PCR-amplification of this conserved region (Jelcic et al., 2004; Leppik et al., 2007; de Villiers et al., 2009; Sospedra et al., 2005; de Villiers and Gunst, unpublished results). Identification of individual TT virus types however requires the amplification of full-length genomes. Thus far 93 full-length genomes of TTVs (ca 3.8 kb) were isolated from human samples (Jelcic et al., 2004; Leppik et al., 2007; de Villiers et al., 2009; present experiments). These included samples obtained from healthy individuals, patients with leukaemia and lymphoma, rheumatoid arthritis, multiple sclerosis and kidney disease. The present invention describes the in vitro replication and transcription of 12 isolates after initial transfection of the genomic DNA and followed by virus propagation using frozen infected cells or purified particles. Intragenomic rearranged subviral molecules μTTV (microTTV) appearing in early passages were cloned and characterized. These also propagated independently in cell culture resulting in novel particle-like structures which are able to infect virus-free 293TT cells.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

Figure 4A:
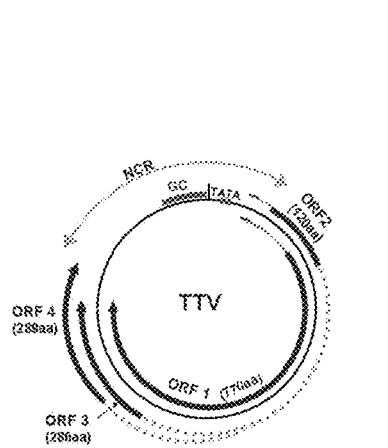
FIGS. 4A and 4B: Schematic outline of the TTV oncogene concept
Figure 4B:
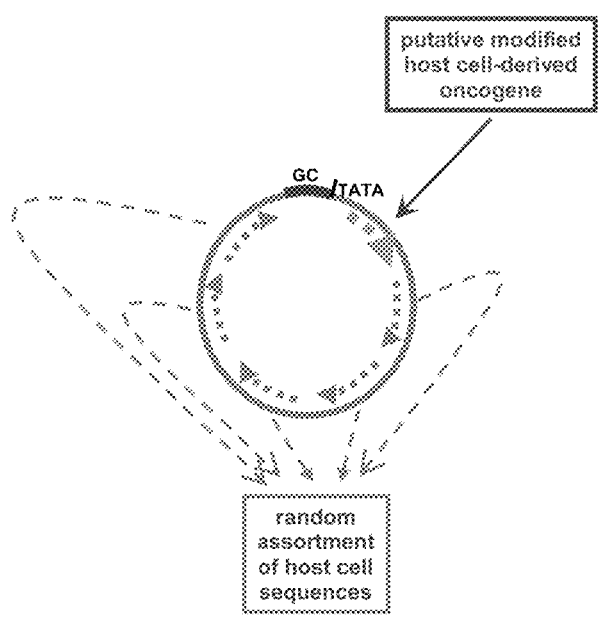

The left part (FIG. 4A) represents the genomic organization of wild-type TTV genomes. The right part (FIG. 4B) envisages the integration of host cell DNA into the single-stranded plasmids.

Figure 5:
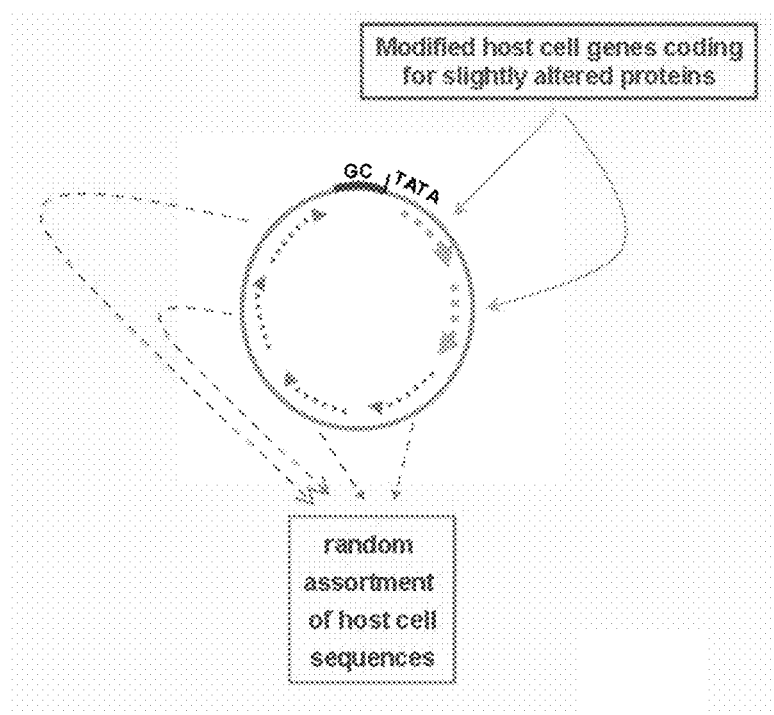

FIG. 5: Schematic outline of the TTV host cell DNA autoimmunity concept

The modified host cell genes should code for immunoreactive antigenic epitopes.

FIG. 6: nnNucleic sequences of 71 base highly conserved region (HCR) from the DNA of 4 different cell lines: zyb2 (SEQ ID NO:228), zyb9 (SEQ ID NO:229), zkb5 (SEQ ID NO:230) and zkb69 (SEQ ID NO:231)

The arrows point to the two sites with variations in the nucleotide sequences.

Figure 7A:
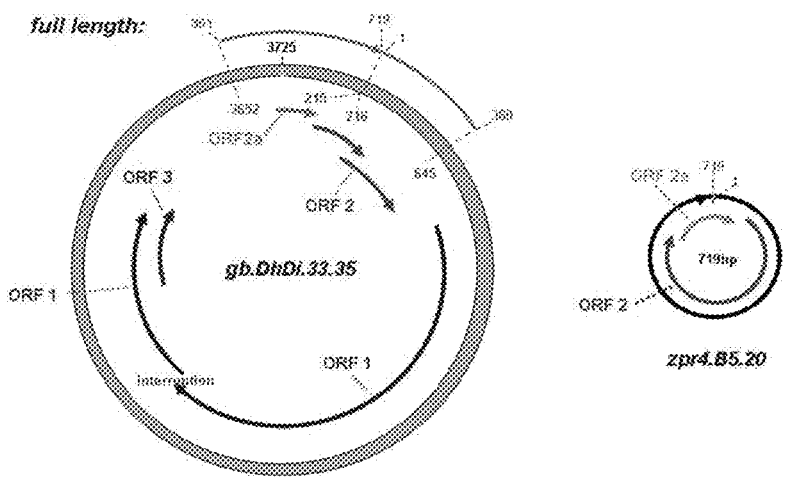
Figure 7B:
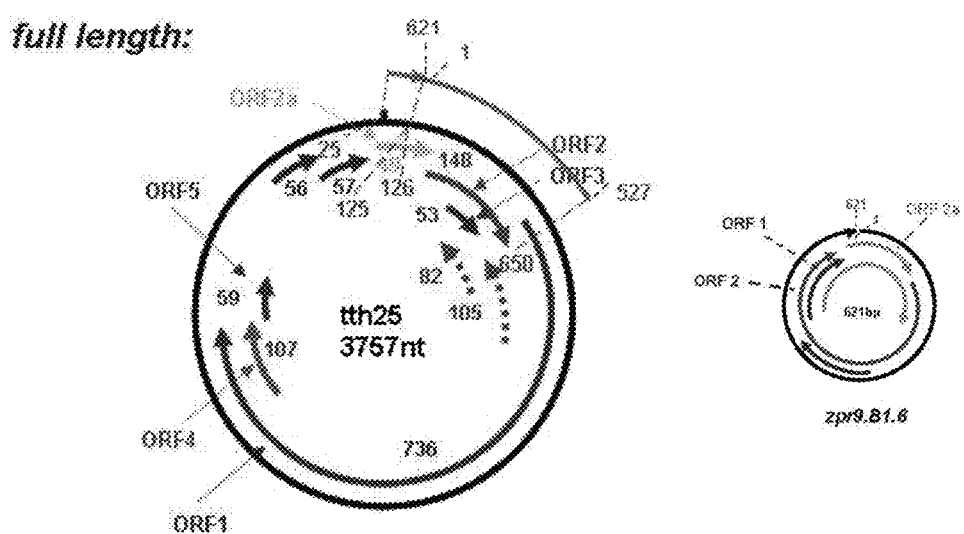
Figure 7C:
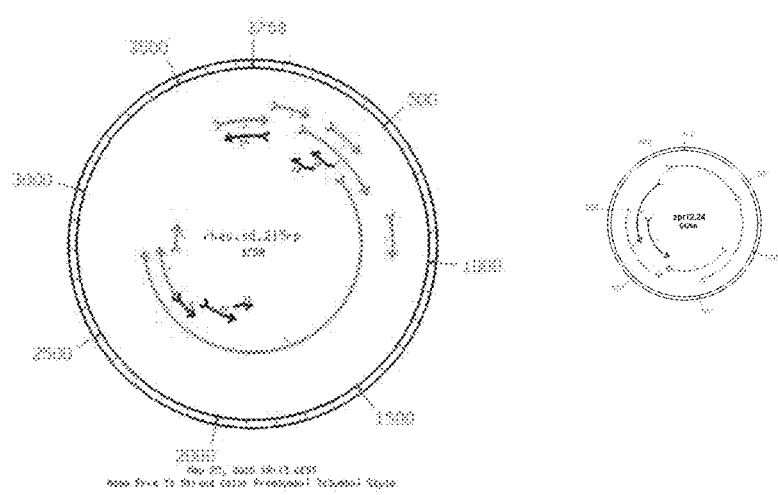
Figures 8E, 8F:
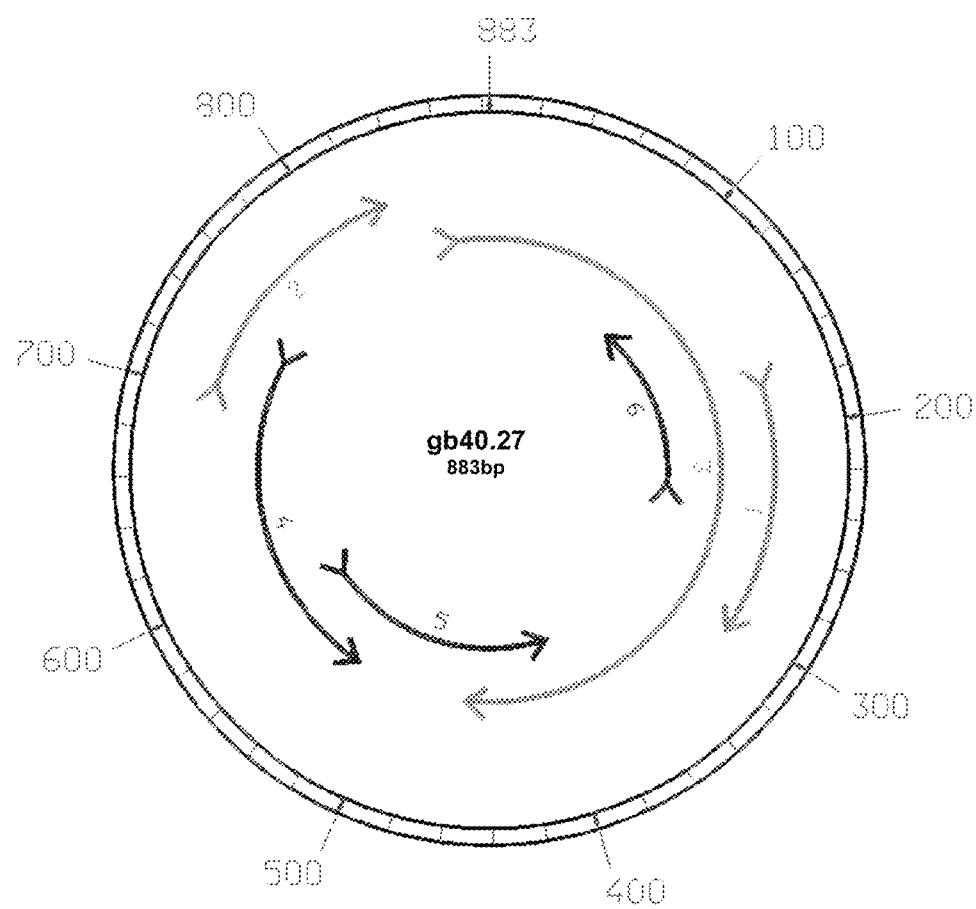

FIGS. 7A-C:
(A) The autonomously replicating 719 base TTV DNA (right) and the complete TTV sequence from which it is derived. The nucleotide composition of both molecules is found in FIGS. 11A+B.
(B) The autonomously replicating 621 base TTV DNA (right) and the complete DNA sequence from which it is derived. The nucleotide composition of both molecules is found in FIGS. 12A+B.
(C) The autonomously replicating 642 base TTV DNA (right) and the complete DNA sequence from which it is derived. The nucleotide composition of both molecules is found in FIGS. 13A+B.

FIGS. 8A-L: Three exemplary chimeric TTV/truncated host cell DNA sequences from brain biopsies of patients with multiple sclerosis
(A-D) Chimeric cellular sequences WV13038 Klon6 (SEQ ID NO:232) derived from chromosome 1 with some homologies to prion and Wilms tumor sequences and the 3' end of myeloid lymphoid leukemia 3 (MLL3) pseudogene. Human DNA sequence from clone RP11-14N7 on chromosome 1. Contains 3' end of a myeloid/lymphoid or mixed lineage leukemia 3 (MLL3) pseudogene, a seven transmembrane helix receptor pseudogene, the 5'-end of a novel gene.
(E-G) Chimeric cellular sequences gb40.27 (SEQ ID NO:233) derived from chromosome 16. Homologies to transcription factor 3 (TF 3C), protein signatures for chemokine receptors and leukotriene B4 receptor.
(H-L) Chimeric cellular sequences derived from chromosome 10, truncated sequence of myosin, reactivity reported for multiple sclerosis patients and those with rheumatoid arthritis (sequence contains both full primers front and back). I) sequence of gb43.40 (SEQ ID NO:234); J) BLAST of gbHhDi43.30 (SEQ ID NO:234) and *homo sapiens* myosin IIIA (SEQ ID NO:235), J+K) BLAST of gb43.30 (SEQ ID NO:236) and human DNA sequence on chromosome 10 (SEQ ID NO:238); L) peptide FASTA of gbDhDi43.30 (SEQ ID NO:239) and ORF2 of Torque teno virus fragment Q9WB12_9VIRU (SEQ ID NO:240); protein sequence of torque teno virus ORF2 (SEQ ID NO:241)

FIGS. 9A-H: Three exemplary chimeric TTV/truncated host cell DNA sequences from cell lines derived from patients with Hodgkin's disease or leukemia
(A-C) Chromosome 1 sequences with part of transgelin 2, the IGSF9 gene for immunoglobulin superfamily member 9, the SLAMS gene. A) sequence of hod11 (SEQ ID NO:242; B+C); strand=plus/plus: BLAST of hodL.VvWw.1.seq (SEQ ID NO:243) and human DNA sequence on chromosome 1 (SEQ ID NO:244); strand=plus/minus: BLAST of hodL.VvWw.1.seq (SEQ ID NO:245) and human DNA sequence on chromosome 1 (SEQ ID NO:246).
(D-F) Translated protein sequences with substantial homology to the oncogenes v-myb (avian myeloblastosis viral oncogene), but also to c-myb. This sequence was amplified with the forward primer at both ends. D-F) sequence of hoht33 (SEQ ID NO:247)
(G-H) Derived from chromosome 10. High homology with "Deleted in malignant 1 Protein" (DMBT), an identified tumor suppressor gene. This sequence was amplified with the forward primer at both ends. Sequence of hoht22 (SEQ ID NO:248)

FIG. 10: Primer sequences used in the reactions described in the Examples, derived from the 71 base HCR. DhDi forward (SEQ ID NO:249), DhDi reverse (SEQ ID NO:250), cd forward (SEQ ID NO:251), cd reverse (SEQ ID NO:252), DfDg (SEQ ID NO:253), DfDg reverse (SEQ ID NO:254).

FIGS. 11A-D:
(A-C) Complete TTV sequence (SEQ ID NO:255) from which autonomously replicating 719 base DNA has been obtained.
(D) Complete sequence (SEQ ID NO:256) of the autonomously replicating 719 base TTV DNA.

FIGS. 12A-D:
(A-C) Complete TTV sequence (tth25) from which autonomously replicating 621 base DNA has been obtained (SEQ ID NO:257).
(D) Complete sequence of the autonomously replicating 621 base TTV DNA (SEQ ID NO: 258).

FIGS. 13A-D:
(A-C) Complete TTV sequence (ttrh215) from which autonomously replicating 642 base DNA has been obtained (SEQ ID NO:259).
(D) Complete sequence of the autonomously replicating 642 base TTV DNA (SEQ ID NO:260).

FIGS. 14A-K: Open reading frames (ORFs) found within the nucleotide sequence of 71 nt
zyb2.1.pep (SEQ ID NO:261), zyb9.1.pep (SEQ ID NO:262), and zkb69.1.pep (SEQ ID NO:263) are starting at the first triplet, zyb2.3.pep (SEQ ID NO:264), zyb9.3.pep (SEQ ID NO:265), zkb5.3.pep (SEQ ID NO:266), and zkb69.3.pep (SEQ ID NO:267) are starting from the third triplet. This region is actively transcribed. A) Sbjct14 (SEQ ID NO:35), B) Q9WSW0 (SEQ ID NO:268), C) Q9WB09_VIRU (SEQ ID NO:269), D) Q98Y39_9VIRU (SEQ ID NO:273, D) Q9WB09_9VIRU (SEQ ID NO:270), E) Q9WB09_9VIRU (SEQ ID NO:271), F) Q9WAY7_9VIRU (SEQ ID NO:272), G) Q98Y39_9VIRU (SEQ ID NO:273), H) Q9WAZ2_9VIRU (SEQ ID NO:274); I) Q9JGT3_9VIRU (SEQ ID NO:275)

Figure 15:
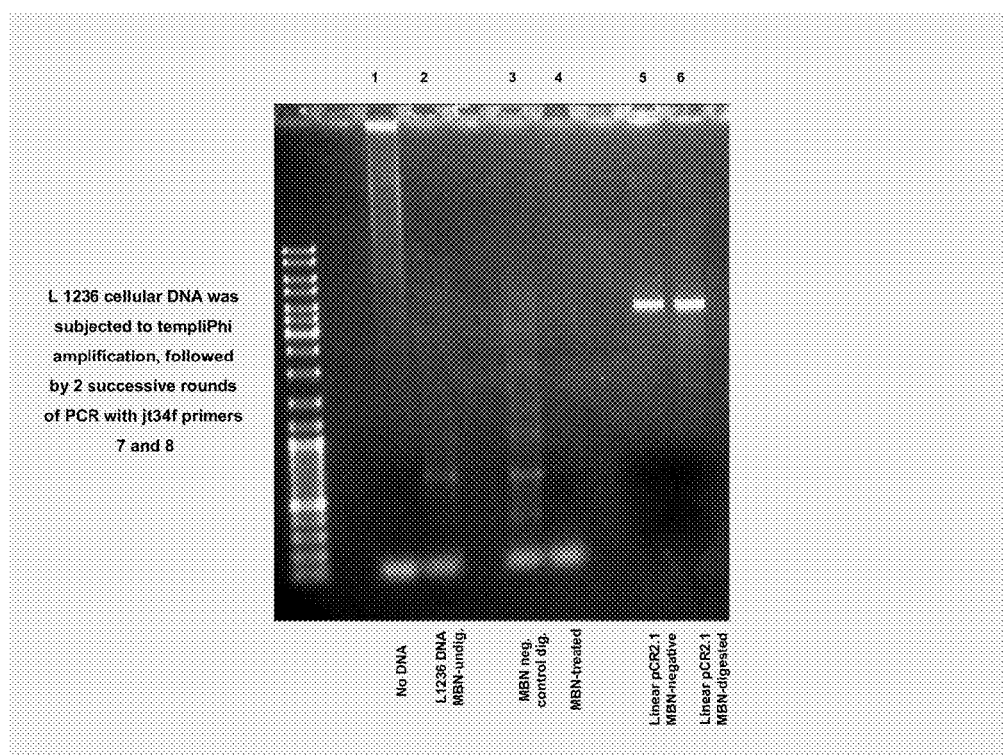
Figure 17A:
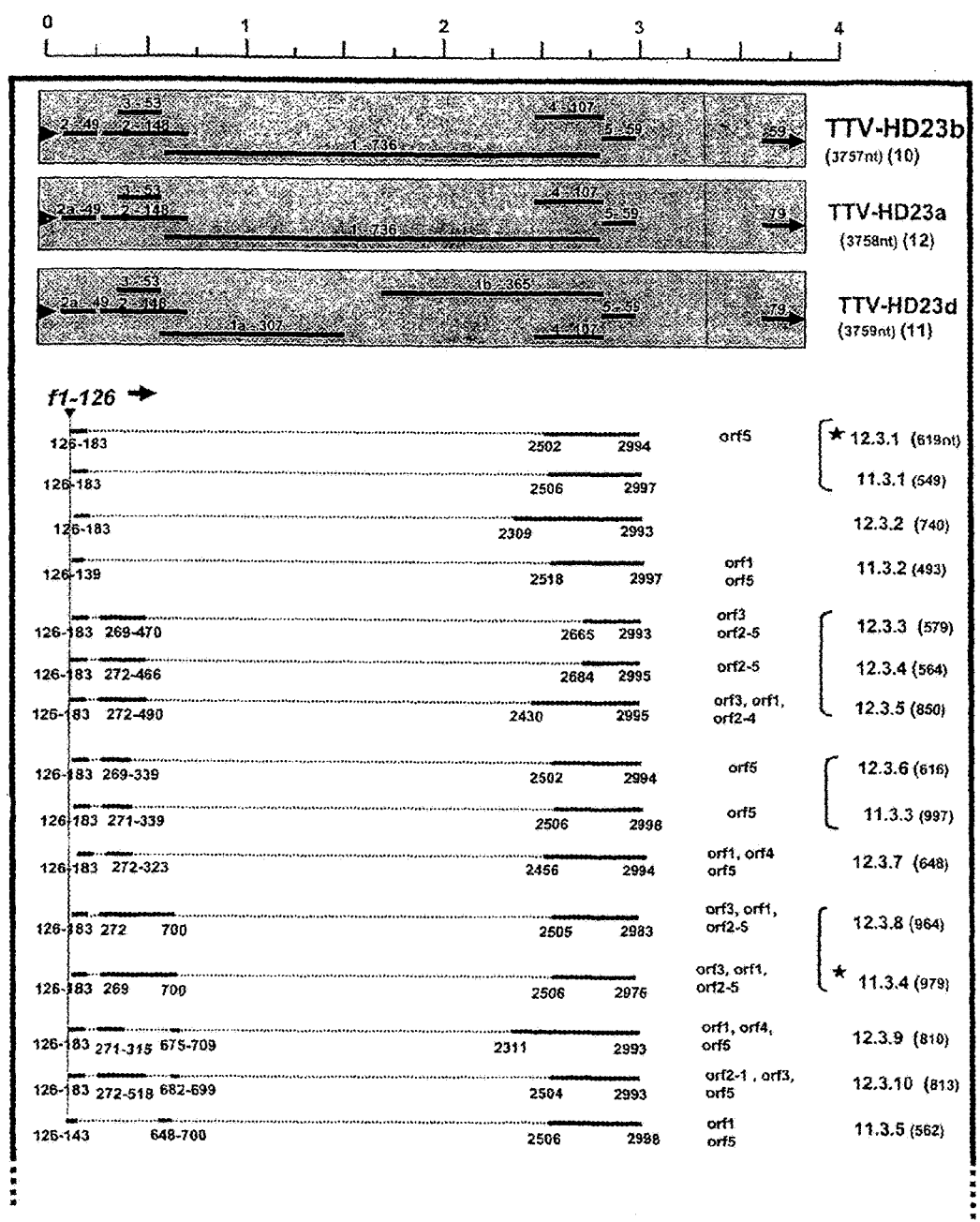
Figure 17B:
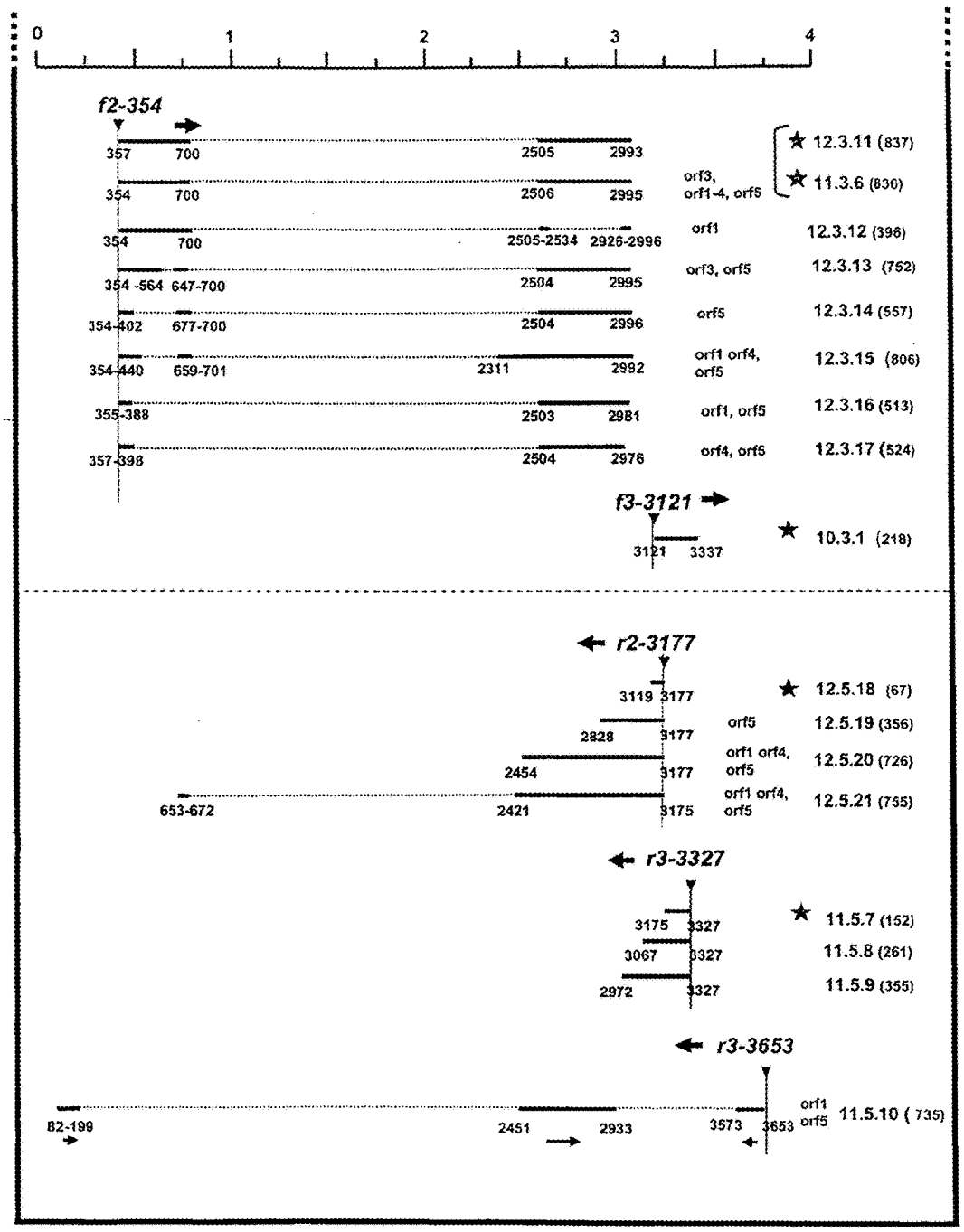
Figure 17C:
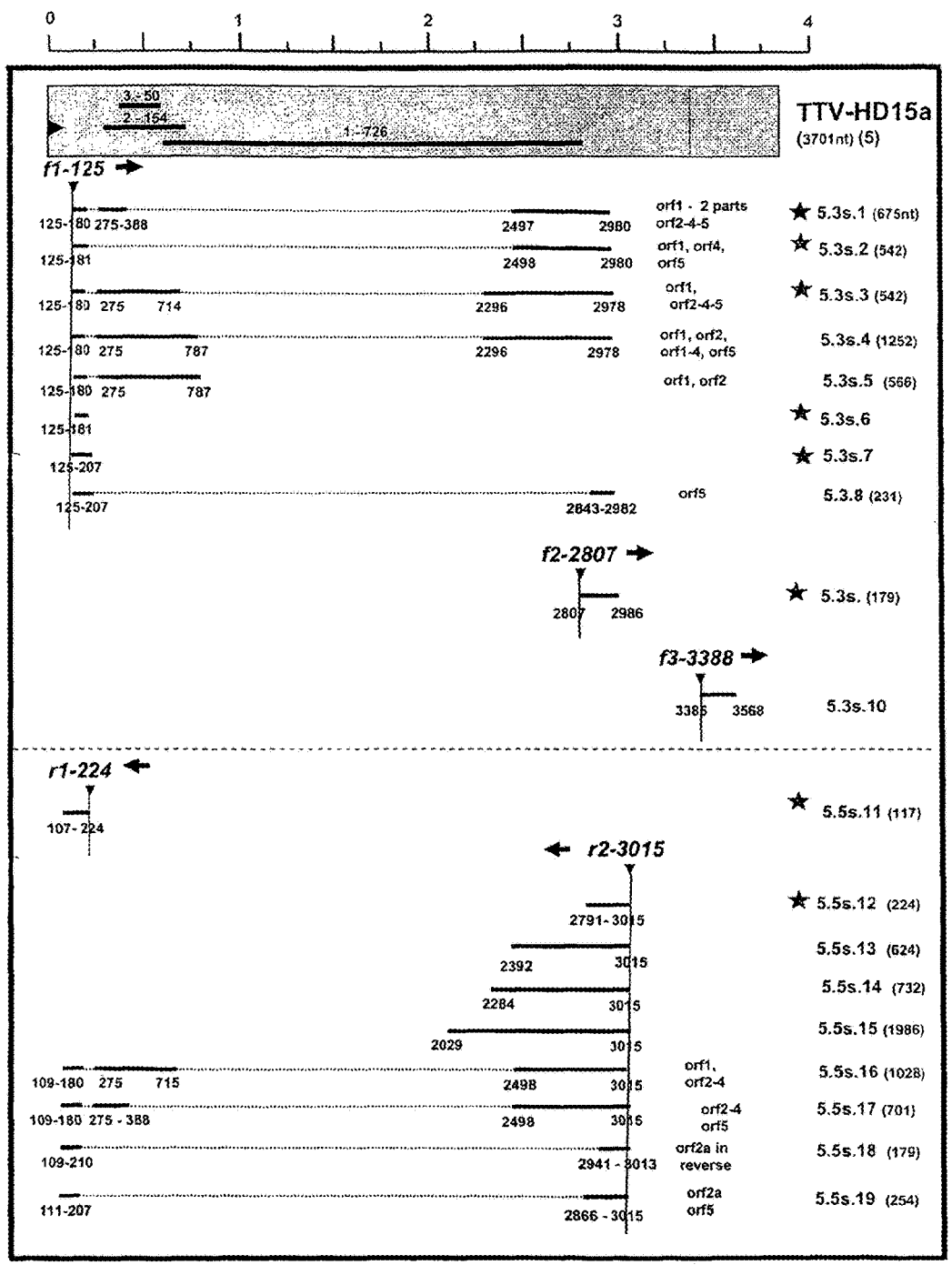
Figure 17D:
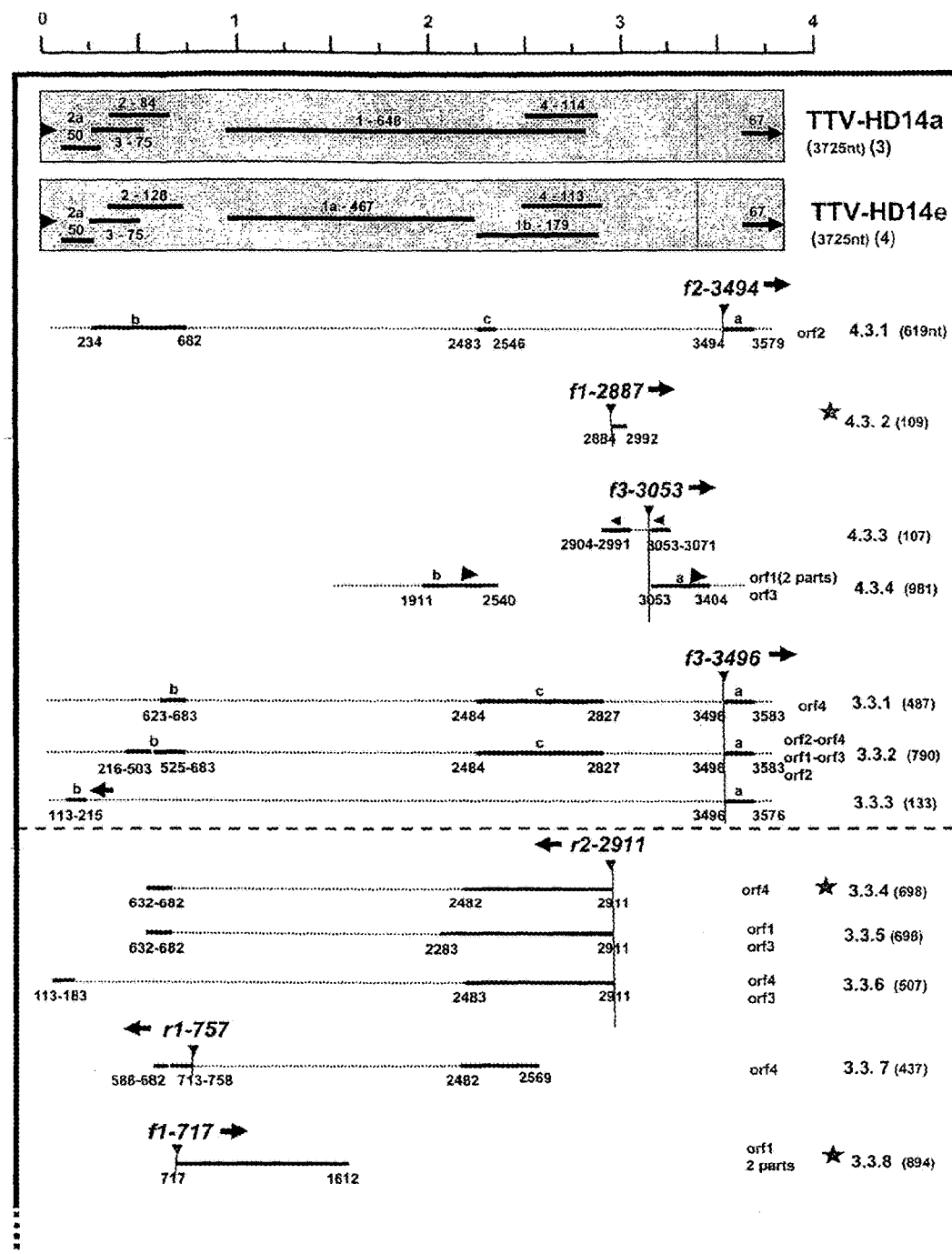
Figure 17E:
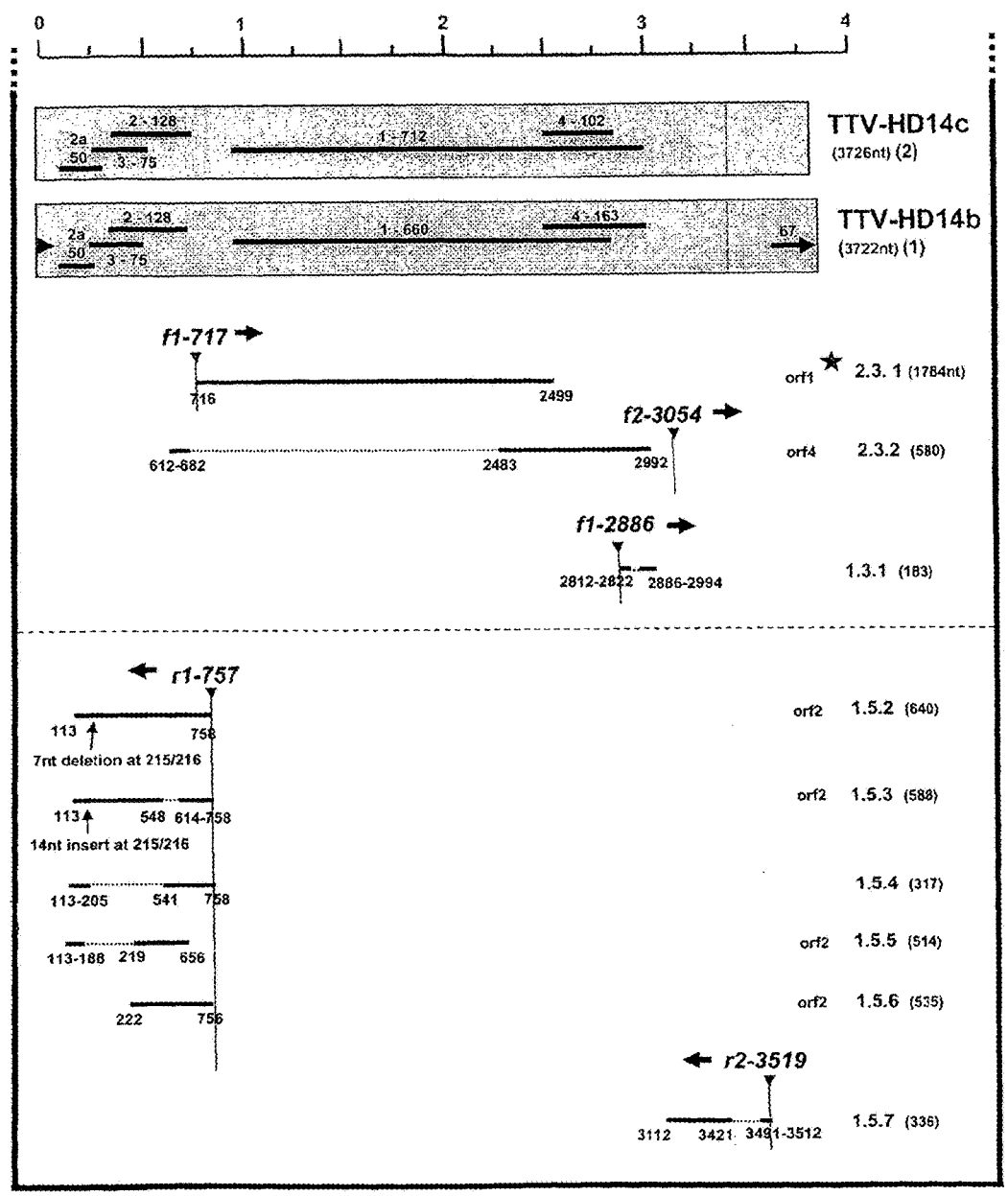
Figure 17F:
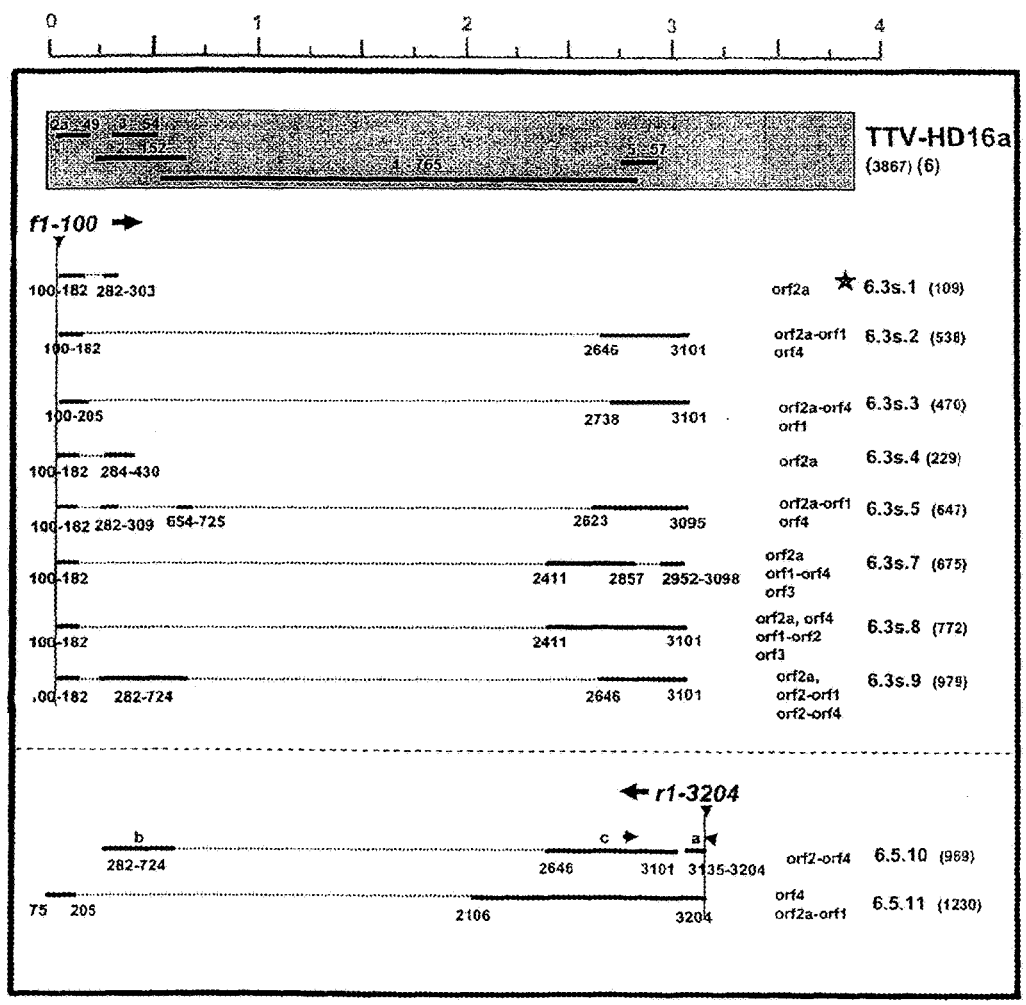
Figure 17G:
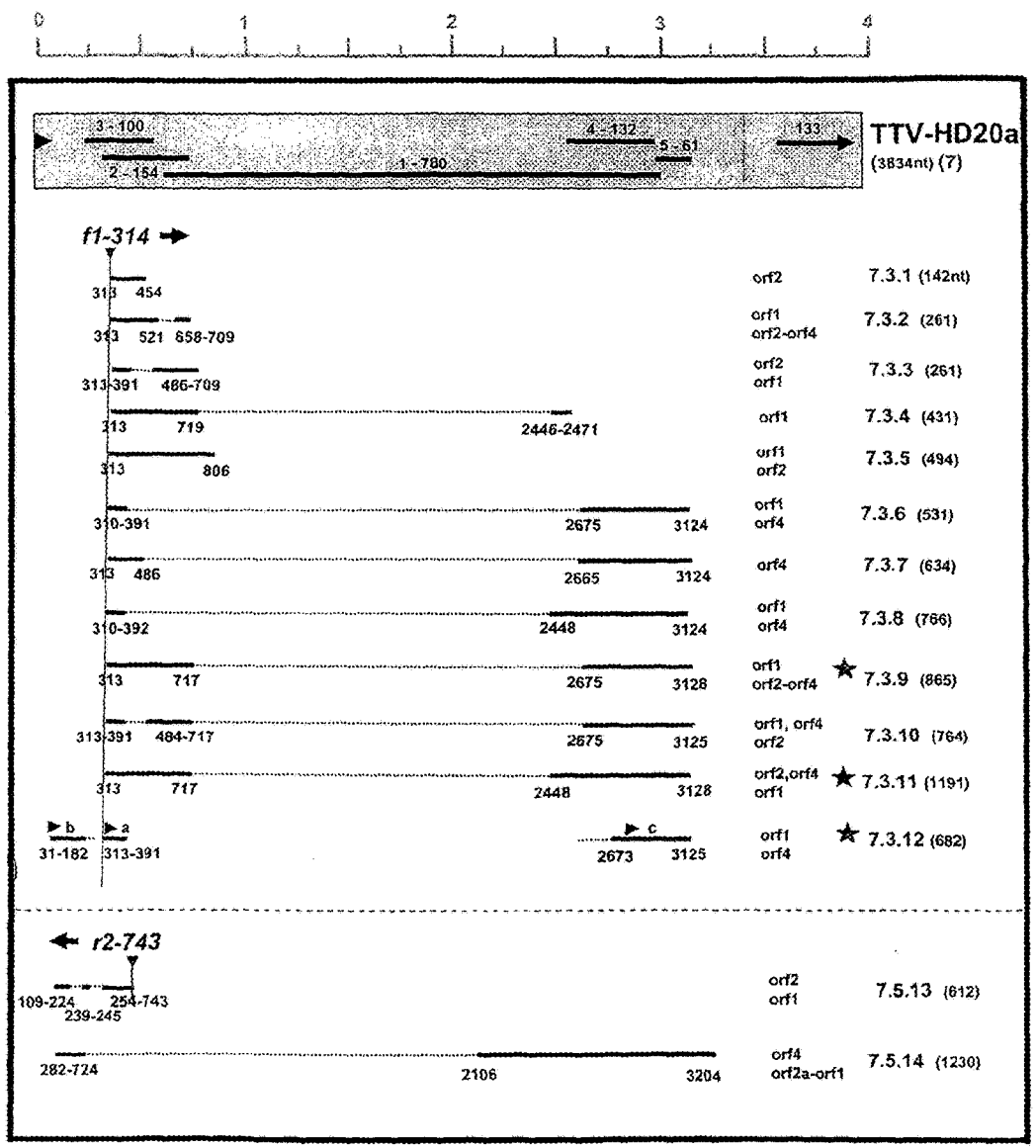

FIG. 15: Digestion of single-stranded DNA by mung-bean nuclease (MBN)
Lanes 2 and 3 show that the amplified DNA may be digested by pre-treatment with MBN. Lanes 5 and 6 demonstrate that plasmid-DNA pretreated in the same way is not digested by MBN.

FIGS. 16A-B: Schematic presentation of the ORF1 of a number of TTV-HD isolates
ORF1 was either divided into one to several smaller ORFs or fused to other ORFs.

FIGS. 17A-G: Transcripts isolated during in vitro replication of TTV-HD isolates
Labelling of individual transcripts indicates "isolate.5'- or 3'-race (s—single strand).no". TTV-isolate numbers (1-12) indicated with respective schematic genome and TTV-HD number. *—transcripts which were more often isolated.

Figure 18:
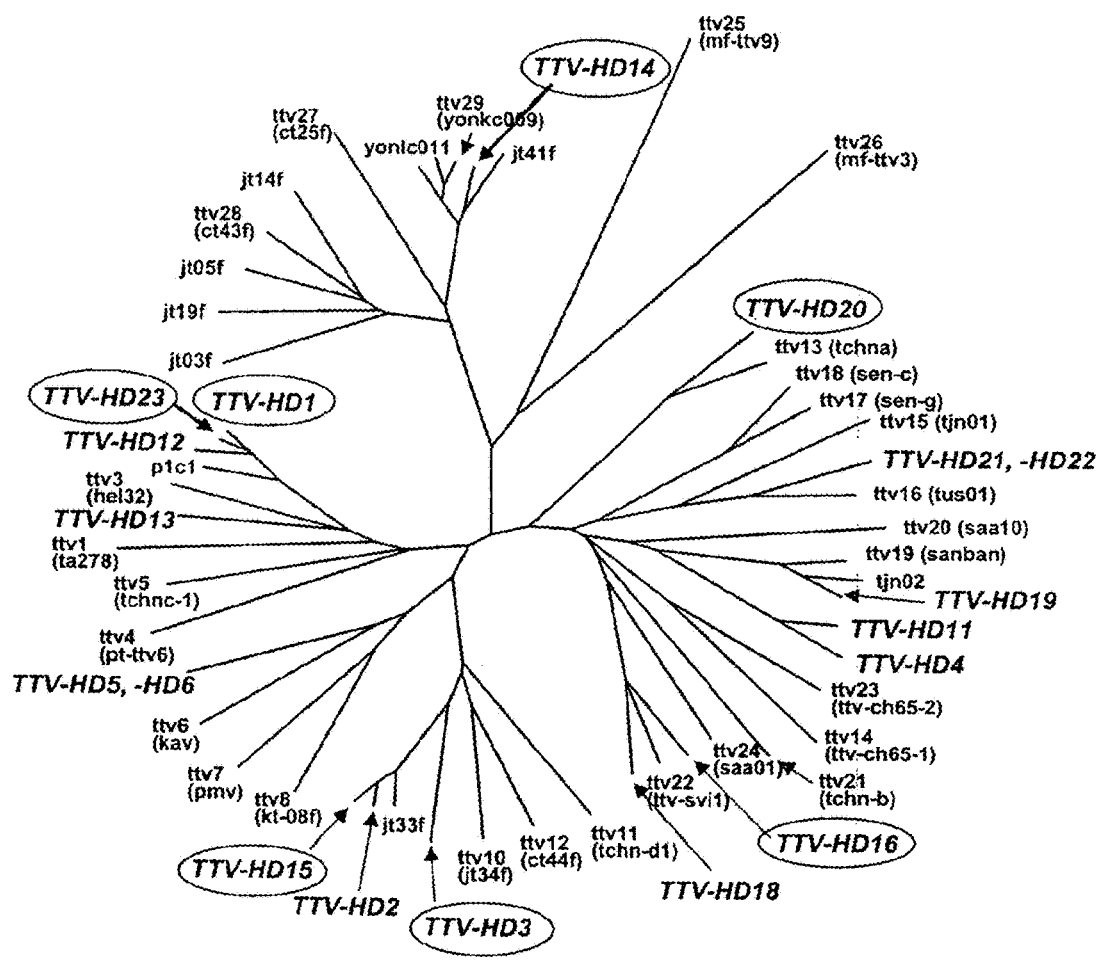

FIG. 18: Phylogenetic tree showing TTV species and isolates of genus Alphatorquevirus, as well as all TTV-HD types
TTV-HD types propagated in in vitro cell cultures are encircled.

Figure 19:
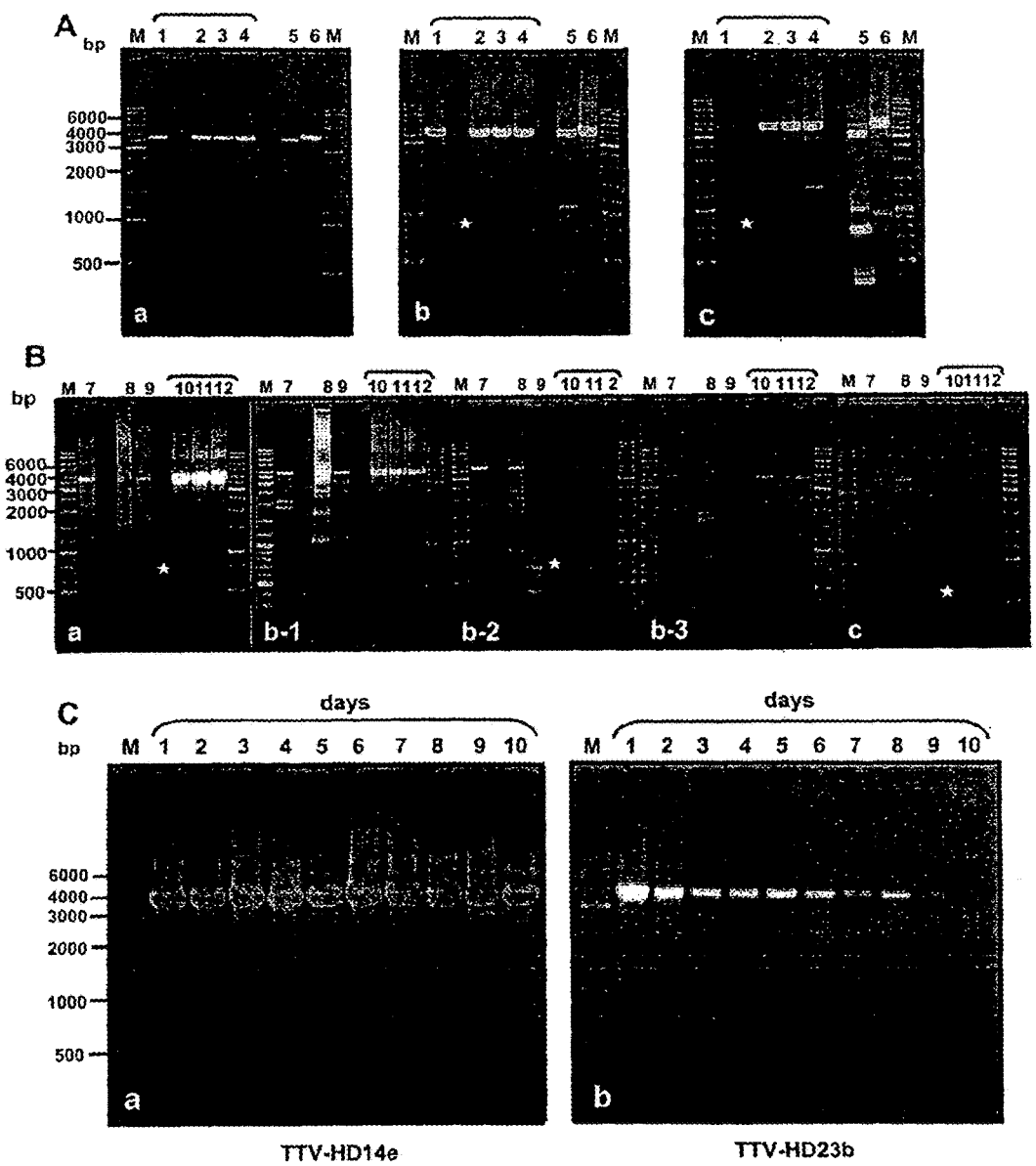

FIGS. 19A-C: Propagation of full-length TTV-HD genomes in 293TT cells
Examples of propagation of
(A) TTV-HD14b, TTV-HD14c, TTV-HD14a, and TTV-HD14e (lanes 1-4), TTV-HD15a (lane 5) and TTV-HD16a (lane 16) after nested PCR amplification;
(B) TTV-HD20a (lane 7), TTV-HD3a (lane 8), TTV-HD1a (lane 9), TTV-HD23b, TTV-HD23d, and TTV-HD23a (lanes 10-12) after single PCR amplification.
a, b and c—examples of propagations, approximately 7 days after infection. b-1, b-2, and b-3 indicate variability observed when propagating same passage.
(C) Daily sampling of TTV-HD14e (nested PCR) and TTV-HD23b cultures.
M—DNA size marker; *—indicate subviral molecules of different cultures.

FIG. 20A-D: Schematic presentation of full-length TTV-HD with their respective μTTV-HD molecules
Numbers indicate ORFs in the DNA genome.

FIGS. 21A-C: Independent propagation of μTTV-HD
μTTV-HD15 replicated stronger after initial transfection, but decreased over time (*-indicate nested PCR amplification). μTTV-HD1 and μTTV-HD23.2 replicated increasingly after additional propagation steps. μTTV-HD23.2 molecules formed during replication of μTTV-HD23.1.

FIGS. 22A-B:
(A) Partially purified virus-like particles
Particles were lysed and content separated on agarose gel.
(B) Partially purified mTTV particles
Particles were lysed and DNA content separated on agarose gel.
3—TTV-HD14a, 5—μTTV-14, 6—TTV-HD16a, 8—TTV-HD3a, 9—μTTV-HD1, 12—TTV-HD23a, 12a—μTTV-HD12.1, 12b—μTTV-HD12.2

DETAILED DESCRIPTION OF THE INVENTION

The ubiquity of torque teno viruses, together with the absence of suitable in vitro culture systems, has hampered progress in investigating this group of viruses. The multitude and heterogeneity of types (Biagini and de Micco, 2010; Okamoto, 2009), as well as their ubiquitous presence in hematopoietic cells (Takahashi et al., 2002; Kanda et al., 1999; Zhong et al., 2002), have added to the delay in gaining information on whether these viruses are involved in the pathogenesis of any disease. A spectrum of TTV types was isolated (Jelcic et al., 2004; Leppik et al., 2007; de Villiers et al., 2009; present invention). Full-length genomes of a number of TTV types were often isolated from an individual sample depending on the composition of primers used for long-distance PCR amplification. The scattered distribution of the new isolates of the present invention on a phylogenetic tree of genus Alphatorquevirus (FIG. 18) indicates their heterogeneity, irrespective of origin. The variation in genome organization resulting from minor differences in sequence identity across the genome was often observed between isolates of the same type and has prompted questions as to the functionality of these modified genes.

Figure 22:
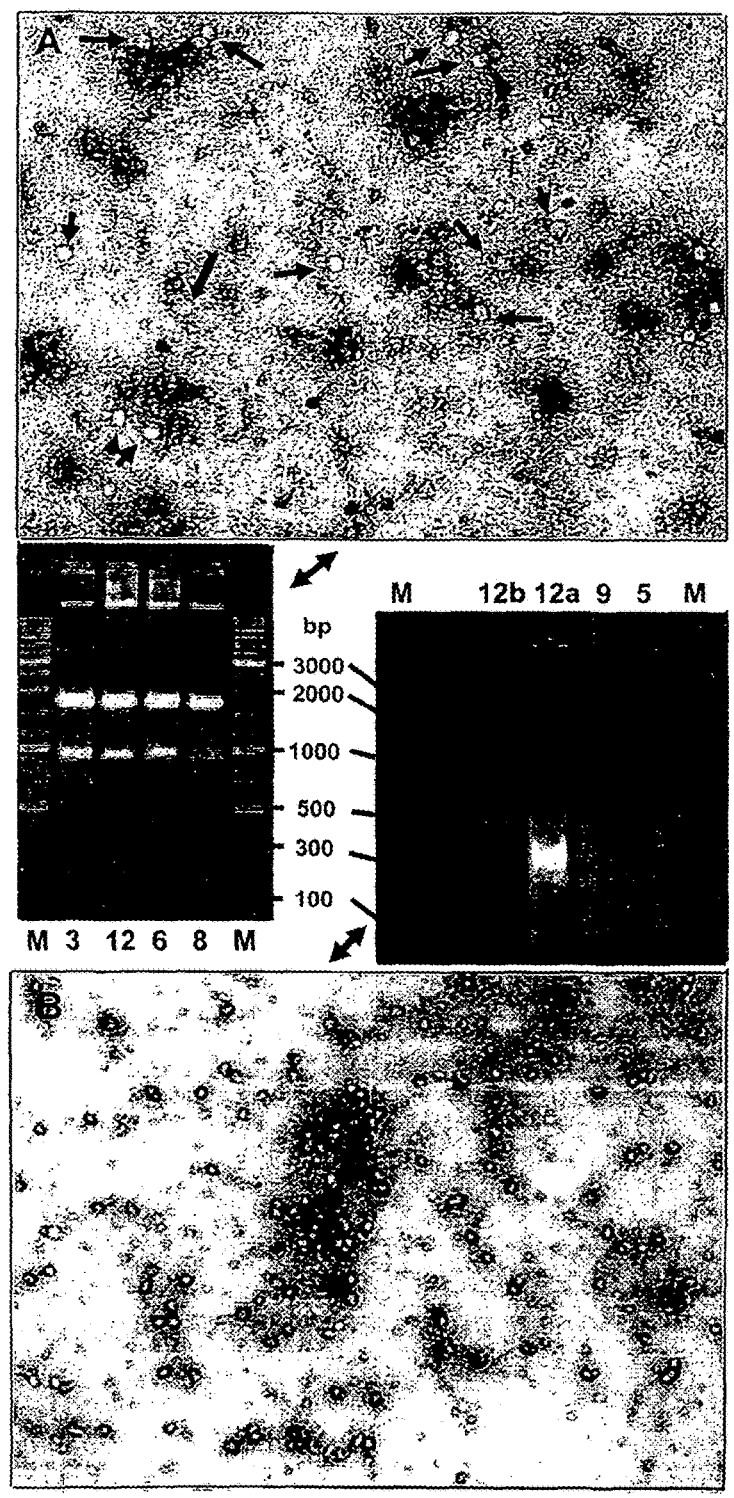

In the past attempts were made to propagate TTV genomes in a number of cell lines and in peripheral blood monocytes under varying in vitro culturing conditions. Moderate success with single isolates was achieved in Hodgkin's lymphoma cell lines and in 293T cells. Replication was however slow and occurred at low levels (Leppik et al., 2007; Leppik and de Villiers, unpublished data). For the studies of the present invention the human embryonic kidney cell line 293TT was engineered to express high-levels of SV-40 large-T antigen (Buck et al., 2005). Transfecting TTV genomes into these cells resulted in virus DNA replication and production of virus-like particles of ca. 30 nm in size (FIG. 22). The structures of these virus-like particles differ from those previously published as TTV particles (Itoh et al., 2000). This is possibly a consequence of the isolation of the latter from faeces.

The differences in the level of DNA replication observed between TTV-isolates cannot presently be explained. Phylogenetic information does not provide an answer. Noticeable is that 6 isolates (TTV-HD14, TTV-HD15 and TTV-HD16) which originated from brain biopsies of patients with multiple sclerosis all replicated much less in the system of the present invention. Virus production (FIG. 22) or virus propagation (FIGS. 19 and 21) did not seem to be influenced despite the varying levels of DNA replication or modifications in the genome organization which included modified ORF1 s. Transcription levels however, seemed to be influenced and fewer of the common transcripts described for other TTV-types were detected in the four TTV-14 isolates than in TTV-HD15a and TTV-HD16a cultures. Previously reported transcripts (Leppik et al., 2007; Kakkola et al., 2009) were isolated from all infected cultures. Interestingly, no transcript was identified which would code for full-length ORF1 protein (suspected to play a major role in coding for the viral capsid, but not yet proven) of any of the TTV-HD types studied, despite the isolation of full-length genome-carrying virus-like particles from all infected cultures. A number of putative protein sequences were identified which may have resulted from fusion products of any two or three genes. Translation strategies known to be used by viruses, such as leaky scanning, re-initiation and ribosomal shunting (Ryabova et al., 2006) might be involved here. Dual coding in alternative reading frames is an additional mechanism which may be involved (Kovacs et al., 2010). Interestingly, transcripts of the control region were also isolated. Here two groups of transcripts were identified. One group involved transcripts spanning at least part of the intergenic region and extending into the rest of the genome covering the known genes. The second group consisted of transcripts varying in length and without recognizable coding capacity. It has been proposed that the nature of the TTV intergenic region with its high GC content may play a role in transcription-dependent replication blockage (Belotserkovskii et al., 2010).

A very prominent observation in the present study is the formation of subviral molecules already early during the replication cycle of the majority of the isolates obtained. Two groups of subviral molecules were distinguished. The formation of multiple subviral DNA molecules ranging in size occurred frequently and extensively in TTV-HD20a-, TTV-HD3a- and TTV-HD1a-infected cultures. Previously similar rearranged subviral molecules were demonstrated in serum samples (Leppik et al., 2007). Transfection into L428 cells (Hodgkin's lymphoma cell line) of a small number of the subviral genomes originating from sera resulted in limited replication and transcription for a few days (de Villiers et al., 2009). Data shown in the present invention indicate a role as defective interfering particles during in vitro replication of the full-length genome. Replication of the full-length genome is reduced during simultaneously increasing levels of subviral molecules (FIG. 19b). Similar subviral molecules were occasionally and inconsistently demonstrated in cultures of the other 9 isolates, but did not influence the replication of the full-length genome. This difference also underlines not only the diversity between TTV types, but also that this phenomenon does not result from PCR artifacts. Similar defective interfering molecules have also been reported in Geminiviruses where they accumulate during improper replication (Jeske, 2009).

The second group of subviral molecules µTTV evolved during replication of TTV isolates TTV-HD14b, TTV-HD14c, TTV-HD14a and TTV-HD14e, TTV-HD15a, TTV-HD16a, TTV-HD1a, TTV-HD23b, TTV-HD23d and TTV-HD23a and remained constant in size and composition during propagation, as evidenced after cloning and sequencing. Their production in the case of the latter 4 isolates seemed to be influenced by culturing conditions. Interestingly, the subviral molecule µTTV-HD1 in the TTV-HD1a infected culture was detectable in the cell culture even after loss of detectable parental full-length genome (FIG. 19c). Two molecules µTTV-HD23.1 (409 bases) and µTTV-HD23.2 (642 bases) were isolated from all 3 TTV-HD23 infected cultures. µTTV-HD23.2 is composed of the µTTV-HD23.1 molecule plus a duplication of 306 nt of the smaller molecule. Subviral molecules (µTTV-HD14) which were isolated from the 4 TTV-HD14 cultures were all identical in sequence and appeared very early after the initial transfection of the parental genome. The production of these smaller molecules did not seem to be influenced by the variation in genome structure between isolates of the same TTV type. All subviral molecules were composed of parts of the parental TTV type, although the genome regions involved, differed. They were all amplified by long-distance PCR using the same back-to-back primers as for amplification of the parental genome. The episomal replication of a TTV subviral molecule isolated from a serum sample over a period of 23 days had previously been observed (de Villiers et al., 2009). Multimeric subviral RNA was demonstrated during this process. The subviral molecules reported in the present invention are able to replicate autonomously, may be propagated in vitro (FIG. 21) and appear to be related to small protein structures observed in these cultures by electronmicroscope (FIG. 22). It is not known whether they are transmitted as part of an infectious TT virus or whether they are induced only after infection by the parent virus and then transmitted by autonomously infecting other cells. Similar subviral DNAs have been associated with the geminivirus disease complex (Stanley, 2004). β-satellites enhance symptom phenotypes in plants. They share a network of protein interactions with geminiviruses and are dependent on them for trans-replication, encapsidation and vector transmission. The only sequence shared between β-satellites and geminiviruses lies in the short origin of replication (Nawaz-ul-Rehman and Fauquet, 2009; Patil and Fauquet, 2010; Paprotka et al., 2010). This is in contrast to the TTV subviral molecules (µTTV) which share almost identical sequences with the parental genome. The cytopathic effect observed during in vitro propagation of the TTV subviral molecules of the present invention points to their possible role as the disease-inducing component of some torque teno viruses. Signature motifs of proteins involved in autoimmune disease have been identified by in silico analyses of putative proteins expressed by these subviral molecules, as well as from virus transcripts isolated from the TTV-infected cultures.

The observation of a DNA encoding a protein containing a signature motif of a mammalian protein associated with cancer or an autoimmune disease linked to the 71 bp highly conserved TT virus region (HCR) is the basis for the following conclusion: The rearranged open reading frames of TTV and μTTV code for antigenic epitopes which mimic cellular protein sequences which are attacked in cancer or autoimmune diseases. Their shared, but not identical sequence should provoke an immune response against these epitopes present also in normal tissue.

The surprising observation of host cell DNA linked to an apparently single-stranded form to TT virus HCR is the basis for the following conclusion: TT viral sequences have not yet been demonstrated as integrated into double-stranded cellular DNA, persisting within host cell chromosomes. Thus, the opposite finding of host cell DNA, linked in a single-stranded state to the TTV HCR should have biological significance. The present data indicate their long-time persistence as episomes in human cancer cell lines, pointing to a role of this persistence in cell proliferation. Two aspects seem to require specific consideration: a possible role of those recombinants in cancer and in autoimmunity.

One possibility is the random integration of host cell sequences into TTV episomes. This may happen after strand displacement in the course of aberrant DNA replication or after reverse transcription of cellular RNA. In case of random integration a larger number of recombinants should be innocuous and harmless for cells carrying these recombinants. A growth-promoting property of transcripts of the TTV HCR, as well as integration and transcription of growth-stimulating host cell genes, their modification in the process of integration or their dysregulation by the TTV HCR however, will result in proliferative consequences. These episomes should acquire immortalizing and under certain conditions transforming properties. In combination with additional modifications of the host cell genome they may direct malignant growth. This mode of action reveals a distant resemblance to the insertion of cellular oncogenes into retroviral genomes.

The previous considerations are summarized in FIG. 4. Obviously, the recombination between the TTV regulatory region and cellular nucleic acids must be a relatively frequent process, since such recombinants are found in the majority of cell lines thus far analyzed. It also should contribute to cell proliferation, otherwise the regular persistence of such molecules, in part over decades of continuous proliferation, would be difficult to explain. It is assumed that this type of recombination is a random process, involving different types of cellular genes. The coding function of the TTV HCR and/or the uptake of genes steering cell proliferation, or blocking the function of proliferation antagonists, or inhibiting cell differentiation should lead to an accumulation of cells containing these types of recombinants. It is envisaged that this, in combination with additional mutational or recombinational events of the cells harbouring such TTV-host cell nucleic acid recombinants, provides a selective advantage for cells carrying such episomes. The presence of the latter would represent a prime risk factor for malignant conversion. In this sense those recombinations should be of general importance for different types of human cancers, although a certain degree of specificity for a limited set of genes would be expected for individual cancer types.

The implications of this model are profound. They reach from cancer prevention, early detection into cancer therapy. The important role of TTV infections and of the persistence of TTV HCR is stressed by the available information. Prevention of these infections should reduce the risk for the development of the described recombinants. The diagnosis of specific recombinants would probably contribute to cancer risk assessment. Profound implications would be expected for cancer therapy: the TTV HCR emerges as the prime determinant for the persistence and maintenance of the single-stranded episomes. Since this region appears to be part of an open reading frame, it should be vulnerable to small interfering RNAs or DNAs. Thus, it offers a suitable target for future therapeutic deliberations.

Two other aspects deserve discussion: certain parallels which seem to exist to retroviral carcinogenesis in rodents and chicken and the use of autonomously replicating TTV-based vector systems for gene therapy. Insertional mutagenesis, the uptake and modification of cellular growth-stimulating genes, rendering them into oncogenes has frequently been analyzed in animal systems. This has thus far not been reported for human cancers. Do TT viruses replace this niche in human and other primate cells? Do TTV compete successfully with retrovirus infections in taking over their role in specific species? The episomal persistence of single-stranded DNA, however, emerges as a remarkable difference to retrovirus-induced carcinogenesis.

Autonomously replicating subviral DNA molecules of approximately 400 bases of TTV origin have been described before. It is tempting to speculate that they or specific TTV-host cell recombinants may represent optimal vector systems for future approaches in gene therapy and for the construction of artificial chromosomes.

The existence of TTV host cell nucleic acid recombinants also permits a novel view on aspects of autoimmune diseases and other chronic diseases (potentially even conditions like arteriosclerosis and Alzheimer's disease). Modification or dys-regulation of cellular proteins may originate from insertional events of cellular genes into single-stranded DNA or to the different HCRs exerted by TTV elements (FIG. 5). They could provide a convenient explanation for autoimmune reactions, even for local ones, like in multiple sclerosis (MS) or Crohn's disease. In the latter two cases in particular, the reactivation of other local infections (potentially herpes-type viruses) would provide a stimulus for the local amplification and gene activity of the respective TTV-host cell nucleic acid recombinants. In MS, this could explain recurrent episodes of disease progression. A model of the autoimmunity concept is depicted in FIG. 5.

Similarly, rearranged TT virus molecules of 719, 642, and 621 bases have been identified which replicate autonomously upon transfection of specific cell lines. Their DNA composition and derivation from specific complete TTV genotypes is shown in FIG. 6. Here the rearrangement results in novel open reading frames in part with epitopes related to those of juvenile diabetes and rheumatoid arthritis.

The models of the present invention for a role of TTV-host cell nucleic acid recombinants is based on the demonstration of the single-stranded chimeric molecules between the TTV HCR and host cell DNA and rearranged autonomously replicating TTV molecules of substantially reduced molecular weights. Both, the TTV oncogene concept and the TTV autoimmunity concept will clearly provide novel approaches to prevention, diagnosis, and in particular to therapy of these conditions and will improve the prognosis of the respective patients.

Unless defined otherwise, all technical and scientific terms used herein have the same meaning as commonly understood by those of ordinary skill in the art to which the invention belongs. Although any methods and materials similar or equivalent to those described herein may be used in the practice or testing of the present invention, preferred methods and materials are described. For the purposes of the present invention, the following terms are defined below.

By "signature motif of a mammalian protein being associated with an autoimmune disease" is meant an amino acid sequence showing striking identity to a motif that may be found in any of the proteins listed in Table 1. Preferably, the length of the signature motif is at least 5 aa, preferably at least 10 aa, more preferably at least 20 aa, and most preferably at least 30 aa and/or the degree of identity of this signature motif to a corresponding motif in a mammalian protein is at least 50%, 60%, 70%, 80%, 90% or 95%.

By "antibody" is meant a protein of the immunoglobulin family that is capable of combining, interacting or otherwise associating with an antigen. The term "antigen" is used herein in its broadest sense to refer to a substance that is capable of reacting in and/or inducing an immune response. Typically, but not necessarily, antigens are foreign to the host animal in which they produce immune reactions.

By "epitope" is meant that part of an antigenic molecule against which a particular immune response is directed. Typically, in an animal, antigens present several or even many antigenic determinants simultaneously. Thus, the terms "epitope" and "antigenic determinant" mean an amino acid sequence that is immunoreactive. Generally an epitope consists of 4, and more usually 5,6,7,8 or 9 contiguous amino acids. However, it should also be clear that an epitope need not be composed of a contiguous amino acid sequence. The immunoreactive sequence may be separated by a linker, which is not a functional part of the epitope. The linker does not need to be an amino acid sequence, but may be any molecule that allows the formation of the desired epitope.

The term "biological sample" as used herein refers to a sample that may be extracted, untreated, treated, diluted or concentrated from an animal. Biological sample refers to any biological sample (tissue or fluid) containing a TTV polynucleic acid of the invention and refers more particularly to blood serum samples, plasma samples, biopsy samples, cerebrospinal fluid samples etc.

By "carrier" is meant any substance of typically high molecular weight to which a non- or poorly immunogenic substance (e.g., a hapten) is naturally or artificially linked to enhance its immunogenicity.

The term "diagnosis" is used herein in its broadest sense to include detection of an antigen reactive to a sub-immunoglobulin antigen-binding molecule. Also included within its scope, is the analysis of disorder mechanisms. Accordingly, the term "diagnosis" includes the use of monoclonal antibodies for research purposes as tools to detect and understand mechanisms associated with a disease or condition of interest. It also includes the diagnostic use of TTV polynucleic acid of the invention for the detection of homologous or complementary RNA transcribed from such molecules.

The term "immunogenicity" is used herein in its broadest sense to include the property of evoking an immune response within an organism. Immunogenicity typically depends partly upon the size of the substance in question, and partly upon how unlike host molecules it is. It is generally considered that highly conserved proteins tend to have rather low immunogenicity.

The term "patient" refers to patients of human or other mammal origin and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

By "pharmaceutically acceptable carrier" is meant a solid or liquid filler, diluent or encapsulating substance that may be safely used in any kind of administration.

The term "related disease or condition" is used herein to refer to a disease or condition that is related anatomically, physiologically, pathologically and/or symptomatically to a reference disease or condition. For example, diseases or conditions may be related to one another by affecting similar anatomical locations (e.g., affecting the same organ or body part), affecting different organs or body parts with similar physiological function (e.g., the oesophagus, duodenum and colon which rely an peristalsis to move food from one end of the alimentary canal to the other), by having similar or overlapping pathologies (e.g., tissue damage or rupture, apoptosis, necrosis) or by having similar or overlapping symptoms (i.e., allergic response, inflammation, lymphocytosis). Thus, for example, an antigen associated with ulcerated colitis may also be associated with perforation of the colon because these disease affects the same organ (i.e., colon).

The term "treating" is used herein in its broadest sense to include both therapeutic and prophylactic (i.e., preventative) treatment designed to ameliorate the disease or condition.

The term "episome" is used herein to refer to a portion of genetic material that may exist independent of the main body of genetic material (chromosome) at some times or continuously and replicate autonomously, while at other times is able to integrate into the chromosome. Examples of episomes include insertion sequences, transposons and the TTV of the invention.

The present invention provides a rearranged TT virus polynucleic acid which may comprise (or consisting of)
(a) a nucleotide sequence shown in FIG. 6;
(b) a nucleotide sequence which shows at least 70%, 80%, 90%, 95% or at least 98% identity to a nucleotide sequence of (a) and is capable of replicating autonomously;
(c) a fragment of a nucleotide sequence of (a) or (b) which is capable of replicating autonomously and/or inducing autonomous replication;
(d) a nucleotide sequence which is the complement of the nucleotide sequence of (a), (b), or (c); or
(e) a nucleotide sequence which is redundant as a result of the degeneracy of the genetic code compared to any of the above-given nucleotide sequences,
wherein, preferably, said nucleotide sequence of (a), (b), (c), (d) or (e) is linked to a polynucleic acid encoding a protein containing a signature motif of a protein being associated with cancer or an autoimmune disease via a phosphodiester bond.

Preferably, the protein is a mammalian protein. Particularly preferably the mammalian protein is a human protein. In another embodiment of the invention the protein is an allergen such as gluten.

The present invention also provides fragments of the nucleotide sequences of the present invention described above that are capable of replicating autonomously. The skilled person may derive at fragments still having the biological activity of the full length molecule without undue experimentation. The lengths of the fragments are not critical, however, fragments having a length of at least 45, 55 or 65 nt are preferred.

The person skilled in the art may easily determine which nucleic acid sequences are related to the nucleotide sequence of FIG. 6 or which fragments are still capable of replicating autonomously by using standard assays or the assays described in the examples, below.

The present invention also provides polynucleic acid sequences which are redundant as a result of the degeneracy of the genetic code compared to any of the above-given nucleotide sequences. These variant polynucleic acid sequences will thus encode the same amino acid sequence as the polynucleic acids they are derived from.

The term "polynucleic acid" refers to a single-stranded or double-stranded nucleic acid sequence. A polynucleic acid may consist of deoxyribonucleotides or ribonucleotides, nucleotide analogues or modified nucleotides, or may have been adapted for therapeutic purposes. Preferably, the rearranged TT virus polynucleic acid is a single-stranded DNA.

Preferably, the rearranged TT virus polynucleic acid of the invention is present as an extrachromosomal episome.

Preferably, the mammalian protein associated with cancer or an autoimmune disease or allergen associated with an autoimmune disease is a protein as shown in Table 1.

TABLE 1

(A) Examples of signature motifs identified in putative proteins resulting from TTV-HD transcripts and full-length genomes Protamine 1 + 2
Leukotriene B4 receptor
AIRE (AutoImmune Regulator)
Gliadin
Neuropeptide Y
CHLAMIDIAOM3 - Chlamidia mol. mimicry - heart disease
Arginine-rich
Opsin
Cyclin kinase
Proxisome (diabetes steroid receptor)
Vasopressin
BDNF factor (brain-derived neurotropic factor)
prepro-orexin
Collagen helix repeat
GIP receptor
Neurotensin
Prion
CD36 antigen (insulin resistance deficiency, artherosclerose)
Calcitonin
Prostanoid
GABA receptor (principal inhibitory neurotransmitter in brain)
Arginine deaminase
Opioid, growth factor receptor
Galanin
Plexin/semamorphin
NURR (rat orphan nuclear hormone receptor)
Brain derived neurotrophin factor (BDN)
Collagenase + endostatin
Aerolysin
Myelin proteolipid
serotonin
Muscarinic receptor
Melanin-conentrating hormone receptor
Sjorgen's syndrome/scleroderma auto-antigen p27
Plexin/semaphoring/integrin type repeat signature
Male specific protein
Gastrin
Collagen
Collagenase metalloprotease
(B) aa sequence alignments
DomainSweep employs a variety of search methods to scan the following protein family databases:
BLOCKS
PFAMA
PRINTS
PRODOM
PROSITE TABLE 1-continued (A) Examples of signature motifs identified in putative proteins resulting from TTV-HD transcripts and full-length genomes

```
SMART
SUPERFAMILY
TIGRFAMS
OPSIN
       gbCsCt38.4ikn.2.154
       OPSINRH3RH4_3: domain 1 of 1, from 46 to 56: score 8.4, E = 5.1       56 (SEQ ID NO: 36)
                   *->iynsFhrGfAlg<-* (SEQ ID NO: 32)
                     y sFhrG+A
       gbCst38.4 46   -YESFHRGHAAF
       zc55s.B4.18dek.281
       OPSINRH3RH4_3: domain 1 of 1, from 19 to 29: score 8.4, E = 5.1       29 (SEQ ID NO: 36)
                   *->iynsFhrGfAlg<-* (SEQ ID NO: 32)
                     y sFhrG+A
       zc55s.B4.1 19  -YESFHRGHAAF
       rheu.cd.215rev.1.736
       OPSINRH3RH4_7: domain 1 of 1, from 665 to 683: score 7.8, E = 5.3    683 (SEQ ID NO: 1)
                   *->R1ELqKR1PWLelnEKave<-* (SEQ ID NO: 33)
                     R+ +q+R1PW+ + +++
       rheu.cd.21 665    RFGVQQRLPWVHSSQETQS
       OPSINRH3RH4_7: domain 1 of 1, from 23 to 41: score 8.2, E = 4.4       41 (SEQ ID NO: 2)
                   *->R1ELqKR1PWLelnEKave<-* (SEQ ID NO: 33)
                     R+ +q+R1PW+ + +++
       zc3r11.B4_   23    RFRVQQRLPWVHSSQETQS
gc;    OPSINRH3RH4
gx;    PR00577
gn;    COMPOUND (7)
ga;    11-SEP-1996; UPDATE 07-JUN-1999
gt;    Opsin RH3/RH4 signature
gp;    PRINTS; PR00237 GPCRRHODOPSN; PR00247 GPCRCAMP; PR00248 GPCRMGR
gp;    PRINTS; PR00249 GPCRSECRETIN; PR00250 GPCRSTE2; PR00899 GPCRSTE3
gp;    PRINTS; PR00251 BACTRLOPSIN
gp;    PRINTS; PR00238 OPSIN; PR00574 OPSINBLUE; PR00575 OPSINREDGRN
gp;    PRINTS; PR00576 OPSINRH1RH2; PR00578 OPSINLTRLEYE; PR01244 PEROPSIN
gp;    PRINTS; PR00666 PINOPSIN; PR00579 RHODOPSIN; PR00239 RHODOPSNTAIL
gp;    PRINTS; PR00667 RPERETINALR
gp;    INTERPRO; IPR000856
gr;    1. APPLEBURY, M.L. AND HARGRAVE, P.A.
gr;    Molecular biology of the visual pigments.
gr;    VISION RES. 26(12) 1881-1895 (1986).
gr;    2. FRYXELL, K.J. AND MEYEROWITZ, E.M.
gr;    The evolution of rhodopsins and neurotransmitter receptors.
gr;    J. MOL. EVOL. 33(4) 367-378 (1991).
gr;    3. ATTWOOD, T.K. AND FINDLAY, J.B.C.
gr;    Design of a discriminating fingerprint for G protein-coupled receptors.
gr;    PROTEIN ENG. 6(2) 167-176 (1993).
gr;    4. ATTWOOD, T.K. AND FINDLAY, J.B.C.
gr;    Fingerprinting G protein-coupled receptors.
gr;    PROTEIN ENG. 7(2) 195-203 (1994).
gr;    5. FRYXELL, K.J. AND MEYEROWITZ, E.M.
```

TABLE 1-continued (A) Examples of signature motifs identified in putative proteins resulting from TTV-HD transcripts and full-length genomes gr; An opsin gene that is expressed only in the R7 photoreceptor cell of
gr; Drosophila.
gr; EMBO J. 6(2) 443-451 (1987).
gr; 6. ZUKER, C.S., MONTELL, C., JONES, K., LAVERTY, T. AND RUBIN, G.M.J.
gr; A rhodopsin gene expressed in photoreceptor cell R7 of the Drosophila
gr; eye-homologies with other signal-transducing molecules.
gr; NEUROSCIENCE 7(5) 1550-1557 (1987).
gr; 7. MONTELL, C., JONES, K., ZUKER, C.S. AND RUBIN, G.M.J.
gr; A second opsin gene expressed in the ultraviolet-sensitive R7
gr; photoreceptor cells of Drosophila melanogaster.
gr; NEUROSCIENCE 7(5) 1558-1566 (1987).
gd; Opsins, the light-absorbing molecules that mediate vision [1,2], are
gd; integral membrane proteins that belong to a superfamily of G protein-
gd; coupled receptors (GPCRs). The activating ligands of the different
gd; superfamily members vary widely in structure and character, yet the
gd; proteins appear faithfully to have conserved a basic structural
gd; framework, believed to consist of 7 transmembrane (TM) helices. Although
gd; the sequences of these proteins are very diverse, reflecting to some
gd; extent this broad range of activating ligands, nevertheless, motifs
gd; have been identified in the TM regions that are characteristic of
gd; virtually the entire superfamily [3,4]. Amongst the exceptions are the
gd; olfactory receptors, which cluster together in a subfamily, which lacks
gd; significant matches with domains 2, 4 and 6. Interestingly, the opsins
gd; also seem to be emerging as increasingly atypical of the superfamily,
gd; clustering most strongly, in phylogenetic analyses, with the olfactory
gd; receptors [4]. The visual pigments comprise an apoprotein (opsin),
gd; covalently linked to the chromophore 11-cis-retinal. The covalent link
gd; is in the form of a protonated Schiff base between the retinal and a
gd; lysine residue located in TM domain 7. Vision is effected through the
gd; absorption of a photon by the chromophore, which is isomerised to the
gd; all-trans form, promoting a conformational change in the protein.
gd; By contrast with vertebrate rhodopsin, which is found in rod cells,
gd; insect photoreceptors are found in the ommatidia that comprise the
gd; compound eyes. Each Drosophila eye has 800 ommatidia, each of which
gd; contains 8 photo-receptor cells (designated R1-R8): R1-R6 are outer
gd; cells, while R7 and R8 are inner cells. Opsins RH3 and RH4 are sensitive
gd; to UV light [5-7]. OPSINRH3RH4 is a 7-element fingerprint that provides
gd; a signature for the RH3 and RH4 opsins. The fingerprint was derived from
gd; an initial alignment of 5 sequences: the motifs were drawn from conserved
gd; sections within either loop or N- and C-terminal regions, focusing on
gd; those areas of the alignment that characterise the RH3/RH4 opsins but
gd; distinguish them from the rest of the rhodopsin-like superfamily-
gd; motifs 1 and 2 lie at the N-terminus; motif 3 spans the first external
gd; loop; motif 4 lies in the second external loop; motif 5 spans the C-
gd; terminal half of TM domain 5; motif 6 lies in the third cytoplasmic
gd; loop; and motif 7 lies at the C-terminus. A single iteration on OWL28.1
gd; was required to reach convergence, no further sequences being identified
gd; beyond the starting set.
gd;

TABLE 1-continued (A) Examples of signature motifs identified in putative proteins resulting from TTV-HD transcripts and full-length genomes

```
c; OPSINRH3RH43
il; 12
it; Opsin RH3/RH4 motif III-1
id; IFNSFHRGFAIY (SEQ ID NO: 3)     OPS4_DROME     109     52
id; IYNSFHRGFALG (SEQ ID NO: 4)     OPS4_DROPS     112     54
id; IYNSFHRGFALG (SEQ ID NO: 4)     OPS4_DROVI     115     54
id; IYNSFHQGYALG (SEQ ID NO: 5)     OPS3_DROME     115     54
id; IYNSFHQGYALG (SEQ ID NO: 5)     OPS3_DROPS     114     54
bb;
fc; OPSINRH3RH43
fl; 12
ft; Opsin RH3/RH4 motif III-2
fd; IYNSFHRGFALG (SEQ ID NO: 4)     OPS4_DROVI     115     54
fd; IYNSFHQGYALG (SEQ ID NO: 5)     OPS3_DROME     115     54
fd; IYNSFHRGFALG (SEQ ID NO: 4)     OPS4_DROPS     112     54
fd; IYNSFHQGYALG (SEQ ID NO: 5)     OPS3_DROPS     114     54
fd; IFNSFHRGFAIY (SEQ ID NO: 3)     OPS4_DROME     109     52
fd; IYNSFHTGFATG (SEQ ID NO: 6)     061474         105     54
fd; IYNSFNTGFATG (SEQ ID NO: 7)     061473         106     54
fd; IYNSFHRGFALG (SEQ ID NO: 8)     OPSV_APIME     105     54
fc; OPSINRH3RH47
fl; 19
ft; Opsin RH4 motif VII-2
fd; RMELQKRCPWLAIDEKAPE (SEQ ID NO: 9)      OPS4_DROVI     346     62
fd; RMELQKRCPWLALNEKAPE (SEQ ID NO: 10)     OPS3_DROME     346     62
fd; RMELQKRCPWLGVNEKSGE (SEQ ID NO: 11)     OPS4_DROPS     343     62
fd; RMELQKRCPWLAISEKAPE (SEQ ID NO: 12)     OPS3_DROPS     345     62
fd; RMELQKRCPWLGVNEKSGE (SEQ ID NO: 13)     OPS4_DROME     342     62
fd; RLELQKRLPWLELQEKPVA (SEQ ID NO: 14)     061474         336     62
fd; RLELQKRLPWLELQEKPIE (SEQ ID NO: 15)     061473         337     62
fd; RLELQKRLPWLELQEKPIS (SEQ ID NO: 16)     OPSV_APIME     336     62
ARG RICH PROSITE-PROFILES
ARG_RICH Arginine-rich region NLS_BP Bipartite nuclear lo
PFSCAN using sequence gbCsCt38.2ikn.1.726
and profile(s) PRFDIR:prosite.prf,
Command Line Parameters used:
-CUTLEV = -1
Score     Raw     seq-f     seq-t     prf-f     prf-t     Name        Description
30.1607   170     4-        67        1-        2         ARG_RICH    Arginine-rich region
4.0000    4       10-       26        1-        17        NLS_BP      Bipartite nuclear lo
4.0000    4       32-       46        1-        17        NLS_BP      Bipartite nuclear lo
5.0000    5       52-       66        1-        17        NLS_BP      Bipartite nuclear lo
PFSCAN using sequence gbDhDi43.4rp.1.765
and profile(s) PRFDIR:prosite.prf, October 15, 2010 15:31
```

TABLE 1-continued (A) Examples of signature motifs identified in putative proteins resulting from TTV-HD transcripts and full-length genomes

```
Command Line Parameters used:
-CUTLEV = -1
  Score   Raw     seq-f     seq-t    prf-f   prf-t   Name       Description
  33.0880 187     9-        73       1-      2       ARG_RICH   Arginine-rich region
PFSCAN using sequence zpr5.B4.12dk.209
Command Line Parameters used:
-CUTLEV = -1
  Score   Raw     seq-f     seq-t    prf-f   prf-t   Name       Description
  30.1607 170     4-        67       1-      2       ARG_RICH   Arginine-rich region
PFSCAN using sequence zc55s.B4.18dek.117
and profile(s) PRFDIR:prosite.prf,
Command Line Parameters used: -CUTLEV = -1
  Score   Raw     seq-f     seq-t    prf-f   prf-t   Name       Description
  18.7959 104     4-        85       1-      2       ARG_RICH   Arginine-rich region
PFSCAN using sequence zc37.B9.2de.p1
Command Line Parameters used: -CUTLEV = -1
  Score   Raw     seq-f     seq-t    prf-f   prf-t   Name       Description
  24.3061 136     7-        86       1-      2       ARG_RICH   Arginine-rich region
Protamine 1 and Protamine 2

BLKPROB Version 5/21/00.1
Database = /gcg/husar/gcgdata/gcgblimps/blocksplus.dat
Query = gbCsCt38.2ikn.1.726                   Length: Size = 726 Amino Acids Family                                                     Strand  Blocks  Combined
                                                                           E-value
IPB000221  Protamine P1                                                    1.3e-09
HSP1_CHICK|P15340  1   ARYRSRTRSRSPRSRRRRRRSGRRRSPRRRRY (SEQ ID NO: 17)
IPB000492  Protamine 2, PRM2                                       1 of 1
HSP2_PIG|P19757  55  HTRRRRSCRRRRRACRHRHRRGCRRIRRRRRCR (SEQ ID NO: 18)  1 of 2  2.2e-09
Query = gbDhDi43.4rp.1.765                    Length: 765

Family                                                     Strand  Blocks  Combined
                                                                           E-value
IPB000221  Protamine P1                                                    1.2e-11
HSP1_DIDMA|P35305  1   ARYRRRSRSRSRYGRRRRRSRSRRRRSRRRR (SEQ ID NO: 19)  1 of 1
IPB000492  Protamine 2, PRM2                                       1 of 2  2.8e-10
HSP2_CALJA|Q28337  69  RRRSRSCRRRRRRSCRYRRRPRRGCRSRRRRRCRR (SEQ ID NO: 20)
Query = rheu.ef.242.746                       Length: 746

Family                                                     Strand  Blocks  Combined
                                                                           E-value
IPB000492  Protamine 2, PRM2                                               1.4e-08
HSP2_CALJA|Q28337  69  RRRSRSCRRRRRRSCRYRRRPRRGCRSRRRRRCRR (SEQ ID NO: 20)  1 of 2
IPB000221  Protamine P1                                            1 of 1  1.5e-07
HSP1_DIDMA|P35305  1   ARYRRRSRSRSRYGRRRRRSRSRRRRSRRRR (SEQ ID NO: 19)
Query = uro705rev.1a.74                       Length: 74
1/1 blocks Combined E-value = 2.8e-12
IPB000221  Protamine P1
HSP1_DIDMA|P35305  1   ARYRRRSRSRSRYGRRRRRSRSRRRRSRRRR (SEQ ID NO: 19)
1/2 blocks Combined E-value = 2.3e-10
IPB000492  Protamine 2, PRM2
HSP2_CALJA|Q28337  69  RRRSRSCRRRRRRSCRYRRRPRRGCRSRRRRRCRR (SEQ ID NO: 20)
Query = zpr5.B4.12dk                          Length: 209
IPB000221  Protamine P1                                            1 of 1  4.1e-10
```

TABLE 1-continued (A) Examples of signature motifs identified in putative proteins resulting from TTV-HD transcripts and full-length genomes

```
HSP1_CHICK|P15340 1      Protamine 2, PRM2      ARYRRSRTRSRSPRSPRSRRRRRSGRRRSPRRRRY (SEQ ID NO: 17)
IPB000492
HSP2_PIG|P19757 55       Protamine 2, PRM2      HTRRRRSCRRRRRACRHRHRRGCRRIRRRRRCR (SEQ ID NO: 18)     1                  7.1e-10
Query = zc55s.B4.18dek.117                      length: 117

Strand  Blocks         Combined
Family                                                                                                     E-value
IPB000492    Protamine 2, PRM2                                                       1      1 of 2         3.4e-05
Q91V94|Q91V94_MESAU63
IPB000221    Protamine P1                       HRRRRSCRRRRRHSCRHRRHRRGCRRSRRRRRCR (SEQ ID NO: 21)  1 of 2
HSP1_MOUSE|P02319 1                                                                                        0.0013
Query = zc37.B9.2de.p1                          ARYRCCRSKSRSRCRRRRRRCRRRRRRCCRRRRR (SEQ ID NO: 22)  1
                                                length: 918

Strand  Blocks         Combined
Family                                                                                                     E-value
IPB000492    Protamine 2, PRM2                  RRRHRSCRRRRRSCRHRHRRGCRTRRRRCRRY (SEQ ID NO: 23)    1      1 of 2      2.8e-05
HSP2_ERYPA|Q9GKM0 69
IPB000221    Protamine P1                       ARYRCCRSPSRSRCRRRRRFYRRRRRCHRRRRR (SEQ ID NO: 24)   1      1 of 1      0.0001
HSP1_CAVPO|P35304 1

Sequences presented as examples:
Full-length genomes (TTV) of:
gbCsCt38.2ikn.1.726                             (TTV-HD15, ORF1 = 726aa)
gbDhDi43.4rp.1.765                              (TTV-HD16, ORF1 = 765aa)
rheu.ef.242.746                                 (TTV-HD19, ORF1 = 746aa)
uro705rev.la.74                                 (TTV-HD18, ORF1a = 74aa)
Full-length genome (μTTV) of:
zpr5.B4.12dk                                    (μTTV-HD15. ORF = 208aa)
Transcripts (from -):
zc55s.B4.18dek.117                              (TTV-HD15, ORF = 117aa)
zc37.B9.2de.p1                                  (TTV-HD20, ORF = 109aa)
GALANIN:

HMMER 2.3.2 (Oct 2003)
Copyright © 1992-2003 HHMI/Washington University School of Medicine
Freely distributed under the GNU General Public License (GPL)

HMM file: smart.hmm
sequence file: gbDhDi33.33ik.1c.417
galanin: domain 1 of 1, from 264 to 367: score -22.9, E = 6.5
            *->atlGLgsPvkekrGwtLnsAGYlLlGPHAidnHRsFsdKhGLtgKREL
               t L P + r + s LGP ++ ++G+ +KR +
gbDhDi33.3   264 STHELPDPDRHPRMLQV-SDPTKLGPKT.-AFHKMDWRRGMLSKRSI       307
            e..pEdearpGsfdrplses.nivrtieflsflhLkeaGaLdrLpg1Pa
               ++ Ed +++pl+ ++n t + L+ L +
gbDhDi33.3   308 KrvQEDSTDDEYVAGPLPRKrNKFDTRVQGPPTPEKESYTLLQALQESGQ    357
            aasseDlers<-* (SEQ ID NO: 31)
               sseD e++
gbDhDi33.3   358 ESSSEDQEQA                                           367 (SEQ ID NO: 25)

gbDfDg33.48ikn.1b.179
galanin: domain 1 of 1, from 26 to 129: score -21.0, E = 3.9
            *->atlGLgsPvkekrGwtLnsAGYlLlGPHAidnHRsFsdKhGLtgKREL
               t L P + r + s LGP + ++ ++G+ +KR +
```

TABLE 1-continued (A) Examples of signature motifs identified in putative proteins resulting from TTV-HD transcripts and full-length genomes

```
gbDfDg33.4       26   STHELPDDRHPRMLQV-SDPTKLGPKTV--FHKMDWRRGMLSKRSI                                      69
                      e..pEdearpGsfdrplses.nivrtiiefLsfLhLkeaGaLdrIpglPa
                      ++ Ed +++pl+ ++n t +L+ L +
gbDfDg33.4       70   KrVQEDSTDDEYVAGPLPRK-NKFDTRVQGPPTPEKESYTLLQALQESGQ                                  119
                      aasseDlers<-* (SEQ ID NO: 31)
                      sseD e++
gbDfDg33.4      120   ESSSEDQEQA                                   129 (SEQ ID NO: 26)
HMM file: smart.hmm
Sequence file: gbDhDi33.32ikn.1.648
galanin: domain 1 of 1, from 495 to 598: score -24.5, E = 9.7
gbDhDi33.3      495   *->atlGLgsPvkekrGWtLnsAGYLLGPHAidnHrsFsdKhGLtgKREL                                  538
                      t L P + r + s LGP + ++ ++G+ +KR +
gbDhDi33.3      539   STHELPDDRHPRMLQV-SDPTKLGPKTV--FHKMDWRRGMLSKRSI
                      .epEdearpGs.fdrplses.nivrtiiefLsfLhLkeaGaLdrIpglPa
                      ++ + G +++pl+ ++n t +L+ L +
gbDhDi33.3      589   kRVQGDSTDGEYVAGPLPRKrNKFDTRVQGPPTPEKESYTLLQALQESGQ                                  588
                      aasseDlers<-* (SEQ ID NO: 31)
                      sseD e++
gbDhDi33.3            ESSSEDQEQA                                   598 (SEQ ID NO: 27)
gbDfDg33.45ikn.1b.210
galanin: domain 1 of 1, from 57 to 160: score -23.1, E = 6.8
gbDfDg33.4       57   *->atlGLgsPvkekrGWtLnsAGYLLGPHAidnHrsFsdKhGLtgKREL                                  100
                      t L P + r + s LGP + ++ ++G+ +KR +
gbDfDg33.4      101   STHELPDDRHPRMLQV-SDPTKLGPKTV--FHKMDWRGMLSKRSI
                      e..pEdearpGsfdrplses.nivrtiiefLsfLhLkeaGaLdrIpglPa
                      ++ Ed +++pl+ ++n t +L+ L +
gbDfDg33.4      151   KrVQEDSTDDEYVAGPLPRK-NKFDTRVQGPPTPEKESYTLLQALQESGQ                                  150
                      aasseDlers<-* (SEQ ID NO: 31)
                      sseD e++
gbDfDg33.4            ESSSEDQEQA                                   160 (SEQ ID NO: 28)
```

PLEXIN/SEMAPHORIN/INTEGRIN TYPE REPEAT SIGNATURES

HMMER 2.3.2 (Oct 2003)
Copyright © 1992-2003 HHMI/Washington University School of Medicine
Freely distributed under the GNU General Public License (GPL)

HMM file: smart.hmm
Sequence file: gbDhDi33.32ikn.1.648
psinew7: domain 1 of 1, from 341 to 394: score -16.8, E = 3.9

```
gbDhDi33.3      341   *->rCsgygv . . ..ti++ttkskClilrdpl . . . CgWCssegrCtrg.erC                            384
                      Cs +++ +t+ s C+l++ p + C W ++Ct ++++
gbDhDi33.3      385   WCSEKSSkldTTKSKCILRDFPLWamaygyCDWVV---KCTGVsSAW                                     394 (SEQ ID NO: 29)
                      derrgsrqnwssgpssqCp<-*  (SEQ ID NO: 30)
                      + +r+ --- Cp
gbDhDi33.3            TDMRI----AI-----ICP
Interpro:       IPR003659                                            Plexin/semaphorin/integrin
```

TABLE 1-continued (A) Examples of signature motifs identified in putative proteins resulting from TTV-HD transcripts and full-length genomes

| Mouse-over to show the element definition. Click to show original data. | Formularbeginn¶ | Mouse-over to sh ¶ | Mouse-over to sh ¶ |
|---|---|---|---|
| | 1  100  200  300  400  500  600 | Formularende¶ | |

SM00423 ▬

IPR003659; IPR016201; (Plexin-like) matches 1383 proteins ShortName Plexin-like FullName Plexin/semaphorin/integrin Type Repeat Signatures SMART: SM00423PSI
¶Children IPR016201 Plexin-like fold (matches 619 proteins)&Found in IPR012013

Integrin beta-4 subunit (matches 9 proteins)
IPR020707 Tyrosine-protein kinase, hepatocyte growth factor receptor (matches 82 proteins)
IPR020739 Tyrosine-protein kinase, MSP receptor (matches 18 proteins) Abstract This is a domain that has been found in plexins, semaphorins and integrins. Plexin is involved in the development of neural and epithelial tissues; semaphorins induce the collapse and paralysis of neuronal growth cones; and integrins may mediate adhesive or migratory functions of epithelial cells. Examples

```
HMM file: smart.hmm
Sequence file: gbDhDi33.3likn.1.712
psinew7: domain 1 of 1, from 341 to 378: score -14.4, E = 2.3

*->rCsgygv...tsCseCllardpygCgWCssegrCtrgerCderrgsr
                    Cs +++ +t+ s C+l++p W ++++Cd
gbDhDi33.3   341 WCSEKSSkldTTKSKCILRDFP---LWA-----MAYGHCD------  372 qnwssgpssqCp<-* (SEQ ID NO: 34)
                 w+ +C+
gbDhDi33.3   373 --WVV---KCT                                       378 (SEQ ID NO: 36)
GASTRIN
```

```
HMM file: prints.hmm
Sequence file: gbDhDi33.32ikn.1.648
Copyright © 1992-2003 HHMI/Washington University School of Medicine
Freely distributed under the GNU General Public License (GPL)

GASTRINR_8: domain 1 of 1, from 541 to 559:
                 *->vaGEDsDGCyvg..LPRsR<-* (SEQ ID NO: 37)
                   v G+ DG yv ++LPR R
gbDhDi33.3   541 VQGDSTDGEYVAgpLPRKR                               559 (SEQ ID NO: 38)
gc; GASTRINR
gx; PR00527
gn; COMPOUND (9)
```

TABLE 1-continued (A) Examples of signature motifs identified in putative proteins resulting from TTV-HD transcripts and full-length genomes

```
ga; 03-JUN-1996; UPDATE 10-JUN-1999
gt; Gastrin receptor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; PRINTS; PR01822 CCYSTOKININR; PR00524 CCYSTOKINIAR
gp; INTERPRO; IPR000314
gr; 1. ATTWOOD, T.K. AND FINDLAY, J.B.C.
gr; Fingerprinting G protein-coupled receptors.
gr; PROTEIN ENG. 7(2) 195-203 (1994).
gd; Gastrins and cholecystokinins (CCKs) are naturally-occurring peptides that
gd; share a common C-terminal sequence, GWMDF; full biological activity
gd; resides in this region [6]. The principal physiological role of gastrin is
gd; to stimulate acid secretion in the stomach; it also has trophic effects on
gd; gastric mucosa [6]. Gastrin is produced from a single gene transcript, and
gd; is found predominantly in the stomach and intestine, but also in vagal
gd; nerves. The CCKB receptor has a widespread distribution in the CNS and
gd; has been implicated in the pathogenesis of panic-anxiety attacks caused
gd; by CCK-related peptides [6]. It has a more limited distribution in the
gd; periphery, where it is found in smooth muscle and secretory glands.
gd; GASTRINR is a 9-element fingerprint that provides a signature for the
gd; gastrin (CCKB) receptors. The fingerprint was derived from an initial
gd; alignment of 5 sequences: the motifs were drawn from conserved sections
gd; within either loop or N- and C-terminal regions, focusing on those areas
gd; of the alignment that characterise the gastrin receptors but distinguish
gd; them from the rest of the rhodopsin-like superfamily - motifs 1 and 2 lie
gd; at the N-terminus; motif 3 spans the first external loop; motif 4 spans
gd; the second cytoplasmic loop; motifs 5 and 6 span the second external loop;
gd; motifs 7 and 8 spans the third cytoplasmic loop; and motif 9 lies at the
gd; C-terminus. Two iterations on OWL28.0 were required to reach convergence,
gd; at which point a true set which may comprise 7 sequences was identified.
gd; Several partial matches were also found, all of which are either gastrin
gd; fragments, or members of the cholecystokinin type A receptor family.
fc; GASTRINR8
fl; 17
ft; Gastrin receptor motif VIII-2
fd; LAGEDGDGCTVQLPRSR (SEQ ID NO: 39)   GASR_RABIT   288   31
fd; VAGEDNDGCTVQLPRSR (SEQ ID NO: 40)   GASR_PRANA   289   30
fd; LAGEDGDGCTVQLPRSR (SEQ ID NO: 39)   GASR_BOVIN   290   31
fd; AVGEDGDGCTVQLPRSR (SEQ ID NO: 41)   GASR_HUMAN   285   26
fd; LAGEDGDGCTVQLPRSR (SEQ ID NO: 39)   GASR_CANFA   289   29
fd; LTGEDSDGCTVQLPRSR (SEQ ID NO: 42)   GASR_MOUSE   291   32
fd; VAGEDSDGCCVQLPRSR (SEQ ID NO: 43)   GASR_RAT     290   31
COLLAGENASE
```

HMMER 2.3.2 (Oct 2003)
Copyright © 1992-2003 HHMI/Washington University School of Medicine
Freely distributed under the GNU General Public License (GPL)
-----------------------------------------------------------------
HMM file: pfam.hmm TABLE 1-continued (A) Examples of signature motifs identified in putative proteins resulting from TTV-HD transcripts and full-length genomes

```
Sequence file: rheu.ef.241.736
Peptidase_M9: domain 1 of 1, from 125 to 412: score -152.5, E = 7.5
                *->msrlaelyllGdsiKgrhDnlWLaaaemlsYyApegkselgidicqa
                   l ly    r n W + +el+ g+ +
rheu.ef.24    125    --TLRILYDEF----TRRMNFWTVSNEDLDLCRYVGCKLIF--FKHP    163
                     kleIaakVlPy..lyeCsgpaa. irsqdltdgqaAsaCdilrnkekdfhq
                     ++ + ++++ +++aa+i + ++ +l h+
rheu.ef.24    164    TVDFIVQINTQppFLDTHLTAAsIHPGIMMLSKRRILIPSLKTRPSRKHR    213
                     vkytGktPVaDDgntrveVgvfvseedykrYSafaSKEVkaqFgrvtdNG
                     v+ V ++ + d  ++S fa t +
rheu.ef.24    214    VVVR----VGAPPLFQDKWYPQSDLCDTVLLSIFA----------TACD    248
                     GmYLEGNPsdagNqvrF  . iAYBeakInadlsigNlehEYthy  . . LDgR
                     +Y G P + v+F+ ++k ++s N+e + thY+++L +
rheu.ef.24    249    LQYPFGSPLTENPCVNFgiLGPHYKKHL-SISSTNDETNKTHYesnLFNK    297
                     fdtYGtFsrnleeshivWweEGfAEYvhYkqgGvPyqaApeliggqskly
                     +Y tF ++ + e G+ v  v ++ + ++g +
rheu.ef.24    298    TELYNTFQTIAQ-----LKETGRTSGVNPNWTSVQNTTPLNQAGNN---A    339
                     lsdvftTTeeGyAElFAGShDtcdRiyRWGYLA.vrf . . mletnHnr
                     ++ + t++ G + d I ++++rf++ + ++l n +
rheu.ef.24    340    QNSRDTWY---K-----GNTYNDNISKLAEITrQRFksatisALP-NYPT    380
                     dveslIvhsRyGhsfafyaylvkllgymYnnefgiw<-* (SEQ ID NO: 45)
                     ++ ++l ++ +G Y+ ++ +g Y g++
rheu.ef.24    381    IMSTDLYEYHSG----IYSSIFLSAGRSYFETTGAY    412  (SEQ ID NO: 44)
rheu.ef.241.736
Peptidase_M9: domain 1 of 1, from 125 to 412: score -152.5, E = 7.5
                *->msrlaelyllGdsiKgrhDnlWLaaaemlsYyApegkselgidicqa
                   l ly    r n W + +el+ g+ +
rheu.ef.24    125    --TLRILYDEF----TRRMNFWTVSNEDLDLCRYVGCKLIF--FKHP    163
                     kleIaakVlPy..lyeCsgpaa. irsqdltdgqaAsaCdilrnkekdfhq
                     ++ + ++++ +++aa+i + ++ +l h+
rheu.ef.24    164    TVDFIVQINTQppFLDTHLTAAsIHPGIMMLSKRRILIPSLKTRPSRKHR    213
                     vkytGktPVaDDgntrveVgvfvseedykrYSafaSKEVkaqFgrvtdNG
                     v+ V ++ + d  ++S fa t +
rheu.ef.24    214    VVVR----VGAPPLFQDKWYPQSDLCDTVLLSIFA----------TACD    248
                     GmYLEGNPsdagNqvrF  . iAYBeakInadlsigNlehEYthy  . . LDgR
                     +Y G P + v+F+ ++ k  ++s N+e + thY+++L +
rheu.ef.24    249    LQYPFGSPLTENPCVNFgiLGPHYKKHL-SISSTNDETNKTHYesnLFNK    297
                     fdtYGtFsrnleeshivWweEGfAEYvhYkqgGvPyqaApeliggqskly
                     +Y tF ++ + e G+ v  v ++ + ++g +
rheu.ef.24    298    TELYNTFQTIAQ-----LKETGRTSGVNPNWTSVQNTTPLNQAGNN---A    339
                     lsdvftTTeeGyAElFAGShDtcdRiyRWGYLA.vrf . . mletnHnr
                     ++ + t++ G + d I ++++rf++ + ++l n +
rheu.ef.24    340    QNSRDTWY---K-----GNTYNDNISKLAEITrQRFksatisALP-NYPT    380
                     dveslIvhsRyGhsfafyaylvkllgymYnnefgiw<-* (SEQ ID NO: 45)
                     ++ ++l ++ +G Y+ ++ +g Y g++
rheu.ef.24    381    IMSTDLYEYHSG----IYSSIFLSAGRSYFETTGAY    412  (SEQ ID NO: 44)

# = GF ID    Peptidase_M9
# = GF AC    PF01752.9
# = GF DE    Collagenase
# = GF AU    Bateman A
```

TABLE 1-continued (A) Examples of signature motifs identified in putative proteins resulting from TTV-HD transcripts and full-length genomes

```
# = GF SE    SWISS-PROT
# = GF RM    7582017
# = GF RT    Molecular analysis of an extracellular protease gene from Vibrio
# = GF RT    parahaemolyticus.
# = GF RA    Lee CY, Su SC, Liaw RB;
# = GF RL    Microbiology 1995; 141: 2569-2576.
# = GF RM    8282691
# = GF RT    Purification and characterization of Clostridium perfringens
# = GF RT    120-kilodalton collagenase and nucleotide sequence of the
# = GF RT    corresponding gene.
# = GF RA    Matsushita O, Yoshihara K, Katayama S, Minami J, Okabe A;
# = GF RL    J Bacteriol 1994; 176: 149-156.
# = GF DR    INTERPRO; IPR013510;
# = GF DR    MEROPS; M9;
# = GF CC    This family of enzymes break down collagens.
COLLAGEN HELIX REPEAT BLKPROB Version 5/21/00.1
================================================================
Database = /gcg/husar/gcgdata/gcgblimps/blocksplus.dat
Copyright © 1992-6 by the Fred Hutchinson Cancer Research Center
If you use BLOCKS in your research, please cite:
Steven Henikoff and Jorja G. Henikoff, Protein Family Classification Based
on Searching a Database of Blocks, Genomics 19: 97-107 (1994).
================================================================
Each numbered result consists of one or more blocks from a PROSITE or PRINTS gbDhDi33.35ikn.2.128.pep
================================================================
                                                                     Combined
Family                                            Strand    Blocks   E-value
IPB008161    Collagen helix repeat                  1       1 of 1   0.0077
>IPB008161 1/1 blocks Combined E-value = 0.0077: Collagen helix repeat
Block       Frame    Location (aa)                          Block E-value
IPB008161     0          49-91                                 0.007
Other reported alignments:

IPB008161                    <-->
O16787|O16787_CAEEL143       GAPGPPGLPGPKGPRGPAGIEGKPGRLGEDNRPGPPGPPGVRG
gbDhDi33.35ikn.2.1 49        GPPRPPPGLDQLNPEGPAGPGGPPAILPALPAPADPEPAPRRG
O16787_CAEEL143 (SEQ ID NO: 46); gbDhDi33.35ikn.2.1 (SEQ ID NO: 47)

Query = rheu.ef.241.148                                  Length: 148                      Type: P
>IPB008161 1/1 blocks (SEQ ID NO: 48) blocks Combined E-value = 0.0075: Collagen helix repeat
Block       Frame    Location (aa)                          Block E-value
IPB008161     0          67-109                                0.0068
```

TABLE 1-continued

Examples of signature motifs identified in putative proteins resulting from TTV-HD transcripts and full-length genomes (A)

```
Other reported alignments:

IPB008161          <->
Q9L470_STAEP    1076    GKPAEPGKPAEPGKPAEPGTPAEPGKPAEPGKPAEPG
                        |||   |||     ||    ||||    |||
rheu.ef.241.148   67    HLATTLGRPPRPGPPGGPRTPQIRnLPALPAPQGEPGDRATWR Q9L470_STAEP (SEQ ID NO: 48);rheu.ef.241.148 (SEQ ID NO: 49)

Query = rheu.ef.238rev.148_2774.sreformat
>IPB008161 1/1 blocks Combined E-value = 0.0075 : Collagen helix repeat
Block    Frame    Location (aa)    Block E-value
IPB008161    0    67-109           0.0068
Other reported alignments:

IPB008161          <->                                                         Length: 148
Q9L470_STAEP    1076    GKPAEPGKPAEPGKPAEPGTPAEPGKPAEPGKPAEPG
                        |||   |||     ||    ||||    |||
rheu.ef.241.148   67    HLATTLGRPPRPGPPGGPRTPQIRnLPALPAPQGEPGDRATWR Q9L470_STAEP (SEQ ID NO: 48);rheu.ef.241.148 (SEQ ID NO: 50)

HMMER 2.3.2 (Oct 2003)
Copyright © 1992-2003 HHMI/Washington University School of Medicine
Freely distributed under the GNU General Public License (GPL)
- - - - - - - - - - - - - - - - - - - - - - - - - - - - - - - - - - - - - - -
HMM file: pfam.hmm
Sequence file: rheu.ef.241.148
Collagen: domain 1 of 1, from 73 to 133: score -74.8, E = 3.5
                *->GppGppGppGppGppGppGppGppaGapGapGppGppGe.pGpPGppGppG
                   G+p +pGppG  p p + p  + ++G++pG++ +G+ G++ + G
rheu.ef.24   73  GRPPRPGPPGGPRTPQIRNLPALPAPQGEPGDRATwRGASGADAAGG
                ppGppGapGapGpp<-*  (SEQ ID NO: 51)
                G++Ga+G
rheu.ef.24  120 DGGERGADGGDPGD                                                119    (SEQ ID NO: 52)
rheu.ef.238rev.148
Collagen Collagen triple helix repeat (20 copies)
Collagen: domain 1 of 1, from 73 to 133: score -74.8, E = 3.5
                *->GppGppGppGppGppGppGppGppaGapGapGppGppGe.pGpPGppGppG
                   G+p +pGppG  p p + p  + ++G++pG++ +G+ G++ + G
rheu.ef.23   73  GRPPRPGPPGGPRTPQIRNLPALPAPQGEPGDRATwRGASGADAAGG
                ppGppGapGapGpp<-*  (SEQ ID NO: 51)
                G++Ga+G
rheu.ef.23  120 DGGERGADGGDPGD                                                119    (SEQ ID NO: 52)
#  =  GF ID   Collagen
#  =  GF AC   PF01391.10
#  =  GF DE   Collagen triple helix repeat (20 copies)
#  =  GF AU   Bateman A, Eddy SR
#  =  GF SE   Swissprot
```

133    (SEQ ID NO: 52)

133    (SEQ ID NO: 52)

TABLE 1-continued (A) Examples of signature motifs identified in putative proteins resulting from TTV-HD transcripts and full-length genomes

```
# = GF TP   Repeat
# = GF BM   hmmbuild -F --prior PRIORHMM_ls.ann SEED.ann
# = GF BM   hmmcalibrate --seed 0 HMM_ls
# = GF BM   hmmbuild -f -F --prior PRIORHMM_fs.ann SEED.ann
# = GF BM   hmmcalibrate --seed 0 HMM_fs
# = GF AM   byscore
# = GF RM   8240831
# = GF RT   New members of the collagen superfamily
# = GF RA   Mayne R, Brewton RG;
# = GF RL   Curr Opin Cell Biol 1993;5:883-890.
# = GF DR   INTERPRO; IPR008160;
# = GF DR   SCOP; 1a9a; fa;
# = GF DR   MIM; 240400;
# = GF DC   Scurvy is associated with collagens.
# = GF CC   Members of this family belong to the collagen superfamily [1].
# = GF CC   Collagens are generally extracellular structural proteins
# = GF CC   involved in formation of connective tissue structure. The
# = GF CC   alignment contains 20 copies of the G-X-Y repeat that forms a
# = GF CC   triple helix. The first position of the repeat is glycine, the
# = GF CC   second and third positions may be any residue but are frequently
# = GF CC   proline and hydroxyproline. Collagens are post translationally
# = GF CC   modified by proline hydroxylase to form the hydroxyproline
# = GF CC   residues. Defective hydroxylation is the cause of scurvy. Some
# = GF CC   members of the collagen superfamily are not involved in
# = GF CC   connective tissue structure but share the same triple helical
# = GF CC   structure.
MALE SPECIFIC SPERM PROTEIN HMMER 2.3.2 (Oct 2003)
Copyright © 1992-2003 HHMI/Washington University School of Medicine
Freely distributed under the GNU General Public License (GPL)

HMM file: pfam.hmm
Sequence file: gbDhDi33.34ik.2.128

MSSP: domain 1 of 1, from 59 to 116: score -9.5, E = 8.9
                    *->vgGPcGPcGPCggpcCGsccsPCg.gpCgPCgpCGpCCgpCCgggCGPC
                       P gp GP g+p+ P ++p P p CG ++g
           gbDhDi33.3       59    QLNPEGPAGPGGPPAIL---PALpAPADPE-PAPRCGGRADGGAAA
                                  GpCGPCCGttekycGl<-*  (SEQ ID NO: 53)
                                  G t l
           gbDhDi33.3      101    GAAADADHTGYEEGDL                         116 (SEQ ID NO: 54)
# = GF ID   MSSP
# = GF AC   PF03940.5
# = GF DE   Male specific sperm protein
This family of drosophila proteins are typified by the
repetitive motif C-G-P.
```

TABLE 1-continued (A) Examples of signature motifs identified in putative proteins resulting from TTV-HD transcripts and full-length genomes

```
MICROBIAL COLLAGENASE METALLOPROTEASE (M9) SIGNATURE

HMMER 2.3.2 (Oct 2003)
Copyright © 1992-2003 HHMI/Washington University School of Medicine
Freely distributed under the GNU General Public License (GPL)

HMM file: prints.hmm
Sequence file: gbDhDi43.4rp.1.765
MICOLLPTASE_1: domain 1 of 1, from 311 to 328: score 5.3, E = 5.7
              *->gletLveflRAGYYvrfyn<-*  (SEQ ID NO: 55)
                 le+ +++ RA Y f++
gbDhDi43.4   311    TLEN-ILYTRASYWNSFHA                328 (SEQ ID NO: 56)
MICOLLPTASE
gx; PR00931
gn; COMPOUND (5)
ga; 09-SEP-1998; UPDATE 07-JUN-1999
gt; Microbial collagenase metalloprotease (M9) signature
gp; PRINTS; PR00756 ALADIPTASE; PR00791 PEPDIPTASEA; PR00730 THERMOLYSIN
gp; PRINTS; PR00787 NEUTRALPTASE; PR00782 LSHMANOLYSIN; PR00997 FRAGILYSIN
gp; PRINTS; PR00786 NEPRILYSIN; PR00765 CRBOXYPTASEA; PR00932 AMINO1PTASE
gp; PRINTS; PR00789 OSIALOPTASE; PR00933 BLYTICPTASE; PR00934 XHISDIPTASE
gp; PRINTS; PR00919 THERMOPTASE; PR00998 CRBOXYPTASET; PR00768 DEUTEROLYSIN
gp; PRINTS; PR00999 FUNGALYSIN; PR01000 SREBPS2PTASE
gp; INTERPRO; IPR002169
gp; PROSITE; PS00142 ZINC_PROTEASE
gp; PFAM; PF00099
gr; 1. RAWLINGS, N.D. AND BARRETT, A.J.
gr; Evolutionary families of metallopeptidases.
gr; METHODS ENZYMOL. 248 183-228 (1995).
gr; 2. RAWLINGS, N.D. AND BARRETT, A.J.
gr; MEROPS - Peptidase Database
gr; http://www.bi.bbsrc.ac.uk/merops/merops.htm
gr; 3. RAWLINGS, N.D. AND BARRETT, A.J.
gr; Family M9 - Clan MA - Microbial collagenase
gr; http://www.bi.bbsrc.ac.uk/merops/famcards/m9.htm
gr; 4. BARRETT, A.J., RAWLINGS, N.D. AND WOESSNER, J.F.
gr; Vibrio collagenase.
gr; IN HANDBOOK OF PROTEOLYTIC ENZYMES, ACADEMIC PRESS, 1998, PP. 1096-1098.
gr; 5. BARRETT, A.J., RAWLINGS, N.D. AND WOESSNER, J.F.
gr; Clostridium collagenases.
gr; IN HANDBOOK OF PROTEOLYTIC ENZYMES, ACADEMIC PRESS, 1998, PP. 1098-1102.
gr; 6. MATSUSHITA, O., YOSHIHARA, K., KATAYAMA, S., MINAMI, J. AND OKABE, A.
gr; Purification and characterization of Clostridium perfringens 120-
gr; kilodalton collagenase and nucleotide sequence of the corresponding gene.
gr; J. BACTERIOL. 176 149-156 (1994).
gd; Metalloproteases are the most diverse of the four main types of protease,
gd; with more than 30 families identified to date [1]. Of these, around
gd; half contain the HEXXH motif, which has been shown in crystallographic
gd; studies to form part of the metal-binding site [1]. The HEXXH motif is
gd; relatively common, but may be more stringently defined for metallo-
```

TABLE 1-continued (A) Examples of signature motifs identified in putative proteins resulting from TTV-HD transcripts and full-length genomes gd; proteases as abXHEbbHbc, where a is most often valine or threonine and
gd; forms part of the S1' subsite in thermolysin and neprilysin, b is an
gd; uncharged residue, and c a hydrophobic residue. Proline is never found
gd; in this site, possibly because it would break the helical structure
gd; adopted by this motif in metalloproteases [1].
gd; Metalloproteases may be split into five groups on the basis of their metal-
gd; binding residues: the first three contain the HEXXH motif, the other two
gd; do not [1]. In the first group, a glutamic acid completes the active site-
gd; these are termed HEXXH+E: all families in this group show some sequence
gd; relationship and have been assigned to clan MA [1]. The second group, which
gd; have a third histidine as the extra metal-binding residue, are termed
gd; HEXXH+H and are grouped into clan MB on the basis of their inter-relation-
gd; ship[1]. In the third group, the additional metal-binding residues are
gd; unidentified. The fourth group is diverse - the metal-binding residues are
gd; known but do not form the HEXXH motif. And the fifth group may comprise the
gd; remaining families where the metal-binding residues are as yet unknown
gd; [1,2]. Microbial collagenases have been identified from bacteria of both the
gd; Vibrio and Clostridium genuses. They are zinc-containing metallopeptidases
gd; that belong to the M25 protease family, which form part of the MA clan
gd; [1,3]. Collagenase is used during bacterial attack to degrade the collagen
gd; barrier of the host during invasion. Vibrio bacteria are non-pathogenic, and
gd; are sometimes used in hospitals to remove dead tissue from burns and ulcers
gd; [4]. Clostrium histolyticum is a pathogen that causes gas gangrene;
gd; nevertheless, the isolated collagenase has been used to treat bed sores [5].
gd; Collagen cleavage occurs at an Xaa+Gly in Vibrio bacteria and at Yaa+Gly
gd; bonds in Clostridium collagenases [4,5].
gd; Analysis of the primary structure of the gene product from Clostridium
gd; perfringens has revealed that the enzyme is produced with a stretch of 86
gd; residues that contain a putative signal sequence [6]. Within this stretch
gd; is found PLGP, an amino acid sequence typical of collagenase substrates.
gd; This sequence may thus be implicated in self-processing of the collagenase [6].
gd; MICOLLPTASE is a 5-element fingerprint that provides a signature for
gd; microbial collagenase zinc metallopeptidases (M9). The fingerprint was
gd; derived from an initial alignment of 4 sequences: the motifs were drawn from
gd; conserved regions spanning virtually the full alignment length - motif 4
gd; includes the region encoded by the PROSITE pattern ZINC PROTEASE (PS00142),
gd; which describes the HEXXH active site; and motif 5 contains the active site
gd; glutamate. Two iterations on OWL31.1 were required to reach convergence,
gd; at which point a true set which may comprise 8 sequences was identified.
tp; COLA_CLOPE 054108 COLA_VIBAL Q46085
tp; COLA_VIBPA
sn; Codes involving 4 elements
st; O86030
tt; COLA_CLOPE MICROBIAL COLLAGENASE PRECURSOR (EC 3.4.24.3) (120 KD
COLLAGENASE-CLOSTRIDIUM
tt; O54108 PUTATIVE SECRETED PROTEASE - STREPTOMYCES COELICOLOR.
tt; COLA_VIBAL MICROBIAL COLLAGENASE PRECURSOR (EC 3.4.24.3) - VIBRIO
ALGINOLYTICUS.
tt; Q46085 COLLAGENASE PRECURSOR - CLOSTRIDIUM HISTOLYTICUM.
tt; COLA_VIBPA MICROBIAL COLLAGENASE PRECURSOR (EC 3.4.24.3) - VIBRIO TABLE 1-continued (A) Examples of signature motifs identified in putative proteins resulting from TTV-HD transcripts and full-length genomes

```
PARAHAEMOLYTICUS.
tt; O86030 COLLAGENASE - VIBRIO CHOLERAE.
ic; MICOLLPTASE1
il; 19
it; Microbial collagenase motif I-1
id; GIPTLVEFLRAGYYLGFYN   (SEQ ID NO: 57)    COLA_CLOPE         159
id; ELETLFLYLRAGYYAEFYN   (SEQ ID NO: 58)    COLA_VIBAL         144
id; VLENLGEFVRAAYYVRYNA   (SEQ ID NO: 59)    COLA_VIBPA          97
id; RLENYGEFIRAAYYVRYNA   (SEQ ID NO: 60)    AF080248            97
bb;
MIC1 microneme protein signature HMMER 2.3.2 (Oct 2003)
Copyright © 1992-2003 HHMI/Washington University School of Medicine
Freely distributed under the GNU General Public License (GPL)
---------------------------------------------------------------
HMM file: prints.hmm
Sequence file: rheu.ef.242.746
MIC1MICRNEME_5: domain 1 of 1, from 448 to 463: score 6.6, E = 4.4
                  *->TyiStkLdVaVGSCHk<-*  (SEQ ID NO: 61)
                     T t+L Va GSC
  rheu.ef.24    448  TKADTQLIVAGGSCKA     463  (SEQ ID NO: 62)

gc; MIC1MICRNEME
gx; PR01744
gn; COMPOUND (7)
ga; 03-JUL-2002
gt; MIC1 microneme protein signature
gr; 1. SIBLEY, L.D., MORDUE, D. AND HOWE, K.
gr; Experimental approaches to understanding virulence in toxoplasmosis.
gr; IMMUNOBIOL. 201 210-224 (1999).
gr; 2. CARRUTHERS, V.B.
gr; Armed and dangerous: Toxoplasma gondii uses an arsenal of secretory
gr; proteins to infect host cells.
gr; PARASITOL.INT. 48 1-10 (1999).
gr; 3. FOURMAUX, M.N., ACHBAROU, A., MERCEREAU-PUIJALON, O., BIDERRE, C.,
gr; BRICHE, I., LOYENS, A., ODBERG-FERRAGUT, C., CAMUS, D. AND DUBREMETZ, J.F.
gr; The MIC1 microneme protein of Toxoplasma gondii contains a duplicated
gr; receptor-like domain and binds to host cell surface.
gr; MOL.BIOCHEM.PARASITOL. 20 201-210 (1996).
gr; 4. LOURENCO, E.V., PEREIRA, S.R., FACA, V.M., COELHO-CASTELO, A.A.,
gr; MINEO, J.R., ROQUE-BARREIRA, M.C., GREENE, L.J. AND PANUNTO-CASTELO, A.
gr; Toxoplasma gondii microneme protein MIC1 is a lactose-binding lectin.
gr; GLYCOBIOL. 11 541-547 (2001).
gr; 5. KELLER, N., NAGULESWARAN, A., CANNAS, A., VONLAUFEN, N., BIENZ, M.,
gr; BJORKMAN, C., BOHNE, W. AND HEMPHILL, A.
gr; Identification of a Neospora caninum microneme protein (NcMIC1) which
gr; interacts with sulphated host cell surface glycosaminoglycans.
gr; INFECT.IMMUN. 70 187-198 (2002).
gd; Toxoplasma gondii is an obligate intracellular apicomplexan protozoan
gd; parasite, with a complex lifestyle involving varied hosts [1]. It has two
```

TABLE 1-continued (A) Examples of signature motifs identified in putative proteins resulting from TTV-HD transcripts and full-length genomes

```
gd; phases of growth: an intestinal phase in feline hosts, and an extra-
gd; intestinal phase in other mammals. Oocysts from infected cats develop
gd; into tachyzoites, and eventually, bradyzoites and zoitocysts in the
gd; extraintestinal host [1]. Transmission of the parasite occurs through
gd; contact with infected cats or raw/undercooked meat; in immunocompromised
gd; individuals, it may cause severe and often lethal toxoplasmosis. Acute
gd; infection in healthy humans may sometimes also cause tissue damage [1].
gd; The protozoan utilises a variety of secretory and antigenic proteins to
gd; invade a host and gain access to the intracellular environment [2]. These
gd; originate from distinct organelles in the T. gondii cell termed micronemes,
gd; rhoptries, and dense granules. They are released at specific times during
gd; invasion to ensure the proteins are allocated to their correct target
gd; destinations [2].
gd; MIC1, a protein secreted from the microneme, is a 456-residue moiety
gd; involved in host cell recognition by the parasite [3]. The protein is
gd; released from the apical pole of T.gondii during infection, and attaches to
gd; host-specific receptors [4]. Recent studies have demonstrated that Mic1 is
gd; a lactose-binding lectin, and utilises this to enhance its binding to host
gd; endothelial cells [4]. A homologue of Mic1 found in Neospora caninum
gd; interacts with sulphated host cell-surface glycosaminoglycans [5].
gd; MIC1MICRNEME is a 7-element fingerprint that provides a signature for the
gd; MIC1 microneme proteins. The fingerprint was derived from an initial
gd; alignment of 2 sequences: the motifs were drawn from conserved regions
gd; spanning the C-terminal portion of the alignment (~380 amino acids). A
gd; single iteration on SPTR40.20f was required to reach convergence, no
gd; further sequences being identified beyond the starting set.
bb;
ic; MIC1MICRNEME5
il; 16
it; MIC1 microneme protein motif V-1
id; TFISTKLDVAVGSCHS  (SEQ ID NO: 63)   O00834       341     133
id; TYSSPQLHVSVGSCHK  (SEQ ID NO: 64)   Q8WRS0       344     138
AUTOIMMUNE REGULATOR (AIRE) SIGNATURE HMMER 2.3.2 (Oct 2003)
Copyright © 1992-2003 HHMI/Washington University School of Medicine
Freely distributed under the GNU General Public License (GPL)
HMM file: prints.hmm
Sequence file: rheu.ef.241.736
AIREGULATOR_4: domain 1 of 1, from 138 to 152: score 6.4, E = 9.2
                   *->DFWRvLFKDYnLERY<-* (SEQ ID NO: 65)
                      FW v D L RY
rheu.ef.24     138  NFWTVSNEDLDLCRY                          152 (SEQ ID NO: 66)
rheu.ef.234rev.628
AIREGULATOR_4: domain 1 of 1, from 30 to 44: score 6.4, E = 9.2
                   *->DFWRvLFKDYnLERY<-* (SEQ ID NO: 65)
                      FW v D L RY
```

TABLE 1-continued (A) Examples of signature motifs identified in putative proteins resulting from TTV-HD transcripts and full-length genomes

```
rheu.ef.23       30    NFWTVSNEDLDLCRY                                                    44 (SEQ ID NO: 67)
rheu.cd.215rev.1.736
AIREGULATOR_4: domain 1 of 1, from 138 to 152: score 6.4, E = 9.2
                *->DFWRvLFKDYnLERY<-* (SEQ ID NO: 65)
                   FW v D L RY
rheu.cd.21      138    NFWTVSNEDLDLCRY                                                   152 (SEQ ID NO: 68)
gc; AIREGULATOR
gx; PR01711
gn; COMPOUND (8)
ga; 13-MAR-2002
gt; Autoimmune regulator (AIRE) signature
gr; 1. The Finnish-German APECED Consortium.
gr; An autoimmune disease, APECED, caused by mutations in a novel gene
gr; featuring two PHD-type zinc-finger domains.
gr; NAT.GENET. 17 399-403 (1997).
gr; 2. MITTAZ, L., ROSSIER, C., HEINO, M., PETERSON, P., KROHN, K.J.E., GOS, A.,
gr; MORRIS, M.A., KUDOH, J., SHIMIZU, N., ANTONARAKIS, S.E. AND SCOT, H.S.
gr; Isolation and chatacterisation of the mouse Aire gene.
gr; BIOCHEM.BIOPHYS.RES.COMMUN. 255 483-490 (1999).
gr; 3. PETERSON, H.M., KUDOH, J., NAGAMINE, K., LAGERSTEDT, A., OVOD, V.,
gr; RANKI, A., RANTALA, I., NIEMINEN, M., TUUKKANEN, J., SCOTT, H.S.,
gr; ANTONARAKIS, S.E., SHIMIZU, N. AND KROHN, K.
gr; Autoimmune regulator is expressed in the cells regulating immune tolerance
gr; in thymous medulla.
gr; BIOCHEM. BIOPHYS. RES. COMMUN. 257 821-825 (1999).
gr; 4. KUMAR, P.G., LALORAYA, M., WANG, C.Y., RUAN, Q.G., SEMIROMI, A.D.,
gr; KAO. K.J. AND SHE, J.X.
gr; The autoimmune regulator (AIRE) is a DNA-binding protein.
gr; J. BIOL. CHEM. 276 41357-41364 (2001).
gd; AIRE (AutoImmune REgulator) is the predicted protein responsible for a rare
gd; autosomal recessively inherited disease termed APECED. APECED, also
gd; called Autoimmune Polyglandular Syndrome type I (APS 1), is the only
gd; described autoimmune disease with established monogenic background, being
gd; localised outside the major histocompatibility complex region. It is
gd; characterised by the presence of two of the three major clinical entities,
gd; chronic mucocutaneus candidiasis, hypoparathyroidism and Addison's disease.
gd; Other immunologically mediated phenotypes, including insulin-dependent
gd; diabetes mellitus (IDDM), gonadal failure, chronic gastritis, vitiligo,
gd; autoimmune thyroid disease, enamel hypoplasia, and alopecia may also
gd; be present. Immunologically, APECED patients have deficient T cell
gd; responses towards Candida antigens, and clinical symptoms both within and
gd; outside the endocrine system, mainly as a result of autoimmunity against
gd; organ-specific autoantigens [1,2].
gd; AIRE has motifs suggestive of a transcriptional regulator protein. It
gd; harbours two zinc fingers of the plant homodomain (PHD) type. A putative
gd; DNA-binding domain, termed SAND, as well as four nuclear receptor binding LXXLL
gd; motifs, an inverted LXXLL domain, and a variant of the latter (FXXLL), hint
gd; that this protein functions as a transcription coactivator. Furthermore, a
gd; highly conserved N-terminal 100-amino acid domain in AIRE shows significant
gd; similarity to the homogeneously staining (HSR) domain of Sp100 and Sp140
```

TABLE 1-continued (A) Examples of signature motifs identified in putative proteins resulting from TTV-HD transcripts and full-length genomes

```
gd; proteins, which has been shown to function as a dimerisation domain in
gd; several Sp-100 related proteins [2-4].
gd; AIRE has a dual subcellular location. It is not only expressed in multiple
gd; immunologically relevant tissues, such as the thymus, spleen, lymph nodes
gd; and bone marrow, but it has also been detected in various other tissues,
gd; such as kidney, testis, adrenal glands, liver and ovary, suggesting that
gd; APECED proteins might also have a function outside the immune system.
gd; However, AIRE is not expressed in the target organs of autoimmune
gd; destruction. At the subcellular level, AIRE may be found in the cell nucleus
gd; in a speckled pattern in domains resembling promyelocytic leukaemia nuclear
gd; bodies, also known as ND10, nuclear dots or potential oncogenic domains
gd; associated with the AIRE homologous nuclear proteins Sp100, Sp140, and
gd; Lysp100. The nuclear localisation of AIRE, in keeping with its predicted
gd; protein domains, suggest that it may regulate the mechanisms involved in the
gd; induction and maintenance of immune tolerance [3,4].
gd; AIREGULATOR is an 8-element fingerprint that provides a signature for the
gd; AIRE autoimmune regulators. The fingerprint was derived from an initial
gd; alignment of 6 sequences: the motifs were drawn from conserved regions
gd; largely spanning the N-terminal and central portions of the alignment,
gd; focusing on those sections that characterise the autoregulators but
gd; distinguish them from those possessing SAND and PHD domains. Two iterations
gd; on SPTR39_17f were required to reach convergence, at which point a true set
gd; which may comprise 14 sequences was identified.
fc; AIREGULATOR4
fl; 15
ft; Autoimmune regulator (AIRE) motif IV-1
fd; DFWRILFKDYNLERY   (SEQ ID NO: 69)   Q9JLM0          77           18
fd; DFWRILFKDYNLERY   (SEQ ID NO: 69)   Q9Z0E3          77           18
fd; DFWRILFKDYNLERY   (SEQ ID NO: 69)   Q9JLX0          77           18
fd; DFWRILFKDYNLERY   (SEQ ID NO: 69)   Q9JLW9          77           18
fd; DFWRILFKDYNLERY   (SEQ ID NO: 69)   Q9JLW8          77           18
fd; DFWRILFKDYNLERY   (SEQ ID NO: 69)   Q9JLW7          77           18
fd; DFWRILFKDYNLERY   (SEQ ID NO: 69)   Q9JLW6          77           18
fd; DFWRILFKDYNLERY   (SEQ ID NO: 69)   Q9JLW5          77           18
fd; DFWRILFKDYNLERY   (SEQ ID NO: 69)   Q9JLW4          77           18
fd; DFWRILFKDYNLERY   (SEQ ID NO: 69)   Q9JLW3          77           18
fd; DFWRILFKDYNLERY   (SEQ ID NO: 69)   Q9JLW2          77           18
fd; DFWRILFKDYNLERY   (SEQ ID NO: 69)   Q9JLW1          77           18
fd; DFWRVLFKDYNLERY   (SEQ ID NO: 70)   AIRE_HUMAN      76           18
fd; DFWRVLFKDYNLERY   (SEQ ID NO: 70)   O75745          76           18
GLIADIN
```

HMMER 2.3.2 (Oct 2003)
Copyright © 1992-2003 HHMI/Washington University School of Medicine
Freely distributed under the GNU General Public License (GPL)
HMM file: prints.hmm
Sequence file: rheu.ef.241.736
GLIADIN_7: domain 1 of 1, from 688 to 708: score 17.7, E = 0.056
  *->PqaqGsvqPqqLPqePeEiRnL<-* (SEQ ID NO: 71)
     qaqGsvq q L q E R L TABLE 1-continued (A) Examples of signature motifs identified in putative proteins resulting from TTV-HD transcripts and full-length genomes

```
rheu.ef.24      688      TQAQGSVQEQLLLQLREQRVL                                708 (SEQ ID NO: 72)
rheu.ef.234rev.628
GLIADIN_7: domain 1 of 1, from 580 to 600: score 17.7, E = 0.056
                         *->PqaqGsvqPqqLPqPeEiRnL<-*         (SEQ ID NO: 71)
                            qaqGsvq q L q E R L
rheu.ef.23      580      TQAQGSVQEQLLLQLREQRVL                                600 (SEQ ID NO: 72)
rheu.cd.215rev.1.736
GLIADIN_7: domain 1 of 1, from 688 to 708: score 18.3, E = 0.037
                         *->PqaqGsvqPqqLPqPeEiRnL<-*         (SEQ ID NO: 71)
                            qaqGsvq q L q E R L
rheu.cd.21      688      TQAQGSVQDQLLLQLREQRVL                                708 (SEQ ID NO: 73)
GLIADIN_7: domain 1 of 1, from 46 to 66: score 18.3, E = 0.037
                         *->PqaqGsvqPqqLPqPeEiRnL<-*         (SEQ ID NO: 71)
                            qaqGsvq q L q E R L
zc3rl1.B4.      46       TQAQGSVQDQLLLQLREQRVL                                66  (SEQ ID NO: 73)
gc;   GLIADIN
gx;   PR00209
gn;   COMPOUND (9)
ga;   21-OCT-1992; UPDATE 19-JUN-1999
gt;   Alpha/beta gliadin family signature
gp;   PRINTS; PR00208 GLIADGLUTEN; PR00211 GLUTELIN; PR00210 GLUTENIN
gp;   INTERPRO; IPR001376
gr;   1. SHEWRY, P. AND MORGAN, M.
gr;   Gluten - proteins that put the springiness into bread and are implicated
gr;   in food intolerance syndromes such as coeliac disease.
gr;   IN PROTEIN POWER AFRC NEWS SUPPLEMENT (1992).
gr;   2. OKITA T.W., CHEESBROUGH V. AND REEVES C.D.
gr;   Evolution and heterogeneity of the alpha-type, beta-type, and gamma-type
gr;   gliadin DNA sequences.
gr;   J. BIOL. CHEM. 260 (13) 8203-8213 (1985).
gr;   3. RAFALSKI J.A.
gr;   Structure of wheat gamma-gliadin genes.
gr;   GENE 43 (3) 221-229 (1986).
gd;   Gluten is the protein component of wheat flour. It consists of numerous
gd;   proteins, which are of 2 different types responsible for different physical
gd;   properties of dough [1]: the glutenins, which are primarily responsible for
gd;   the elasticity, and the gliadins, which contribute to the extensibility.
gd;   The gliadins themselves are of different types (e.g., alpha/beta or gamma)
gd;   and, like the glutenins, contain repetitive sequences [2] that form loose
gd;   helical structures, but they are usually associated with more extensive
gd;   non-repetitive regions, which are compact and globular [3].
gd;   GLIADIN is a 9-element fingerprint that provides a signature for the
gd;   alpha/beta gliadins. The fingerprint was derived from an initial align-
gd;   ment of 5 sequences: motifs 2 and 3 encode the Gln/Pro-rich tandem repeats.
gd;   Two iterations on OWL18.0 were required to reach convergence, at which
gd;   point a true set which may comprise 14 sequences was identified. Several
gd;   partial matches were also found: 3 of these are alpha/beta gliadin
gd;   fragments: GDA1_WHEAT and B22364 both lack the C-terminal part of the
gd;   sequence bearing the last 2 motifs, and GDA8_WHEAT lacks the N-terminal
gd;   part of the sequence bearing the first 3 motifs.
```

TABLE 1-continued (A) Examples of signature motifs identified in putative proteins resulting from TTV-HD transcripts and full-length genomes

```
gd;  In addition to the alpha/beta gliadin fragments, a number of other partial
gd;  matches were identified: these included gamma-gliadins, low molecular
gd;  weight glutenins, avenins, secalins, and so on. Most of these fail to
gd;  match, or at least match only poorly, those motifs that encode the tandem
gd;  repeats - clearly they are characterised by their own distinctive
gd;  signatures in this region. The fingerprint thus provides reasonable
gd;  discrimination between the alpha/beta type gliadins and the gamma type and
gd;  related proteins.
c;   GLIADIN7
fl;  21
ft;  Gliadin motif VII-2
fd;  PQAQGSVQPQQLPQFEEIRNL  (SEQ ID NO: 74)   GDA9_WHEAT   259  6
fd;  PQAQGSVQPQQLPQFEEIRNL  (SEQ ID NO: 74)   GDA6_WHEAT   246  6
fd;  PQAQGSVQPQQLPQFEEIRNL  (SEQ ID NO: 74)   Q41509       239  6
fd;  PQAQGSVQPQQLPQFEEIRNL  (SEQ ID NO: 74)   Q41531       241  6
fd;  PQAQGSVQPQQLPQFEEIRNL  (SEQ ID NO: 74)   GDA0_WHEAT   238  6
fd;  PQAQGSVQPQQLPQFAEIRNL  (SEQ ID NO: 75)   GDA7_WHEAT   263  6
fd;  PQAQGSVQPQQLPQFAEIRNL  (SEQ ID NO: 75)   Q41546       263  6
fd;  PQAQGSFQPQQLPQFEEIRNL  (SEQ ID NO: 76)   GDA2_WHEAT   243  6
fd;  PQAQGSVQPQQLPQFEEIRNL  (SEQ ID NO: 74)   Q41632       246  6
fd;  PQAQGSVQPQQLPQFEEIRNL  (SEQ ID NO: 74)   Q41530       240  6
fd;  PQAQGSFQPQQLPQFEEIRNL  (SEQ ID NO: 76)   Q41529       263  6
fd;  PQAQGSVQPQQLPQFAEIRNL  (SEQ ID NO: 75)   GDA5_WHEAT   269  6
fd;  PQAQGSVQPQQLPQFAEIRNL  (SEQ ID NO: 75)   Q41545       268  6
fd;  PQTQGSVQPQQLPQFEEIRNL  (SEQ ID NO: 155)  GDA4_WHEAT   239  6
fd;  PQAQGSVQPQQLPQFEEIRNL  (SEQ ID NO: 77)   GDA3_WHEAT   249  6
                                                           232  6
NEUROPEPTIDE Y2 RECEPTOR SIGNATURE HMMER 2.3.2 (Oct 2003)
Copyright © 1992-2003 HHMI/Washington University School of Medicine
Freely distributed under the GNU General Public License (GPL)
HMM file: prints.hmm
Sequence file: rheu.ef.241.736
NRPEPTIDEY2R_9: domain 1 of 1, from 664 to 677: score 8.9, E = 3.1
              *->AFLsAFRCEqRLDAiHs<-* (SEQ ID NO: 78)
              sAFR qR+ +Hs
rheu.ef.24     664    ---SAFRVQQRVPWVHS                       677 (SEQ ID NO: 79)
rheu.ef.234rev 628
NRPEPTIDEY2R_9: domain 1 of 1, from 556 to 569: score 8.9, E = 3.1
              *->AFLsAFRCEqRLDAiHs<-* (SEQ ID NO: 78)
              sAFR qR+ +Hs
rheu.ef.23     556    ---SAFRVQQRVPWVHS                       569 (SEQ ID NO: 79)
NRPEPTIDEY2R_9: domain 1 of 1, from 22 to 35: score 7.2, E = 6.3
              *->AFLsAFRCEqRLDAiHs<-* (SEQ ID NO: 78)
              s FR qRL +Hs
zc3rl1.B4      22     ---SRFRVQQRLPWVHS                       35  (SEQ ID NO: 80)
gc;  NRPEPTIDEY2R
gx;  PR01014
gn;  COMPOUND (11)
```

TABLE 1-continued (A) Examples of signature motifs identified in putative proteins resulting from TTV-HD transcripts and full-length genomes

```
ga; 30-NOV-1998; UPDATE 07-JUN-1999
gt; Neuropeptide Y2 receptor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; PRINTS; PR01012 NRPEPTIDEYR; PR01013 NRPEPTIDEY1R; PR01015
NRPEPTIDEY4R
gp; PRINTS; PR01016 NRPEPTIDEY5R; PR01017 NRPEPTIDEY6R
gp; INTERPRO; IPR001358
gr; 1. ATTWOOD, T.K. AND FINDLAY, J.B.C.
gr; Fingerprinting G protein-coupled receptors.
gr; PROTEIN ENG. 7 (2) 195-203 (1994).
gr; 2. ATTWOOD, T.K. AND FINDLAY, J.B.C.
gr; G protein-coupled receptor fingerprints.
gr; 7TM, VOLUME 2, EDS. G. VRIEND AND B. BYWATER (1993).
gr; 3. BIRNBAUMER, L.
gr; G proteins in signal transduction.
gr; ANNU. REV. PHARMACOL. TOXICOL. 30 675-705 (1990).
gr; 4. CASEY, P.J. AND GILMAN, A.G.
gr; G protein involvement in receptor-effector coupling.
gr; J. BIOL. CHEM. 263 (6) 2577-2580 (1988).
gr; 5. ATTWOOD, T.K. AND FINDLAY, J.B.C.
gr; Design of a discriminating fingerprint for G protein-coupled receptors.
gr; PROTEIN ENG. 6 (2) 167-176 (1993).
gr; 6. WATSON, S. AND ARKINSTALL, S.
gr; Neuropeptide Y.
gr; IN THE G PROTEIN-LINKED RECEPTOR FACTSBOOK, ACADEMIC PRESS, 1994,
PP. 194-198.
gd; G protein-coupled receptors (GPCRs) constitute a vast protein family that
gd; encompasses a wide range of functions (including various autocrine, para-
gd; crine and endocrine processes). They show considerable diversity at the
gd; sequence level, on the basis of which they may be separated into distinct
gd; groups. Applicants use the term clan to describe the GPCRs, as they embrace
gd; a group of families for which there are indications of evolutionary,
gd; relationship but between which there is no statistically significant
gd; similarity in sequence [1,2]. The currently known clan members include the
gd; rhodopsin-like GPCRs, the secretin-like GPCRs, the cAMP receptors, the
gd; fungal mating pheromone receptors, and the metabotropic glutamate receptor
gd; family. The rhodopsin-like GPCRs themselves represent a widespread protein
gd; family that includes hormone, neurotransmitter and light receptors, all of
gd; which transduce extracellular signals through interaction with guanine
gd; nucleotide-binding (G) proteins. Although their activating ligands vary
gd; widely in structure and character, the amino acid sequences of the
gd; receptors are very similar and are believed to adopt a common structural
gd; framework which may comprise 7 transmembrane (TM) helices [3-5].
gd; Neuropeptide Y (NPY) is one of the most abundant peptides in mammalian
gd; brain, inducing a variety of behavioural effects (e.g., stimulation of food
gd; intake, anxiety, facilitation of learning and memory, and regulation of the
gd; cardiovascular and neuroendocrine systems) [6]. In the periphery, NPY
gd; stimulates vascular smooth muscle contraction and modulates hormone
```

TABLE 1-continued (A) Examples of signature motifs identified in putative proteins resulting from TTV-HD transcripts and full-length genomes

```
gd; secretion. NPY has been implicated in the pathophysiology of hypertension,
gd; congestive heart failure, affective disorders and appetite regulation [6].
gd; Several pharmacologically distinct neuropeptide Y receptors have been
gd; characterised, designated NPY Y1-Y6. High densities of Y2 receptors are
gd; present in rat hippocampus and are also found in high levels in superficial
gd; layers of cortex, certain thalamic nuclei, lateral septum, and anterior
gd; olfactory nuclei; lower levels are found in striatum [6]. The receptors are
gd; found in high levels in smooth muscle (e.g., vas deferens and intestine),
gd; kidney proximal tubules and in cell lines [6]. They are believed to have a
gd; predominantly presynaptic location, and are involved in inhibition of
gd; adenylyl cyclase and voltage dependent calcium channels via a pertussis-
gd; toxin-sensitive G protein, probably of the Go/Gi class [6].
gd; NRPEPTIDEY2R is an 11-element fingerprint that provides a signature for
gd; neuropeptide Y2 receptors. The fingerprint was derived from an initial
gd; alignment of 2 sequences: the motifs were drawn from conserved sections
gd; within either loop or TM regions, focusing on those areas of the alignment
gd; that characterise the Y2 receptors but distinguish them from the rest of
gd; the neuropeptide Y family - motifs 1-3 span the N-terminus, leading into
gd; TM domain 1; motifs 4 and 5 span the C-terminus of TM domain 4 and the
gd; second external loop; motifs 6 and 7 span the C-terminus of TM domain 5
gd; and the third cytoplasmic loop; motif 8 spans the C-terminus of TM domain 6
gd; and the third external loop; and motifs 9-11 reside at the C-terminus. Two
gd; iterations on OWL30.2 were required to reach convergence, at which point
gd; a true set which may comprise 5 sequences was identified. Two partial
gd; matches were also found: OAU83458 is an ovine neuropeptide Y2 receptor
gd; fragment that matches motifs 4-6; and AF054870 is a rat neuropeptide Y2
gd; receptor fragment that matches motifs 5 and 6.
fc; NRPEPTIDEY2R9
fl; 17
ft; Neuropeptide Y2 receptor motif IX-2
fd; AFLSAFRCEQRLDAIHS (SEQ ID NO: 81)    NY2R_HUMAN    335    29
fd; AFLSAFRCEQRLDAIHS (SEQ ID NO: 81)    NY2R_BOVIN    338    29
fd; AFLSAFRCEQRLDAIHS (SEQ ID NO: 81)    NY2R_MOUSE    339    29
fd; AFLSAFRCEQRLDAIHS (SEQ ID NO: 81)    NY2R_PIG      337    29
AEROLYSIN
```

```
HMMER 2.3.2 (Oct 2003)
Copyright © 1992-2003 HHMI/Washington University School of Medicine
Freely distributed under the GNU General Public License (GPL)

HMM file: prints.hmm
sequence file: rheu.ef.241.736
AEROLYSIN_7: domain 1 of 1, from 602 to 621: score 3.4, E = 9.3
           *->wDKRYiPGEvKwWDWnWtiq<-* (SEQ ID NO: 81)
              +D +Y+ Ev W W
rheu.ef.24     602    VDPKYVTPEVTMHSWDIRRG    621 (SEQ ID NO: 83)
rheu.ef.234rev.628
AEROLYSIN_7: domain 1 of 1, from 494 to 513: score 3.4, E = 9.3
           *->wDKRYiPGEvKwWDWnWtiq<-* (SEQ ID NO: 82)
              +D +Y+ Ev W W
```

TABLE 1-continued (A) Examples of signature motifs identified in putative proteins resulting from TTV-HD transcripts and full-length genomes

```
rheu.ef.23      494    VDPKYVTPEVTWHSWDIRRG                                           513 (SEQ ID NO: 83)
HMM file: prints.hmm
Sequence file: uro742rev.109r
AEROLYSIN_7: domain 1 of 1, from 65 to 84: score 3.6, E = 8.6
       *->wDKRYiPGEvKwWDWnWtiq<-*     (SEQ ID NO: 82)
          + G K W  WnW +
uro742rev.       65    FAWVLASGTAKCWSWNWSAR                                            84 (SEQ ID NO: 84)
AEROLYSIN_7: domain 1 of 1, from 65 to 84: score 3.6, E = 8.6
       *->wDKRYiPGEvKwWDWnWtiq<-*     (SEQ ID NO: 82)
          + G K W  WnW +
zc37.B9.2d       65    FAWVLASGTAKCWSWNWSAR                                            84 (SEQ ID NO: 84)
gc; AEROLYSIN
gx; PR00754
gn; COMPOUND (9)
ga; 25-AUG-1997; UPDATE 06-JUN-1999
gt; Aerolysin signature
gp; INTERPRO; IPR001776
gp; PROSITE; PS00274 AEROLYSIN
gp; PFAM; PF01117 Aerolysin
gr; 1. PARKER, M.W., BUCKLEY, J.T., POSTMA, J.P., TUCKER, A.D., LEONARD, K.,
gr; PATTUS, F. AND TSERNOGLOU, D.
gr; Structure of the aeromonas toxin proaerolysin in its water-soluble and
gr; membrane-channel states.
gr; NATURE 367 292-295 (1994).
gd; Aerolysin is responsible for the pathogenicity of Aeromonas hydrophila, a
gd; bacterium associated with diarrhoeal diseases and deep wound infections [1].
gd; In common with other microbial toxins, the protein changes in a multi-step
gd; process from a water-soluble form to produce a transmembrane channel that
gd; destroys sensitive cells by breaking their permeability barriers [1].
gd; The structure of proaerolysin has been determined to 2.8A resolution and
gd; shows the protoxin to adopt a novel fold [1]. Images of an aerolysin
gd; oligomer derived from electron microscopy have helped to construct a
gd; model of the protein and to outline a mechanism by which it might insert
gd; into lipid bilayers to form ion channels [1].
gd; AEROLYSIN is a 9-element fingerprint that provides a signature for the
gd; aerolysins. The fingerprint was derived from an initial alignment of 10
gd; sequences: the motifs were drawn from conserved regions spanning virtually
gd; the full alignment length. A single iteration on OWL29.4 was required to
gd; reach convergence, no further sequences being identified beyond the
gd; starting set. A single partial match was found, CLOALPTOX, a related
gd; alpha-toxin from Clostridium septicum that matches motifs 4 and 6.
gd;
fc; AEROLYSIN7
fl; 20
ft; Aerolysin motif VII-2
fd; WDKRYIPGEVKWWDWNWTIQ  (SEQ ID NO: 85)     ERA_AERHY      382  21
fd; WDKRYIPGEVKWWDWNWTIQ  (SEQ ID NO: 85)     Q4063          382  21
fd; WDKRYIPGEVKWWDWNWTIQ  (SEQ ID NO: 85)     AER3_AERHY     382  21
fd; WDKRYIPGEVKWWDWNWTIQ  (SEQ ID NO: 85)     AER5_AERHY     382  21
fd; WDKRYIPGEVKWWDWNWTIQ  (SEQ ID NO: 85)     AER4_AERHY     382  21
```

TABLE 1-continued (A) Examples of signature motifs identified in putative proteins resulting from TTV-HD transcripts and full-length genomes

| | | | | | |
|---|---|---|---|---|---|
| fd; WDKRYIPGEVKWWDWNWTIQ | (SEQ ID NO: 85) | P94128 | 382 | 21 | |
| fd; WDKRYLPGEMKWWDWNWAIQ | (SEQ ID NO: 85) | AERA_AERTR | 382 | 21 | |
| fd; WDKRYLPGEMKWWDWNWAIQ | (SEQ ID NO: 85) | O85370 | 382 | 21 | |
| fd; VDKRYIPGEVKWWDWNWTIS | (SEQ ID NO: 85) | AERA_AERSA | 383 | 21 | |
| fd; VDKRYIPGEVKWWDWNWTIS | (SEQ ID NO: 85) | AERA_AERSO | 382 | 21 | |

OREXIN:

```
HMMER 2.3.2 (Oct 2003)
Copyright © 1992-2003 HHMI/Washington University School of Medicine
Freely distributed under the GNU General Public License (GPL)1
- - - - - - - - - - - - - - - - - - - - - - - - - - - - - - - - - - - - - - - - - - - - - - - - - - - - - - - - - - - - - - - - - - -
HMM file: pfam.hmm
Sequence file: rheu.ef.241.148
Orexin: domain 1 of 1, from 10 to 122: score -38.9, E = 4.1
              *->mnlPsaKvsWAavtlLLLLLLLpPAlLslGvdAqPLPDCCRqKtCsC
rheu.ef.24  10    RKVLLQTVRAAKKARRLLGMMWQPPVHNVPGIERNWYESCFRSHAAVC
                 RLYELLHGAGnHAAGiLtLGK.RRPGPPGLqGRLLqAsGnHAAGiLt
                 ++ G nH A tLG++ RPGPPG G i
rheu.ef.24  57    GCGDFV-GHINHLAT--TLGRpPRPGPPG----------GPRTPQI-89
                 mGRRAGAElePrlCPGRRClaAaAsalAPrGrsrv<-* (SEQ ID NO: 88)
                 R A ++P+ PG R As G+ +
rheu.ef.24  90    --RNLPALPAPQGEPGDRATWRGASGADAAGGDGG      122 (SEQ ID NO: 89)
rheu.ef.238rev.148
Orexin: domain 1 of 1, from 10 to 122: score -38.9, E = 4.1
              *->mnlPsaKvsWAavtlLLLLLLLpPAlLslGvdAqPLPDCCRqKtCsC
rheu.ef.23  10    RKVLLQTVRAAKKARRLLGMMWQPPVHNVPGIERNWYESCFRSHAAVC
                 RLYELLHGAGnHAAGiLtLGK.RRPGPPGLqGRLLqAsGnHAAGiLt
                 ++ G nH A tLG++ RPGPPG G i
rheu.ef.23  57    GCGDFV-GHINHLAT--TLGRpPRPGPPG----------GPRTPQI-89
                 mGRRAGAElePrlCPGRRClaAaAsalAPrGrsrv<-* (SEQ ID NO: 88)
                 R A ++P+ PG R As G+ +
rheu.ef.23  90    --RNLPALPAPQGEPGDRATWRGASGADAAGGDGG      122 (SEQ ID NO: 89)

# = GF ID      Orexin
# = GF AC      PF02072.7
# = GF DE      Prepro-orexin
# = GF AU      Mian N, Bateman A
# = GF SE      IPR001704
# = GF TP      Family
OREX_HUMAN/1-131

MNLPSTKVSWAAVTLLLLLLLPPALLSSSGAAAQPLPDCCRQKTCSCRLYELLHGAGN
                 HAAGILTLGKRRSGPPGLQGRLQRLLQASGNHAAGILTMGRRAGAEPAPRPCLGRRC
                 SAPAAASVAPGGQSGI (SEQ ID NO: 90)
```

TABLE 1-continued (A) Examples of signature motifs identified in putative proteins resulting from TTV-HD transcripts and full-length genomes

```
GIP RECEPTOR

HMMER 2.3.2 (Oct 2003)
Copyright © 1992-2003 HHMI/Washington University School of Medicine
Freely distributed under the GNU General Public License (GPL)
-----------------------------------------------------------------------
HMM file: prints.hmm
Sequence file: rheu.ef.241.148
GIPRECEPTOR_7: domain 1 of 1, from 76 to 97: score 7.9, E = 3.7
                  *->PrlGPYlGdqtltLwnq.ALAA<-* (SEQ ID NO: 91)
                     Pr+GP G +t+ ++n +AL A
     rheu.ef.24   76  PRPGPPGGPRTPQIRNLpALpA                97 (SEQ ID NO: 92)
     rheu.ef.238rev
GIPRECEPTOR_7: domain 1 of 1, from 76 to 97: score 7.9, E = 3.7
                  *->PrlGPYlGdqtltLwnq.ALAA<-* (SEQ ID NO: 91)
                     Pr+GP G +t+ ++n +AL A
     rheu.ef.23   76  PRPGPPGGPRTPQIRNLpALpA                97 (SEQ ID NO: 92)
GIPRECEPTOR
gx; PR01129
gn; COMPOUND (11)
ga; 22-MAY-1999
gt; Gastric inhibitory polypeptide receptor precursor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; INTERPRO; IPR001749
gr; 1. ATTWOOD, T.K. AND FINDLAY, J.B.C.
gr; Fingerprinting G protein-coupled receptors.
gr; PROTEIN ENG. 7 (2) 195-203 (1994).
gr; 2. ISHIHARA T., NAKAMURA S., KAZIRO, Y., TAKAHASHI, T., TAKAHASHI, K.
gr; AND NAGATA, S.
gr; Molecular cloning and expression of a cDNA encoding the secretin receptor
gr; EMBO J. 10 1635-1641 (1991).
gr; 3. LIN, H.Y., HARRIS, T.L., FLANNERY, M.S., ARUFFO, A., KAJI, E.H.,
gr; GORN, A., KOLAKOWSKI, L.F., LODISH, H.F. AND GOLDRING, S.R.
gr; Expression cloning of adenylate cyclase-coupled calcitonin receptor
gr; SCIENCE 254 1022-1024 (1991).
gr; 4. JUEPPNER, H., ABOU-SAMRA, A.-B., FREEMAN, M., KONG, X.F.,
gr; SCHIPANI, E., RICHARDS, J., KOLALOWSKI, L.F., HOCK, J., POTTS, J.T.,
gr; KRONENBERG, H.M. AND SEGRE, G.E.
gr; A G protein linked receptor for parathyroid hormone and parathyroid
gr; hormone-related peptide.
gr; SCIENCE 254 1024-1026 (1991).
gr; 5. ISHIHARA, T., SHIGEMOTO, R., MORI, K., TAKAHASHI, K. AND NAGATA, S.
gr; Functional expression and tissue distribution of a novel receptor for
gr; vasoactive intestinal polypeptide.
gr; NEURON 8 (4) 811-819 (1992).
gr; 6. VOLZ, A., GOKE, R., LANKAT-BUTTGEREIT, B., FEHMANN, H.C., BODE, H.P.
gr; AND GOKE, B.
gr; Molecular cloning, functional expression, and signal transduction of the
```

TABLE 1-continued (A) Examples of signature motifs identified in putative proteins resulting from TTV-HD transcripts and full-length genomes

| | | |
|---|---|---|
| gr; | GIP-receptor cloned from a human insulinoma. | |
| gr; | FEBS LETT. 373 (1) 23-9 (1995). | |
| gd; | G protein-coupled receptors (GPCRs) constitute a vast protein family that | |
| gd; | encompasses a wide range of functions (including various autocrine, para- | |
| gd; | crine and endocrine processes). They show considerable diversity at the | |
| gd; | sequence level, on the basis of which they may be separated into distinct | |
| gd; | groups. Applicants use the term clan to describe the GPCRs, as they embrace | |
| gd; | a group of families for which there are indications of evolutionary | |
| gd; | relationship,but between which there is no statistically significant | |
| gd; | similarity in sequence [1]. The currently known clan members include the | |
| gd; | rhodopsin-like GPCRs, the secretin-like GPCRs, the cAMP receptors, the | |
| gd; | fungal mating pheromone receptors, and the metabotropic glutamate receptor | |
| gd; | family. The secretin-like GPCRs include secretin [2], calcitonin [3], | |
| gd; | parathyroid hormone/parathyroid hormone-related peptides [4] and vasoactive | |
| gd; | intestinal peptide [5], all of which activate adenylyl cyclase and the | |
| gd; | phosphatidyl-inositol-calcium pathway. The amino acid sequences of the | |
| gd; | receptors contain high proportions of hydrophobic residues grouped into 7 | |
| gd; | domains, in a manner reminiscent of the rhodopsins and other receptors | |
| gd; | believed to interact with G proteins. However, while a similar 3D framework | |
| gd; | has been proposed to account for this, there is no significant sequence | |
| gd; | similarity between these families: the secretin-like receptors thus bear | |
| gd; | their own unique '7TM' signature. | |
| gd; | Glucose-dependent insulinotropic polypeptide (GIP) plays an important role | |
| gd; | in the regulation of postprandial insulin secretion and proinsulin gene | |
| gd; | expression of pancreatic beta-cells [6]. The human GIP-receptor encodes a | |
| gd; | 7TM protein that is similar to the human glucagon-like peptide 1(GLP-1) | |
| gd; | receptor. It is hoped that an understanding of GIP-receptor regulation and | |
| gd; | signal transduction will shed light on the hormone's failure to exert its | |
| gd; | biological action at the pancreatic B-cell in type II diabetes mellitus.\| | |
| gd; | GIPRECEPTOR is an 11-element fingerprint that provides a signature for | |
| gd; | gastric inhibitory polypeptide receptors. The fingerprint was derived from | |
| gd; | an initial alignment of 3 sequences: the motifs were drawn from conserved | |
| gd; | regions spanning the full alignment length, focusing on those sections | |
| gd; | that characterise the gastric inhibitory polypeptide receptors but | |
| gd; | distinguish them from the rest of the secretin-like superfamily - motifs 1-6 | |
| gd; | span the N-terminal domain; motif 7 resides in the loop between TM domains 2\| | |
| gd; | and 3; motif 8 spans the loop between TM domains 3 and 4; motif 9 spans the | |
| gd; | C-terminal portion of TM domain 6 and | |
| gd; | loop between TM domains 4 and 5; and motifs 10 and 11 reside at the | |
| gd; | C-terminus. A single iteration on SPTR37_9f was required to reach | |
| gd; | convergence, no further sequences being identified beyond the starting set. | |
| gd; | Two partial matches were also found, secretin and glucagon receptors | |
| bb; | that match motifs 1, 8 and 9. | |
| fc; | GIPRECEPTOR7 | |
| fl; | 21 | |
| ft; | Gastric inhibitory polypeptide receptor precursor motif VII-1 | |
| fd; | PTLGPYPGDRTLTLRNQALAA (SEQ ID NO: 93) | 92 |
| fd; | PPLGPYTGNQTPTLWNQALAA (SEQ ID NO: 94) GIPR_MESAU | 56 |
| fd; | PPLGPYTGNQTPTLWNQALAA (SEQ ID NO: 94) GIPR_RAT | 192 56 |
| fd; | PRPGPYLGDQALALWNQALAA (SEQ ID NO: 95) GIPR_HUMAN | 195 56 |

TABLE 1-continued (A) Examples of signature motifs identified in putative proteins resulting from TTV-HD transcripts and full-length genomes

```
PRION
HMMER 2.3.2 (Oct 2003)
Copyright © 1992-2003 HHMI/Washington University School of Medicine
Freely distributed under the GNU General Public License (GPL)
HMM file: prints.hmm
Sequence file: rheu.ef.241.148
PRION_2: domain 1 of 1, from 68 to 89: score 5.4, E = 8.6
            *->snggsrypgqGSPGGNRYPpq<-*  (SEQ ID NO: 96)
               + r+p +G PGG R P
rheu.ef.24      68  LATTLGRPPRGPPGGPRTPQI                              89  (SEQ ID NO: 97)
rheu.ef.238rev.148
PRION_2: domain 1 of 1, from 68 to 89: score 5.4, E = 8.6
            ->snggsrypgqGSPGGNRYPpq<-*  (SEQ ID NO: 96)
              r+p +G PGG R P
rheu.ef.23      68  LATTLGRPPRGPPGGPRTPQI                              89  (SEQ ID NO: 97)
gc; PRION
gx; PR00341
gn; COMPOUND (8)
ga; 19-OCT-1992; UPDATE 07-JUN-1999
gt; Prion protein signature
gp; INTERPRO: IPR000817
gp; PROSITE; PS00291 PRION_1; PS00706 PRION_2
gp; PFAM: PF00377 prion
gr; 1. STAHL, N. AND PRUSINER, S.B.
gr; Prions and prion proteins.
gr; FASEB J. 5 2799-2807 (1991).
gr; 2. BRUNORI, M., CHIARA SILVESTRINI, M. AND POCCHIARI, M.
gr; The scrapie agent and the prion hypothesis.
gr; TRENDS BIOCHEM. SCI. 13 309-313 (1988).
gr; 3. PRUSINER, S.B.
gr; Scrapie prions.
gr; ANNU. REV. MICROBIOL. 43 345-374 (1989).
gd; Prion protein (PrP) is a small glycoprotein found in high quantity in the
gd; brain of animals infected with certain degenerative neurological diseases,
gd; such as sheep scrapie and bovine spongiform encephalopathy (BSE), and the
gd; human dementias Creutzfeldt-Jacob disease (CJD) and Gerstmann-Straussler
gd; syndrome (GSS). PrP is encoded in the host genome and is expressed both in
gd; normal and infected cells. During infection, however, the PrP molecules
gd; become altered and polymerise, yielding fibrils of modified PrP protein.
gd; PrP molecules have been found on the outer surface of plasma membranes of
gd; nerve cells, to which they are anchored through a covalent-linked
gd; glycolipid, suggesting a role as a membrane receptor. PrP is also expressed
gd; in other tissues, indicating that it may have different functions depending
gd; on its location.
gd; The primary sequences of PrP's from different sources are highly similar:
gd; all bear an N-terminal domain containing multiple tandem repeats of a
gd; Pro/Gly rich octapeptide; sites of Asn-linked glycosylation; an essential
gd; disulphide bond; and 3 hydrophobic segments. These sequences show some
gd; similarity to a chicken glycoprotein, thought to be an acetylcholine
```

TABLE 1-continued

Examples of signature motifs identified in putative proteins resulting from TTV-HD transcripts and full-length genomes (A)

gd; receptor-inducing activity (ARIA) molecule. It has been suggested that
gd; changes in the octapeptide repeat region may indicate a predisposition to
gd; disease, but it is not known for certain whether the repeat may
gd; meaningfully be used as a fingerprint to indicate susceptibility.
gd; PRION is an 8-element fingerprint that provides a signature for the prion
gd; proteins. The fingerprint was derived from an initial alignment of 5
gd; sequences: the motifs were drawn from conserved regions spanning virtually
gd; the full alignment length, including the 3 hydrophobic domains and the
gd; octapeptide repeats (WGQPHGGG). Two iterations on OWL18.0 were required
gd; to reach convergence, at which point a true set which may comprise 9
gd; sequences was identified. Several partial matches were also found: these
gd; include a fragment (PRIO_RAT) lacking part of the sequence bearing the first
gd; motif, and the PrP homologue found in chicken - this matches well with only
gd; 2 of the 3 hydrophobic motifs (1 and 5) and one of the other conserved
gd; regions (6), but has an N-terminal signature based on a sextapeptide repeat
gd; (YPHNPG) rather than the characteristic PrP octapeptide.
c; PRION2
fl; 22
ft; Prion protein motif II-2
fd; WNTGGSRYPGQGSPGGNRYPPQ    PRIO_COLGU    31    8
(SEQ ID NO: 98)
fd; WNTGGSRYPGQGSPGGNRYPPQ    PRIO_MACFA    31    8
(SEQ ID NO: 98)
fd; WNTGGSRYPGQGSPGGNRYPPQ    PRIO_CEREL    34    9
(SEQ ID NO: 98)
fd; WNTGGSRYPGQGSPGGNRYPPQ    PRIO_ODOHE    34    9
(SEQ ID NO: 98)
fd; WNTGGSRYPGQGSPGGNRYPPQ    PRIO_GORGO    31    8
(SEQ ID NO: 98)
fd; WNTGGSRYPGQGSPGGNRYPPQ    PRIO_PANTR    31    8
(SEQ ID NO: 98)
fd; WNTGGSRYPGQGSPGGNRYPPQ    PRIO_HUMAN    34    9
(SEQ ID NO: 98)
fd; WNTGGSRYPGQGSPGGNRYPPQ    O46648        34    9
(SEQ ID NO: 98)
fd; WNTGGSRYPGQGSPGGNRYPPQ    PRIO_SHEEP    34    9
(SEQ ID NO: 98)
fd; WNTGGSRYPGQGSPGGNRYPPQ    PRIO_CALJA    31    8
(SEQ ID NO: 98)
fd; WNTGGSRYPGQGSPGGNRYPPQ    PRIO_BOVIN    34    9
(SEQ ID NO: 98)
fd; WNTGGSRYPGQGSPGGNRYPPQ    PRP2_BOVIN    34    9
(SEQ ID NO: 98)
fd; WNTGGSRYPGQGSPGGNRYPPQ    PRIO_ATEPA    31    8
(SEQ ID NO: 98)
fd; WNTGGSRYPGQGSPGGNRYPPQ    PRIO_SAISC    31    8
(SEQ ID NO: 98)
fd; WNTGGSRYPGQGSPGGNRYPPQ    PRIO_PREFR    31    8
(SEQ ID NO: 98)
fd; WNTGGSRYPGQGSPGGNRYPPQ    PRIO_PONPY    31    8
(SEQ ID NO: 98)
fd; WNTGGSRYPGQGSPGGNRYPPQ    O75942        31    8
(SEQ ID NO: 98)

TABLE 1-continued (A) Examples of signature motifs identified in putative proteins resulting from TTV-HD transcripts and full-length genomes

| Motif | Protein | Col3 | Col4 |
|---|---|---|---|
| fd; WNTGGSRYPGQGSPGGNRYPPQ (SEQ ID NO: 98) | PRIO_CAPHI | 34 | 9 |
| fd; WNTGGSRYPGQGSPGNLYPPQ (SEQ ID NO: 99) | PRIO_CEBAP | 31 | 8 |
| fd; WNTGGSRYPGQGSPGGNRYPPQ (SEQ ID NO: 98) | PRIO_CAMDR | 34 | 9 |
| fd; WNTGGSRYPGQGSPGGNRYPPQ (SEQ ID NO: 98) | PRIO_FELCA | 34 | 9 |
| fd; WNTGGSRYPGQGSPGGNRYPSQ (SEQ ID NO: 100) | PRP1_TRAST | 34 | 9 |
| fd; WNTGGSRYPGQGSSPGGNRYPPQ (SEQ ID NO: 101) | PRIO_RABIT | 32 | 9 |
| fd; WNTGGSRYPGQGSPGGNRYPPQ (SEQ ID NO: 101) | PRP2_TRAST | 34 | 9 |
| fd; WNTGGSRYPGQGSPGGNRYPPQ (SEQ ID NO: 101) | PRIO_PIG | 34 | 9 |
| fd; WNTGGSRYPGQGSPGGNRYPPQ (SEQ ID NO: 101) | PRIO_CANFA | 34 | 9 |
| fd; WNTGGSRYPGQGSPGGNRYPPQ (SEQ ID NO: 101) | PRIO_CRIGR | 31 | 8 |
| fd; WNTGGSRYPGQGSPGGNRYPPQ (SEQ ID NO: 101) | PRIO_CRIMI | 31 | 8 |
| fd; WNTGGSRYPGQGSPGGNRYPPQ (SEQ ID NO: 101) | Q15216 | 31 | 8 |
| fd; WNTGGSRYPGQGSPGGNRYPPQ (SEQ ID NO: 101) | PRIO_RAT | 31 | 8 |
| fd; WNTGGSRYPGQGSPGGNRYPPQ (SEQ ID NO: 101) | PRIO_CERAE | 31 | 8 |
| fd; WNTGGSRYPGQGSPGGNRYPPQ (SEQ ID NO: 101) | PRIO_MUSPF | 34 | 9 |
| fd; WNTGGSRYPGQGSPGGNRYPPQ (SEQ ID NO: 101) | PRIO_MUSVI | 34 | 9 |
| fd; WNTGGSRYPGQGSPGGNRYPPQ (SEQ ID NO: 101) | PRIO_MESAU | 31 | 8 |
| fd; WNTGGSRYPGQGSPGGNRYPPQ (SEQ ID NO: 101) | PRIO_MOUSE | 31 | 8 |
| fd; NTGGGSRYPGQGSPGGNRYPPQ (SEQ ID NO: 102) | O46593 | 34 | 9 |
| fd; SGGSNRYPGQPGSPGGNRYPGW (SEQ ID NO: 103) | PRIO_TRIVU | 37 | 12 | bb;
NEUROTENSIN

HMMER 2.3.2 (Oct 2003)
Copyright © 1992-2003 HHMI/Washington University School of Medicine
Freely distributed under the GNU General Public License (GPL)
HMM file: prints.hmm
sequence file: rheu.ef.241.148
NEUROTENSN2R_1: domain 1 of 1, from 68 to 80: score 6.8, E = 8.7
            *->mEtsspwPPRPsp<-* (SEQ ID NO: 104)
              + t +PPRP p TABLE 1-continued (A) Examples of signature motifs identified in putative proteins resulting from TTV-HD transcripts and full-length genomes

```
rheu.ef.24        68  LATTLGRPPRPGP                                                 80 (SEQ ID NO: 105)
rheu.ef.238rev.148
NEUROTENSN2R_1: domain 1 of 1, from 68 to 80: score 6.8, E = 8.7
                      *->mEtsspwPPRPsp<-* (SEQ ID NO: 104)
                         + t +PPRP p
rheu.ef.23        68  LATTLGRPPRPGP                                                 80 (SEQ ID NO: 105)
c;  NEUROTENSN2R
gx; PR01481
gn; COMPOUND (6)
ga; 12-MAR-2001
gt; Neurotensin type 2 receptor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; PRINTS; PR01479 NEUROTENSINR; PR01480 NEUROTENSN1R
gr; 1. ATTWOOD, T.K. AND FINDLAY, J.B.C.
gr; Fingerprinting G protein-coupled receptors.
gr; PROTEIN ENG. 7 (2) 195-203 (1994).
gr; 2. ATTWOOD, T.K. AND FINDLAY, J.B.C.
gr; G protein-coupled receptor fingerprints.
gr; 7TM, VOLUME 2, EDS. G. VRIEND AND B. BYWATER (1993).
gr; 3. BIRNBAUMER, L.
gr; G proteins in signal transduction.
gr; ANNU. REV. PHARMACOL. TOXICOL. 30 675-705 (1990).
gr; 4. CASEY, P.J. AND GILMAN, A.G.
gr; G protein involvement in receptor-effector coupling.
gr; J. BIOL. CHEM. 263 (6) 2577-2580 (1988).
gr; 5. ATTWOOD, T.K. AND FINDLAY, J.B.C.
gr; Design of a discriminating fingerprint for G protein-coupled receptors.
gr; PROTEIN ENG. 6 (2) 167-176 (1993).
gr; 6. WATSON, S. AND ARKINSTALL, S.
gr; Neurotensin.
gr; IN THE G PROTEIN-LINKED RECEPTOR FACTSBOOK, ACADEMIC PRESS, 1994, PP. 199-201.
gr; 7. VINCENT, J-P., MAZELLA, J. AND KITABGI, P.
gr; Neurotensin and neurotensin receptors.
gr; TRENDS PHARMACOL. SCI. 20 (7) 302-309 (1999).
gr; 8. VITA, N., OURY-DONAT, F., CHALON, P., GUILLEMOT, M., KAGHAD, M., BACHY,
gr; A., THURNEYSSEN, O., GARCIA, S., POINOT-CHAZEL, C., CASELLAS, P., KEANE, P.,
gr; LE FUR, G., MAFFRAND, J.P., SOUBRIE, P., CAPUT, D. AND FERRARA, P.
gr; Neurotensin is an antagonist of the human neurotensin NT2 receptor expressed
gr; in Chinese hamster ovary cells.
gr; EUR. J. PHARMACOL. 360 (2-3) 265-272 (1998).
gr; 9. YAMADA, M., YAMADA, M., LOMBET, A., FORGEZ, P. AND ROSTENE, W.
gr; Distinct functional characteristics of levocabastine sensitive rat
gr; neurotensin NT2 receptor expressed in Chinese hamster ovary cells.
gr; LIFE SCI. 62 (23) PL 375-380 (1998).
gd; G protein-coupled receptors (GPCRs) constitute a vast protein family that
gd; encompasses a wide range of functions (including various autocrine,
gd; paracrine and endocrine processes). They show considerable diversity at the
gd; sequence level, on the basis of which they may be separated into distinct
```

TABLE 1-continued (A) Examples of signature motifs identified in putative proteins resulting from TTV-HD transcripts and full-length genomes gd; groups. Applicants use the term clan to describe the GPCRs, as they embrace
gd; a group of families for which there are indications of evolutionary
gd; relationship, but between which there is no statistically significant
gd; similarity in sequence [1,2]. The currently known clan members include the
gd; rhodopsin-like GPCRs, the secretin-like GPCRs, the cAMP receptors, the fungal
gd; mating pheromone receptors, and the metabotropic glutamate receptor family.
gd; The rhodopsin-like GPCRs themselves represent a widespread protein family
gd; that includes hormone, neurotransmitter and light receptors, all of
gd; which transduce extracellular signals through interaction with guanine
gd; nucleotide-binding (G) proteins. Although their activating ligands vary
gd; widely in structure and character, the amino acid sequences of the
gd; receptors are very similar and are believed to adopt a common structural
gd; framework which may comprise 7 transmembrane (TM) helices [3-5].
gd; Neurotensin is a 13-residue peptide transmitter, sharing significant
gd; similarity in its 6 C-terminal amino acids with several other neuropeptides,
gd; including neuromedin N. This region is responsible for the biological
gd; activity, the N-terminal portion having a modulatory role. Neurotensin is
gd; distributed throughout the central nervous system, with highest levels in
gd; the hypothalamus, amygdala and nucleus accumbens. It induces a variety of
gd; effects, including: analgesia, hypothermia and increased locomotor activity.
gd; It is also involved in regulation of dopamine pathways. In the periphery,
gd; neurotensin is found in endocrine cells of the small intestine, where it
gd; leads to secretion and smooth muscle contraction [6].
gd; The existence of 2 neurotensin receptor subtypes, with differing affinities
gd; for neurotensin and differing sensitivities to the antihistamine
gd; levocabastine, was originally demonstrated by binding studies in rodent
gd; brain. Two neurotensin receptors (NT1 and NT2) with such properties have
gd; since been cloned and have been found to be G protein-coupled receptor
gd; family members [7].
gd; The NT2 receptor was cloned from rat, mouse and human brains based on its
gd; similarity to the NT1 receptor. The receptor was found to be a low affinity,
gd; levocabastine sensitive receptor for neurotensin. Unlike the high affinity,
gd; NT1 receptor, NT2 is insensitive to guanosine triphosphate and has low
gd; sensitivity to sodium ions [7]. Highest levels of expression of the receptor
gd; are found in the brain, in regions including: the olfactory system, cerebral
gd; and cerebellar cortices, hippocampus and hypothalamic nuclei. The
gd; distribution is distinct from that of the NT1 receptor, with only a few
gd; areas (diagonal band of Broca, medial septal nucleus and suprachiasmatic
gd; nuclei) expressing both receptor subtypes [7]. The receptor has also been
gd; found at lower levels in the kidney, uterus, heart and lung [8]. Activation
gd; of the NT2 receptor by non-peptide agonists suggests that the receptor may
gd; couple to phospholipase C, phospholipase A2 and MAP kinase. A functional
gd; response to neurotensin, however, is weak [9] or absent, and neurotensin
gd; appears to act as an antagonist of the receptor [8]. It has been suggested
gd; that a substance other than neurotensin may act as the natural ligand for
gd; this receptor [8].
gd; NEUROTENSN2R is a 6-element fingerprint that provides a signature for the
gd; neurotensin type 2 receptors. The fingerprint was derived from an initial
gd; alignment of 3 sequences: the motifs were drawn from conserved sections
gd; within the N-terminus and loop regions, focusing on those areas of the TABLE 1-continued (A) Examples of signature motifs identified in putative proteins resulting from TTV-HD transcripts and full-length genomes

```
gd;   alignment that characterise the neurotensin type 2 receptors but distinguish
gd;   them from the rest of neurotensin receptor family - motifs 1 and 2 span the
gd;   N-terminus; motifs 3 and 4 span the second external loop; and motifs 5 and 6
gd;   span the third cytoplasmic loop. A single iteration on SPTR39_15f was
gd;   required to reach convergence, no further sequences being identified beyond
gd;   the starting set.
bb;
fc;   NEUROTENSN2R1
fl;   13
ft;   Neurotensin type 2 receptor motif I-1
fd;   METSSPWPPRPSP (SEQ ID NO: 106) NTR2_RAT          1
fd;   METSSLWPPRPSP (SEQ ID NO: 107) NTR2_MOUSE        1
fd;   METSSPRPPRPSS (SEQ ID NO: 108) NTR2_HUMAN        1
ORPHAN NUCLEAR RECEPTOR (4A NUCLEAR RECEPTOR) FAMILY SIGNATURE HMMER 2.3.2 (Oct 2003)
Copyright © 1992-2003 HHMI/Washington University School of Medicine
Freely distributed under the GNU General Public License (GPL)
HMM file: prints.hmm
sequence file: uro742rev.1.780
NUCLEARECPTR_5: domain 1 of 1, from 326 to 341: score 7.2, E = 5
            *->PvnLlnaLVRahvDStP<-* (SEQ ID NO: 109)
               + + n++VRAh+D+
uro742rev.    326   -TFITNSMVRAHIDADK             341 (SEQ ID NO: 110)
gc;   NUCLEARECPTR
gx;   PR01284
gn;   COMPOUND (11)
ga;   16-FEB-2000
gt;   Orphan nuclear receptor (4A nuclear receptor) family signature
gp;   PRINTS; PR00398 STRDHORMONER; PR00047 STROIDFINGER
gp;   PRINTS; PR01285 HMRNUCRECPTR; PR01286 NORNUCRECPTR; PR01287 NURRNUCRCPTR
gr;   1. NUCLEAR RECEPTORS NOMENCLATURE COMMITTEE
gr;   A unified nomenclature system for the nuclear receptor superfamily.
gr;   CELL 97 161-163 (1999).
gr;   2. NISHIKAWA, J-I., KITAURA, M., IMAGAWA, M. AND NISHIHARA, T.
gr;   Vitamin D receptor contains multiple dimerisation interfaces that
gr;   are functionally different.
gr;   NUCLEIC ACIDS RES. 23 (4) 606-611 (1995).
gr;   3. DE VOS, P., SCHMITT, J., VERHOEVEN, G. AND STUNNENBERG, G.
gr;   Human androgen receptor expressed in HeLa cells activates transcription
gr;   in vitro.
gr;   NUCLEIC ACIDS RES. 22 (7) 1161-1166 (1994).
gr;   4. OHKURA, N., HIJIKURO, M., YAMAMOTO, A. AND MIKI, K.
gr;   Molecular cloning of a novel thyroid/steroid receptor superfamily gene from
gr;   cultured rat neuronal cells.
gr;   BIOCHEM. BIOPHYS. RES. COMMUN. 205 1959-1965 (1994).
gr;   5. LAW, S.W., CONNEELY, O.M., DEMAYO, F.J. AND O'MALLEY, B.W.
gr;   Identification of a new brain-specific transcription factor, NURR1.
gr;   MOL. ENDOCRINOL. 2129-2135 (1992).
gr;   6. WILSON, T.E., PAULSEN, R.E., PADGETT, K.A. AND MILBRANDT, J.
```

TABLE 1-continued (A) Examples of signature motifs identified in putative proteins resulting from TTV-HD transcripts and full-length genomes gr; Participation of non-zinc finger residues in DNA binding by two nuclear
gr; orphan receptors.
gr; SCIENCE 256 107-110 (1992).
gr; 7. CLARK, J., BENJAMIN, H., GILL, S., SIDHAR, S., GOODWIN, G., CREW, J.,
gr; GUSTERSON, B.A., SHIPLEY, J. AND COOPER, C.S.
gr; Fusion of the EWS gene to CHN, a member of the steroid/thyroid receptor
gr; gene superfamily, in a human myxoid chondrosarcoma.
gr; ONCOGENE 12 229-235 (1996).
gd; Steroid or nuclear hormone receptors (NRs) constitute an important super-
gd; family of transcription regulators that are involved in widely diverse
gd; physiological functions, including control of embryonic development, cell
gd; differentiation and homeostasis [1]. Members of the superfamily include the
gd; steroid hormone receptors and receptors for thyroid hormone, retinoids,
gd; 1,25-dihydroxy-vitamin D3 and a variety of other ligands. The proteins
gd; function as dimeric molecules in nuclei to regulate the transcription of
gd; target genes in a ligand-responsive manner [2,3]. In addition to C-terminal
gd; ligand-binding domains, these nuclear receptors contain a highly-conserved,
gd; N-terminal zinc-finger that mediates specific binding to target DNA
gd; sequences, termed ligand-responsive elements. In the absence of ligand,
gd; steroid hormone receptors are thought to be weakly associated with nuclear
gd; components; hormone binding greatly increases receptor affinity.
gd; NRs are extremely important in medical research, a large number of them
gd; being implicated in diseases such as cancer, diabetes, hormone resistance
gd; syndromes, etc. [1]. While several NRs act as ligand-inducible transcription
gd; factors, many do not yet have a defined ligand and are accordingly termed
gd; "orphan" receptors. During the last decade, more than 300 NRs have been
gd; described, many of which are orphans, which cannot easily be named due to
gd; current nomenclature confusions in the literature. However, a new system
gd; has recently been introduced in an attempt to rationalise the increasingly
gd; complex set of names used to describe superfamily members [1].
gd; Novel members of the steroid receptor superfamily designated NOR-1 (neuron
gd; derived orphan receptor) [4], Nurr1 (Nur-related factor 1) [5], and NGFI-B
gd; [6] have been identified from forebrain neuronal cells undergoing apoptosis,
gd; from brain cortex, and from lung, superior cervical ganglia and adrenal
gd; tissue respectively. The NOR-1 protein binds to the B1a response-element,
gd; which has been identified as the target sequence of the Nur77 family,
gd; suggesting that three members of the Nur77 family may transactivate common
gd; target gene(s) at different situations [4]. Ewing's sarcoma is characterised
gd; by chromosomal translocations that involve the NOR protein [7].
gd; NUCLEARECPTR is an 11-element fingerprint that provides a signature for the
gd; orphan nuclear receptor family. The fingerprint was derived from an initial
gd; alignment of 11 sequences: the motifs were drawn from conserved regions
gd; spanning virtually the full alignment length, focusing on those sections
gd; that characterise members of the nuclear receptor family but distinguish
gd; them from the rest of the steroid hormone receptor superfamily - motifs 1-3
gd; lie N-terminal to the zinc finger domain; motifs 4 and 5 lie between the
gd; zinc fingers and putative ligand-binding domain; motifs 6 and 7 encode the
gd; N- and C-terminal extremities of the ligand-binding domain; and motifs 8-11
gd; reside at the C-terminus. A single iteration on SPTR37_10f was required to
gd; reach convergence, no further sequences being identified beyond the starting TABLE 1-continued (A) Examples of signature motifs identified in putative proteins resulting from TTV-HD transcripts and full-length genomes

```
gd; set. Several partial matches were found, all of which appear to be N- or
gd; C-terminally truncated homologues.
fc; NUCLEARECPTR5
fl; 17
ft; Orphan nuclear receptor family motif V-1
fd;   PANLLTSLVRAHLDSGP    (SEQ ID NO: 111)    NR41_HUMAN    361    6
fd;   PANLLTSLVRAHLDSGP    (SEQ ID NO: 111)    NR41_CANFA    361    6
fd;   PVSLISALVRAHVDSNP    (SEQ ID NO: 112)    NR42_RAT      361    10
fd;   PVSLISALVRAHVDSNP    (SEQ ID NO: 112)    NR42_MOUSE    361    10
fd;   PVSLISALVRAHVDSNP    (SEQ ID NO: 112)    NR42_HUMAN    361    10
fd;   PTNLLTSLIRAHLDSGP    (SEQ ID NO: 113)    NR41_RAT      360    6
fd;   PTNLLTSLIRAHLDSGP    (SEQ ID NO: 113)    NR41_MOUSE    364    6
fd;   PVDLIINSLVRAHIDSIP   (SEQ ID NO: 114)    NR42_XENLA    340    6
fd;   PVCMMNALVRALTDSTP    (SEQ ID NO: 115)    O97726        412    15
fd;   PICMMNALVRALTDSTP    (SEQ ID NO: 116)    NR43_HUMAN    395    15
fd;   PICMMNALVRALTDATP    (SEQ ID NO: 117)    NR43_RAT      397    15
BRAIN DERIVED NEUROTROPHIC FACTOR SIGNATURE (BDN)

HMMER 2.3.2 (Oct 2003)
Copyright © 1992-2003 HHMI/Washington University School of Medicine
Freely distributed under the GNU General Public License (GPL)
HMM file: prints.hmm
Sequence file: uro742rev.1.780
BDNFACTOR_3: domain 1 of 2, from 496 to 512: score 3.1, E = 42
              *->PLLFLLEEYKnYLDAAn<-*  (SEQ ID NO: 118)
                 PL LL Y YL+
uro742rev.  496  PLWALLNGYVDYLETQI                              512  (SEQ ID NO: 119)
BDNFACTOR_3: domain 2 of 2, from 690 to 706: score 7.7, E = 5.7
              *->PLLFLLEEYKnYLDAAn<-*  (SEQ ID NO: 118)
                 PLLFL EY+ AA
uro742rev.  690  PLLFLPSEYQREDGAAE                              706  (SEQ ID NO: 120)
gc; BDNFACTOR
gx; PR01912
gn; COMPOUND (5)
ga; 29-AUG-2008
gt; Brain derived neurotrophic factor signature
gp; PRINTS; PR00268 NGF; PR01913 NGFBETA; PR01914 NEUROTROPHN3
gp; PRINTS; PR01915 NEUROTROPHN4; PR01916 NEUROTROPHN6
gp; PDB; 1BND; 1B8M
gp; SCOP; 1BND; 1B8M
gp; CATH; 1BND; 1B8M
gp; MIM; 113505
gr; 1. HOFER, M., PAGLIUSI, S.R., HOHN, A., LEIBROCK, J. AND BARDE, Y.A.
gr; Regional distribution of brain-derived neurotrophic factor messenger RNA in
gr; the adult mouse brain.
gr; EMBO J. 9 (8) 2459-2464 (1990).
gr; 2. KOYAMA, J.I., INOUE, S., IKEDA, K. AND HAYASHI, K.
gr; Purification and amino acid sequence of a nerve growth factor from the
gr; venom of Vipera russelli russelli.
gr; BIOCHIM. BIOPHYS. ACTA 1160 287-292 (1992).
```

TABLE 1-continued (A) Examples of signature motifs identified in putative proteins resulting from TTV-HD transcripts and full-length genomes gr; 3. INOUE, S., ODA, T., KOYAMA, J., IKEDA, K. AND HAYASHI, K.
gr; Amino acid sequences of nerve growth factors derived from cobra venoms.
gr; FEBS LETT. 279 (1) 38-40 (1991).
gr; 4. BARDE, Y., EDGAR, D. AND THOENEN, H.
gr; Purification of a new neurotrophic factor from mammalian brain.
gr; EMBO J. 1 549-553 (1982).
gr; 5. HIBBERT, A., KRAMER, B., MILLER, F. AND KAPLAN, D.
gr; The localization, trafficking and retrograde transport of BDNF bound to
gr; p75NTR in sympathetic neurons.
gr; MOL. CELL. NEUROSCI. 32 387-402 (2006).
gr; 6. LINNARSSON, S., BJORKLUND, A. AND ERNFORS, P.
gr; Learning deficit in BDNF mutant mice.
gr; EUR. J. NEUROSCI. 9 2581-2587 (1997).
gr; 7. LEBRUN, B., BARIOHAY, B., MOYSE, E. AND JEAN, A.
gr; Brain-derived neurotrophic factor (BDNF) and food intake regulation: a
gr; minireview.
gr; AUTON. NEUROSCI. 126-127 30-38 (2006).
gr; 8. KOZISEK, M., MIDDLEMAS, D. AND BYLUND, D.
gr; Brain-derived neurotrophic factor and its receptor tropomyosin-related
gr; kinase B in the mechanism of action of antidepressant therapies.
gr; PHARMACOL. THER. 117 30-51 (2008).
gd; During the development of the vertebrate nervous system, many neurons
gd; become redundant (because they have died, failed to connect to target
gd; cells, etc.) and are eliminated. At the same time, developing neurons send
gd; out axon outgrowths that contact their target cells [1]. Such cells control
gd; their degree of innervation (the number of axon connections) by the
gd; secretion of various specific neurotrophic factors that are essential for
gd; neuron survival. One of these is nerve growth factor (NGF), which is
gd; involved in the survival of some classes of embryonic neuron (e.g., peri-
gd; pheral sympathetic neurons) [1]. NGF is mostly found outside the central
gd; nervous system (CNS), but slight traces have been detected in adult CNS
gd; tissues, although a physiological role for this is unknown [1]; it has also
gd; been found in several snake venoms [2,3]. Proteins similar to NGF include
gd; brain-derived neurotrophic factor (BDNF) and neurotrophins 3 to 7, all of
gd; which demonstrate neuron survival and outgrowth activities.
gd; Originally purified from pig brain [4], the neurotrophin BDNF is expressed
gd; in a range of tissues and cell types in the CNS and periphery. It exerts
gd; its effects by binding to neurotrophic tyrosine kinase receptor type 2
gd; (NTRK2; also called TrkB) and the low affinity nerve growth factor receptor,
gd; p75NTR. While the former receptor mediates the neurotrophin's prosurvival
gd; functions, activation of p75NTR by BDNF has been shown to promote apoptosis
gd; and to inhibit axonal growth [5].
gd; BDNF is a key regulator of synaptic plasticity, and plays an important role
gd; in learning and memory [6]. Several lines of evidence suggest that it is
gd; also involved in the control of food intake and body weight [7]. A number
gd; of clinical studies have demonstrated an association between aberrant BDNF
gd; levels and disorders and disease states, such as depression, epilepsy,
gd; bipolar disorder, Parkinson's disease and Alzheimer's disease [8].
gd; BDNFACTOR is a 5-element fingerprint that provides a signature for brain-
gd; derived neurotrophic factor. The fingerprint was derived from an initial TABLE 1-continued (A) Examples of signature motifs identified in putative proteins resulting from TTV-HD transcripts and full-length genomes gd; alignment of 33 sequences: the motifs were drawn from conserved regions
gd; spanning virtually the full alignment length - motif 1 includes part of the
gd; signal sequence. Three iterations on SPTR55_38f were required to reach
gd; convergence, at which point a true set which may comprise 47 sequences was
gd; identified. A single partial match was also found, Q6YNR1_HUMAN, a human
gd; BDNF splice variant that fails to match motifs 4 and 5.
fc; BDNFACTOR3
fl; 17
ft; Brain derived neurotrophic factor motif III-3
fd; PLLFLLEEYKNYLDAAN    A2AII2_MOUSE      115    31
fd; PLLFLLEEYKNYLDAAN    Q8CCH9_MOUSE      107    31
fd; PLLFLLEEYKNYLDAAN    Q6YNR3_HUMAN      113    31
fd; PLLFLLEEYKNYLDAAN    Q6YNR2_HUMAN      120    31
fd; PLLFLLEEYKNYLDAAN    Q59BQ1_HUMAN      105    31
fd; PLLFLLEEYKNYLDAAN    Q54IP3_MOUSE      107    31
fd; PLLFLLEEYKNYLDAAN    BDNF_URSML        105    31
fd; PLLFLLEEYKNYLDAAN    BDNF_URSAR        105    31
fd; PLLFLLEEYKNYLDAAN    BDNF_SPECI        105    31
fd; PLLFLLEEYKNYLDAAN    BDNF_SELTH        105    31
fd; PLLFLLEEYKNYLDAAN    BDNF_RAT          107    31
fd; PLLFLLEEYKNYLDAAN    BDNF_PROLO        105    31
fd; PLLFLLEEYKNYLDAAN    BDNF_PIG          110    31
fd; PLLFLLEEYKNYLDAAN    BDNF_PANTR        105    31
fd; PLLFLLEEYKNYLDAAN    BDNF_MOUSE        107    31
fd; PLLFLLEEYKNYLDAAN    BDNF_HUMAN        105    31
fd; PLLFLLEEYKNYLDAAN    BDNF_FELCA        105    31
fd; PLLFLLEEYKNYLDAAN    BDNF_CANFA        105    31
fd; PLLFLLEEYKNYLDAAN    BDNF_BOVIN        108    31
fd; PLLFLLEEYKNYLDAAN    BDNF_AILME        105    31
fd; PLLFLLEEYKNYLDAAN    BDNF_AILFU        105    31
fd; PLLFLLEEYKNYLDAAN    A7LA92_HUMAN      187    31
fd; PLLFLLEEYKNYLDAAN    A7LA85_HUMAN      134    31
fd; PLLFLLEEYKNYLDAAN    BDNF_CAVPO        113    31
fd; PLLFLLEEYKNYLDAAN    BDNF_HORSE        105    31
fd; PLLFLLEEYKNYLDAAN    Q8VHH4_MOUSE      107    31
fd; PLLFLLEEYKNYLDAAN    Q6DN19_HUMAN      105    31
fd; PLLFLLEEYKNYLDAAN    BDNF_LIPVE        106    31
fd; PLLFLLEEYKNYLDAAN    BDNF_CHICK        105    30
fd; PLLFLLEEYKNYLDAAN    Q8AV78_NIPNI      104    30
fd; PLLFLLEEYKNYLDAAN    Q4JHT7_POEGU      104    30
fd; PLLFLLEEYKNYLDAAN    A4L7M3_BOMOR      105    30
fd; PLLFLLEEYKNYLDAAN    Q63ZM5_XENLA      105    30
fd; PLLFLLEEYKNYLDAAN    A3FPG9_XENTR      105    30
fd; PLLFLLEEYKNYLDAAN    Q8QG75_9SAUR      104    30
fd; PLLFLLEEYKNYLDAAN    Q8QG76_9SAUR      104    30
fd; PLLFLLEEYKNYLDAAN    A4L7M4_9SALA      105    30
fd; PLLFLLEEYKNYLDAAN    A4L7M5_SALSL      105    30
fd; PLLFLLEEYKNYLDAAN    A2ICR4_AMBME      104    30
fd; PLLFLLEEYKNYLDAAN    Q8QG77_9SALA      105    30
fd; PLLFLLEEYKNYLDAAN    Q6NZO1_DANRE      128    47

TABLE 1-continued (A) Examples of signature motifs identified in putative proteins resulting from TTV-HD transcripts and full-length genomes

```
fd;   PLLFLLEEYKNYLDAAN       Q9YH42_DANRE       128        47
fd;   PLLFLLEEYKNYLDAAN       Q8JGW4_PAROL       127        48
fd;   PLLFLLEEYKNYLDAAN       Q06B76_DICLA       127        48
fd;   PLLFLLEEYKNYLDAAN       BDNF_CYPCA         128        47
fd;   PLLFLLEEYKNYLDAAN       Q8QG74_9SAUR       104        30
fd;   PLLFLLEEYKNYLDAAN       BDNF_XIPMA         127        48
(SEQ ID NO: 118)
CALCITONIN

HMMER 2.3.2 (Oct 2003)
Copyright © 1992-2003 HHMI/Washington University School of Medicine
Freely distributed under the GNU General Public License (GPL)
HMM file: prints.hmm
Sequence file: uro742rev.154
CALCITONINR_2: domain 1 of 1, from 91 to 108: score 6.0, E = 9.4
          *->kCYDRmqLPpYeGEGpY<-*  (SEQ ID NO: 121)
             R+ LP+Y GEGp
uro742rev.       91    TPVRRLLPLPSYPGEGPQ       108 (SEQ ID NO: 122)
CALCITONINR_2: domain 1 of 1, from 72 to 89: score 6.0, E = 9.4
          *->kCYDRmqLPpYeGEGpY<-*  (SEQ ID NO: 121)
             R+ LP+Y GEGp
zc37.B9.2d       72    TPVRRLLPLPSYPGEGPQ       89  (SEQ ID NO: 122)
gc;   CALCITONINR
gx;   PR00361
gn;   COMPOUND (6)
ga;   15-APR-1995; UPDATE 06-JUN-1999
gt;   Calcitonin receptor signature
gp;   PRINTS; PR00237 GPCRRHODOPSN; PR00247 GPCRCAMP; PR00248 GPCRMGR
gp;   PRINTS; PR00249 GPCRSECRETIN; PR00250 GPCRSTE2; PR00899 GPCRSTE3
gp;   PRINTS; PR00251 BACTRLOPSIN
gp;   PRINTS; PR01350 CTRFAMILY; PR01351 CGRPRECEPTOR
gp;   INTERPRO; IPR001688
gr;   1. ATTWOOD, T.K. AND FINDLAY, J.B.C.
gr;   Fingerprinting G protein-coupled receptors.
gr;   PROTEIN ENG. 7 (2) 195-203 (1994).
gr;   2. ISHIHARA T., NAKAMURA S., KAZIRO, Y., TAKAHASHI, T., TAKAHASHI, K.
gr;   AND NAGATA, S.
gr;   Molecular cloning and expression of a cDNA encoding the secretin receptor.
gr;   EMBO J. 10 1635-1641 (1991).
gr;   3. LIN, H.Y., HARRIS, T.L., FLANNERY, M.S., ARUFFO, A., KAJI, E.H.,
gr;   GORN, A., KOLAKOWSKI, L.F., LODISH, H.F. AND GOLDRING, S.R.
gr;   Expression cloning of adenylate cyclase-coupled calcitonin receptor.
gr;   SCIENCE 254 1022-1024 (1991).
gr;   4. JUEPPNER, H., ABOU-SAMRA, A.-B., FREEMAN, M., KONG, X.F.,
gr;   SCHIPANI, E., RICHARDS, J., KOLALOWSKI, L.F., HOCK, J., POTTS, J.T.,
gr;   KRONENBERG, H.M. AND SEGRE, G.E.
gr;   A G protein linked receptor for parathyroid hormone and parathyroid
gr;   hormone-related peptide.
gr;   SCIENCE 254 1024-1026 (1991).
gr;   5. ISHIHARA, T., SHIGEMOTO, R., MORI, K., TAKAHASHI, K. AND NAGATA, S.
```

TABLE 1-continued (A) Examples of signature motifs identified in putative proteins resulting from TTV-HD transcripts and full-length genomes gr; Functional expression and tissue distribution of a novel receptor for
gr; vasoactive intestinal polypeptide.
gr; NEURON 8 (4) 811-819 (1992).
gr; 6. WATSON, S. AND ARKINSTALL, S.
gr; Calcitonin.
gr; IN THE G PROTEIN-LINKED RECEPTOR FACTSBOOK, ACADEMIC PRESS, 1994, PP. 74-76.
gr; 7. NJUKI, F., NICHOLL, C.G., HOWARD, A., MAK, J.C., BARNES, P.J.,
gr; GIRGIS, S.I. AND LEGON, S.A.
gr; A new calcitonin-receptor-like sequence in rat pulmonary blood vessels.
gr; CLIN. SCI. 85 (4) 385-388 (1993).
gd; G protein-coupled receptors (GPCRs) constitute a vast protein family that
gd; encompasses a wide range of functions (including various autocrine, para-
gd; crine and endocrine processes). They show considerable diversity at the
gd; sequence level, on the basis of which they may be separated into distinct
gd; groups. Applicants use the term clan to describe the GPCRs, as they embrace a
gd; group of families for which there are indications of evolutionary
gd; relationship, but between which there is no statistically significant
gd; similarity in sequence [1]. The currently known clan members include the
gd; rhodopsin-like GPCRs, the secretin-like GPCRs, the cAMP receptors, the fungal
gd; mating pheromone receptors, and the metabotropic glutamate receptor family.
gd; The secretin-like GPCRs include secretin [2], calcitonin [3], parathyroid
gd; hormone/parathyroid hormone-related peptides [4] and vasoactive intestinal
gd; peptide [5], all of which activate adenylyl cyclase and the phosphatidyl-
gd; inositol-calcium pathway. The amino acid sequences of the receptors contain
gd; high proportions of hydrophobic residues grouped into 7 domains, in a manner
gd; reminiscent of the rhodopsins and other receptors believed to interact with
gd; G proteins. However, while a similar 3D framework has been proposed to
gd; account for this, there is no significant sequence identity between these
gd; families: the secretin-like receptors thus bear their own unique '7TM'
gd; signature.
gd; The major physiological role of calcitonin is to inhibit bone resorption
gd; thereby leading to a reduction in plasma Ca++ [6]. Further, it enhances
gd; excretion of ions in the kidney, prevents absorption of ions in the
gd; intestine, and inhibits secretion in endocrine cells (e.g. pancreas and
gd; pituitary). In the CNS, calcitonin has been reported to be analgesic
gd; and to suppress feeding and gastric acid secretion. It is used to treat
gd; Paget's disease of the bone. Calcitonin receptors are found predominantly
gd; on osteoclasts or on immortal cell lines derived from these cells. It is
gd; found in lower amounts in the brain (e.g. in hypothalamus and pituitary
gd; tissues) and in peripheral tissues (e.g. testes, kidney, liver and
gd; lymphocytes). It has also been described in lung and breast cancer cell
gd; lines. The predominant signalling pathway is activation of adenylyl cyclase
gd; through Gs, but calcitonin has also been described to have both stimulatory
gd; and inhibitory actions on the phosphoinositide pathway.
gd; CALCITONINR is a 6-element fingerprint that provides a signature for the
gd; calcitonin receptors. The fingerprint was derived from an initial alignment
gd; of 6 sequences: the motifs were drawn from conserved sections within either
gd; loop or TM regions, focusing on those areas of the alignment that
gd; characterise the calcitonin receptors but distinguish them from the rest
gd; of the secretin-like family - motifs 1-3 were drawn from the N-terminal TABLE 1-continued (A) Examples of signature motifs identified in putative proteins resulting from TTV-HD transcripts and full-length genomes

```
gd; region leading into the first TM domain; motif 4 lies at the C-terminus of
gd; the second TM domain following into the loop region; motif 5 is N-terminal
gd; to the seventh TM region; and motif 6 was drawn from the C-terminus. Two
gd; iterations on OWL25.2 were required to reach convergence, at which point a
gd; true set which may comprise 9 sequences was identified. A single partial
gd; match was also found, RNCLR, a new calcitonin-like receptor from rat
gd; pulmonary blood vessels [7].
fc; CALCITONINR2
fl; 18
ft; Calcitonin receptor motif II-2
fd; KCYDRIQQLPPYEGEGPY (SEQ ID NO: 123)              CALR_RAT      54   1
fd; KCYDRMEQLPPYQGEGPY (SEQ ID NO: 124)              CALR_RABIT    54   1
fd; KCYDRMQQLPAYQGEGPY (SEQ ID NO: 125)              CALR_HUMAN    54   1
fd; KCYDRIHQLPSYEGEGLY (SEQ ID NO: 126)              CALR_MOUSE    54   1
fd; RCYDRMQQLPPYEGEGPY (SEQ ID NO: 127)              CALR_CAVPO    54   1
fd; RCYDRMQKLPPYQGEGLY (SEQ ID NO: 128)              CALR_PIG      55   1
LEUKOTRIENE B4 TYPE 1 RECEPTOR BLKPROB Version 5/21/00.1
Database = /gcg/husar/gcgdata/gcgblimps/blocksplus.dat
Copyright © 1992-6 by the Fred Hutchinson Cancer Research Center
If you use BLOCKS in your research, please cite:
Steven Henikoff and Jorja G. Henikoff, Protein Family Classification Based
on Searching a Database of Blocks, Genomics 19: 97-107 (1994).
Each numbered result consists of one or more blocks from a PROSITE or PRINTS
group found in the query sequence. One set of the highest-scoring blocks that
are in the correct order and separated by distances comparable to the BLOCKS
database is selected for analysis. If this set includes multiple blocks
the probability that the lower scoring blocks support the highest scoring
block is reported. Maps of the database blocks and query sequence are shown:
< indicates the sequence has been truncated to fit the page
: indicates the minimum distance between blocks in the database
. indicates the maximum distance between blocks in the database
The maps are aligned on the highest scoring block. The alignment of the
query sequence with the sequence closest to it in the BLOCKS database
is shown. Upper case in the query sequence indicates at least one
occurrence of the residue in that column of the block.
Query = uro705rev.1a.74           Length: 74              Type: P C       Combined
Size = 74 Amino Acids
Blocks Searched = 29068
Alignments Done = 2896529
Cutoff combined expected value for hits = 0
Cutoff block expected value for repeats/other = 0
```

TABLE 1-continued (A) Examples of signature motifs identified in putative proteins resulting from TTV-HD transcripts and full-length genomes

```
Family                                                              Strand    Blocks      E-value
IPB003983 Leukotriene B4 type 1 receptor sign                         1       1 of 6      0.0042
>IPB003983 1/6 blocks Combined E-value = 0.0042: Leukotriene B4 type 1
receptor signature
Block        Frame    Location (aa)                    Block E-value
IPB003983C     0        25-41                             0.0046
Other reported alignments:
                                       |--- 141 amino acids---|
            IPB003983 AAA::::BB::::::::::::::::::::::::::::CCC:::DDD:::::::::EEEFF
uro705rev.1a.74_12                                          ::::CCC IPB003983C       <->C         (202,207).24
Q9WTK1|Q9WTK1_CAVPO207         SRLRVRRFHRRRRTGR (SEQ ID NO: 129)
                               ||  ||  ||||  ||
uro705rev.1a.74_12  25         lRRrRpRRplRRRRrGR (SEQ ID NO: 130)

rheu.cd.215rev.1.736  Combined E-value = 0.0094: Leukotriene B4 type 1
receptor signature
Block        Frame    Location (aa)                    Block E-value
IPB003983C     0        28-44                             0.0096
Other reported alignments:
                                       |--- 141 amino acids---|
            IPB003983 AAA::::BB::::::::::::::::::::::::::::CCC:::DDD:::::::::EEEFF
rheu.cd.215rev.1.7                                          ::::CCC IPB003983C       <->C         (202,207).27
LT4R1_RAT|Q9R0Q2 206           GRRLQARFRFRSRRTGR (SEQ ID NO: 131)
                               |||   ||  ||| ||
rheu.cd.215rev.1.7  28         rRRrpARRFRaRRRvrR (SEQ ID NO: 132)

zpr5.B4.12dk.209     Length: 209        Type: P
Family                                                              Strand    Blocks      Combined
                                                                                          E-value
IPB003983 Leukotriene B4 type 1 receptor sign                         1       1 of 6      0.0078
zpr5.B4.12dk
>IPB003983 1/6 blocks Combined E-value = 0.0078: Leukotriene B4 type 1 receptor
signature
Block        Frame    Location (aa)                    Block E-value
IPB003983C     0        32-48                             0.0081
```

TABLE 1-continued (A) Examples of signature motifs identified in putative proteins resulting from TTV-HD transcripts and full-length genomes Other reported alignments:

```
                  |--- 141 amino acids---|
      IPB003983 AAA:::::BB::::::::::::::::::CCC:::DDD:::::::::EEEFF
zpr5.B4.12dk.209_2                                   ::::CCC IPB003983C         <->C        (202,207):31
Q9WTK1|Q9WTK1_CAVPO207         SRRLRVRRFHRRRRTGR (SEQ ID NO: 129)
                               |||  |||| ||||  |
zpr5.B4.12dk.209_2 32          rRRpRrRvRRRRRRwrR (SEQ ID NO: 133)
```

SJOGREN'S SYNDROME/SCLERODERMA AUTOANTIGEN 1 (AUTOANTIGEN P27)

HMMER 2.3.2 (Oct 2003)
Copyright © 1992-2003 HHMI/Washington University School of Medicine
Freely distributed under the GNU General Public License (GPL)
HMM file: pfam.hmm
Sequence file: rheu.cd.21lrev.164 (SEQ ID NO: 135)
Auto_anti-p27: domain 1 of 1, from 117 to 156: score -12.1, E = 4.6 (SEQ ID NO: 134)

```
                 *->eiskkmaelllkGatMLdehCpkCgtPLFrlKdGkvfCPiCe-.*
                    + ++ ++++l + L++ +kC ++ +r + Gk  fC +Ce
rheu.ed.21    11    HT-AVKGQPGLGTGRALGKALKKCAFAGLR-RKGKCFCKVCE         156
# = GF ID   Auto_anti-p27
# = GF AC   PF06677.4
# = GF DE   Sjogren's syndrome/scleroderma autoantigen 1 (Autoantigen p27)
# = GF AU   Moxon SJ
# = GF SE   Pfam-B_21881 (release 10.0)
# = GF TP   Family
# = GF RN   [1]
# = GF RM   9486406
# = GF RT   cDNA cloning of a novel autoantigen targeted by a minor subset
# = GF RT   of anti-centromere antibodies.
# = GF RA   Muro Y, Yamada T, Himeno M, Sugimoto K;
# = GF RL   Clin Exp Immunol 1998; 111: 372-376.
# = GF DR   INTERPRO; IPR009563;
# = GF CC   This family consists of several Sjogren's syndrome/scleroderma
# = GF CC   autoantigen 1 (Autoantigen p27) sequences. It is thought that
# = GF CC   the potential association of anti-p27 with anti-centromere
# = GF CC   antibodies suggests that autoantigen p27 might play a role in
# = GF CC   mitosis [1].
```

TABLE 1-continued (A) Examples of signature motifs identified in putative proteins resulting from TTV-HD transcripts and full-length genomes

```
VASOPRESSIN

HMMER 2.3.2 (Oct 2003)
Copyright © 1992-2003 HHMI/Washington University School of Medicine
Freely distributed under the GNU General Public License (GPL)
HMM file: prints.hmm
Sequence file: uro742rp.132
VASOPRSNV2R_6: domain 1 of 1, from 7 to 26: score 7.4, E = 9.1
                   *->RaGgrRrGrRtGsPsEGArv<-*   (SEQ ID NO: 136)
                      R rRrG t s sE A
uro742rp.1        7   RNASRRRGSSTASTSEEASL                       26 (SEQ ID NO: 137)
VASOPRSNV2R_6: domain 1 of 1, from 7 to 26: score 7.4, E = 9.1
                   *->RaGgrRrGrRtGsPsEGArv<-*   (SEQ ID NO: 136)
                      R rRrG t s sE A
zc37.B8.10        7   RNASRRRGSSTASTSEEASL                       26 (SEQ ID NO: 137)
VASOPRSNV1BR_4: domain 1 of 1, from 130 to 149: score 3.0, E = 7.1
                   *->TQAgRverrGWRTWDksSsS<-*   (SEQ ID NO: 138)
                      Q + +e R WD++
zc35s.B2.9       130  AQDWAEEYTACRYWDRPPRT                      149 (SEQ ID NO: 139)
gc; VASOPRSNV2R
gx; PR00898
gn; COMPOUND (8)
ga; 15-APR-1998; UPDATE 07-JUN-1999
gt; Vasopressin V2 receptor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; PRINTS; PR00896 VASOPRESSINR
gp; PRINTS; PR00752 VASOPRSNV1AR; PR00897 VASOPRSNV1BR; PR00665 OXYTOCINR
gp; INTERPRO; IPR000161
gr; 1. ATTWOOD, T.K. AND FINDLAY, J.B.C.
gr; Fingerprinting G protein-coupled receptors.
gr; PROTEIN ENG. 7 (2) 195-203 (1994).
gr; 2. ATTWOOD, T.K. AND FINDLAY, J.B.C.
gr; G protein involvement in receptor-effector coupling.
gr; J. BIOL. CHEM. 263 (6) 2577-2580 (1988).
gr; 3. ATTWOOD, T.K. AND FINDLAY, J.B.C.
gr; G protein-coupled receptor fingerprints.
gr; 7TM, VOLUME 2, EDS. G. VRIEND AND B. BYWATER (1993).
gr; 3. BIRNBAUMER, L.
gr; G proteins in signal transduction.
gr; ANNU. REV. PHARMACOL. TOXICOL. 30 675-705 (1990).
gr; 4. CASEY, P.J. AND GILMAN, A.G.
gr; G protein involvement in receptor-effector coupling.
gr; J. BIOL. CHEM. 263 (6) 2577-2580 (1988).
gr; 5. ATTWOOD, T.K. AND FINDLAY, J.B.C.
gr; Design of a discriminating fingerprint for G protein-coupled receptors.
gr; PROTEIN ENG. 6 (2) 167-176 (1993).
gr; 6. WATSON, S. AND ARKINSTALL, S.
gr; Vasopressin and oxytocin.
gr; IN THE G PROTEIN-LINKED RECEPTOR FACTSBOOK, ACADEMIC PRESS, 1994, PP. 284-291.
gd; G protein-coupled receptors (GPCRs) constitute a vast protein family
gd; that encompasses a wide range of functions (including various autocrine,
```

TABLE 1-continued (A) Examples of signature motifs identified in putative proteins resulting from TTV-HD transcripts and full-length genomes gd; paracrine and endocrine processes). They show considerable diversity at the
gd; sequence level, on the basis of which they may be separated into distinct
gd; groups. Applicants use the term clan to describe the GPCRs, as they embrace
gd; a group of families for which there are indications of evolutionary
gd; relationship, but between which there is no statistically significant
gd; similarity in sequence [1, 2]. The currently known clan members include the
gd; rhodopsin-like GPCRs, the secretin-like GPCRs, the cAMP receptors, the fungal
gd; mating pheromone receptors, and the metabotropic glutamate receptor family.
gd; The rhodopsin-like GPCRs themselves represent a widespread protein family
gd; that includes hormone, neurotransmitter and light receptors, all of
gd; which transduce extracellular signals through interaction with guanine
gd; nucleotide-binding (G) proteins. Although their activating ligands vary
gd; widely in structure and character, the amino acid sequences of the
gd; receptors are very similar and are believed to adopt a common structural
gd; framework which may comprise 7 transmembrane (TM) helices [3-5].
gd; Vasopressin and oxytocin are members of the neurohypophyseal hormone family
gd; found in all mammalian species [6]. They are present in high levels in the
gd; posterior pituitary. Vasopressin has an essential role in the control of
gd; the water content of the body, acting in the kidney to increase water and
gd; sodium absorption [6]. In higher concentrations, vasopressin stimulates
gd; contraction of vascular smooth muscle, stimulates glycogen breakdown in the
gd; liver, induces platelet activation, and evokes release of corticotrophin
gd; from the anterior pituitary [6]. Vasopressin and its analogues are used
gd; clinically to treat diabetes insipidus [6].
gd; The V2 receptor is found in high levels in the osmoregulatory epithelia of
gd; the terminal urinary tract, where it stimulates water reabsorption [6]. It
gd; is also present in lower levels in the endothelium and blood vessels of some
gd; species, where it induces vasodilation [6]. In the CNS, binding sites are
gd; found in the subiculum, with lower levels in caudate-putamen and islands
gd; of Calleja [6]. The receptor is involved in an effector pathway that forms
gd; cAMP through activation of Gs [6].
gd; VASOPRSNV2R is an 8-element fingerprint that provides a signature for
gd; vasopressin V2 receptors. The fingerprint was derived from an initial
gd; alignment of 4 sequences: the motifs were drawn from short conserved
gd; sections spanning the full alignment length, focusing on those regions
gd; that characterise the vasopressin V2 receptors but distinguish them from
gd; the rest of the vasopressin family - motifs 1 and 2 reside at the N-terminus;
gd; motif 3 spans the first cytoplasmic loop; motif 4 spans the second
gd; cytoplasmic loop; motifs 5 and 6 span the third cytoplasmic loop; and
gd; motifs 7 and 8 reside at the C-terminus. A single iteration on OWL30.1 was
gd; required to reach convergence, no further sequences being identified
gd; beyond the starting set.
fc; VASOPRSNV2R6
fl; 20
ft; Vasopressin V2 receptor motif VI-2
fd; RAGRRRRGHRTGSPSEGAHV (SEQ ID NO: 140)    O88721    V2R_RAT      243  2
fd; RAGRRRRGRRTGSPSEGAHV (SEQ ID NO: 141)              V2R_PIG      243  2
fd; RAGGHRGGRRAGSPREGARV (SEQ ID NO: 142)              V2R_HUMAN    242  2
fd; RPGGRRRGRRTGSPGEGAHV (SEQ ID NO: 143)    O77808                 243  2
fd; RAGGCRGGHRTGSPSEGARV (SEQ ID NO: 144)                           242  2

TABLE 1-continued (A) Examples of signature motifs identified in putative proteins resulting from TTV-HD transcripts and full-length genomes

```
fd;   RAGGPRRGCRPGSPAEGARV (SEQ ID NO: 145)            V2R_BOVIN                242    2
gc;   VASOPRSNV1BR
gx;   PR00897
gn;   COMPOUND (9)
ga;   15-APR-1998; UPDATE 07-JUN-1999
gt;   Vasopressin V1B receptor signature
gp;   PRINTS; PR00237 GPCRRHODOPSN; PR00247 GPCRCAMP; PR00248 GPCRMGR
gp;   PRINTS; PR00249 GPCRSECRETIN; PR00250 GPCRSTE2; PR00899 GPCRSTE3
gp;   PRINTS; PR00251 BACTRLOPSIN
gp;   PRINTS; PR00896 VASOPRESSINR
gp;   PRINTS; PR00752 VASOPRSNV1AR; PR00898 VASOPRSNV2R; PR00665 OXYTOCINR
gp;   INTERPRO; IPR000628
gr;   1. ATTWOOD, T.K. AND FINDLAY, J.B.C.
gr;   Fingerprinting G protein-coupled receptors.
gr;   PROTEIN ENG. 7 (2) 195-203 (1994).
gr;   2. ATTWOOD, T.K. AND FINDLAY, J.B.C.
gr;   G protein-coupled receptor fingerprints.
gr;   7TM, VOLUME 2, EDS. G. VRIEND AND B. BYWATER (1993).
gr;   3. BIRNBAUMER, L.
gr;   G proteins in signal transduction.
gr;   ANNU. REV. PHARMACOL. TOXICOL. 30 675-705 (1990).
gr;   4. CASEY, P.J. AND GILMAN, A.G.
gr;   G protein involvement in receptor-effector coupling.
gr;   J. BIOL. CHEM. 263 (6) 2577-2580 (1988).
gr;   5. ATTWOOD, T.K. AND FINDLAY, J.B.C.
gr;   Design of a discriminating fingerprint for G protein-coupled receptors.
gr;   PROTEIN ENG. 6 (2) 167-176 (1993).
gr;   6. WATSON, S. AND ARKINSTALL, S.
gr;   Vasopressin and oxytocin.
gr;   IN THE G PROTEIN-LINKED RECEPTOR FACTSBOOK, ACADEMIC PRESS, 1994, PP. 284-291.
gd;   VASOPRSNV1BR is a 9-element fingerprint that provides a signature for
gd;   vasopressin V1B receptors. The fingerprint was derived from an initial
gd;   alignment of 3 sequences: the motifs were drawn from short conserved
gd;   sections spanning the full alignment length, focusing on those regions
gd;   that characterise the vasopressin V1B receptors but distinguish them from
gd;   the rest of the vasopressin family - motif 1 lies at the N-terminus; motif
gd;   2 lies in the second cytoplasmic loop; motif 3 lies in the second external
gd;   loop; motifs 4 and 5 span the third cytoplasmic loop; motif 6 lies in the
gd;   third external loop; and motifs 7-9 reside in the C-terminal domain. A
gd;   single iteration on OWL30.1 was required to reach convergence, no further
gd;   sequences being identified beyond the starting set.
fc;   VASOPRSNV1BR4
fl;   20
ft;   Vasopressin V1B receptor motif IV-2
fd;   TQAWRVGGGWRTWDRPSPS (SEQ ID NO: 146)              V1BR_HUMAN               234   48
fd;   TQAGRERRGWRTWDKSSSS (SEQ ID NO: 147)              V1BR_RAT                 234   48
```

TABLE 1-continued (A) Examples of signature motifs identified in putative proteins resulting from TTV-HD transcripts and full-length genomes

```
MELANIN-CONCENTRATING HORMONE 2 RECEPTOR SIGNATURE

HMMER 2.3.2 (Oct 2003)
Copyright © 1992-2003 HHMI/Washington University School of Medicine
Freely distributed under the GNU General Public License (GPL)
HMM file: prints.hmm
sequence file: uro742rp.133
MCH2RECEPTOR_5: domain 1 of 1, from 69 to 86: score 5.9, E = 7.1
           *->LvqPFRLtrWRtRYKtIRin<-*  (SEQ ID NO: 147)
             F +t+WRt + + n
uro742rp.1    69    --RPFCITKWRTSFLFFKNN              86   (SEQ ID NO: 147)
gc; MCH2RECEPTOR
gx; PR01784
gn; COMPOUND (9)
ga; 25-SEP-2002
gt; Melanin-concentrating hormone 2 receptor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; PRINTS; PR01507 MCH1RECEPTOR; PR01783 MCHRECEPTOR
gr; 1. ATTWOOD, T.K. AND FINDLAY, J.B.C.
gr; Fingerprinting G protein-coupled receptors.
gr; PROTEIN ENG. 7 (2) 195-203 (1994).
gr; 2. ATTWOOD, T.K. AND FINDLAY, J.B.C.
gr; G protein-coupled receptor fingerprints.
gr; 7TM, VOLUME 2, EDS. G. VRIEND AND B. BYWATER (1993).
gr; 3. BIRNBAUMER, L.
gr; G proteins in signal transduction.
gr; ANNU. REV. PHARMACOL. TOXICOL. 30 675-705 (1990).
gr; 4. CASEY, P.J. AND GILMAN, A.G.
gr; G protein involvement in receptor-effector coupling.
gr; J. BIOL. CHEM. 263 (6) 2577-2580 (1988).
gr; 5. ATTWOOD, T.K. AND FINDLAY, J.B.C.
gr; Design of a discriminating fingerprint for G protein-coupled receptors.
gr; PROTEIN ENG. 6 (2) 167-176 (1993).
gr; 6. CHAMBERS, J., AMES, R.S., BERGSMA, D., MUIR, A., FITZGERALD, L.R.,
gr; HERVIEU, G., DYTKO, G.M., FOLEY, J.J., MARTIN, J., LIU, W.S., PARK, J.,
gr; ELLIS, C., GANGULY, S., KONCHAR, S., CLUDERAY, J., LESLIE, R., WILSON, S.
gr; AND SARAU, H.M.
gr; Melanin-concentrating hormone is the cognate ligand for the orphan G
gr; protein-coupled receptor SLC-1.
gr; NATURE 400 261-265 (1999).
gr; 7. SAITO, Y., NOTHACKER, H.-P., WANG, Z., LIN, S.H.S., LESLIE, F. AND
gr; CIVELLI, O.
gr; Molecular characterization of the melanin-concentrating-hormone receptor.
gr; NATURE 400 265-269 (1999).
gr; 8. SAITO, Y., NOTHACKER, H.-P. AND CIVELLI, O.
gr; Melanin-concentrating hormone receptor: an orphan receptor fits the key.
gr; TRENDS ENDOCRINOL. METAB. 11 (8) 299-303 (2000).
gr; 9. HILL, J., DUCKWORTH, M., MURDOCK, P., RENNIE, G., SABIDO-DAVID, C., AMES,
```

TABLE 1-continued (A) Examples of signature motifs identified in putative proteins resulting from TTV-HD transcripts and full-length genomes gr; R.S., SZEKERES, P., WILSON, S., BERGSMA, D.J., GLOGER, I.S., LEVY, D.S.,
gr; CHAMBERS, J.K. AND MUIR, A.I.
gr; Molecular cloning and functional characterization of MCH2, a novel human MCH
gr; receptor.
gr; J.BIOL.CHEM. 276(23) 20125-20129 (2001).
gd; G protein-coupled receptors (GPCRs) constitute a vast protein family that
gd; encompasses a wide range of functions (including various autocrine,
gd; para-crine and endocrine processes). They show considerable diversity at the
gd; sequence level, on the basis of which they may be separated into distinct
gd; groups. Applicants use the term clan to describe the GPCRs, as they embrace
gd; a group of families for which there are indications of evolutionary
gd; relationship, but between which there is no statistically significant
gd; similarity in sequence [1,2]. The currently known clan members include the
gd; rhodopsin-like GPCRs, the secretin-like GPCRs, the cAMP receptors, the fungal
gd; mating pheromone receptors, and the metabotropic glutamate receptor family.
gd; The rhodopsin-like GPCRs themselves represent a widespread protein family
gd; that includes hormone, neurotransmitter and light receptors, all of
gd; which transduce extracellular signals through interaction with guanine
gd; nucleotide-binding (G) proteins. Although their activating ligands vary
gd; widely in structure and character, the amino acid sequences of the
gd; receptors are very similar and are believed to adopt a common structural
gd; framework which may comprise 7 transmembrane (TM) helices [3-5].
gd; Melanin-concentrating hormone (MCH) is a cyclic peptide originally
gd; identified in teleost fish [6,7]. In fish, MCH is released from the
gd; pituitary and causes lightening of skin pigment cells through pigment
gd; aggregation [6,8]. In mammals, MCH is predominantly expressed in the
gd; hypothalamus, and functions as a neurotransmitter in the control of a range
gd; of functions [8]. A major role of MCH is thought to be in the regulation of
gd; feeding: injection of MCH into rat brains stimulates feeding; expression of
gd; MCH is upregulated in the hypothalamus of obese and fasting mice; and mice
gd; lacking MCH are lean and eat less [6]. MCH and alpha melanocyte-stimulating
gd; hormone (alpha-MSH) have antagonistic effects on a number of physiological
gd; functions. Alpha-MSH darkens pigmentation in fish and reduces feeding in
gd; mammals, whereas MCH increases feeding [6,8].
gd; Two G protein-coupled receptors, MCH1 and MCH2, have recently been
gd; identified as receptors for the hormone.
gd; The expression profile of MCH2 is similar to that of MCH1, with highest
gd; levels being found in the brain. However, expression of MCH2 is
gd; significantly lower than MCH1 in the pituitary, hypothalamus, locus
gd; coeruleus, medulla oblongata, and cerebellum [9]. Binding of MCH to the
gd; receptor causes a pertussis toxin-insensitive increase in intracellular
gd; calcium, suggesting coupling to Gq proteins [9].
gd; MCH2RECEPTOR is a 9-element fingerprint that provides a signature for the
gd; melanin-concentrating hormone 2 receptor. The fingerprint was derived from
gd; an initial alignment of 5 sequences: the motifs were drawn from conserved
gd; sections within N- and C-terminal and loop regions, focusing on those areas
gd; of the alignment that characterise the MCH2 receptors but distinguish them
gd; from the rest of the MCH receptor family - motifs 1 and 2 span the
gd; N-terminus; motif 3 encodes the first cytoplasmic loop; motif 4 lies in the
gd; first external loop; motif 5 spans the second cytoplasmic loop, leading into TABLE 1-continued (A) Examples of signature motifs identified in putative proteins resulting from TTV-HD transcripts and full-length genomes

```
gd; TM domain 4; motif 6 resides in the second external loop; motif 7 spans the
gd; third cytoplasmic loop; motif 8 is located at the N-terminus of TM domain 7;
gd; and motif 9 encodes the C-terminus. Two iterations on SPTR40_22f were
gd; required to reach convergence, at which point a true set which may comprise
gd; 6 sequences was identified.
fc; MCH2RECEPTOR5
fl; 20
ft; Melanin-concentrating hormone 2 receptor motif V-2 (SEQ ID NO: 150)
fd; LVQPFRLTSWRTRYKTIRIN   Q8MJ88    135   29 (SEQ ID NO: 150)
fd; LVQPFRLTRWRTRYKTIRIN   Q969V1    135   29 (SEQ ID NO: 237)
fd; LVQPFRLTRWRTRYKTIRIN   Q9BXA8    135   29 (SEQ ID NO: 237)
fd; LVQPFRLTSWRTRYKTIRIN   Q8SQ54    135   29 (SEQ ID NO: 150)
fd; LVQPFRLTSWRTRYKTIRIN   Q8MIN7    135   29 (SEQ ID NO: 150)
fd; LVQPFRLTSWRTRYKTIRIN   Q8MIP5    135   29 (SEQ ID NO: 150)
PROSTANOID EP1 RECEPTOR SIGNATURE HMMER 2.3.2 (Oct 2003)
Copyright © 1992-2003 HHMI/Washington University School of Medicine
Freely distributed under the GNU General Public License (GPL)
-------------------------------------------------------------
HMM file: prints.hmm
Sequence file: uro742rev.107r
PRSTNOIDEP1R_4: domain 1 of 1, from 1 to 18: score 8.4, E = 4.7
          *->isLGPpGGWRgAL.LAGL<-*  (SEQ ID NO: 151)
             ++LGP GG R+ L +AG
uro742rev.     1 MGLGPSGGNRKTLfIAGK                  18 (SEQ ID NO: 152)
PRSTNOIDEP1R_4: domain 1 of 1, from 1 to 18: score 8.4, E = 4.7
          *->isLGPpGGWRgAL.LAGL<-*  (SEQ ID NO: 151)
             ++LGP GG R+ L +AG
zc37.B8.10     1 MGLGPSGGNRKTLfIAGK                  18 (SEQ ID NO: 152)
gc; PRSTNOIDEP1R
gx; PR00580
gn; COMPOUND (7)
ga; 25-SEP-1996; UPDATE 07-JUN-1999
gt; Prostanoid EP1 receptor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; PRINTS; PR00428 PROSTAGLNDNR; PR00581 PRSTNOIDEP2R; PR00582
PRSTNOIDEP3R
gp; PRINTS; PR00583 PRSTNOIDE31R; PR00584 PRSTNOIDE32R; PR00585
PRSTNOIDE33R
gp; PRINTS; PR00586 PRSTNOIDEP4R; PR00854 PRSTNOIDDPR; PR00855
PRSTNOIDFPR
gp; PRINTS; PR00856 PRSTNOIDIPR
gp; INTERPRO; IPR000708
gr; 1. ATTWOOD, T.K. AND FINDLAY, J.B.C.
gr; Fingerprinting G protein-coupled receptors.
gr; PROTEIN ENG. 7 (2) 195-203 (1994).
gr; 2. ATTWOOD, T.K. AND FINDLAY, J.B.C.
```

TABLE 1-continued (A) Examples of signature motifs identified in putative proteins resulting from TTV-HD transcripts and full-length genomes

```
gr;  G protein-coupled receptor fingerprints.
gr;  7TM, VOLUME 2, EDS. G. VRIEND AND B. BYWATER (1993).
gr;  3. BIRNBAUMER, L.
gr;  G proteins in signal transduction.
gr;  ANNU. REV. PHARMACOL. TOXICOL. 30 675-705 (1990).
gr;  4. CASEY, P.J. AND GILMAN, A.G.
gr;  G protein involvement in receptor-effector coupling.
gr;  J. BIOL. CHEM. 263 (6) 2577-2580 (1988).
gr;  5. ATTWOOD, T.K. AND FINDLAY, J.B.C.
gr;  Design of a discriminating fingerprint for G protein-coupled receptors.
gr;  PROTEIN ENG. 6 (2) 167-176 (1993).
gr;  6. WATSON, S. AND ARKINSTALL, S.
gr;  Prostanoids.
gr;  IN THE G PROTEIN-LINKED RECEPTOR FACTSBOOK, ACADEMIC PRESS, 1994, PP. 239-251.
gd;  G protein-coupled receptors (GPCRs) constitute a vast protein family that
gd;  encompasses a wide range of functions (including various autocrine, para-
gd;  crine and endocrine processes). They show considerable diversity at the
gd;  sequence level, on the basis of which they may be separated into distinct
gd;  groups. Applicants use the term clan to describe the GPCRs, as they embrace
gd;  a group of families for which there are indications of evolutionary
gd;  relationship, but between which there is no statistically significant
gd;  similarity in sequence [1,2]. The currently known clan members include the
gd;  rhodopsin-like GPCRs, the secretin-like GPCRs, the cAMP receptors, the fungal
gd;  mating pheromone receptors, and the metabotropic glutamate receptor family.
gd;  The rhodopsin-like GPCRs themselves represent a widespread protein family
gd;  that includes hormone, neurotransmitter and light receptors, all of
gd;  which transduce extracellular signals through interaction with guanine
gd;  nucleotide-binding (G) proteins. Although their activating ligands vary
gd;  widely in structure and character, the amino acid sequences of the
gd;  receptors are very similar and are believed to adopt a common structural
gd;  framework which may comprise 7 transmembrane (TM) helices [3-5].
gd;  Prostanoids (prostaglandins (PG) and thromboxanes (TX)) mediate a wide
gd;  variety of actions and play important physiological roles in the cardio-
gd;  vascular and immune systems, and in pain sensation in peripheral systems
gd;  [6]. PGI2 and TXA2 have opposing actions, involving regulation of the
gd;  interaction of platelets with the vascular endothelium, while PGE2, PGI2
gd;  and PGD2 are powerful vasodilators and potentiate the action of various
gd;  autocoids to induce plasma extravasation and pain sensation. To date,
gd;  evidence for at least 5 classes of prostanoid receptor has been obtained.
gd;  However, identification of subtypes and their distribution is hampered by
gd;  expression of more than one receptor within a tissue, coupled with poor
gd;  selectivity of available agonists and antagonists.
gd;  EP1 receptors mediate contraction of gastrointestinal smooth muscles in
gd;  various species, and relaxation of airway and uterine smooth muscles,
gd;  especially in rodents [6]. The receptors activate the phosphoinositide
gd;  pathway via a pertussis-toxin-insensitive G protein, probably of the
gd;  Gq/G11 class [6].
gd;  PRSTNOIDEP1R is a 7-element fingerprint that provides a signature for the
gd;  prostanoid EP1 receptors. The fingerprint was derived from an initial
gd;  alignment of 2 sequences: the motifs were drawn from conserved sections
```

TABLE 1-continued (A) Examples of signature motifs identified in putative proteins resulting from TTV-HD transcripts and full-length genomes

```
gd; within either loop or N- and C-terminal regions, focusing on those areas of
gd; the alignment that characterise the prostanoid EP1 receptors but distinguish
gd; them from the rest of the rhodopsin-like superfamily - motif 1 lies at the
gd; N-terminus; motif 2 spans the first cytoplasmic loop; motif 3 spans the
gd; first external loop; motif 4 lies in the second external loop; motif 5 lies
gd; in the third cytoplasmic loop; and motifs 6 and 7 span the C-terminus. A
gd; single iteration on OWL28.2 was required to reach convergence, no further
gd; sequences being identified beyond the starting set.
gd;
fc; PRSTNOIDEP1R4
fl; 17
ft; Prostanoid EP1 receptor motif IV-2
fd; ISLGPRGGWRQALLAGL (SEQ ID NO: 153)        PE21_MOUSE              192             73
fd; ISLGPPGGWRQALLAGL (SEQ ID NO: 153)        PE21_RAT                192             73
fd; IGLGPPGGWRQALLAGL (SEQ ID NO: 154)        PE21_HUMAN              190             73
CYCLINKINASE
```

```
HMMER 2.3.2 (Oct 2003)
Copyright © 1992-2003 HHMI/Washington University School of Medicine
Freely distributed under the GNU General Public License (GPL)
HMM file: prints.hmm
Sequence file: rheu.cd.215rev.1.736
CYCLINKINASE_3: domain 1 of 1, from 662 to 676: score 9.3, E = 3.1
                      *->EWRslGvqqslGWvh<-* (SEQ ID NO: 157)
                       E + Gvqq l Wvh
rheu.cd.21     662     ESSRFGVQQRLPWVH                    676 (SEQ ID NO: 158)
gc; CYCLINKINASE
gx; PR00296
gn; COMPOUND (4)
ga; 07-OCT-1994; UPDATE 07-JUN-1999
gt; Cyclin-dependent kinase regulatory subunit signature
gp; INTERPRO; IPR000789
gp; PROSITE; PS00944 CKS_1; PS00945 CKS_2
gp; PFAM; PF01111 CKS
gr; 1. BRIZUELA, L., DRAETTA, G. AND BEACH, D.
gr; p13suc1 acts in the fission yeast cell division cycle as a component of the
gr; p34cdc2 protein kinase.
gr; EMBO J. 6 3507-3514 (1987).
gr; 2. PARGE, H.E., ARVAI, A.S., MURTARI, D.J., REED, S.I. AND TAINER, J.A.
gr; Human CksHs2 atomic structure: a role for its hexameric assembly in cell
gr; cycle control.
gr; SCIENCE 262 387-395 (1993).
gr; 3. TANG, Y. AND REED, S.I.
gr; The Cdk-associated protein Cks1 functions both in G1 and G2 in Saccharomyces
gr; cerevisiae.
gr; GENES DEV. 7 822-832 (1993).
gd; In eukaryotes, cyclin-dependent protein kinases interact with cyclins to
gd; regulate cell cycle progression, and are required for the G1 and G2 stages
gd; of cell division [1]. The proteins bind to a regulatory subunit (cyclin-
gd; dependent kinase regulatory subunit, or CKS), which is essential for their
```

TABLE 1-continued (A) Examples of signature motifs identified in putative proteins resulting from TTV-HD transcripts and full-length genomes gd; function [2]. The regulatory subunits exist as hexamers, formed by the
gd; symmetrical assembly of 3 interlocked homodimers, creating an unusual
gd; 12-stranded beta-barrel structure [2]. Through the barrel centre runs a
gd; 12A diameter tunnel, lined by 6 exposed helix pairs [3]. Six kinase units
gd; may be modelled to bind the hexameric structure, which may thus act as a
gd; hub for cyclin-dependent protein kinase multimerisation [2,3].
gd; CYCLINKINASE is a 4-element fingerprint that provides a signature for
gd; cyclin-dependent kinase regulatory subunits. The fingerprint was derived
gd; from an initial alignment of 4 sequences: the motifs were drawn from
gd; conserved regions encompassing virtually the full alignment length, motifs
gd; 1, 2 and 4 spanning the regions encoded by PROSITE patterns CKS_1 (PS00944)
gd; and CKS_2 (PS00945). Two iterations on OWL24.0 were required to reach
gd; convergence, at which point a true set which may comprise 5 sequences was
gd; identified
fc; CYCLINKINASE3
fl; 15
ft; Cyclin-dependent kinase regulatory subunit motif III-2
fd; EWRRLGVQQSLGWVH (SEQ ID NO: 159)    CKS2_XENLA        42        7
fd; EWRNLGVQQSQGWVH (SEQ ID NO: 160)    CKS1_HUMAN        42        7
fd; EWRRLGVQQSLGWVH (SEQ ID NO: 159)    CKS2_HUMAN        42        7
fd; EWRRLGVQQSLGWVH (SEQ ID NO: 159)    CKS2_MOUSE        42        7
fd; EWRSIGVQQSHGWIH (SEQ ID NO: 161)    CKS1_PATVU        42        7
fd; EWRSIGVQQSRGWIH (SEQ ID NO: 162)    CKS1_DROME        41        7
fd; EWRSIGVQQSQGWVH (SEQ ID NO: 163)    CKS1_PHYPO        42        7
fd; EWRQLGVQQSQGWVH (SEQ ID NO: 164)    CKS1_LEIME        67        7
fd; EWRAIGVQQSRGWVH (SEQ ID NO: 165)    O23249            40        7
fd; EWRGLGITQSLGWQH (SEQ ID NO: 166)    O60191            73        16
fd; EWRGLGITQSLGWEM (SEQ ID NO: 167)    CKS1_SCHPO        69        16
fd; EWRGLGITQSLGWEH (SEQ ID NO: 168)    CKS1_YEAST        73        16
fd; EWRSLGIQQSPGWMH (SEQ ID NO: 169)    CKS1_CAEEL        44        7
PEROXISOME PROLIFERATOR-ACTIVATED RECEPTOR (1C NUCLEAR RECEPTOR) SIGNATURE HMMER 2.3.2 (Oct 2003)
Copyright © 1992-2003 HHMI/Washington University School of Medicine
Freely distributed under the GNU General Public License (GPL)
HMM file: prints.hmm
sequence file: rheu.cd.215rev.1.736
PROXISOMEPAR_7: domain 1 of 1, from 721 to 733: score 8.0, E = 5.7
                *->KtEtdasLHPLLq<-* (SEQ ID NO: 170)
                   K + sLHPLL
rheu.cd.21    721  KVQAGHSLHPLLS                         733 (SEQ ID NO: 171)
gc; PROXISOMEPAR
gx; PR01288
gn; COMPOUND (7)
ga; 19-FEB-2000
gt; Peroxisome proliferator-activated receptor (1C nuclear receptor) signature TABLE 1-continued (A) Examples of signature motifs identified in putative proteins resulting from TTV-HD transcripts and full-length genomes

```
gp; PRINTS; PR00398 STRDHORMONER; PR00047 STROIDFINGER
gp; PRINTS; PR01289 PROXISOMPAAR; PR01290 PROXISOMPABR; PR01291
PROXISOMPAGR
gr; 1. NUCLEAR RECEPTORS NOMENCLATURE COMMITTEE
gr; A unified nomenclature system for the nuclear receptor superfamily.
gr; CELL 97 161-163 (1999).
gr; 2. NISHIKAWA, J-I., KITAURA, M., IMAGAWA, M. AND NISHIHARA, T.
gr; Vitamin D receptor contains multiple dimerisation interfaces that
gr; are functionally different.
gr; NUCLEIC ACIDS RES. 23 (4) 606-611 (1995).
gr; 3. DE VOS, P., SCHMITT, J., VERHOEVEN, G. AND STUNNENBERG, G.
gr; Human androgen receptor expressed in HeLa cells activates transcription
gr; in vitro.
gr; NUCLEIC ACIDS RES. 22 (7) 1161-1166 (1994).
gr; 4. KREY, G., KELLER, H., MAHFOUDI, A., MEDIN, J., OZATO, K., DREYER, C.
gr; AND WAHLI, W.
gr; Xenopus peroxisome proliferator activated receptors: genomic organization,
gr; response element recognition, heterodimer formation with retinoid X receptor
gr; and activation by fatty acids.
gr; J. STEROID BIOCHEM. MOL. BIOL. 47 65-73 (1993).
gr; 5. DREYER, C., KREY, G., KELLER, H., GIVEL, F., HELFTENBEIN, G.
gr; AND WAHLI, W.
gr; Control of the peroxisomal beta-oxidation pathway by a novel family
gr; of nuclear hormone receptors.
gr; CELL 68 879-887 (1992).
gd; steroid or nuclear hormone receptors (NRs) constitute an important super-
gd; family of transcription regulators that are involved in widely diverse
gd; physiological functions, including control of embryonic development, cell
gd; differentiation and homeostasis [1]. Members of the superfamily include the
gd; steroid hormone receptors and receptors for thyroid hormone, retinoids,
gd; 1,25-dihydroxy-vitamin D3 and a variety of other ligands. The proteins
gd; function as dimeric molecules in nuclei to regulate the transcription of
gd; target genes in a ligand-responsive manner [2,3]. In addition to C-terminal
gd; ligand-binding domains, these nuclear receptors contain a highly-conserved,
gd; N-terminal zinc-finger that mediates specific binding to target DNA
gd; sequences, termed ligand-responsive elements. In the absence of ligand,
gd; steroid hormone receptors are thought to be weakly associated with nuclear
gd; components; hormone binding greatly increases receptor affinity.
gd; NRs are extremely important in medical research, a large number of them
gd; being implicated in diseases such as cancer, diabetes, hormone resistance
gd; syndromes, etc. [1]. While several NRs act as ligand-inducible transcription
gd; factors, many do not yet have a defined ligand and are accordingly termed
gd; "orphan" receptors. During the last decade, more than 300 NRs have been
gd; described, many of which are orphans, which cannot easily be named due to
gd; current nomenclature confusions in the literature. However, a new system
gd; has recently been introduced in an attempt to rationalise the increasingly
gd; complex set of names used to describe superfamily members [1].
gd; Peroxisome proliferator-activated receptors (PPAR) are ligand-activated
gd; transcription factors that belong to the nuclear hormone receptor
gd; superfamily. Three cDNAs encoding PPARs have been isolated from Xenopus
```

TABLE 1-continued (A) Examples of signature motifs identified in putative proteins resulting from TTV-HD transcripts and full-length genomes gd; laevis: xPPAR alpha, beta and gamma [4]. All three xPPARs appear to be
gd; activated by both synthetic peroxisome proliferators and naturally occurring
gd; fatty acids, suggesting a common mode of action for all members of this
gd; subfamily of receptors [4]. Furthermore, the multiplicity of the receptors
gd; suggests the existence of hitherto unknown cellular signalling pathways for
gd; xenobiotics and putative endogenous ligands [5].
gd; PROXISOMEPAR is a 7-element fingerprint that provides a signature for
gd; peroxisome proliferator-activated receptors. The fingerprint was derived
gd; from an initial alignment of 11 sequences: the motifs were drawn from
gd; conserved regions spanning virtually the full alignment length, focusing on
gd; those sections that characterise the PPAR family but distinguish it from the
gd; rest of the steroid hormone receptor superfamily - motifs 1 and 2 lie
gd; C-terminal to the zinc finger domain; and motifs 3-7 span the putative
gd; ligand-binding domain. Three iterations on SPTR37_10f were required to
gd; reach convergence, at which point a true set which may comprise 19 sequences
gd; was identified. A single partial match was also found, the Xenopus beta
gd; peroxisome proliferator activated receptor, PPAS_XENLA, which fails to
gd; match the first motif.
fc; PROXISOMEPAR7
fl; 13
ft; Peroxisome proliferator-activated receptor motif VII-3
fd; KTETDMSLHPLLQ (SEQ ID NO: 172) O18924       486    16
fd; KTETDMSLHPLLQ (SEQ ID NO: 172) Q15832       486    16
fd; KTETDMSLHPLLQ (SEQ ID NO: 172) PPAT_HUMAN   456    16
fd; KTETDMSLHPLLQ (SEQ ID NO: 172) O62807       485    16
fd; KTETDMSLHPLLQ (SEQ ID NO: 172) O18971       486    16
fd; KTETDMSLHPLLQ (SEQ ID NO: 172) PPAT_RABIT   456    16
fd; KTETDMSLHPLLQ (SEQ ID NO: 172) O77815       485    16
fd; KTETDMSLHPLLQ (SEQ ID NO: 172) O88275       456    16
fd; KTETDMSLHPLLQ (SEQ ID NO: 172) PPAT_MOUSE   456    16
fd; KTETDMSLHPLLQ (SEQ ID NO: 172) Q15180       456    16
fd; KTEADMCLHPLLQ (SEQ ID NO: 173) PPAR_XENLA   487    16
fd; KTETDAALHPLLQ (SEQ ID NO: 174) PPAR_XENLA   458    16
fd; KTESDAALHPLLQ (SEQ ID NO: 175) PPAR_HUMAN   455    16
fd; KTESDAALHPLLQ (SEQ ID NO: 175) PPAR_RAT     449    16
fd; KTESDAALHPLLQ (SEQ ID NO: 175) PPAR_MOUSE   449    16
fd; KTETETSLHPLLQ (SEQ ID NO: 176) PPAS_HUMAN   449    16
fd; KTESDAALHPLLQ (SEQ ID NO: 177) PPAR_CAVPO   422    16
fd; KTESETLLHPLLQ (SEQ ID NO: 178) PPAS_MOUSE   448    15
fd; KTESETLLHPLLQ (SEQ ID NO: 178) Q62879       421    16
MUSCARINIC M1 RECEPTOR SIGNATURE                         421    16

HMMER 2.3.2 (Oct 2003)
Copyright © 1992-2003 HHMI/Washington University School of Medicine
Freely distributed under the GNU General Public License (GPL)
HMM file: prints.hmm
Sequence file: rheu.cd.215rev.1.736
MUSCRINICMR_4: domain 1 of 2, from 161 to 177: score 0.9, E = 98
          *->KmPmvDpEAgAPtKgPPk<-* (SEQ ID NO: 179)
             K P vD q t qPP TABLE 1-continued (A) Examples of signature motifs identified in putative proteins resulting from TTV-HD transcripts and full-length genomes

```
rheu.cd.21      161    KHPTVDFMVQINT-QPPF                 177 (SEQ ID NO: 180)
gc; MUSCRINICM1R
gx; PR00538
gn; COMPOUND (6)
ga; 01-JUN-1996; UPDATE 07-JUN-1999
gt; Muscarinic M1 receptor signature
gp; PRINTS; PR00237 GPCRRHODOPSN; PR00247 GPCRCAMP; PR00248 GPCRMGR
gp; PRINTS; PR00249 GPCRSECRETIN; PR00250 GPCRSTE2; PR00899 GPCRSTE3
gp; PRINTS; PR00251 BACTRLOPSIN
gp; PRINTS; PR00243 MUSCARINICR; PR00539 MUSCRINICM2R; PR00540
MUSCRINICM3R
gp; PRINTS; PR00541 MUSCRINICM4R; PR00542 MUSCRINICM5R
gp; INTERPRO; IPR002228
gr; 1. ATTWOOD, T.K. AND FINDLAY, J.B.C.
gr; Fingerprinting G protein-coupled receptors.
gr; PROTEIN ENG. 7 (2) 195-203 (1994).
gr; 2. ATTWOOD, T.K. AND FINDLAY, J.B.C.
gr; G protein-coupled receptor fingerprints.
gr; 7TM, VOLUME 2, EDS. G. VRIEND AND B. BYWATER (1993).
gr; 3. BIRNBAUMER, L.
gr; G proteins in signal transduction.
gr; ANNU. REV. PHARMACOL. TOXICOL. 30 675-705 (1990).
gr; 4. CASEY, P.J. AND GILMAN, A.G.
gr; G protein involvement in receptor-effector coupling.
gr; J. BIOL. CHEM. 263 (6) 2577-2580 (1988).
gr; 5. ATTWOOD, T.K. AND FINDLAY, J.B.C.
gr; Design of a discriminating fingerprint for G protein-coupled receptors.
gr; PROTEIN ENG. 6 (2) 167-176 (1993).
gr; 6. KERLAVAGE, A.R., FRASER, C.M., CHUNG, F-Z. AND VENTER, J.C.
gr; Molecular structure and evolution of adrenergic and cholinergic receptors.
gr; PROTEINS 1 287-301 (1986).
gr; 7. WATSON, S. AND ARKINSTALL, S.
gr; Acetylcholine.
gd; IN THE G PROTEIN-LINKED RECEPTOR FACTSBOOK, ACADEMIC PRESS, 1994, PP. 7-18.
gd; G protein-coupled receptors (GPCRs) constitute a vast protein family that
gd; encompasses a wide range of functions (including various autocrine, para-
gd; crine and endocrine processes). They show considerable diversity at the
gd; sequence level, on the basis of which they may be separated into distinct
gd; groups. Applicants use the term clan to describe the GPCRs, as they embrace
gd; a group of families for which there are indications of evolutionary
gd; relationship, but between which there is no statistically significant
gd; similarity in sequence [1, 2]. The currently known clan members include the
gd; rhodopsin-like GPCRs, the secretin-like GPCRs, the cAMP receptors, the fungal
gd; mating pheromone receptors, and the metabotropic glutamate receptor family.
gd; The rhodopsin-like GPCRs themselves represent a widespread protein family
gd; that includes hormone, neurotransmitter and light receptors, all of
gd; which transduce extracellular signals through interaction with guanine
gd; nucleotide-binding (G) proteins. Although their activating ligands vary
gd; widely in structure and character, the amino acid sequences of the
gd; receptors are very similar and are believed to adopt a common structural
```

TABLE 1-continued (A) Examples of signature motifs identified in putative proteins resulting from TTV-HD transcripts and full-length genomes

```
gd;  framework which may comprise 7 transmembrane (TM) helices [3-5].
gd;  The muscarinic acetylcholine receptors, present in the central nervous
gd;  system, spinal cord motoneurons and autonomic preganglia, modulate a
gd;  variety of physiological functions, including airway, eye and intestinal
gd;  smooth muscle contractions; heart rate; and glandular secretions. The
gd;  receptors mediate adenylate cyclase attenuation, calcium and potassium
gd;  channel activation, and phosphatidyl inositol turnover [6]. This diversity
gd;  may result from the occurrence of multiple receptor subtypes (of which 5
gd;  are currently known, designated M1 to M5), which have been classified
gd;  based on observed differences in ligand binding to receptors in membranes
gd;  from several tissues.
gd;  The M1 receptor is found in high levels in neuronal cells of the CNS; it
gd;  is particularly abundant in the cerebral cortex and hippocampus [7]. Its
gd;  distribution largely overlaps with that of M3 and M4 subtypes. In the
gd;  periphery, M1 receptors are found in autonomic ganglia and certain
gd;  secretory glands, and they are also found in cell lines. No truly selective
gd;  agonist has been described [7].
gd;  MUSCRINICM1R is a 6-element fingerprint that provides a signature for the
gd;  muscarinic M1 receptors. The fingerprint was derived from an initial
gd;  alignment of 4 sequences. The motifs were drawn from conserved sections
gd;  within either loop or N- and C-terminal regions, focusing on those areas
gd;  of the alignment that characterise the M1 receptors but distinguish them
gd;  from the rest of the muscarinic receptor family - motif 1 lies at the N-
gd;  terminus; motifs 2-5 span the third cytoplasmic loop; and motif 6 lies
gd;  at the C-terminus. A single iteration on OWL28.0 was required to reach
gd;  convergence, no further sequences being identified beyond the starting set.
fc;  MUSCRINICM1R4
fl;  18
ft;  Muscarinic M1 receptor motif IV-2
fd;  KMPMVDPEAQAPTKQPPR  (SEQ ID NO: 181)     ACM1_HUMAN    303    3
fd;  KMPMVDPEAQAPTKQPPK  (SEQ ID NO: 182)     ACM1_MOUSE    303    3
fd;  KMPMVDSEAQAPTKQPPK  (SEQ ID NO: 183)     ACM1_RAT      303    3
fd;  KMPMVDPEAQAPTKQPPR  (SEQ ID NO: 181)     ACM1_MACMU    303    3
fd;  KMPMVDPEAQAPAKQPPR  (SEQ ID NO: 184)     ACM1_PIG      303    3
METABOTROPIC GAMMA-AMINOBUTYRIC ACID (GABA) TYPE B2 RECEPTOR SIGNATURE transcript zc35s.B3.3e.172:
GABAB2RECPTR_1: domain 1 of 1, from 111 to 129: score 5.9, E = 6.4
                *->LAPGAWGWaRGAPRPPPss<-*  (SEQ ID NO: 185)
                   + P W + P+PPPs+
zc35s.B3.3       111     VGPEQWLFPERKPKPPPSA          129 (SEQ ID NO: 186)
gc;  GABAB2RECPTR
gx;  PR01178
gn;  COMPOUND (13)
ga;  18-SEP-1999
gt;  Metabotropic gamma-aminobutyric acid type B2 receptor signature
gp;  PRINTS; PR00237 GPCRRHODOPSN; PR00247 GPCRCAMP; PR00249
GPCRSECRETIN
gp;  PRINTS; PR00250 GPCRSTE2; PR00899 GPCRSTE3; PR00251 BACTRLOPSIN
gp;  PRINTS; PR00592 CASENSINGR; PR00593 MTABOTROPICR
```

TABLE 1-continued (A) Examples of signature motifs identified in putative proteins resulting from TTV-HD transcripts and full-length genomes gp; PRINTS; PR01176 GABABRECEPTR; PR01177 GABAB1RECPTR
gp; INTERPRO; IPR002457
gr; 1. KAUPMANN, K., HUGGEL, K., HEID, J., FLOR, P.J., BISCHOFF, S., MICKEL,
gr; S.J., MCMASTER, G., ANGST, C., BITTIGER, H., FROESTL, W. AND BETTLER, B.
gr; Expression cloning of GABA(B) receptors uncovers similarity to metabotropic
gr; glutamate receptors.
gr; NATURE 386 239-246 (1997).
gr; 2. KAUPMANN, K., SCHULER, V., MOSBACHER, J., BISCHOFF, S., BITTIGER, H.,
gr; HEID, J., FROESTL, W., LEONHARD, S., PFAFF, T., KARSCHIN, A. AND BETTLER,
gr; B. Human gamma-aminobutyric acid type B receptors are differentially
gr; expressed and regulate inwardly rectifying K+ channels.
gr; PROC. NATL. ACAD. SCI. U.S.A. 95 (25) 14991-14996 (1998).
gr; 3. WHITE, J.H., WISE, A., MAIN, M.J., GREEN, A., FRASER, N.J., DISNEY, G.H.,
gr; BARNES, A.A., EMSON, P., FOORD, S.M. AND MARSHALL, F.H.
gr; Heterodimerization is required for the formation of a functional GABA(B)
gr; receptor.
gr; NATURE 396 679-82 (1998).
gd; GABA (gamma-amino-butyric acid) is the principal inhibitory neurotransmitter
gd; in the brain, and signals through ionotropic (GABA(A)/GABA(C)) and
gd; metabotropic (GABA(B)) receptor systems [1]. The GABA(B) receptors have
gd; been cloned, and photoaffinity labelling experiments suggest that they
gd; correspond to two highly conserved receptor forms in the vertebrate nervous
gd; system [1].
gd; GABA(B) receptors are involved in the fine tuning of inhibitory synaptic
gd; transmission [2]. Presynaptic receptors inhibit neurotransmitter release by
gd; down-regulating high-voltage activated Ca2+ channels, while postsynaptic
gd; receptors decrease neuronal excitability by activating a prominent inwardly
gd; rectifying K+ (Kir) conductance that underlies the late inhibitory post-
gd; synaptic potentials [2]. GABA(B) receptors negatively couple to adenylyl
gd; cyclase and show sequence similarity to the metabotropic receptors for the
gd; excitatory neurotransmitter L-glutamate.
gd; A new subtype of the GABA(B) receptor (GABA(B)R2) has been identified by
gd; EST database mining [3]. Yeast two-hybrid screening has shown that the new
gd; subtype forms heterodimers with GABA(B)R1 via an interaction at their
gd; intracellular C-terminal tails [3]. On expression with GABA(B)R2 in HEK293T
gd; cells, GABA(B)R1 is terminally glycosylated and expressed at the cell
gd; surface. Co-expression of the receptors produces a fully functional GABA(B)
gd; receptor at the cell surface; this receptor binds GABA with a high affinity
gd; equivalent to that of the endogenous brain receptor [3]. Such results
gd; indicate that, in vivo, functional brain GABA(B) receptors may be hetero-
gd; dimers of GABA(B)R1 and GABA(B)R2.
gd; GABAB2RECPTR is a 13-element fingerprint that provides a signature for
gd; type 2 GABA(B) receptors. The fingerprint was derived from an initial
gd; alignment of 2 sequences: the motifs were drawn from conserved regions
gd; spanning virtually the full alignment length, focusing on those sections
gd; that characterise the type 2 receptors but distinguish them from the rest
gd; of the GABA(B) receptor family. A single iteration on SPTR37_10f was TABLE 1-continued (A) Examples of signature motifs identified in putative proteins resulting from TTV-HD transcripts and full-length genomes

```
gd; required to reach convergence, no further sequences being identified
gd; beyond the starting set.
fc; GABAB2RECPTR1
fl; 19
ft; GABAB2 receptor motif I-1
fd; LAPGAWGWARGAPRPPPSS (SEQ ID NO: 187)        O75899    35
fd; LAPGAWGWTRGAPRPPPSS (SEQ ID NO: 188)        O88871    34
ARGININE DEIMINASE SIGNATURE ARGDEIMINASE_6: domain 1 of 1, from 57 to 75: score 8.0, E = 6.8
               *->seLsrGrggprcmsmplvR<-* (SEQ ID NO: 189)
                  s L+rG g pr s p++
zc35s.B3.3    57  SPLGRGAGEPRRTSTPVAA                75 (SEQ ID NO: 156)
gc; ARGDEIMINASE
gx; PR01466
gn; COMPOUND (6)
ga; 08-JAN-2001
gt; Bacterial arginine deiminase signature
gp; PRINTS; PR00102 OTCASE
gp; PFAM; PF02726 Arg_deiminase
gp; INTERPRO; IPR003876
gr; 1. BROWN, D.M., UPCROFT, J.A., EDWARDS, M.R. AND UPCROFT, P.
gr; Anaerobic bacterial metabolism in the ancient eukaryote Giardia duodenalis.
gr; INT. J. PARASITOL. 28 149-64 (1998).
gr; 2. HARASAWA, R., KOSHIMIZU, K., KITAGAWA, M., ASADA, K. AND KATO, I.
gr; Nucleotide sequence of the arginine deiminase gene of Mycoplasma hominis.
gr; MICROBIOL. IMMUNOL. 36 661-665 (1992).
gr; 3. KANAOKA, M., KAWANAKA, C., NEGORO, T., FUKITA, Y., TAYA, K. AND AGUI, H.
gr; Cloning and expression of the antitumor glycoprotein gene of Streptococcus
gr; pyogenes Su in Escherichia coli.
gr; AGRIC. BIOL. CHEM. 51 2641-2648 (1987).
gr; 4. DEGNAN, B.A., PALMER, J.M., ROBSON, T., JONES, C.E., FISCHER, M.,
gr; GLANVILLE, M., MELLOR, G.D., DIAMOND, A.G., KEHOE, M.A. AND GOODACRE, J.A.
gr; Inhibition of human peripheral blood mononuclear cell proliferation by
gr; Streptococcus pyogenes cell extract is associated with arginine deiminase
gr; activity.
gr; INFECT. IMMUN. 66 3050-3058 (1998).
gd; The arginine dihydrolase (AD) pathway is found in many prokaryotes and some
gd; primitive eukaryotes, an example of the latter being Giardia [1]. The three-
gd; enzyme anaerobic pathway breaks down L-arginine to form 1 mol of ATP, carbon
gd; dioxide and ammonia. In simpler bacteria, the first enzyme, arginine
gd; deiminase, may account for up to 10% of total cell protein [1].
gd; Arginine deiminase catalyses the conversion of L-arginine to L-citrulline
gd; and ammonia. As well as producing energy via ATP, the ammonia also serves
gd; to protect the bacteria against acid damage, and the citrulline generated
gd; may be used in other biosynthetic pathways [2]. A streptococcal acid
gd; glycoprotein (SAGP) has also been shown to function as an arginine
gd; deiminase [3].
gd; Recently, another function of this enzyme has been discovered [4]. It has a
gd; potent anti-tumour effect, and may inhibit antigen, superantigen, or mitogen-
```

TABLE 1-continued (A) Examples of signature motifs identified in putative proteins resulting from TTV-HD transcripts and full-length genomes gd; stimulated human peripheral blood mononuclear cell proliferation [4].
gd; Another function of the protein may be to inhibit cell proliferation by
gd; cell cycle arrest and apoptosis induction. It has thus been hypothesized
gd; that recombinant arginine deiminase could be used as a novel anti-tumour
gd; agent [4].
gd; ARGDEIMINASE is a 6-element fingerprint that provides a signature for
gd; the bacterial arginine deiminase protein family. The fingerprint was
gd; derived from an initial alignment of 4 sequences: the motifs were drawn from
gd; conserved regions spanning the full alignment length (~430 amino acids). Two
gd; iterations on SPTR37_10f were required to reach convergence, at which point
gd; a true set which may comprise 13 sequences was identified. Three partial
gd; matches were also found: P75475 and P75474 are Mycoplasma pneumoniae arginine
gd; deiminases that match the first three and the last three motifs respectively;
and Q48294 is a Halobacterium salinarium arginine deiminase that matches motifs
2 and 6.
bb;
c; ARGDEIMINASE6
fl; 19
ft; Bacterial arginine deiminase motif VI-2
fd; SELSRGRGGPRCMSMPLIR   (SEQ ID NO: 190)   O51896        388  8
fd; SELSRGRGGPRCMSMPLIR   (SEQ ID NO: 190)   Q46254        392  8
fd; SELVRGRGGPRCMSMPFER   (SEQ ID NO: 191)   SAGP_STRPY    389  8
fd; SELSRGRGGPRCMSMSLVR   (SEQ ID NO: 192)   O51781        389  8
fd; GELSRGRGGPRCMSMPLYR   (SEQ ID NO: 193)   O86131        391  8
fd; SELSRGRGGPRCMSMPLVR   (SEQ ID NO: 192)   O53088        388  8
fd; GELGRGRGGHCMTCPIVR    (SEQ ID NO: 194)   ARCA_PSEAE    394  8
fd; NQLSLGMGNARCMSMPLSR   (SEQ ID NO: 195)   ARCA_MYCHO    385  8
fd; SELGRGRGGHCMTCPIWR    (SEQ ID NO: 196)   O31017        387  8
fd; NQLSLGMGNARCMSMPLSR   (SEQ ID NO: 195)   ARCA_MYCAR    386  8
fd; GELGRGRGGHCMTCPIVR    (SEQ ID NO: 197)   ARCA_PSEPU    397  8
fd; SELGTGRGGPRCMSCPAAR   (SEQ ID NO: 198)   O05585        381  8
fd; SELGRGPSGPLEMVCSLWR   (SEQ ID NO: 199)   ARCA_MYCPN    419  8
OPIOID GROWTH FACTOR RECEPTOR REPEAT HMMER 2.3.2 (Oct 2003)
Copyright © 1992-2003 HHMI/Washington University School of Medicine
Freely distributed under the GNU General Public License (GPL)
HMM file: pfam.hmm
Sequence file: zc37.B9.2de.p2
OGFr_III: domain 1 of 1, from 186 to 207: score 8.2, E = 3.6
                 *->sPsEtPGPrPA..GParDEPAE<-* (SEQ ID NO: 200)
                    +tP P PA +GP+r +P E
   zc37.B9.2d    186  RAASTPVPTPALrGPTRQDPGE    207 (SEQ ID NO: 201)
= GF ID   OGFr_III
= GF AC   PF04680.5
= GF DE   Opioid growth factor receptor repeat
= GF PI   OGFr_repeat;
= GF AU   Waterfield DI, Finn RD
= GF SE   Pfam-B_4529 (release 7.5)
= GF GA   33.30 0.00; 25.00 25.00;

TABLE 1-continued (A) Examples of signature motifs identified in putative proteins resulting from TTV-HD transcripts and full-length genomes

```
# = GF TC    40.70 0.30; 28.20 35.60;
# = GF NC    30.90 18.10; 17.10 16.10;
# = GF TP    Repeat
# = GF BM    hmmbuild -FHMM ls.ann SEED.ann
# = GF BM    hmmcalibrate --seed 0 HMM_ls
# = GF BM    hmmbuild -f -FHMM_fs.ann SEED.ann
# = GF BM    hmmcalibrate --seed 0 HMM_fs
# = GF AM    globalfirst
# = GF RN    [1]
# = GF RM    11890982
# = GF RT    The biology of the opioid growth factor receptor (OGFr).
# = GF RA    Zagon IS, Verderame MF, McLaughlin PJ;
# = GF RL    Brain Res Brain Res Rev 2002; 38: 351-376.
# = GF DR    INTERPRO; IPR006770;
# = GF CC    Proline-rich repeat found only in a human opioid growth factor
# = GF CC    receptor [1].
ADHESION MOLECULE CD36 SIGNATURE HMMER 2.3.2 (Oct 2003)
Copyright © 1992-2003 HHMI/Washington University School of Medicine
Freely distributed under the GNU General Public License (GPL)
HMM file: prints.hmm
Sequence file: zc3r11.B4.10d.pl
CD36ANTIGEN_3: domain 1 of 1, from 11 to 29: score 6.3, E = 7.7
            *->WiFDvqnPdevaknsskikvkqR<-*   (SEQ ID NO: 202)
               vq P+e  ss+ +v+qR
zc3r11.B4.    11   ---NVQDPEE-QNESSRFPVQQR            29 (SEQ ID NO: 203)
gc; CD36ANTIGEN
gx; PR01610
gn; COMPOUND (13)
ga; 23-DEC-2001
gt; Adhesion molecule CD36 signature
gp; PRINTS; PR01609 CD36FAMILY; PR01611 LIMPII
gp; MIM; 173510
gr; 1. OKUMURA, T. AND JAMIESON, G.A.
gr; Platelet glycocalicin. Orientation of glycoproteins on the human platelet
gr; surface.
gr; J. BIOL. CHEM. 251 5944-5949 (1976).
gr; 2. NICHOLSON, A.C., FEBBRAIO, M., HAN, J., SILVERSTEIN, R.L. AND
gr; HAJJAR, D.P.
gr; CD36 in atherosclerosis. The role of a class B macrophage scavenger receptor.
gr; ANN. N.Y. ACAD. SCI. 902 128-131 (2000).
gr; 3. SILVERSTEIN, R.L. AND FEBBRAIO, M.
gr; CD36 and atherosclerosis.
gr; CURR. OPIN. LIPIDOL. 11 483-491 (2000).
gr; 4. SAVILL, J., HOGG, N., REN, Y. AND HASLETT, C.
gr; Thrombospondin cooperates with CD36 and the vitronectin receptor
gr; in macrophage recognition of neutrophils undergoing apoptosis.
gr; J. CLIN. INVEST. 90 1513-1522 (1989).
gr; 5. TANDON, NN., KRALISZ, U. AND JAMIESON, GA.
```

TABLE 1-continued (A) Examples of signature motifs identified in putative proteins resulting from TTV-HD transcripts and full-length genomes gr; Identification of glycoprotein IV (CD36) as a primary receptor
gr; for platelet-collagen adhesion.
gr; J. BIOL. CHEM. 264 7576-7583 (1989).
gr; 6. MCGREGOR, J.L., CATIMEL, B., PARMENTIER, S., CLEZARDIN, P.,
gr; DECHAVANNE, M. AND LEUNG, L.L.
gr; Rapid purification and partial characterization of human platelet
gr; glycoprotein IIIb. Interaction with thrombospondin and its role in platelet
gr; aggregation.
gr; J. BIOL. CHEM. 264 501-506 (1989).
gr; 7. BARNWELL, J.W., ASCH, A.S., NACHMAN, R.L., YAMAYA, M., AIKAWA, M. AND
gr; INGRAVALLO, P.
gr; A human 88-KD membrane glycoprotein (CD36) functions in vitro as a receptor
gr; for a cytoadherence ligand on Plasmodium falciparum-infected erythrocytes.
gr; J. CLIN. INVEST. 84 765-772 (1989).
gr; 8. BULL, H.A., BRICKELL, P.M. AND DOWD, P.M.
gr; Src-related protein tyrosine kinases are physically associated with the
gr; surface antigen CD36 in human dermal microvascular endothelial cells.
gr; FEBS LETT. 351 41-44 (1994).
gr; 9. MIYAOKA, K., KUWASAKO, T., HIRANO, K., NOZAKI, S., YAMASHITA, S.
gr; AND MATSUZAWA, Y.
gr; CD36 deficiency associated with insulin resistance.
gr; LANCET 357 686-687 (2001).
gd; CD36 is a transmembrane, highly glycosylated, 88kDa glycoprotein [1]
gd; expressed by monocytes, macrophages, platelets, microvascular endothelial
gd; cells and adipose tissue [2]. It is a multifunctional receptor that binds
gd; to oxidised LDL (OxLDL), long chain fatty acids, anionic phospholipids,
gd; apoptotic cells, thrombospondin (TSP), collagen and Plasmodium falciparum-
gd; infected erythrocytes [2].
gd; CD36 has numerous cellular functions. It is a type B scavenger receptor,
gd; playing a major role in the uptake of OxLDL by macrophages [3]. The lipid-
gd; rich macrophages are then differentiated into foam cells and contribute to
gd; the formation of atherosclerotic lesions [3]. In addition, CD36 of macro-
gd; phages, together with TSP and the integrin alphav beta3, may phagocytose
gd; apoptotic neutrophils [4]. Furthermore, the protein is one of the receptors
gd; of collagen in platelet adhesion and aggregation [5,6]. CD36 may also
gd; mediate cytoadherence of Plasmodium falciparum-infected erythrocytes to the
gd; endothelium of post-capillary venules of different organs [7]. Moreover,
gd; cytoplasmic CD36 plays an important role in signal transduction by inter-
gd; acting with Src family tyrosine kinases [8]. Deficiency in CD36 in Asian
gd; and African populations has been associated with insulin resistance [9].
gd; CD36 is a 13-element fingerprint that provides a signature for the CD36
gd; adhesion molecules. The fingerprint was derived from an initial alignment
gd; of 4 sequences, focusing on those sections that characterise CD36 adhesion
gd; molecules but distinguish them from the rest of the CD36 family: motif 1
gd; spans the first putative, N-terminal TM domain; motifs 2-12 reside in the
gd; extracellular domain; and motif 13 spans the second putative, C-terminal TABLE 1-continued (A) Examples of signature motifs identified in putative proteins resulting from TTV-HD transcripts and full-length genomes

```
gd; TM domain. Two iterations on SPTR40_18f were required to reach convergence,
gd; at which point a true set which may comprise 6 sequences was identified.
bb;
fc; CD36ANTIGEN3
fl; 23
ft; Adhesion molecule CD36 motif III-2
fd; WVFDVQNPEEVAKNSSKIKVIQR (SEQ ID NO: 204)         CD36_RAT       65    18
fd; WIFDVQNPDDVAKNSSKIKVKQR (SEQ ID NO: 205)         CD36_MOUSE     65    18
fd; WIFDVQNPDEVTVNSSKIKVKQR (SEQ ID NO: 206)         CD36_BOVIN     65    18
fd; WIFDVQNPQEVMMNSSNIQVKQR (SEQ ID NO: 207)         CD36_HUMAN     65    18
fd; WIFDVQNPDEVAVNSSKIKVKQR (SEQ ID NO: 208)         CD36_MESAU     65    18
fd; WIFDVQNPEEVAKNSSKIKVKQR (SEQ ID NO: 209)         O35754         66    18
MYELIN PROTEOLIPID PROTEIN (PLP) SIGNATURE
------------------------------------------------------------------------------------
HMMER 2.3.2 (Oct 2003)
Copyright © 1992-2003 HHMI/Washington University School of Medicine
Freely distributed under the GNU General Public License (GPL)
------------------------------------------------------------------------------------
HMM file: prints.hmm
Sequence file: zc312.B11.20d.trrev4_8009.sreformat
MYELINP0_5: domain 1 of 1, from 70 to 91: score -0.1, E = 9.3
               *->GVVlGAiIGGvVLGvVLLlvlllYLv<-*
                  1G iIGGv G VLL + +l +
     zc312.B11  70    -MLGRIIGGV-GCVLLELXGLGVR   91
zc312.B11 (SEQ ID NO: 211)
gc; MYELINPLP0:5 (SEQ ID NO: 210)
gx; PR00214
gn; COMPOUND (7)
ga; 11-JUL-1994; UPDATE 07-JUN-1999
gt; Myelin proteolipid protein (PLP) signature
gp; INTERPRO; IPR001614
gp; PROSITE; PS00575 MYELIN_PLP_1; PS01004 MYELIN_PLP_2
gp; BLOCKS; BL00575
gp; PFAM; PF01275 Myelin_PLP
gr; 1. SAKAMOTO, Y., KITAMURA, K., YOSHIMURA, K., NISHIJIMA, T. AND UYEMURA, K.
gr; Complete amino acid sequence of P0 protein in bovine peripheral nerve
gr; myelin.
gr; J. BIOL. CHEM. 262 4208-4214 (1987).
gr; 2. SHAW, S.Y., LAURSEN, R.A. AND LEES, M.B.
gr; Identification of thiol groups and a disulfide crosslink site in bovine
gr; myelin proteolipid protein.
gr; FEBS LETT. 250 306-310 (1989).
gr; 3. DIEHL, H.J., SCHAICH, M., BUDZINSKI, R.M. AND STOFFEL, W.
gr; Individual exons encode the integral membrane domains of human myelin
gr; proteolipid protein.
gr; PROC. NATL. ACAD. SCI. U.S.A. 83 9807-9811 (1986).
gd; The myelin sheath is a multi-layered membrane, unique to the nervous system,
gd; that functions as an insulator to greatly increase the velocity of axonal
gd; impulse conduction [1]. Myelin proteolipid protein (PLP) is the major
gd; protein found in the sheath of central nervous system nerves [2]. It spans
```

TABLE 1-continued (A) Examples of signature motifs identified in putative proteins resulting from TTV-HD transcripts and full-length genomes

```
gd; the membrane 4 times [3] and is thought to play a role in the formation or
gd; maintenance of the multi-lamellar structure. The protein contains several
gd; cysteine residues, some involved in the formation of disulphide bonds,
gd; others being palmitoylated [2]. Mutations in PLP result in neurological
gd; disorders, such as Pelizaeus-Merzbacher disease in humans, 'jimpy' in
gd; mice, and 'shaking pup' in dogs.
gd; MYELINPLP is a 7-element fingerprint that provides a signature for myelin
gd; proteolipid proteins. The fingerprint was derived from an initial alignment
gd; of 4 sequences: motifs 1, 2, 5 and 7 encode the 4 transmembrane (TM)
gd; domains - motif 4 includes the region encoded by PROSITE pattern MYELIN_PLP_1
gd; (PS00575), which is located between the second and third TM segments
gd; and contains 2 Cys residues that are palmitoylated; motif 7 includes part
gd; of the region encoded by PROSITE pattern MYELIN_PLP_2 (PS01004). Two
gd; iterations on OWL23.2 were required to reach convergence, at which point a
gd; true set which may comprise 9 sequences was identified. Several partial
gd; matches were also found, all of which are either deletion mutants or myelin
gd; PLP fragments.
gd; An update on SPTR37_9f identified a true set of 8 sequences, and 9
gd; partial matches.
CHLAMIDIAOM CHLAMIDIAOM (SEQ ID NO: 212)
RHEU.CD.21 (SEQ ID NO: 213)
HMMER 2.3.2 (Oct 2003)
Copyright © 1992-2003 HHMI/Washington University School of Medicine
Freely distributed under the GNU General Public License (GPL)
-------------------------------------------------------------------
HMM file: prints.hmm
Sequence file: rheu.cd.212rp.365_22305.sreformat
CHLAMIDIAOM3_3: domain 1 of 1, from 88 to 100: score 4.6, E = 9.7

*->CgsYvPsCskpcG-*
                        C +Y+ C k G
     rheu.cd.21   88    CTGYTEFCAKYTG     100 gr; 3. BACHMAIER, K., NEU, N. DE LA MAZA, L.M., PAL, S., HESSEL, A. AND
gr; PENNINGER, J.M.
gr; Chlamydia infections and heart disease linked through antigenic mimicry.
gr; SCIENCE 283 1335-1339 (1999).
bb;
bb;
gd; Three cysteine-rich proteins (also believed to be lipoproteins) make up the
gd; extracellular matrix of the Chlamydial outer membrane [1]. They are involved
gd; in the essential structural integrity of both the elementary body (EB) and
gd; recticulate body (RB) phase. As these bacteria lack the peptidoglycan layer
gd; common to most Gram-negative microbes, such proteins are highly important
gd; in the pathogenicity of the organism.
gd; The largest of these is the major outer membrane protein (momp), and
gd; constitutes around 60% of the total protein for the membrane [2]. CMP2
gd; is the second largest, with a molecular mass of 58kDa, while the CMP3
gd; protein is ~15kDa [1]. MOMP is believed to elicit the strongest immune
```

TABLE 1-continued

| (A) Examples of signature motifs identified in putative proteins resulting from TTV-HD transcripts and full-length genomes |
|---|
| gd; response, and has recently been linked to heart disease through its sequence<br>gd; similarity to a murine heart-muscle specific alpha myosin [3].<br>gd;<br>gd; The CMP3 family plays a structural role in the outer membrane during<br>gd; the EB stage of the Chlamydial cell, and different biovars show a small, yet<br>gd; highly significant, change at peptide charge level [1]. Members of this<br>gd; family include *C. trachomatis*, *C. pneumoniae*, and *C. psittaci*.<br>gd;<br>gd; CHLAMIDIAOM3 is a 3-element fingerprint that provides a signature for<br>gd; the Chlamydial cysteine-rich outer membrane 3 protein (CMP3) family.<br>gd; The fingerprint was derived from an initial alignment of 3 sequences: the<br>gd; motifs were drawn from conserved regions spanning the full alignment length<br>gd; (~90 amino acids). Two iterations on SPTR37_10f were required to reach<br>gd; convergence, at which point a true set comprising 8 sequences was<br>gd; identified.<br>;<br>; |

The present invention also relates to an oligonucleotide primer which may comprise or consisting of part of a polynucleic acid as defined above, with said primer being able to act as primer for specifically sequencing or specifically amplifying TT virus HCR polynucleic acid of the invention and attached cellular (host) DNA sequences.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow priming the synthesis of the extension products. Preferably the primer is about 5-50 nucleotides. Specific length and sequence will depend on the complexity of the required DNA or RNA targets, as well as on the conditions of primer use such as temperature and ionic strength.

The fact that amplification primers do not have to match exactly with corresponding template sequence to warrant proper amplification is amply documented in the literature. The amplification method used may be polymerase chain reaction (PCR), ligase chain reaction (LCR), nucleic acid sequence-based amplification (NASBA), transcription-based amplification system (TAS), strand displacement amplification (SDA) or amplification by means of Qβ replicase or any other suitable method to amplify nucleic acid molecules using primer extension. During amplification, the amplified products may be conveniently labelled either using labelled primers or by incorporating labelled nucleotides.

Labels may be isotopic (32P, 35S, etc.) or non-isotopic (biotin, digoxigenin, etc.). The amplification reaction is repeated between 20 and 70 times, advantageously between 25 and 45 times.

Any of a variety of sequencing reactions known in the art may be used to directly sequence the viral genetic information and determine the orf by translating the sequence of the sample into the corresponding amino acid sequence. Exemplary sequencing reactions include those based on techniques developed by Sanger or Maxam and Gilbert. It is also contemplated that a variety of automated sequencing procedures may be utilized when performing the subject assays including sequencing by mass spectrometry (see, for example: PCT publication WO 94/16101). It will be evident to one skilled in the art that, for example the occurrence of only two or three nucleic bases needs to be determined in the sequencing reaction.

Preferably, these primers are about 5 to 50 nucleotides long, more preferably from about 10 to 25 nucleotides. Most preferred are primers having a length of at least 13 bases.

In a preferred embodiment, a primer of the present invention has a nucleotide sequence as shown in Table 2.

TABLE 2

Primers used to generate complete TTV-HD genomes and μTTV-HD subviral genomes by long distance PCR amplification

| TTV | Primer | Nucleotide number | Sequence |
|---|---|---|---|
| TTV-jt34f (acc no AB064607) | jt34f-1s | 223-247 | 5'-GGCCGGGCCA TGGGCAAGGC TCTTA-3' (SEQ ID NO: 214) |
| | jt34f-2as | 195-222 | 5'-AGTCAAGGGG CAATTCGGGC TCGGGACT-3' (SEQ ID NO: 215) |
| | jt34f-5s | 205-222 | 5'-CAATTCGGGC TCGGGACT-3' (SEQ ID NO: 216) |
| | jt34f-6as | 186-204 | 5'-ACACACCGCA GTCAAGGGG-3' (SEQ ID NO: 217) |
| | jt34f-7s | 205-223 | 5'-CAATTCGGGC TCGGGACTG-3' (SEQ ID NO: 218) |
| | jt34f-8as | 181-204 | 5'-AGTTTACACA CCGCAGTCAA GGGG-3' (SEQ ID NO: 219) |
| TTV-HD1 (acc no AJ620222) | th25-1s | 126-156 | 5'-CCGCAGCGAG AACGCCACGG AGGGAGATCC T-3' (SEQ ID NO: 220) |
| | tth25-2as | 95-125 | 5'-ACTTCCGAAT GGCTGAGTTT TCCACGCCCG T-3' (SEQ ID NO: 221) |
| TTV-HD3 (acc no AJ620231) | tth8-1s | 133-164 | 5'-AGAGGAGCCA CGGCAGGGGA TCCGAACGTC CT-3' (SEQ ID NO: 222) |
| | tth8-2as | 102-132 | 5'-CTTACCGACT CAAAAACGAC GGGCAGGCGC C (SEQ ID NO: 223) |
| TTV-HD4 (acc no AJ620226) | tth4-1s | 129-156 | 5'-CAGCGAGAAC GCCACGGAGG GAGATCCT-3' (SEQ ID NO: 224) |
| | tth4-2as | 101-128 | 5'-GAATGGCTGA GTTTTCCACG CCCGTCCG-3' (SEQ ID NO: 225) |
| TTV-t3pb (acc. no AF247138) | t3pb-1s | 209-226 | 5'-CAATTCGGGC ACGGGACT-3' * (SEQ ID NO: 226) |
| | t3pb-2as | 185-208 | 5'-AGTTTACACA CCGAAGTCAA GGGG-3' (SEQ ID NO: 227) |

* A - TTV-t3pb sequence has a T at this position

The present invention also relates to an oligonucleotide probe which may comprise or consisting of part of a rearranged TT virus polynucleic acid as defined above, with said probe being able to act as a hybridization probe for specific detection of a TTV nucleic acid according to the invention.

The term "probe" refers to single stranded sequence-specific oligonucleotides which have a sequence which is complementary to the target sequence of the rearranged TTV polynucleic acid to be detected.

Preferably, these probes are about 5 to 50 nucleotides long, more preferably from about 10 to 25 nucleotides. Most preferred are probes having a length of at least 13 bases.

The probe may be labelled or attached to a solid support.

The term "solid support" may refer to any substrate to which an oligonucleotide probe may be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The oligonucleotides according to the present invention, used as primers or probes may also contain or consist of nucleotide analoges such as phosphorothioates, alkylphosphoriates or peptide nucleic acids or may contain intercalating agents. These modifications will necessitate adaptions with respect to the conditions under which the oligonucleotide should be used to obtain the required specificity and sensitivity. However, the eventual results will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The polynucleic acids of the invention may be comprised in a composition of any kind. Said composition may be for diagnostic, therapeutic or prophylactic use.

Also included within the present invention are sequence variants of the polynucleic acids as selected from any of the nucleotide sequences with said sequence variants containing either deletions and/or insertions of one or more nucleotides, especially insertions or deletions of 1 or more codons, mainly at the extremities of oligonucleotides (either 3' or 5'), or substitutions of some non-essential nucleotides by others (including modified nucleotides an/or inosine).

Figure 1:
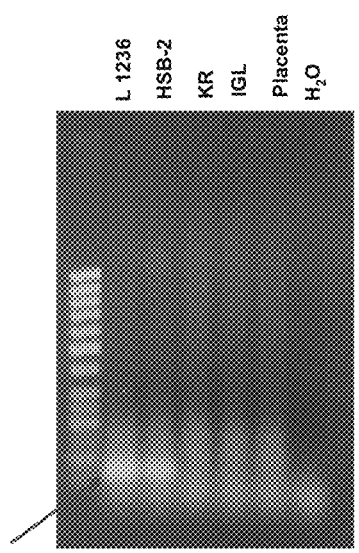
FIG. 1: PCR amplification of a 71 base fragment containing the highly conserved TTV region (HCR) in 4 different cell lines, L1236 (EBV-negative Hodgkin's lymphoma line), HSB-2 (acute lymphoblastic leukemia line), KR and IGL (melanoma cell lines) and placenta DNA

Rearranged TTV polynucleic acid sequences according to the present invention which are similar to the sequences as shown in FIG. 1 may be characterized and isolated according to any of the techniques known in the art, such as amplification by means of sequence-specific primers, hybridization with sequence-specific probes under more or less stringent conditions, sequence determination of the genetic information of TTV, etc.

The present invention also relates to a recombinant expression vector which may comprise a rearranged TTV polynucleic acid of the invention as defined above operably linked to prokaryotic, eukaryotic or viral transcription and translation control elements.

The term "vector" may comprise a plasmid, a cosmid, an artificial chromosome, a phage, or a virus or a transgenic non-human animal. Particularly useful for vaccine development may be TT virus recombinant molecules, BCG or adenoviral vectors, as well as avipox recombinant viruses.

The term "recombinantly expressed" used within the context of the present invention refers to the fact that the polypeptides of the present invention are produced by recombinant expression methods be it in prokaryotes, or lower or higher eukaryotes as discussed in detail below.

The term "lower eukaryote" refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluiveromyces, Pichia* (e. g. *Pichia pastoris*), *Hansenula* (e. g. *Hansenula* polymorph), *Schwaniomyces, Schizosaccharomyces, Yarowia, Zygosaccharomyces* and the like. *Saccharomyces cerevisiae, S. carlsbergensis* and *K. lactis* are the most commonly used yeast hosts, and are convenient fungal hosts.

The term "higher eukaryote" refers to host cells derived from higher animals, such as mammals, reptiles, insects, and the like. Presently preferred higher eukaryote host cells are derived from Chinese hamster (e. g. CHO), monkey (e. g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic non-human animals.

The term "prokaryotes" refers to hosts such as *E. coli, Lactobacillus, Lactococcus, Salmonella, Streptococcus, Bacillus subtilis* or *Streptomyces*. Also these hosts are contemplated within the present invention.

The term "host cell" refers to cells which may be or have been, used as recipients for a recombinant vector or other transfer polynucleotide, and include the progeny of the original cell which has been transfected.

It is understood that the progeny of a single parental cell may not necessarily be completely identical in morphology or in genomic or total DNA complement as the original parent, due to natural, accidental, or deliberate mutation or recombination.

The term "replicon" is any genetic element, e. g., a plasmid, a chromosome, a virus, a cosmid, etc., that behaves as an autonomous unit of polynucleotide replication within a cell, i. e., capable of replication under its own control.

The term "vector" is a replicon further which may comprise sequences providing replication and/or expression of a desired open reading frame.

The term "control element" refers to polynucleotide sequences which are necessary to effect the expression of coding sequences to which they are ligated. The nature of such control sequences differs depending upon the host organism; in prokaryotes, such control sequences generally include promoter, ribosomal binding site, splicing sites and terminators; in eukaryotes, generally, such control sequences include promoters, splicing sites, terminators and, in some instances, enhancers. The term "control elements" is intended to include, at a minimum, all components whose presence is necessary for expression, and may also include additional components whose presence is advantageous, for example, leader sequences which govern secretion.

The term "promoter" is a nucleotide sequence which is comprised of consensus sequences which allow the binding of RNA polymerase to the DNA template in a manner such that mRNA production initiates at the normal transcription initiation site for the adjacent structural gene.

The expression "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The segment of the rearranged TTV DNA encoding the desired sequence inserted into the vector sequence may be attached to a signal sequence. Said signal sequence may be that from a non-TTV source, but particularly preferred constructs according to the present invention contain signal sequences appearing in the TTV genome before the respective start points of the proteins.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. For vaccination of humans the avipox and Ankara Modified Virus (MVA) are particularly useful vectors.

Also known are insect expression transfer vectors derived from baculovirus *Autographa californica* nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

The present invention also relates to a host cell as defined above transformed with a recombinant vector as defined above.

The present invention also relates to a polypeptide having an amino acid sequence encoded by a rearranged TTV polynucleic acid as defined above, or a part or an analogue thereof being substantially similar and biologically equivalent. Preferably, this polypeptide is encoded by the nucleotide sequence which encodes the protein containing a signature motif of a mammalian protein.

The term "polypeptide" refers to a polymer of amino acids and does not refer to a specific length of the product. Thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, peptide nucleic acid (PNA), etc.), polypeptides with substituted linkages, as well as other modifications known in the art, both naturally occurring and non-naturally occurring.

By "biologically equivalent" as used throughout the specification and claims, it is meant that the compositions are immunogenically equivalent to the polypeptides of the invention as defined above and below.

By "substantially homologous" as used throughout the specification and claims to describe polypeptides, it is meant a degree of homology in the amino acid sequence to the polypeptides of the invention. Preferably the degree of homology is in excess of 70%, preferably in excess of 80%, with a particularly preferred group of proteins being in excess of 90% or even 95% homologous with the polypeptides of the invention.

The term "analogue" as used throughout the specification to describe the polypeptides of the present invention, includes any polypeptide having an amino acid residue sequence substantially identical to a sequence specifically shown herein in which one or more residues have been conservatively substituted with a biologically equivalent residue. Examples of conservative substitutions include the substitution of one nonpolar (hydrophobic) residue such as isoleucine, valine, leucine or methionine for another, the substitution of one polar (hydrophillic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to the protein or peptide of the invention.

"Chemical derivative" refers to a protein or peptide having one or more residues chemically derivatized by reaction of a functional side group. Examples of such derivatized molecules include but are not limited to, those molecules in which free amino groups have been derivatized to form amine hydrochlorides, p-toluene sulfonyl groups, carbobenzoxy groups, tbutyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Those proteins or peptides are also included as chemical derivatives which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The polypeptides of the present invention also include any polypeptide having one or more additions and/or deletions or residues relative to the sequence of a polypeptide whose sequence is shown herein, so long as the polypeptide is biologically equivalent to the polypeptides of the invention.

The polypeptides according to the present invention contain preferably at least 3, preferably 4 or 5 contiguous amino acids, 6 or 7 preferably however at least 8 contiguous amino acids, at least 10 or at least 15.

The polypeptides of the invention may be prepared by classical chemical synthesis. The synthesis may be carried out in homogeneous solution or in solid phase. For instance, the synthesis technique in homogeneous solution which may be used is the one described by Houbenweyl in the book entitled "Methode der organischen Chemie" (Method of organic chemistry) edited by E. Wunsh, vol. 15-I et II. THIEME. Stuttgart 1974.

The polypeptides of the invention may also be prepared in solid phase according to for example the methods described by Atherton and Shepard in their book entitled "Solid phase peptide synthesis" (IRL Press, Oxford, 1989).

The polypeptides according to this invention may also be prepared by means of recombinant DNA techniques as for example described by Maniatis et al., Molecular Cloning: A Laboratory Manual, New York, Cold Spring Harbor Laboratory, 1982.

The present invention also relates to a method for production of a recombinant polypeptide as defined above, which may comprise: (a) transformation of an appropriate cellular host with a recombinant vector, in which a polynucleic acid or a part thereof as defined above has been inserted under the control of the appropriate regulatory elements, (b) culturing said transformed cellular host under conditions enabling the expression of said insert, and (c) harvesting said polypeptide.

The present invention also relates to an antibody raised upon immunization with at least one polypeptide as defined above, with said antibody being specifically reactive with any of said polypeptides, and with said antibody being preferably a monoclonal antibody. The term "antibody", preferably, relates to antibodies which consist essentially of pooled monoclonal antibodies with different epitopic specifities, as well as distinct monoclonal antibody preparations. Monoclonal antibodies are made from an antigen containing, e.g., a polypeptide encoded by the TTV polynucleic acid of the invention or a fragment thereof by methods well known to those skilled in the art. As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less nonspecific tissue binding than an intact antibody. Thus, these fragments are preferred, as well as the products of a FAB or other immunoglobulin expression library. Moreover, antibodies useful for the purposes of the present invention include chimerical, single chain, and humanized antibodies.

Preferably, the antibody or antigen binding fragment thereof carries a detectable label. The antibody/fragment may be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

The present invention also relates to a diagnostic kit for use in determining the presence of a TT virus polynucleic acid or polypeptide of the invention, said kit which may comprise a primer, a probe, and/or an antibody of the invention.

Alternatively, the present invention also relates to a method for the detection of a rearranged TTV polynucleic acid according to the invention present in a biological sample, which may comprise: (a) optionally extracting sample polynucleic acid, (b) amplifying the polynucleic acid as described above with at least one primer as defined above, optionally a labelled primer, and (c) detecting the amplified polynucleic acids.

The term "polynucleic acid" may also be referred to as analyte strand and corresponds to a single- or double-stranded polynucleic acid molecule.

The term "labelled" refers to the use of labelled nucleic acids. This may include the use of labelled nucleotides incorporated during the polymerase step of the amplification or labelled primers, or by any other method known to the person skilled in the art.

The present invention also relates to a method for the detection of a rearranged TTV polynucleic acid according to the invention present in a biological sample, which may comprise: (a) optionally extracting sample polynucleic acid, (b) hybridizing the polynucleic acid as described above with at least one probe as defined above, and (c) detecting the hybridized polynucleic acids.

The hybridization and washing conditions are to be understood as stringent and are generally known in the art (e. g. Maniatis et al., Molecular Cloning: A Laboratory Manual, New York, Cold Spring Harbor Laboratory, 1982). However, according to the hybridization solution (SSC, SSPE, etc.), these probes should be hybridized at their appropriate temperature in order to attain sufficient specificity.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i. e. nucleotides not essential to discriminate between types) by others (including modified nucleotides or inosine) these probes or variants thereof may be caused to hybridize specifically at the same hybridization conditions (i. e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions.

Suitable assay methods for purposes of the present invention to detect hybrids formed between the oligonucleotide probes and the polynucleic acid sequences in a sample may comprise any of the assay formats known in the art, such as the conventional dot-blot format, sandwich hybridization or reverse hybridization. For example, the detection may be accomplished using a dot blot format, the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the polynucleic acids of the sample and the oligonucleotide probes according to the present invention may be used.

The present invention also relates to a method for detecting a polypeptide encoded by a rearranged TTV polynucleic acid of the present invention or an antibody against said polypeptide present in a biological sample, which may comprise: (a) contacting the biological sample for the presence of such polypeptide or antibody as defined above, and (b) detecting the immunological complex formed between said antibody and said polypeptide.

The immunoassay methods according to the present invention may utilize antigens from different domains of the new and unique polypeptide sequences of the present invention. It is within the scope of the invention to use for instance single or specific oligomeric antigens, dimeric antigens, as well as combinations of single or specific oligomeric antigens. The TTV antigens of the present invention may be employed in virtually any assay format that employs a known antigen to detect antibodies. Of course, a format that denatures the TTV conformational epitope should be avoided or adapted. A common feature of all of these assays is that the antigen is contacted with the body component suspected of containing TTV antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that may be used are nitrocellulose (e. g., in membrane or microtiter well form), polyvinyl chloride (e. g., in sheets or microtiter wells), polystyrene latex (e. g., in beads or microtiter plates, polyvinylidine fluoride (known as Immunolon), diazotized paper, nylon membranes, activated beads, and Protein A beads. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of TTV antibodies in the antibody-antigen complexes is directly monitored. This may be accomplished by determining whether (labelled) anti-xenogeneic (e. g. anti-human) antibodies which recognize an epitope on anti-TTV antibodies will bind due to complex formation. In a competitive format, the amount of TTV antibodies in the sample is deduced by monitoring the competitive effect on the binding of a known amount of labeled antibody (or other competing ligand) in the complex.

Complexes formed which may comprise anti-TTV antibody (or in the case of competitive assays, the amount of competing antibody) are detected by any of a number of known techniques, depending on the format. For example, unlabeled TTV antibodies in the complex may be detected using a conjugate of anti-xenogeneic Ig complexed with a label (e. g. an enzyme label).

In an immunoprecipitation or agglutination assay format the reaction between the TTV antigens and the antibody forms a network that precipitates from the solution or suspension and forms a visible layer or film of precipitate. If no anti-TTV antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen/antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles.

The solid phase selected may include polymeric or glass beads, nitrocellulose, microparticles, microwells of a reaction tray, test tubes and magnetic beads. The signal generating compound may include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin.

The above methods are useful for evaluating the risk of developing diseases like cancer or an autoimmune disease due to the deleterious effects of the presence of a (subgenomic) TTV polynucleotide sequence linked to a particular host gene or gene fragment within the patient's cells and allow taking appropriate counter measures.

The present invention also relates to an antisense oligonucleotide or iRNA specific for a rearranged TT virus polynucleic acid of the invention.

The generation of suitable antisense oligonucleotides or iRNAs includes determination of a site or sites within the rearranged TT virus polynucleic acid for the antisense interaction to occur such that the desired effect, e.g., inhibition of expression of the polypeptide, will result. A preferred intragenic site is (a) the region encompassing the translation initiation or termination codon of the open reading frame (ORF) of the gene or (b) a region of the mRNA which is a "loop" or "bulge", i.e., not part of a secondary structure. Once one or more target sites have been identified, oligonucleotides are chosen which are sufficiently complementary to the target, i.e., hybridize sufficiently well and with sufficient specificity, to give the desired effect. In the context of this invention, "hybridization" means hydrogen bonding, which may be Watson-Crick, Hoogsteen or reversed Hoogsteen hydrogen bonding, between complementary nucleoside or nucleotide bases. "Complementary" as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which may hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

"Oligonucleotide" (in the context of antisense compounds) refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention comprise from about 8 to about 50 nucleobases (i.e. from about 8 to about 50 linked nucleosides). Particularly preferred antisense compounds are antisense oligonucleotides, even more preferably those which may comprise from about 15 to about 25 nucleobases. Antisense compounds include ribozymes, external guide sequences (EGS), oligonucleotides (oligozymes), and other short catalytic RNAs or catalytic oligonucleotides which hybridize to the target nucleic acid and inhibit its expression. The antisense compounds also include an iRNA which may comprise a sense sequence and an antisense sequence, wherein the sense and antisense sequences form an RNA duplex and wherein the antisense sequence may comprise a nucleotide sequence sufficiently complementary to the nucleotide sequence of the TT virus polynucleic acid of the present invention.

Alternatively, the invention provides a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, herpes virus, vaccinia, or, more preferably, an RNA virus such as a retrovirus. Even more preferably, the retroviral vector is a derivative of a murine or avian retrovirus. Examples of such retroviral vectors which may be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance may be provided, e.g., by using helper cell lines that contain plasmids encoding all of the structural genes of the retrovirus under the control of regulatory sequences within the LTR. Suitable helper cell lines are well known to those skilled in the art. Said vectors may additionally contain a gene encoding a selectable marker so that the transduced cells may be identified. Moreover, the retroviral vectors may be modified in such a way that they become target specific. This may be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957.

In order to achieve expression only in the target organ, the DNA sequences for transcription of the antisense oligonucleotides may be linked to a tissue specific promoter and used for gene therapy. Such promoters are well known to those skilled in the art.

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which may result in increased stability are known to the person skilled in the art, preferably such modification is a phosphorothioate linkage.

A preferred oligonucleotide mimetic is an oligonucleotide mimetic that has been shown to have excellent hybridization properties, and is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Modified oligonucleotides may also contain one or more substituted or modified sugar moieties. Preferred oligonucleotides comprise one of the following at the 2' position: OH; F; 0-, S-, or N-alkyl; 0-, S-, or N-alkenyl; 0-, S- or N-alkynyl; or 0-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. A particularly preferred modified sugar moiety is a 2'-O-methoxyethyl sugar moiety.

Antisense oligonucleotides of the invention may also include nucleobase modifications or substitutions. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine etc., with 5-methylcytosine substitutions being preferred since these modifications have been shown to increase nucleic acid duplex stability.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, a thiocholesterol, an aliphatic chain, e.g., dodecandiol or undecyl residues, a phospholipid, a polyamine or a polyethylene glycol chain, or adamantane acetic acid, a palmityl moiety, or an octadecylamine or hexylamino-carbonyl-oxycholesterol moiety.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results may often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

The present invention also relates to a pharmaceutical composition which may comprise an antibody or antisense oligonucleotide of the invention and a suitable excipient, diluent or carrier. Preferably, in a pharmaceutical composition, such compound as described above is combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers may be formulated by conventional methods and the active compound may be administered to the subject at an effective dose.

An "effective dose" refers to an amount of the active ingredient that is sufficient to prevent the disease or to affect the course and the severity of the disease, leading to the reduction or remission of such pathology. An "effective dose" useful for treating and/or preventing these diseases or disorders may be determined using methods known to one skilled in the art.

Administration of the suitable compositions may be effected by different ways, e.g. by intravenous, intraperitoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

In a preferred embodiment of the present invention, the disease that may be prevented/treated is an autoimmune disease (or an early stage thereof) such as multiple sclerosis (MS) or any other neurological disease, asthma, polyarthritis, diabetes, lupus erythematosus, celiac disease, colitis ulcerosa, or Crohn's disease. The term "autoimmune disease" also may comprise as yet unknown autoimmune diseases.

The present invention also provides
(a) a method for the generation of a database for determining the risk to develop cancer or an autoimmune disease, which may comprise the following steps
    (i) determining the nucleotide sequence of a genomic host cell DNA linked to rearranged TT virus polynucleic acids according to the invention and being preferably present in episomal form, if present, in a sample from a patient suffering from at least one of said diseases; and
    (ii) compiling sequences determined in step (a) associated with said diseases in a database; as well as
(b) a method for evaluating the risk to cancer or an autoimmune disease of a patient suspected of being at risk of developing such disease, which may comprise the following steps:
    (i) determining the nucleotide sequence of a genomic host cell DNA linked to a rearranged TT virus polynucleic acid according to the invention and being preferably present in episomal form, if present, in a sample from said patient; and
    (ii) comparing sequences determined in step (a) with the sequences compiled in the database generated to the method described above, wherein the absence of a genomic host cell DNA linked to a TT virus polynucleic acid or the presence only of host cell DNA linked to a TT virus polynucleic acid not represented in said database indicates that the risk of developing such disease is decreased or absent.

Finally, the present invention also provides a process for the in vitro replication and propagation of Torque teno viruses (TTV), preferably a rearranged TTV according to the present invention, which may comprise the following steps:
(a) transfecting linearized TTV DNA into 293TT cells expressing high levels of SV40 large T antigen, preferably at least levels as reported in Buck et al. (2004);
(b) harvesting the cells and isolating cells showing the presence of TTV DNA;
(c) culturing the cells obtained in step (b) for at least three days, preferably at least one week or longer, depending on experimental conditions and TTV type concerned; and
(d) harvesting the cells of step (c).

Although the present invention and its advantages have been described in detail, it should be understood that various changes, substitutions and alterations may be made herein without departing from the spirit and scope of the invention as defined in the appended claims.

The present invention will be further illustrated in the following Examples which are given for illustration purposes only and are not intended to limit the invention in any way.

Example 1

Materials and Methods
(A) TT Virus Isolation and Characterization

The isolation of TT virus isolates TTV-HD3a (tth8, accession no AJ620231) and TTV-HD1a (tth25, acc. no AJ620222) was previously described (Jelcic et al., 2004). Full-length genomic sequences of both TTV-HD3a and TTV-HD1a were cloned into the vector pUC18 using restriction enzymes SalI (Leppik et al., 2007) and EcoR1, respectively. Additional TTV sequences were identified in human samples by DNA nested amplification using primers NG472/NG352 and NG473/NG351 as previously described (Peng et al., 2002; Leppik et al., 2007). The limited availability of DNA for a number of biopsy and serum samples required prior amplification using rolling circle amplification with a TempliPhi Kit (GE Healthcare). All amplified products were cloned and sequenced (Leppik et al., 2007). Samples harbouring TT virus DNA were subsequently subjected to long distance-PCR amplification using TaKaRa LA Taq enzyme (TAKARA BIO INC., Japan) and respective primers which had been designed based on the initially identified TTV DNA sequences. These back-to-back primers included the following combinations: tth25-1s and tth25-2as, jt34f-1s and jt34f-2as, jt34f-7s and jt34f-8as, jt34f-5s and jt34f-6as, tth4-1s and tth4-2as, t3pb-1s and t3pb-2as, as well as tth8-1s and tth-2as (Table 2). Long-PCR amplification was performed using a touchdown stepwise reaction as described previously (Leppik et al., 2007) with the exception of primer combinations t3pb-1/2, jt34f-5/6 and tth4. PCR conditions for PCR amplification with t3pb-1/2 and jt34f-5/6-primers were an initial denaturation at 94° C. for 1 min, followed by 30 cycles of 94° C. for 30 sec, annealing at 65° C. for 1 min and elongation at 72° C. for 4 min with a final elongation at 72° C. for 10 min. PCR conditions for amplification with tth4 primers were similar except that annealing was performed at 68° C. All obtained amplicons in the range of 3.8 kb were eluted and purified after gel electrophoresis, cloned into vector pCR2.1 (TA-Cloning-Kit, Invitrogen) and propagated in NovaBlue Singles Competent Cells (Merck Chemicals, UK). All full-length genomes were sequenced through both strands. A total of 53 full-length genomes was obtained.

(B) Sequence Analyses and Phylogeny

DNA sequences were compared to TTV sequences available in all databanks using the HUSAR software package (Jelcic et al., 2004). The ICTV recently classified TT viruses into the family Anelloviridae based on the DNA sequence of large open reading frame 1 (ORF1) (Biagini and de Micco, 2010). Characterizing the genomes of the isolates obtained revealed rearrangement of sequences in the ORF1 region. The full-length genomes of the genus Alphatorquevirus and the isolates were therefore subjected to phylogenetic analyses as previously described (Jelcic et al., 2004). The phylogenetic tree (FIG. 4) was displayed using the Treeview program of the University of Glasgow. Translated ORFs were analyzed for homologous proteins and functional domains by using ProtSweep (del Val et al., 2004).

(C) Cell Culture and Transfection

The human embryonic kidney cell line 293TT (Buck et al., 2004) was maintained in DMEM supplemented with 10% fetal calf serum, 1% Glutamax, 1% non-essential amino acids (both Invitrogen, Karlsruhe, Germany) and 400 µg/ml Hygromycin B (Roche Diagnostics, Mannheim). Linearized virus DNA (2 µg per well on 6-well plates) was transfected into cells grown without Hygromycin B using Lipofectamine reagent (Invitrogen) according to the manufacturer's instructions (Fei et al., 2005). Culture medium (2 ml) was supplemented with 800 µl Opti-MEM prior to incubation for 4 hours at 37° C. Transfected cultures were subsequently incubated with fresh medium containing Hygromycin B and propagated when confluency was reached. Full-length genomes of 12 TTV isolates were transfected, maintained and harvested in parallel at all times. TT virus genomes included TTV-HD14a, TTV-HD14b, TTV-HD14c, TTV-HD14e, TTV-HD15a, TTV-HD16a, TTV-HD20a, TTV-HD3a, TTV-HD1a, TTV-HD23a, TTV-HD23b and TTV-HD23d (Table 3).

TABLE 3

| TT full-length genomes | (3, 8 kb) | subviral genomes |
|---|---|---|
| tth25 | HD1a | µTTV-HD1 - zpr9.B1.6 (621 nt) |
| tth3 | HD1b | |
| tth9 | HD1c | |
| tth16 | HD1d | |
| tth17 | HD1e | |
| tth26 | HD1f | |
| tth27 | HD1g | |
| tth31 | HD1h | |
| tth5 | HD2a | |
| tth14 | HD2b | |
| tth29 | HD2c | |
| tth8 | HD3a | |
| tth7 | HD3b | |
| tth13 | HD3c | |
| tth19 | HD3d | |
| tth22g4 | HD3e | |
| tth23 | HD3f | |
| tth4 | HD4 | |
| tth10 | HD5a | |
| tth11g2 | HD5b | |
| tth18 | HD5c | |
| tth21 | HD5d | |
| tth6 | HD6a | |
| tth20 | HD6b | |
| tt32c2 | HD7 | |
| tt32b8 | HD8 | |
| sle1957 | HD9 | |
| sle1931 | HD10a | |
| sle1932 | HD10b | |
| sle2045 | HD10c | |
| sle2037 | HD11 | |
| sle2065 | HD12a | |
| sle2057 | HD12b | |
| sle2058 | HD12c | |
| sle2061 | HD12d | |
| sle2072 | HD12e | |
| gB20.33 | HD13a | |
| gB20.58 | HD13b | |
| gB21.51 | HD13c | |
| gbDhDi33.32 | HD14a | µTTV-HD14.1 - zpr4.B5.20 (719 nt) |
| gbCuCv33.2 | HD14b | µTTV-HD14.2 - zpr4.B6.125 (1224 nt) |
| gbDhDi33.31 | HD14c | |
| gbDhDi33.33 | HD14d | |
| gbDhDi33.35 | HD14e | |
| gbDhDi32.36 | HD14f | |
| gbDfDg33.45 | HD14g | |
| gbDfDg33.48 | HD14h | |
| gbDfDg33.49 | HD14i | |
| gbCsCt38.1 | HD15b | |
| gbCsCt38.2 | HD15a | µTTV-HD15 - zpr5.B4.12 (913 nt) |
| gbCsCt38.4 | HD15c | |
| gbCsCt38.6 | HD15d | |
| gbCsCt43.2 | HD16a | |
| gbCsCt43.1 | HD16b | |
| gbCsCt43.3 | HD16c | |
| gbCsCt43.5 | HD16d | |
| gbCsCt43.6 | HD16e | |
| gbCuCv43.1 | HD16f | |
| gbCuCv43.4 | HD16g | |
| gbDhDi43.1 | HD16h | |
| gbDhDi43.4 | HD16i | |
| gbDhDi43.6 | HD16j | |
| gbDhDi43.7 | HD16k | |
| gbDhDi43.22 | HD16l | |
| uro702 | HD17 | |
| uro703 | HD18a | |
| uro705 | HD18b | |
| rheu242 | HD19 | |
| uro960 | HD20a | |
| uro742 | HD20b | |
| uro745 | HD20c | |
| uro746 | HD20d | |
| uro953 | HD20e | |
| uro958 | HD20f | |
| rheu111 | HD21 | |
| rheu112 | HD22 | |
| rheu215 | HD23a | |

TABLE 3-continued

| TT full-length genomes | (3, 8 kb) | subviral genomes |
|---|---|---|
| rheu210 | HD23b | µTTV-HD23.1 - zpr12.B2.22 (401 nt) |
| rheu211 | HD23c | µTTV-HD23.2 - zpr12.B5.24 (642 nt) |
| rheu212 | HD23d | |
| rheu213 | HD23e | |
| rheu214 | HD23f | |
| rheu231 | HD24b | |
| rheu232 | HD24a | |
| rheu234 | HD24c | |
| rheu236 | HD24d | |
| rheu238 | HD24e | |
| rheu241 | HD24f | |

Virus DNA was released from the vector prior to transfection. Controls included transfection with vector alone and cells transfected with 1× TE. Transfected cells and culture medium were frozen at −80° C. and samples for DNA and RNA extraction taken at each time point during propagation. DNA was extracted with phenol-chloroform-isoamylalcohol and RNA using the RNeasy Mini Kit (Qiagen, Hilden, Germany). Replication of virus DNA was monitored and demonstrated by long-PCR amplification as described above. All transfection experiments were performed 3 times with 6 week intervals between primary transfections. Frozen cells or purified virus preparations were passaged between 4 to 6 times.

(D) Virus Propagation, Purification and Electronmicroscopy

Transfected cells were harvested from flasks by shaking followed by centrifugation for 10 min at 200 g. Cell pellets were resuspended in DPBS-Mg (Invitrogen) and separated on a 27-33-39% Optiprep (Sigma, St. Louis, Mo.) step gradients for 3.5 hr at 234,000 g (Buck et al., 2005). Gradients were fractionated and screened for the presence of virus DNA by gel electrophoresis of lysed aliquots. Aliquots were lysed with proteinase K, 0.25 mM EDTA and 0.5% SDS for 10 min at 56° C. immediately prior to loading onto the gel. The supernatant of the re-suspended cells were alternatively filtered through a 0.22 µm filter. Aliquots of gradient fractions, as well as filtered supernatants were frozen at −80° C. for use as inoculum. Filtered aliquots were pelleted. Pellets were subjected to negative staining and visualized by electronmicroscopy. Cloned subviral µTTV genomes were transfected into 293TT in the same way as the full-length genomes. The cultures were propagated over several weeks. Cells were partially removed by scraping off part of the monolayer cells while allowing outgrowth of the remaining cells. Removed cells were pelleted and supernatant was filtered through a 0.22 µm filter before visualization in the electron microscopy. Cell pellets were treated as described above prior to centrifugation and separation through Optiprep gradients. Aliquots were lysed and the DNA visualized after gel electrophoresis.

(E) Transcription Analyses

Transcripts of TTV-HD full-length genomes were analysed using two different approaches. 5'- and 3"-RACE products were generated from single-as well as double-stranded cDNA. Single-stranded 5"-RACE-Ready and 3'-RACE-Ready cDNAs were respectively synthesized from 1 µg purified total RNA in a 10 µl reaction mix using the SMARTer™RACE cDNA Amplification Kit (Clontech cat#634923) in which RNA is reverse transcribed by SMARTScribe™ Reverse Transcriptase at 42° C. for 90 min. 3'RACE-CDS primer A was used for the synthesis of 3'RACE-Ready cDNA, whereas the 5'RACE-CDS primer A and SMARTer IIA oligonucleotide were used for the synthesis of 5'-RACE-Ready cDNA. Double-stranded cDNA was concomitantly synthesized. Here full-length single stranded cDNA was initially synthesized using the SMARTer™PCR cDNA Synthesis Kit (Clontech cat#634925) according to the manufacturer's protocol. Purified total RNA (1 µg) was transcribed using SMARTScribe™ Reverse Transcriptase and primers 3' SMART CDS PrimerIIA and SMARTer

| IIA | TTV | primer | Nucleotide number | transcript |
|---|---|---|---|---|

Oligonucleotide. These primers both contain a non-template nucleotide stretch thereby creating an extended template. Second-strand cDNA amplification was obtained by long distance PCR amplification (LD PCR) with 5'PCR Primer IIA and the Advantage 2 polymerase mix (Clontech cat#639201). PCR amplification was performed at follows: 15 sec at 95° C., 30 sec at 65° C. and 3 min at 68° C. per cycle and ranging number of cycles in order to determine optimal conditions.

5'- and 3'-RACE PCR amplification was performed using 5'-RACE-Ready or 3'-RACE-Ready cDNA, respectively, or double-stranded cDNA template in both cases. RACE-PCR was performed using Advantage 2 polymerase mix, a universal primer A mix (UPM) from the SMARTer™RACE cDNA Amplification Kit and forward and reverse primers fitting to the respective TTV types (Table 4).

TABLE 4

Nucleotide positions of primers used for PCR amplification in RACE

| TTV | primer | Nucleotide number | transcript |
|---|---|---|---|
| TTV-HD14b | 1-f1 | 716-743 | + |
| | 1-f3 | 2886-2912 | + |
| | 1-r1 | 757-730 | + |
| | 1-r2 | 3521-3492 | + |
| TTV-HD14c | 2-f1 | 716-743 | + |
| | 2-f2 | 3054-3082 | + |
| | 2-r3 | 2912-2885 | + |
| TTV-HD14a | 3-f1 | 717-744 | + |
| | 3-f2 | 2890-2917 | + |
| | 3-f3 | 3496-3521 | + |
| | 3-r1 | 745-720 | − |
| | 3-r2 | 2914-2887 | + |
| TTV-HD14e | 4-f1 | 2887-2914 | + |
| | 4-f2 | 3494-3519 | + |
| | 4-f3 | 3053-3080 | + |
| | 4-r1 | 757-730 | + |
| | 4-r2 | 2911-2884 | + |
| TTV-HD15a | 5-f1 | 125-149 | + |
| | 5-f2 | 2807-2834 | + |
| | 5-f3 | 3388-3415 | + |
| | 5-r1 | 224-197 | + |
| | 5-r2 | 3014-2987 | + |
| | 5-r3 | 3425-3398 | − |
| TTV-HD16a | 6-f1 | 100-127 | + |
| | 6-f2 | 3145-3172 | + |
| | 6-f3 | 3564-3591 | − |
| | 6-r1 | 3204-3182 | + |
| | 6-r2 | 3443-3418 | − |
| TTV-HD20a | 7-f1 | 314-341 | + |
| | 7-f2 | 3025-3052 | + |
| | 7-r1 | 227-200 | + |
| | 7-r2 | 743-716 | + |
| | 7-r3 | 3332-3305 | − |

TABLE 4-continued

Nucleotide positions of primers used for PCR amplification in RACE

| TTV | primer | Nucleotide number | transcript |
|---|---|---|---|
| TTV-HD23b | 10-f1 | 113-139 | − |
|  | 10-f3 | 3121-3148 | + |
| TTV-HD23d | 11-f1 | 126-148 | + |
|  | 11-f2 | 354-381 | + |
|  | 11-f3 | 3397-3422 | − |
|  | 11-r1 | 226-199 | + |
|  | 11-r2 | 3653-3626 | + |
|  | 11-r3 | 3327-3302 | + |
| TTV-HD23a | 12-f1 | 126-148 | + |
|  | 12-f2 | 354-381 | + |
|  | 12-r2 | 3177-3150 | + |
|  | 12-r3 | 3326-3301 | + |

Conditions for amplification were: 29 cycles of 30 sec at 94° C., annealing for 30 sec at 68° C. and elongation for 3 min at 72° C., with a final extension for 15 min at 72° C. All products were analysed by gel electrophoresis, purified after gel elution, cloned into vector pCR2.1 (Invitrogen cat#K2020-40) and sequenced. Two additional controls were performed in order to control for non-specific amplification. In one control amplification was performed using only one TTV-specific primer and in the second using the UPM primer alone. No products were detected in either of these.

Example 2

Demonstration of the Persistence of TTV DNA in Cells from Tissue Culture Lines Derived from Malignant Tumors Cell lines derived from malignant tumors possess one advantage over primary tumor biopsy material. They commonly represent pure preparations of cancer cells, whereas primary materials are commonly contaminated by normal mesenchymal cells, by cells of the hematopoietic system and normal epithelial cells. On the other hand, one disadvantage of tissue culture lines may arise from the selection of specific clones growing under tissue culture conditions and the acquisition of secondary genetic modifications in the course of long-term cultivation. In addition, fetal calf sera may pose a risk due to the introduction of cattle viruses which survive serum inactivation procedures (e.g. bovine polyomavirus); see Table 5 summarizing these advantages/disadvantages.

TABLE 5

Analysis of primary tumor biopsies vs established cell lines for TTV-related sequences

| Biopsies | | Cell lines | |
|---|---|---|---|
| Advantage | Disadvantage | Advantage | Disadvantage |
| Authentic materials | Contaminated by admixture of normal cells Search for TTV sequences clouded by the uniform presence of TTV in the peripheral blood Availability limited | Pure preparations of cancer cells Available in unlimited amounts | Selection of specific Clones adapted to tissue culture conditions Secondary genetic changes during long-term cultivation Use of fetal calf serum poses the risk of contaminations with cattle viruses |

Attempts to find TTV DNA in human primary tumor materials suffers from one disadvantage: the plurality of TTV genotypes in human material. This renders it virtually impossible to identify a specific genotype as an etiologic agent for a human cancer type. For these reasons studies on the persistence of TTV DNA sequences in cells derived from cancer tissue culture lines were initiated. Thus far the results have been extremely surprising: PCR primers used to discover regions of the TTV large open reading frame have been entirely unsuccessful. However, other primer combinations, discovering exclusively a short GC-rich regulatory region of the TTV genome of about 71 bases, detected this sequence in a larger number of cell lines (FIG. 1). This regulatory region is highly conserved among different TTV genotypes and is not present in the human genome data bank.

In a first series of experiments the same sequence was discovered in a number of additional cell lines. These included the following lines:

MCF7 (breast cancer line);
HAK-1, KMH-2, L1236 (all Epstein-Barr virus negative Hodgkin's lymphoma lines);
Y69 (Epstein-Barr virus negative B-lymphoma)
HSB-2 (acute lymphocytic leukemia);
P3HR-1 (Epstein-Barr virus-positive Burkitt's lymphoma);
BJAB (Epstein-Barr virus negative Burkitt's lymphoma);
Ng (EBV-immortalized B lymphoblasts from a patient with multiple sclerosis)-

Figure 2:
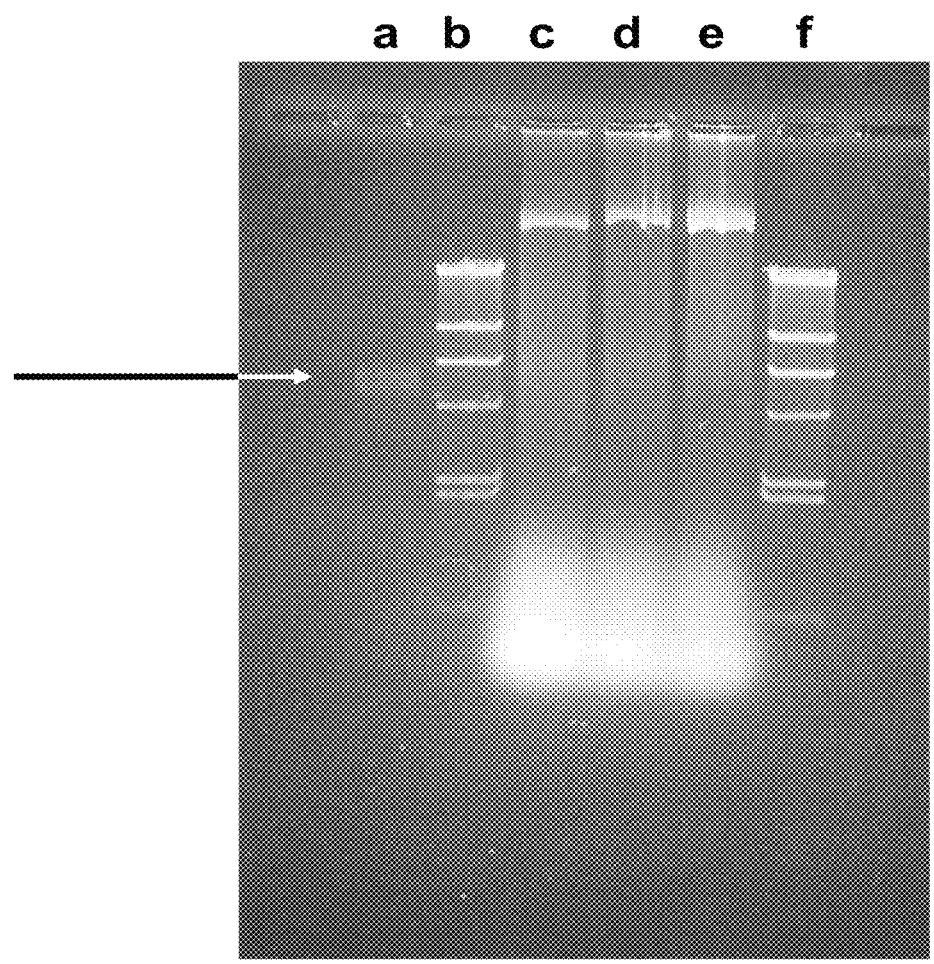
FIG. 2: Spooled DNA remaining in the supernatant of L1236 cells after precipitation and removal of high molecular weight DNA and RNase digestion Two bands are visible in the region between 4.3 and 6.6 base bands.

Besides these 9 positive lines, two melanoma cell lines (IGL and KR, FIG. 1) and human placenta DNA were negative in initial experiments. Interestingly, after removal of spooled DNA from L1236 cells and RNase treatment of the remaining solution, besides mitochondrial DNA two faint bands of similar size became visible banding between positions 4.3-6.6 kb (double-stranded DNA size marker) in the agarose gels (FIG. 2). Analysis of these sequences revealed again the presence of the TTV regulatory region. Mung-bean nuclease, digesting selectively single-stranded DNA, completely abolished the cellular DNA-containing bands from four multiple sclerosis biopsies in contrast to double-stranded control DNA, underlining the single-stranded nature of the former. Similar studies are presently conducted for isolates from tumor DNA.

Example 3

Analyses of Chimeric TTV/Truncated Host Cell DNA Sequences

Figure 3:
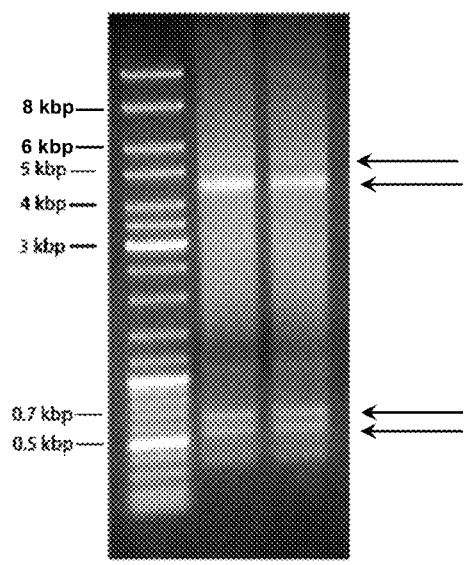
FIG. 3: Outwards-directed long-PCR, using primers of the 71 base TTV HCR region in HSB-2 DNA Two bands are visible in regions corresponding to 4.5 to 7 kb. In addition, bands emerge in the region corresponding to 0.4 to 0.7 kb.

Initially, all attempts failed to use primers in outwards orientation starting within the regulatory region in order to find flanking TT viral DNA, surrounding this region. Invariably, however, human cellular DNA was demonstrated in the respective clones (FIG. 3).

The human genes in these clones and their arrangements within the single-stranded episomal DNA, obviously controlled by the TTV 71 base region, are presently being analyzed. The available data indicate a substantial variation in the uptake of commonly truncated host cell genes. Their possible conversion into growth-stimulating oncogenes or into functions interfering with tumorsuppressor genes requires functional tests which are presently under investigation. The same accounts for rearranged TTV virus sequences. Some of the available data are presented in FIGS. 7, 8, 9, and 11 to 13.

Example 4

Identification and Characterization of TTV Genomes

Initial amplification of the short conserved GC-rich region of TT viruses in serum and biopsy samples led to the identification of TTV DNA in the majority of cases. Subsequent amplification of the complete genome is necessary to identify specific TTV types as many share exact DNA homology in the amplified 71 bp lying in the control region, but differ as much as 60-80% in sequence identity in the rest of their genomes. A number of back-to-back primer combinations was designed on sequences obtained during the course of the investigations (Table 2). Long distance PCR amplification was performed on TTV DNA positive samples. Amplicons ranging between 3 to 4 kb were cloned and sequenced. TTV DNA positive samples originated from healthy subjects as well as patients with leukaemia, multiple sclerosis, rheumatoid arthritis and kidney disease. Part of these data has previously been described (Leppik et al., 2007; Sospedra et al., 2005; de Villiers et al., 2009).

A total of 53 full-length DNA genomes were characterized. As many as 12 distinct full-length isolates were identified after sequencing 19 genomes from a single biopsy. The genome organization of different isolates of one TTV type varied despite low diversity of nucleotides (ranging from 1-4%). Although the large open reading frame ORF1 was mainly involved, differences within the noncoding region and other genes were also noted. These data confirmed earlier observations (Jelcic et al., 2004; Leppik et al., 2007; de Villiers et al., 2009). Modifications in the ORF1 included premature stop codons leading to separate smaller ORFs in this region, considerable sequence diversity in the hypervariable region (Nishizawa et al., 1999; Jelcic et al., 2004) or absence of a stop codon resulting in a larger ORF1 than present in the prototype (FIG. 16). The official classification of the family Anelloviridae is based on comparisons of the ORF1 DNA sequences (Biagini and de Micco, 2010). Due to the ORF1 modifications in the isolates obtained, the full-length genomic sequences was included in the phylogenetic analyses presented here. The aim of this analysis was to gain an overview of the isolates TTV-HD in relation to established TTV species (FIG. 18). All previous isolates are included in this tree as well (Jelcic et al., 2004; Leppik et al., 2007; de Villiers et al., 2009).

Example 5

In Vitro Replication of TTV-HD

Attempts to associate torque teno virus infection with the pathogenesis of a specific disease have repeatedly been reported in the past. Samples from a large range of diseases have been analysed. In vitro investigations were hampered by negative attempts to identify a cell culture system in which these viruses may readily be propagated over longer time periods. Virus particles were initially characterized with the help of density gradients and immunoglobulin aggregates (reviewed in Okamoto, 2009) and later visualized from sera and feces (Itoh et al., 2000). Torque teno viruses occur predominantly in cells of the hematopoietic system (Okamoto, 2009). The first isolates were obtained from the spleen of a patient with Hodgkin's lymphoma (Jelcic et al., 2004). Therefore, the L428 cell line was used in initial attempts to demonstrate in vitro replication and transcription of TTV-HD3a. Replication of the full-length genome for up to 7 days after transfection of the linearized virus DNA was achieved (Leppik et al., 2007). In order to extend this period of replication, full-length TTV genomes were transfected into the human embryonic kidney cell line 293TT which was engineered to express high levels of SV40 large T antigen (Buck et al., 2004). Secondly, it was decided to include 12 full-length isolates in this study in order to determine whether 1) variations in the ORF1 would influence replication and formation of virus particles, 2) divergent TTV types vary in their mode of replication. Great care was taken in propagating all 12 isolates in parallel in order to exclude variation as far as possible which may occur during handling.

The following isolates were chosen for transfection and propagation: TTV-HD3a (Leppik et al., 2007) and TTV-HD1a (Jelcic et al., 2004). TTV-HD1a is closest related to species TTV3 (hel32) and TTV-HD3a to species TTV12 (ct44f) (FIG. 4). TTV-HD16a (species TTV22-related), TTV-HD15a (species TTV12-related), TTV-HD14a, TTV-HD14b, TTV-HD14c and TTV-HD14e (species TTV29-related) were all isolated from brain biopsies from patients with multiple sclerosis. TTV-HD20a (species TTV13-related) originated from kidney tissue and TTV-HD23a, TTV-HD23b and TTV-HD23d (species TTV3-related) were amplified from serum taken from patients with rheumatoid arthritis. The sequences of TTV-HD14a, TTV-HD14b, TTV-HD14c and TTV-HD14e vary between 1-2% in their full-length genomes. The prototype is TTV-HD14a with an intact ORF1 of 648 amino acids (aa) in size. The ORF1 of TTV-HD14b is 660aa in size with only 554aa sharing identity to TTV-HD14a ORF1, whereas the rest of the ORF indicates fusion to ORF4 (after de Schmidt and Noteborn, 2009). Similarly, TTV-HD14c ORF1 is 712aa and constitutes an ORF1 (first 645aa) fused to ORF5. TTV-HD14e ORF1 is interrupted resulting in 2 ORFs of 467aa and 179aa in size. The TTV-HD23b, TTV-HD23d and TTV-HD23a genomes vary only between 1-3% in sequence identity, but their ORF1 genes differ as follows: TTV-HD23a ORF1 as prototype is 736aa in size, TTV-HD23b ORF1 DNA sequence varies from that of TTV-HD23a in the hypervariable region by 18.4% (34.2% in amino acids). TTV-HD23b and TTV-HD23d DNA sequences differ only 1% in overall identity, but the TTV-HD23d ORF1 is interrupted resulting in 2 ORFs 307aa and 365aa in size (FIG. 16).

Transfections were performed on semi-confluent 293TT cells. The nature of this cell line with its many rounded cells attached to the monolayer does not permit a clear-cut identification of cytopathic effects. Cells were passaged when confluent or when cells started to detach from the surface. Flasks were shaken to loosen all cells. Cells were centrifuged and aliquots frozen, as well as used for DNA and RNA extraction and electron microscopic analyses. Frozen infected cells were initially used to re-infect new 293TT cultures as re-infection failed if cells had previously been trypsinized at the time of harvest. Virus replication was monitored by performing long-distance PCR on DNA extracted from infected cells. Periods between re-infection and cell harvest varied between 3 to 7 days, depending on culture density. No obvious morphological differences were noted between cultures of different TTV isolates. Re-infection during the course of one experiment was performed several times using frozen cell aliquots frozen. In vitro propagation of TT viruses has not been described before. Restriction enzyme digestion was performed on cellular DNA obtained from the initially transfected samples to remove any residual bacteria-generated virus DNA. Long PCR amplification results indicated de novo replication of virus DNA. Examples of these TTV DNA amplicons using infected cellular DNA as template are presented in FIG. 19.

Long distance PCR amplification of the full-length DNA molecules indicated considerable differences between cultures. Second round amplifications (using the same primers as in the first round) were necessary on all cultures infected with isolates from brain biopsies, i.e. TTV-HD16a, HD15a and the 4 individual TTV-HD14 isolates (FIG. 19A), despite their divergence (45-50% nucleotide homology) according to the phylogenetic analyses (FIG. 18). Modifications in ORF1 did not seem to influence amplification or propagation as visualized in the amplification of the full-length DNA (FIG. 21A a-c). Additional DNA amplicons varying in size were observed in HD15a-infected cultures. The occurrence of these molecules increased during subsequent propagation with a concomitant reduction in the full-length genome (FIG. 21A a-c lane 5). Applicants previously reported subviral molecules of a similar nature in human serum samples (Leppik et al., 2007). Similar off-sized amplicons were also occasionally noted in TTV-HD16a-infected cultures (lane 6) and rarely in TTV-HD14 cultures (lanes 1-4).

Large differences were noted in the behaviour of the other 6 isolates. This variation was also evident between experiments and passages (FIG. 19B b1, b2, b3) reflecting an apparent high sensitivity to very minor modifications in culturing conditions. The initially replicating full-length genome (3.8 kb) was lost during propagation (FIG. 19B a-c) in concurrence with prominent subgenomic amplicons ranging in size in TTV-HD20a-, TTV-HD3a- and TTV-HD1a-infected cells (lanes 7-9, FIG. 19B). Amounts of input DNA used for long-distance PCR amplification, as well as of amplicons loaded onto gels were the same for all cultures. The high level of DNA amplicons of isolates TTV-HD23b, TTV-HD23d and TTV-HD23a after a single round of long-distance PCR may therefore indicate a stronger replication potential during early passages.

Due to the differences observed between the two groups of isolates, it was investigated whether variations could be observed during serial sampling. Equivalent passages of TTV-HD14e and TTV-HD23b were propagated in parallel and samples were taken daily. Long-distance amplification indicated a constant replication of TTV-HD14e (visible after two rounds of DNA amplification) in contrast to the decreasing replication of TTV-HD23b (visible already after a single round of DNA amplification) which was lost after 10 days in culture (FIG. 19C). These cultures were not passaged and morphological differences between cultures were not noticeable.

Example 6

In Vitro Formation, Replication and Characterization of μTTV Subviral Molecules

Figure 20:
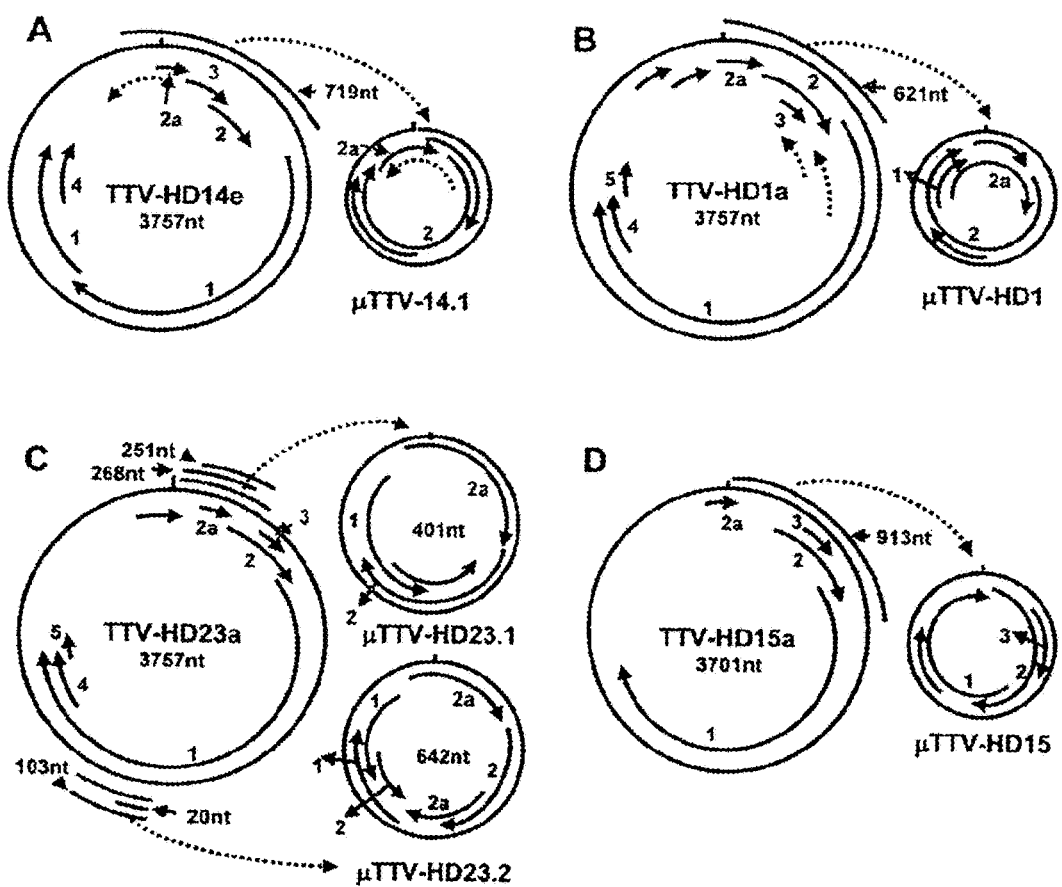
Figure 21:
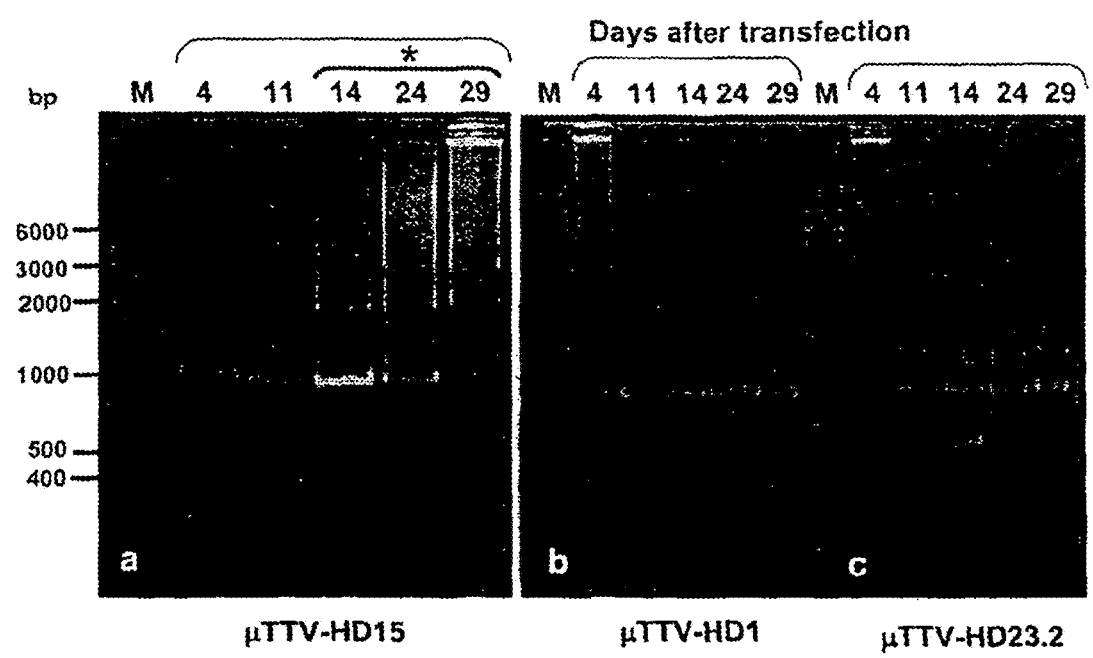

The appearance of smaller DNA amplicons of a constant size in cultures from isolates TTV-HD14b, TTV-HD14c, TTV-HD14d and TTV-HD14e, as well as TTV-HD1a and the 3 TTV-HD23 isolates, was already noted early after transfection and was maintained during passages (FIGS. 19A and B). They were cloned and characterized. These subviral DNA molecules (μTTV-HD14, 719 bases in size) from TTV-HD14b and the 3 TTV-HD14 isolates were all identical in DNA sequence and represented circular subgenomic rearranged molecules originating from the parental TTV-HD14 genome (FIG. 20A). Similarly, a rearranged subviral DNA molecule (μTTV-HD1, 621 bases) originated from the parental TTV-HD1a genome (FIG. 20B). Interestingly, replication of μTTV-HD1 was maintained during passages, despite the disappearance of the full-length TTV-HD1a genome. This presence or absence of the subviral molecules in TTV-HD23 cultures indicates a possible influence of culturing conditions. Here these molecules ranged from 400 to 900 bases in size with an increased level of 642 and 401 base molecules. Characterization of the cloned molecules indicated an apparent evolutionary preferred maturation process as a segment of the 401 base subviral molecule (μTTV-HD23.1) was duplicated in the 642 base subviral DNA (μTTV-HD23.2; FIG. 20C). Multiple versions of this segment were present in larger molecules. Subviral genomes originating from TTV-HD23b, TTV-HD23d as well as TTV-HD23a cultures, were all identical in DNA sequence. Transfection of these subviral rearranged molecules in 293TT cells resulted in replication of their genomes (FIG. 21) as visualized after PCR amplification. Interestingly, the respective μTTV reacted exactly in the same way as the parental genomes, i.e. genomic μTTV-HD15 DNA initial replication was strong, but was subsequently only visualized after nested PCR amplification (FIG. 21). Small protein-like structures 10 nm in size were visible by electron microscopy after filtration (0.22 μm) of the culture medium from these cell cultures (FIG. 22).

Example 7

Purification of Virus-Like Particles (Complete Genomes and μuTTV)

Attempts to purify virus particles were initiated after second round re-infections. Crude cell extracts were centrifuged on 27-33-39% Opti-prep step gradients (Buck et al., 2005). Aliquots of gradient fractions were lysed prior to separation by gel electrophoresis. Gradient fractions indicating virus DNA were frozen at −80° C. and used for further re-infections. Two DNA bands at the 2 kb and 1.0 kb level of the double-stranded DNA size marker were clearly visible (FIG. 8A). The exact sizes of these DNA molecules could not be determined as suitable single-stranded DNA markers are not available. Cell suspensions were, in addition, filtered through a 0.22 μm filter prior to gradient centrifugation. Negative staining of these samples indicated virus-like particles of approximately 30 nm in size (FIG. 8). Similarly protein structures (ca. 10 nm in size) were seen after filtration of the culture medium after propagation of the μTTV-HD genomes (FIG. 22). These filtrates were lysed and the DNA separated on agarose gels (FIG. 22).

Example 8

In Vitro Transcription

Detailed transcription patterns of TTV have been reported for the isolates TTV-P1C1 (Müller et al., 2008), TTV-HEL32 (Qiu et al., 2005; Kakkola et al., 2009) and TTV-HD3a (Leppik et al., 2007). Three main mRNA species (1.0, 1.2 and 3.0 kb) had earlier been reported in bone marrow cells (Okamoto et al., 2000a) and in COS1 cells (Kamahora et al., 2000). Predictions for use of initiation codons according to Kozak rules (Jelcic et al., 2004) in combination with use of alternative splice acceptor and donor sites (Leppik et al., 2007) indicated the involvement of non-conserved mechanisms during transcription of torque teno viruses. The transcription of the isolates was investigated by using single-, as well as double-stranded cDNA as templates for 3"- and 5"RACE mapping. Double-stranded cDNA reduces the possibility for the formation of non-specific hybrids. In addition, primers (forward and reverse) were selected which were located within the intergenic regions, instead of commonly used gene-specific primers. This was done in aim of covering the expression of any unpredicted genes in the TTV genome. RNA from all cultures was extracted on day 7 after transfection. RNA from control transfections with vector alone was included to control for false positive amplification. The transcription analyses were repeated to control for a suitable time point for harvesting mRNA by extracting RNA 48 hours after transfection in the case of isolate TTV-HD14e. Transcription patterns observed did not differ between day 2 and day 7. All results obtained in the transcription analyses are presented in FIG. 17.

Abundant transcripts were isolated from TTV-HD23 infected cultures. Their transcription patterns, as well as those for TTV-HD20a, TTV-HD15a, TTV-HD16a were in general similar to previously described transcription patterns (reviewed in Kakkola et al., 2009). An exception is the absence of a full-length ORF1 transcript from all of the isolates. This is surprising in view of the fact that virus-like particles are concomitantly being produced. Transcripts covering sections of the ORF1 gene (either the 5'- or the 3'-ends) and which could code for smaller proteins, were present (examples in FIG. 17). In silico analyses for putative proteins revealed additional information from what have to date been reported. Examples are splicing (fusions) between either ORF2 or ORF2a with ORF1 or with ORF5 in TTV-HD16a (6.3s.2, 6.3s.3, 6.3s.9), Splicing between ORF1 and ORF5 is another possibility (6.3.7). Short transcripts covering the region of ORF2 in TTV-HD20a may also be expressed as a smaller ORF1 protein (7.3.5, 7.3.4, 7.5.13) (FIG. 17). Transcripts were in addition obtained using primers (forward or reverse) located in the control region. Two observations were made. Reverse primers resulted in spliced or non-spliced transcripts covering extended regions of the genome (12.5.19, 12.5.20, 12.5.21, 5.5s.16, 5.5s.17, 5.5s.18, 5.5s.19) or transcripts varying in length which did not have any coding capacity (5.5s.12, 5.5s.13, 5.5s.14, 5.5s.15, 11.5.7, 11.5.8, 11.5.9). Amplification with forward primers in this region resulted in other short non-coding transcripts or spliced transcripts with coding capacity even as distant as ORF5 (4.3.4, 3.3.1, 3.3.2) (FIG. 17).

LIST OF REFERENCES

1. Belotserkovskii, B. P., Liu, R., Tornaletti, S., Krasilnikova, M. M., Mirkin, S. M. and Hanawalt, P. C. 2010. Mechanisms and implications of transcription blockage by guanine-rich DNA sequences. Proc. Natl. Acad. Sci USA. 107:12816-12821.
2. Biagini, P., and P. de Micco. 2010. La famille des Anelloviridae: virus TTV et genres apparentés. Virologie 14:3-16.
3. Biagini, P., Charrel, R. N., de Micco, P., and X. de Lamballerie. 2003. Association of TT virus primary infection with rhinitis in a newborn. Clin. Infect. Dis. 36:128-129.
4. Buck, C. B., Pastrana, D. V., Lowy, D. R., and J. T. Schiller. 2004. Efficient intracellular assembly of papillomaviral vectors. J. Virol. 78:751-757.
5. Buck, C. B., Pastrana, D. V., Lowy, D. R., and J. T. Schiller. 2005. Generation of HPV pseudovirions using transfection and their use in neutralization assays. Methods Mol. Med. 119:445-462.
6. Del Val, C., Mehrle, A., Falkenhahn, M., Seiler, M., Glatting, K-H., Poustka, A., Suhai, S., and S. Wiemann. 2004. High-throughput protein analysis integrating bioinformatics and experimental assays. Nucleic Acid Res. 32:742-748.
7. de Schmidt, M. H., and M. H. M. Noteborn. 2009. Apoptosis-inducing proteins in chicken anemia virus and TT virus. Curr. Topics Microbiol. Immunol. 331:131-149.
8. de Villiers, E-M., Kimmel, R., Leppik, L., and K. Gunst. 2009. Intragenomic rearrangement in TT viruses: a possible role in the pathogenesis of disease. Curr. Topics Microbiol. Immunol. 331:91-107.
9. de Villiers, E-M., Schmidt, R., Delius, H., and H. zur Hausen. 2002. Heterogeneity of TT virus related sequences isolated from human tumor biopsy specimens. J. Mol. Med. 80:44-50.
10. Fei, J-W., Wei, Q-X., Angel, P., and E-M. de Villiers. 2005. Differential enhancement of a cutaneous HPV promoter by p63, Jun and mutant p53. Cell Cycle 4:689-696.
11. Garbuglia, A. R., Iezzi, T., Capobianchi, M. R., Pignoloni, P., Pulsoni, A., Sourdis, J., Pescarmona, E., Vitolo, D., and F. Mandelli. 2003. Detection of TT virus in lymph node biopsies of B-cell lymphoma and Hodgkin's disease, and its association with EBV infection. Int. J. Immunopathol. Pharmacol. 16:109-118.
12. Itoh, Y., Takahashi, M., Fukuda, M., Shibayama, T., Ishikawa, T., Tsuda, F., Tanaka, T., Nishizawa, T., and H. Okamoto. 2000. Visualization of TT virus particles recovered from the sera and feces of infected humans. Biochem. Biophys. Res. Commun 279:718-724.
13. Jelcic, I., Hotz-Wagenblatt, A., Hunziker, A., zur Hausen, H., and E-M. de Villiers. 2004. Isolation of multiple TT virus genotypes from spleen biopsiey tissue from a Hodgkin's disease patient: Genome reorganization and diversity in the hypervariable region. J. Virol. 78:7498-7507.
14. Jeske, H. 2009. Geminiviruses. Curr Top Microbiol Immunol. 331:185-226
15. Kakkola, L., Bondén, H., Hedman, L., Kivi, N., Moisala, S. Julin, J., Ylä-Liedenpohja, Miettinen, S., Kantola, K., Hedman, K., and M. Söderlund-Venermo. 2008. Expression of all six human Torque teno virus (TTV) proteins in bacteria and in insect cells, and analysis of their IgG responses. Virology 382:182-189.
16. Kakkola, L., Hedman, K., Qiu, J., Pintel, D., and M. Söderlund-Venermo. 2009. Replication of and protein synthesis by TT viruses. Curr. Topics Microbiol. Immunol. 331: 53-64.
17. Kakkola, L., Tommiska, J., Boele, L. C. L., Miettinen, S., Blom, T., Kekarainen, T., Qiu, J., Pintel, D., Hoeben, R C., Hedman, K., and M. Söderlund-Venermo. 2007. Construction and biological activity of a full-length molecular clone of human Torque teno virus (TTV) genotype 6. FEBS. J. 274:4719-4730.
18. Kamada, K., Kamahora, T., Kabat, P., and S. Hino. 2004. Transcriptional regulation of TT virus: promoter and enhancer regions in the 1.2-kb noncoding region. Virology 321:341-348.
19. Kamahora, T., Hino, S., and H. Miyata. 2000. Three spliced mRNAs of TT virus transcribed from a plasmid containing the entire genome in COS1 cells. J. Virol 74:9980-9986.
20. Kanda, Y., Tanaka, Y., Kami, M., Saito, T., Asai, T., Izutsu, K., Yuji, S., Ogawa, S., Honda, H., Mitani, K., Ciba, S., Yasaki, Y., and H. Hirai. 1999. TT virus in bone marrow transplant recipients. Blood 93: 2485-2490.
21. Kazi, A., Miyata, H., Kurokawa, K., Khan, M. A., Kamahora, T., Katamine, S., and S. Hino. 2000. High frequency of postnatal transmission of TT virus in infancy. Arch. Virol. 145:535-540.

22. Kovacs, E., Tompa, P., Liliom, K., and L. Kalmar. 2010. Dual coding in alternative reading frames correlates with intrinsic protein disorder. Proc. Natl. Acad. Sci. U.S.A 107:5429-5434
23. Leppik, L., Gunst, K., Lehtinen, M., Dillner, J., Streker, K., and E-M. de Villiers. 2007. In vivo and in vitro intragenomic rearrangement of TT viruses. J Virol 81:9346-9356.
24. Maggi, F., Andreoli, E., Riente, L., Meschi, S., Rocchi, J., Delle Sedie, A., Vatteroni, M L., Ceccherini-Nelli, L., Specter, S., and M. Bendinelli. 2007. Torquetenovirus in patients with arthritis. Rheumatology 46:885-886.
25. Maggi, F., Focosi, D., Albani, M., Lanini, L., Vatteroni, M L, Petrini, M., Ceccherini-Nelli, L., Pistello, M., and M Bendinelli. 2010. Role of hematopoietic cells in the maintenance of chronic human torquetenovirus plasma viremia. J. Virol. 84:6891-6893.
26. Maggi, F., Fornai, C., Vatteroni, M L., Siciliano, G., Menichetti, F., Tascini, C., Specter, S., Pistello, M., and M. Bendinelli. 2001a. Low prevalence of TT virus in the cerebrospinal fluid of viremic patients with central nervous system disorders. J. Med. Virol. 65:418-422
27. Maggi, F., Fornai, C., Zaccaro, L., Morrica, A., Vatteroni, M. L., Isola, P., Marchi, S., Ricchiuti, A., Pistello, M., and M. Bendinelli. 200 lb. TT virus (TTV) loads associated with different peripheral blood cell types and evidence for TT replication in activated mononuclear cells. J. Med. Virol. 64:190-194.
28. Maggi, F., Pifferi, M., Fornai, C., Andreoli, A., Tempestini, E., Vatteroni, M., Presciuttini, S., Marchi, S., Pietrobelli, A., Boner, A., Pistello, M., and M. Bendinelli. 2003a. TT virus in the nasal secretions of children with acute respiratory disease: relations to viremia and disease severity. J. Virol. 77:2418-2425.
29. Maggi, F., Pifferi, M., Tempestini, E., Fornai, C., Lanini, L., Andreoli, E., Vatteroni, M., Presciuttini, S., Pietrobelli, A., Boner, A., Pistello, M., and M. Bendinelli. 2003b. TT virus loads and lymphocyte subpopulations in children with acute respiratory diseases. J. Virol 77:9081-9083.
30. Mariscal, L. F., Lopez-Alcorocho, J. M., Rodriguez-Inigo, E., Ortiz-Movilla, N., de Lucas, S., Bartolome, J., and V. Carreno. 2002. TT virus replicates in stimulated but not in nonstimulated peripheral blood mononuclear cells. Virology 301:121-129.
31. Müller, B., März, A., Doberstein, K., Finsterbusch, T., and A. Mankertz. 2008. Gene expression of the human Torque Teno Virus isolate P/1C1. Virology 381:36-45.
32. Nawaz-ul-Rehman, M. S., and C. M. Fauquet. 2009. Evolution of geminiviruses and their satellites. FEBS Letter 583:1825-1832.
33. Nishizawa, T., Okamoto, K., Konishi, H., Yoshikawa, H., Miyakawa, Y., and M. Mayumi. 1997. A novel DNA virus (TTV) associated with elevated transaminase levels in posttransfusion hepatitis of unknown etiology. Biochem. Biophys. Res. Commun. 241:92-97.
34. Ninomiya, M., Nishizawa, T., Takahashi, M., Lorenzo, F. R., Shimosegawa, T., and H. Okamoto. 2007. Identification and genomic characterization of a novel human torque teno virus of 3.2 kb. J. Gen. Virology 88:1939-1944.
35. Ninomiya, M., Takahashi, M., Nishizawa, T., Shimosegawa, T., and H. Okamoto. 2008. Development of PCR assays with nested primers specific for differential detection of three human anelloviruses and early acquisition of dual or triple infection during infancy. J. Clin. Microbiol. 46:507-514.
36. Okamoto, H. 2009. History of discoveries and pathogenicity of TT viruses. Curr. Top. Microbiol. Immunol. 331:1-20.
37. Okamoto, H., Nishizawa, T., Tawara, A., Takahashi, M., Kishimoto, J., Sai, T., and Y. Sugai. 2000a. TT virus mRNAs detected in the bone marrow cells from an infected individual. Biochem. Biophys. Res. Commun. 279:700-707.
38. Okamoto, H., Takahashi, M., Kato, N., Fukuda, M., Tawara, A., Fukuda, S., Tanaka, T., Miyakawa, Y., and M. Mayumi. 2000b. Sequestration of TT virus of restricted genotypes in peripheral blood mononuclear cells. J. Virol. 74:10236-10239.
39. Okamoto, H., Takahashi, M., Nishizawa, T., Tawara, A., Sugai, Y., Sai, T., Tanaka, T., and F. Tsuda. 2000c. Replicative forms of TT virus DNA in bone marrow cells. Biochem. Biophys. Res. Commun. 270:657-662.
40. Okamoto, H., Ukita, M., Nishizawa, T., Kishimoto, J., Hoshi, Y., Mizuo, H., Tanka, T., Miyakawa, Y., and M. Mayumi. 2000d. Circular double-stranded forms of TT virus DNA in the liver. J. Virol. 74:5161-5167.
41. Paprotka, T., Metzler, V., and H. Jeske. 2010. The first DNA 1-like a satellite in association with New World begomovirus in natural infections. Virology 404:148-157.
42. Patil, B. L, and C. M. Fauquet. 2010. Differential interaction between cassava mosaic geminivirus and geminivirus satellites. J. Gen. Virol. 91:1871-1882.
43. Peng, Y. H., Nishizawa, T., Takahashi, T., Ishikawa, T., Yoshikawa, A., and H. Okamoto. 2002. Analysis of the entire genomes of thirteen TT virus variants classifiable into the fourth and fifth genetic groups, isolated from viremic infants. Arch. Virol. 147:21-41.
44. Pifferi, M., Maggi, F., Andreoli, E., Lanini, L., Marco, E D., Fornai, C., Vatteroni, M L., Pistello, M., Ragazzo, V., Macchia, P., Boner, A., and M. Bendinelli. 2005. Associations between nasal torquetenovirus load and spitometric indices in children with asthma. J. Infect. Dis. 192: 1141-1148.
45. Qiu, J., Kakkola, L., Cheng, F., Ye, C., Söderlund-Venermo, M., Hedman, K., and D. J. Pintel. 2005. Circovirus TT virus genotype 6 expresses six proteins following transfection of a full-length clone. J. Virol. 79:6506-6510.
46. Ryabova, L. A., Pooggin, M., and T. Hohn. 2006. Translation reinitiation and leaky scanning in plant viruses. Virus Res. 119:52-62.
47. Saunders, K., Bedford, I. D., Briddon, R. W., Markham, P. G., Wong, S. M., and J. Stanley. 2000. A unique virus complex causes *Ageratum* yellow vein disease. Proc. Natl. Acad. Sci. USA 97:6890-6895.
48. Shiramizu, B., Yu, Q., Hu, N., Yanagihara, R., and V. R. Nerurkar. 2002. Investigation of TT virus in the etiology of pediatric acute lymphoblastic leukaemia. Pediatr. Hematol. Oncol. 19:543-551.
49. Sospedra, M., Zhao, Y., zur Hausen, H., Muraro, P. A., Hamashin, C., de Villiers, E. M., Pinilla, C., and R. Martin. 2005. Recognition of conserved amino acid motifs of common viruses and ist role in autoimmunity. PLoS Pathog. 1:e41.
50. Stanley, J. 2004. Subviral DNAs associated with geminivirus disease complexes. Vet. Microbiol 98:121-129.
51. Takahashi, M., Asabe, S., Gotanda, Y., Kishimoto, J., Tsuda, F., and H. Okamoto. 2002. TT virus is distributed in various leukocyte subpopulations at distinct levels, with the highest viral load in granulocytes. Biochem. Biophys. Res. Commun. 290:242-248.

52. Takahashi, K., Iwasa, Y., Hijikata, M., and S. Mishiro. 2000. Identification of a new human DNA virus (TTV-like mini virus, TLMV) intermediately related to TT virus and chicken anemia virus. Arch. Virol. 145:979-993.
53. Zhong, S., Yeo, W., Tang, M., Liu, C., Lin, X. R., Ho, W. M., Hui, P., and P. J. Johnson. 2002. Frequent detection of the replicative form of TT virus DNA in peripheral blood mononuclear cells and in bone marrow cells in cancer patients. J. Med. Virol. 66:428-434.
54. zur Hausen H., and E-M. de Villiers. 2005. Virus target cell conditioning model to explain some epidemiologic characteristics of childhood leukemias and lymphomas. Int. J. Cancer 115:1-5.

The invention is further described by the following numbered paragraphs:

1. 1. A rearranged TT virus polynucleic acid comprising
   (a) a nucleotide sequence shown in FIG. 6;
   (b) a nucleotide sequence which shows at least 70% identity to a nucleotide sequence of (a) and is capable of replicating autonomously and/or inducing autonomous replication;
   (c) a fragment of a nucleotide sequence of (a) or (b) which is capable of replicating autonomously;
   (d) a nucleotide sequence which is the complement of the nucleotide sequence of (a), (b), or (c); or
   (e) a nucleotide sequence which is redundant as a result of the degeneracy of the genetic code compared to any of the above-given nucleotide sequences.

2. The rearranged TT virus polynucleic acid of paragraph 1 consisting of
   (a) a nucleotide sequence shown in FIG. 6;
   (b) a nucleotide sequence which shows at least 70% identity to a nucleotide sequence of (a) and is capable of replicating autonomously and/or inducing autonomous replication;
   (c) a fragment of a nucleotide sequence of (a) or (b) which is capable of replicating autonomously;
   (d) a nucleotide sequence which is the complement of the nucleotide sequence of (a), (b), or (c); or
   (e) a nucleotide sequence which is redundant as a result of the degeneracy of the genetic code compared to any of the above-given nucleotide sequences.

3. The rearranged TT virus polnucleic acid of paragraph 1 or 2, wherein said nucleotide sequence of (a), (b), (c), (d) or (e) is linked to a polynucleic acid encoding a polypeptide containing a signature motif of a mammalian protein or allergen being associated with cancer or an autoimmune disease.

4. The rearranged TT virus polynucleic acid of any one of paragraphs 1 to 3 which is present as a single- or double-stranded extrachromosomal episome.

5. The rearranged TT virus polynucleic acid of any one of paragraphs 1 to 4 which is a single-stranded DNA.

6. The rearranged TT virus polynucleic acid of any one of paragraphs 1 to 5 which is linked to a host cell DNA.

7. The rearranged TT virus polynucleic acid of paragraph 6 having at least one of the following properties:
   (a) growth-stimulation;
   (b) oncogene function;
   (c) tumor suppressor gene-like function; or
   (d) stimulation of autoimmune reactions.

8. The TT virus polynucleic acid of any one of paragraphs 1 to 7 comprising a nucleotide sequence being selected from the group of nucleotide sequences shown in FIGS. 8, 9 and 11 to 13.

9. The rearranged TT virus of any one of paragraphs 1 to 8, wherein said polypeptide is a polypeptide as shown in Table 1.

10. An oligonucleotide primer comprising part of a polynucleic acid according to any one of paragraphs 1 to 7, with said primer being able to act as primer for specifically sequencing or specifically amplifying said polynucleic acid.

11. The oligonucleotide primer of paragraph 10 having a nucleotide sequence being selected from the group consisting of the nucleotide sequences shown in Table 2 and FIG. 10.

12. An oligonucleotide probe comprising part of a polynucleic acid according to any one of paragraphs 1 to 9, wherein said probe can specifically hybridize to said polynucleic acid.

13. The oligonucleotide probe of paragraph 12 having a nucleotide sequence being selected from the group consisting of the nucleotide sequences shown in Table 2 and FIG. 10.

14. The oligonucleotide probe of paragraph 12 or 13, which is detectably labelled or attached to a solid support.

15. The oligonucleotide primer of paragraph 10 or 11 or the oligonucleotide probe of any one of paragraphs 12 to 14 having a length of at least 13 bases.

16. An expression vector comprising a rearranged TT virus polynucleic acid of any one of paragraphs 1 to 9 operably linked to prokaryotic, eukaryotic or viral transcription and translation control elements.

17. The expression vector of paragraph 16 which is an artificial chromosome.

18. A host cell transformed with an expression vector according to paragraph 16 or 17.

19. A polypeptide being encoded by a rearranged TT virus polynucleic acid of any one of paragraphs 1 to 9.

20. An antibody or fragment thereof specifically binding to a polypeptide of paragraph 19.

21. The antibody or fragment thereof of paragraph 20, wherein said antibody or fragment is detectably labelled.

22. A diagnostic kit for use in determining the presence of a rearranged TT virus polynucleic acid of any one of paragraphs 1 to 9, or a polypeptide of paragraph 19, said kit comprising a primer according to paragraph 10, 11 or 15, a probe according to any one of paragraphs 12 to 15, or an antibody according to paragraph 20 or 21.

23. Use of a primer according to paragraph 10, 11 or 15, a probe according to any one of paragraphs 12 to 15, a polypeptide of paragraph 19, or an antibody according to paragraph 20 or 21 for the preparation of a diagnostic composition for the diagnosis of a predisposition or an early stage of cancer or an autoimmune disease.

24. A method for the detection of a rearranged TTV polynucleic acid according to any one of paragraphs 1 to 9 in a biological sample, comprising: (a) optionally extracting sample polynucleic acid, (b) amplifying the polynucleic acid as described above with at least one primer according to paragraph 10 or 11, optionally a labelled primer, and (c) detecting the amplified polynucleic acid.

25. A method for the detection of a rearranged TTV polynucleic acid according to any one of paragraphs 1 to 9 in a biological sample, comprising: (a) optionally extracting sample polynucleic acid, (b) hybridizing the polynucleic acid as described above with at least one probe according to any one of paragraphs 12 to 15, optionally a labelled probe, and (c) detecting the hybridized polynucleic acid.

26. A method for detecting a polypeptide of paragraph 19 or an antibody of paragraph 20 or 21 present in a biological sample, comprising: (a) contacting the biological sample for the presence of such polypeptide or antibody as defined above, and (b) detecting the immunological complex formed between said antibody and said polypeptide.

27. An antisense oligonucleotide reducing or inhibiting the expression of a rearranged TT virus polynucleic acid of any one of paragraphs 1 to 9.

28. The antisense oligonucleotide of paragraph 27, which is an iRNA comprising a sense sequence and an antisense sequence, wherein the sense and antisense sequences form an RNA duplex and wherein the antisense sequence comprises a nucleotide sequence sufficiently complementary to the nucleotide sequence of the rearranged TT virus polynucleic acid of any one of paragraphs 1 to 9.

29. A pharmaceutical composition comprising the antibody of paragraph 20 or 21, or the antisense oligonucleotide of paragraph 27 or 28 and a suitable pharmaceutical carrier.

30. Use of the antibody of paragraph 20 or 21, or the antisense oligonucleotide of paragraph 27 or 28 for the preparation of a pharmaceutical composition for the prevention or treatment of cancer or an autoimmune disease or early stages thereof.

31. The antibody of paragraph 20 or 21 or the antisense oligonucleotide of paragraph 27 or 28 for use in a method of preventing or treating cancer or an autoimmune disease or early stages thereof.

32. Use according to paragraph 30 or 31, wherein said autoimmune disease is multiple sclerosis (MS), asthma, polyarthritis, diabetes, lupus erythematodes, celiac disease, colitis ulcerosa, or Crohn's disease.

33. Use according to paragraph 30 or 31, wherein said cancer is breast cancer, colorectal cancer, pancreatic cancer, cervical cancer, Hodgkin's lymphoma, B-lymphoma, acute lymphocytic leukaemia, or Burkitt's lymphoma.

34. A vaccine comprising a rearranged TT virus polynucleic acid of any one of paragraphs 1 to 9, or a polypeptide according to paragraph 19.

35. The rearranged TT virus polynucleic acid of any one of paragraphs 1 to 9, or the polypeptide of paragraph 19 for use in a method of immunizing a mammal against a TT virus infection.

36. A method for the generation of a database for determining the risk to develop cancer or an autoimmune disease, comprising the following steps (a) determining the nucleotide sequence of a host cell DNA linked to a rearranged TT virus polynucleic acid according to any one of paragraphs 1 to 9 and being present in episomal form, if present, in a sample from a patient suffering from at least one of said diseases; and (b) compiling sequences determined in step (a) associated with said diseases in a database.

37. A method for evaluating the risk to develop cancer or an autoimmune disease of a patient suspected of being at risk of developing such disease, comprising the following steps (a) determining the nucleotide sequence of genomic host cell DNA linked to a rearranged TT virus polynucleic acid according to any one of paragraphs 1 to 9 and being present in episomal form, if present, in a sample from said patient; and (b) comparing sequences determined in step (a) with the sequences compiled in the database generated to the method of paragraph 36, wherein the absence of a host cell DNA linked to a TT virus polynucleic acid or the presence only of genomic host cell DNA linked to a TT virus polynucleic acid not represented in said database indicates that the risk of developing such disease is decreased or absent.

38. A process for the in vitro replication and propagation of Torque teno viruses (TTV) comprising the following steps:

(a) transfecting linearized TTV DNA into 293TT cells expressing high levels of SV40 large T antigen;

(b) harvesting the cells and isolating cells showing the presence of TTV DNA;

(c) culturing the cells obtained in step (b) for at least three days; and (d) harvesting the cells of step (c).

39. The process of paragraph 38, wherein the TTV is a rearranged TTV according to any one of paragraphs 1 to 9. Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An expression vector comprising a rearranged torque teno virus (TTV) polynucleic acid comprising one of the nucleotide sequences of SEQ ID NOs: 228-231, wherein said nucleotide sequence is linked to a polynucleic acid encoding a polypeptide containing a signature motif of a mammalian protein being associated with cancer or an autoimmune disease, wherein the signature motif is at least 10 aa and has a degree of identity to a corresponding signature motif in a mammalian protein of at least 90% and said signature motif is selected from the group consisting of a protamine 1 signature motif having one of the sequences of SEQ ID NOs:17, 19, 22, and 241, a protamine 2 signature motif having one of the sequences of SEQ ID NOs:18, 20, 21, and 23, an opsin signature motif having one of the sequences of SEQ ID NOs: 1-16, and 36, a galanin signature motif having one of the SEQ ID NOs:26-28, a male specific protein signature motif having one of the SEQ ID NOs:53-54, a gastrin signature motif having one of the SEQ ID NOs:38-43, a collagen signature motif having one of the SEQ ID NOs:46-52, a collagenase metalloprotease signature motif having one of the SEQ ID NOs:44-45, a microbial collagenase metalloprotease (M9) signature motif having one of the SEQ ID NOs:55-60, a MIC1 microneme protein signature motif having one of the SEQ ID NOs:61-64: autoimmune regulator (AIRE) signature having one of the SEQ ID NOs:66-70, a gliadin signature motif having one of the SEQ ID NOs:72-77 and 155, a neuropeptide Y2 receptor signature motif having one of the SEQ ID NOs:79-81, an aerolysin signature motif having one of the SEQ ID NOs: 83-87, an orexin signature motif having one of the SEQ ID NOs:89-95, a prion signature motif having one of the SEQ ID NOs:97-103, a neurotensin signature motif having one of the SEQ ID NOs:105-108, an orphan nuclear receptor (4A nuclear receptor) family signature motif having one of the SEQ ID NOs:110-117, a brain derived neurotrophic factor (BDN) signature motif having one of the SEQ ID NOs:118-119, a calcitonin signature motif having one of the SEQ ID NOs:121-128, a leukotrine B4 type 1 receptor signature motif having one of the SEQ ID NOs:129-135, a vasopressin signature motif having one of the SEQ ID NOs:136-147, a melanin concentrating hormone 2 receptor signature motif having one of the SEQ ID NOs:149-150, a prostanoid EP1 receptor signature motif having one of the SEQ ID NOs: 152-154, a cyclin kinase signature motif having one of the SEQ ID NOs:158-169, a peroxisome proliferator-activated receptor signature motif having one of the SEQ ID NOs: 171-178, a muscarinic M1 receptor signature motif having one of the SEQ ID NOs:180-184, a metabotropic gamma-aminobutyric acid type B2 receptor signature motif having one of the SEQ ID NOs:186-188, an argininge deiminase signature motif having one of the SEQ ID NOs:156 and 190-199, an opioid growth factor receptor repeat signature motif having the SEQ ID NO:201, an adhesion molecule CD36 signature motif having one of the SEQ ID NOs:203-209, a myelin proteolipid protein signature motif having the SEQ ID NO:211, and a chlamidiaom signature motif having the SEQ ID NO:213, wherein the rearranged TTV polynucleic acid is operably linked to prokaryotic, eukaryotic or viral transcription and translation control elements and comprising nucleic acid sequence providing expression of a desired open reading frame.

2. The expression vector of claim 1 which is selected from the group consisting of plasmid, cosmid, artificial chromosome, phage and virus.

3. The expression vector of claim 2, wherein the vector is selected from the group consisting of TT virus recombinant molecules, BCG, adenoviral vectors and avipox recombinant viruses.

4. A process for in vitro replication and propagation of a rearranged Torque teno virus (TTV) polynucleic acid comprising the following steps: (a) transfecting the expression vector according to claim 1 into 293TT cells expressing high levels of SV40 large T antigen, (b) harvesting the cells and isolating cells showing the presence of TTV DNA according to claim 1, (c) culturing the cells obtained in step (b) for at least three days, and (d) harvesting the cells of step (c).

* * * * *

SEQUENCE LISTING

```
<160> NUMBER OF SEQ ID NOS: 275

<210> SEQ ID NO 1
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized domain"
      /organism="Artificial Sequence"

<400> SEQUENCE: 1

Arg Phe Gly Val Gln Gln Arg Leu Pro Trp Val His Ser Ser Gln Glu
1               5                   10                  15

Thr Gln Ser

<210> SEQ ID NO 2
<211> LENGTH: 19
<212> TYPE: PRT
<213> ORGANISM: Artificial Sequence
```

```
<220> FEATURE:
<221> NAME/KEY: SOURCE
<222> LOCATION: 1..19
<223> OTHER INFORMATION: /mol_type="protein"
      /note="synthesized domain"
      /organism="Artificial Sequence"

<400> SEQUENCE: 2

Arg Phe Arg Val Gln Gln Arg Leu Pro Trp Val His Ser Ser Gln Glu
1               5                   10                  15

Thr Gln Ser

<210> SEQ ID NO 3
<211> LENGTH: 12
<212> TYPE: PRT
<213> ORGANISM: Artificial Sequence
<220> FEATURE:
<221> NAME/KEY: SOURCE
<222> LOCATION: 1..12
<223> OTHER INFORMATION: /mol_type="protein"
      /note="synthesized opsin motif"
      /organism="Artificial Sequence"

<400> SEQUENCE: 3

Ile Phe Asn Ser Phe His Arg Gly Phe Ala Ile Tyr
1               5                   10

<210> SEQ ID NO 4
<211> LENGTH: 12
<212> TYPE: PRT
<213> ORGANISM: Artificial Sequence
<220> FEATURE:
<221> NAME/KEY: SOURCE
<222> LOCATION: 1..12
<223> OTHER INFORMATION: /mol_type="protein"
      /note="synthesized opsin motif"
      /organism="Artificial Sequence"

<400> SEQUENCE: 4

Ile Tyr Asn Ser Phe His Arg Gly Phe Ala Leu Gly
1               5                   10

<210> SEQ ID NO 5
<211> LENGTH: 12
<212> TYPE: PRT
<213> ORGANISM: Artificial Sequence
<220> FEATURE:
<221> NAME/KEY: SOURCE
<222> LOCATION: 1..12
<223> OTHER INFORMATION: /mol_type="protein"
      /note="synthesized opsin motif"
      /organism="Artificial Sequence"

<400> SEQUENCE: 5

Ile Tyr Asn Ser Phe His Gln Gly Tyr Ala Leu Gly
1               5                   10

<210> SEQ ID NO 6
<211> LENGTH: 12
<212> TYPE: PRT
<213> ORGANISM: Artificial Sequence
<220> FEATURE:
<221> NAME/KEY: SOURCE
<222> LOCATION: 1..12
<223> OTHER INFORMATION: /mol_type="protein"
      /note="synthesized opsin motif"
      /organism="Artificial Sequence"

<400> SEQUENCE: 6
```

Ile Tyr Asn Ser Phe His Thr Gly Phe Ala Thr Gly
1               5                   10

<210> SEQ ID NO 7
<211> LENGTH: 12
<212> TYPE: PRT
<213> ORGANISM: Artificial Sequence
<220> FEATURE:
<221> NAME/KEY: SOURCE
<222> LOCATION: 1..12
<223> OTHER INFORMATION: /mol_type="protein"
      /note="synthesized opsin motif"
      /organism="Artificial Sequence"

<400> SEQUENCE: 7

Ile Tyr Asn Ser Phe Asn Thr Gly Phe Ala Thr Gly
1               5                   10

<210> SEQ ID NO 8
<211> LENGTH: 12
<212> TYPE: PRT
<213> ORGANISM: Artificial Sequence
<220> FEATURE:
<221> NAME/KEY: SOURCE
<222> LOCATION: 1..12
<223> OTHER INFORMATION: /mol_type="protein"
      /note="synthesized opsin motif"
      /organism="Artificial Sequence"

<400> SEQUENCE: 8

Ile Tyr Asn Ser Phe Asn Thr Gly Phe Ala Leu Gly
1               5                   10

<210> SEQ ID NO 9
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsin motif"
      /organism="Artificial Sequence"

<400> SEQUENCE: 9

Arg Met Glu Leu Gln Lys Arg Cys Pro Trp Leu Ala Ile Asp Glu Lys
1               5                   10                  15

Ala Pro Glu

<210> SEQ ID NO 10
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsin motif"
      /organism="Artificial Sequence"

<400> SEQUENCE: 10

Arg Met Glu Leu Gln Lys Arg Cys Pro Trp Leu Ala Leu Asn Glu Lys
1               5                   10                  15

Ala Pro Glu

<210> SEQ ID NO 11
<211> LENGTH: 19
<212> TYPE: PRT

```
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsin motif"
      /organism="Artificial Sequence"

<400> SEQUENCE: 11

Arg Met Glu Leu Gln Lys Arg Cys Pro Trp Leu Gly Val Asn Glu Lys
1               5                   10                  15

Ser Gly Glu

<210> SEQ ID NO 12
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsin motif"
      /organism="Artificial Sequence"

<400> SEQUENCE: 12

Arg Met Glu Leu Gln Lys Arg Cys Pro Trp Leu Ala Ile Ser Glu Lys
1               5                   10                  15

Ala Pro Glu

<210> SEQ ID NO 13
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsin motif"
      /organism="Artificial Sequence"

<400> SEQUENCE: 13

Arg Leu Glu Leu Gln Lys Arg Cys Pro Trp Leu Gly Val Asn Glu Lys
1               5                   10                  15

Ser Gly Glu

<210> SEQ ID NO 14
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsin motif"
      /organism="Artificial Sequence"

<400> SEQUENCE: 14

Arg Leu Glu Leu Gln Lys Arg Leu Pro Trp Leu Glu Leu Gln Glu Lys
1               5                   10                  15

Pro Val Ala

<210> SEQ ID NO 15
<211> LENGTH: 19
<212> TYPE: PRT
<213> ORGANISM: Artificial Sequence
<220> FEATURE:
<221> NAME/KEY: SOURCE
```

```
<222> LOCATION: 1..19
<223> OTHER INFORMATION: /mol_type="protein"
      /note="synthesized opsin motif"
      /organism="Artificial Sequence"

<400> SEQUENCE: 15

Arg Leu Glu Leu Gln Lys Arg Leu Pro Trp Leu Glu Leu Gln Glu Lys
1               5                   10                  15

Pro Ile Glu

<210> SEQ ID NO 16
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsin motif"
      /organism="Artificial Sequence"

<400> SEQUENCE: 16

Arg Leu Glu Leu Gln Lys Arg Leu Pro Trp Leu Glu Leu Gln Glu Lys
1               5                   10                  15

Pro Ile Ser

<210> SEQ ID NO 17
<211> LENGTH: 34
<212> TYPE: PRT
<213> ORGANISM: Artificial Sequence
<220> FEATURE:
<221> NAME/KEY: SOURCE
<222> LOCATION: 1..34
<223> OTHER INFORMATION: /mol_type="protein"
      /note="synthesized protamine P1"
      /organism="Artificial Sequence"

<400> SEQUENCE: 17

Ala Arg Tyr Arg Arg Ser Arg Thr Arg Ser Arg Ser Pro Arg Ser Arg
1               5                   10                  15

Arg Arg Arg Arg Arg Ser Gly Arg Arg Arg Ser Pro Arg Arg Arg Arg
                20                  25                  30

Arg Tyr

<210> SEQ ID NO 18
<211> LENGTH: 35
<212> TYPE: PRT
<213> ORGANISM: Artificial Sequence
<220> FEATURE:
<221> NAME/KEY: SOURCE
<222> LOCATION: 1..35
<223> OTHER INFORMATION: /mol_type="protein"
      /note="synthesized protamine 2"
      /organism="Artificial Sequence"

<400> SEQUENCE: 18

His Thr Arg Arg Arg Arg Ser Cys Arg Arg Arg Arg Arg Arg Ala Cys
1               5                   10                  15

Arg His Arg Arg His Arg Arg Gly Cys Arg Arg Ile Arg Arg Arg Arg
                20                  25                  30

Arg Cys Arg
            35

<210> SEQ ID NO 19
<211> LENGTH: 34
```

-continued

<212> TYPE: PRT
<213> ORGANISM: Artificial Sequence
<220> FEATURE:
<221> NAME/KEY: SOURCE
<222> LOCATION: 1..34
<223> OTHER INFORMATION: /mol_type="protein"
      /note="synthesized protamine P1"
      /organism="Artificial Sequence"

<400> SEQUENCE: 19

Ala Arg Tyr Arg Arg Ser Arg Ser Arg Ser Arg Ser Arg Tyr Gly
1               5                   10                  15

Arg Arg Arg Arg Arg Ser Arg Ser Arg Arg Arg Ser Arg Arg Arg
                20                  25                  30

Arg Arg

<210> SEQ ID NO 20
<211> LENGTH: 35
<212> TYPE: PRT
<213> ORGANISM: Artificial Sequence
<220> FEATURE:
<221> NAME/KEY: SOURCE
<222> LOCATION: 1..35
<223> OTHER INFORMATION: /mol_type="protein"
      /note="synthesized protamine 2"
      /organism="Artificial Sequence"

<400> SEQUENCE: 20

Arg Arg Arg Ser Arg Ser Cys Arg Arg Arg Arg Arg Ser Cys Arg
1               5                   10                  15

Tyr Arg Arg Pro Arg Arg Gly Cys Arg Ser Arg Arg Arg Arg Arg
                20                  25                  30

Cys Arg Arg
        35

<210> SEQ ID NO 21
<211> LENGTH: 35
<212> TYPE: PRT
<213> ORGANISM: Artificial Sequence
<220> FEATURE:
<221> NAME/KEY: SOURCE
<222> LOCATION: 1..35
<223> OTHER INFORMATION: /mol_type="protein"
      /note="synthesized protamine 2"
      /organism="Artificial Sequence"

<400> SEQUENCE: 21

His Arg Arg Arg Arg Ser Cys Arg Arg Arg Arg Arg His Ser Cys Arg
1               5                   10                  15

His Arg Arg Arg His Arg Arg Gly Cys Arg Arg Ser Arg Arg Arg
                20                  25                  30

Arg Cys Arg
        35

<210> SEQ ID NO 22
<211> LENGTH: 34
<212> TYPE: PRT
<213> ORGANISM: Artificial Sequence
<220> FEATURE:
<221> NAME/KEY: SOURCE
<222> LOCATION: 1..34
<223> OTHER INFORMATION: /mol_type="protein"
      /note="synthesized HSP1_mouse"
      /organism="Artificial Sequence"

<400> SEQUENCE: 22

Ala Arg Tyr Arg Cys Cys Arg Ser Lys Ser Arg Ser Arg Cys Arg Arg
1               5                   10                  15

Arg Arg Arg Arg Cys Arg Arg Arg Arg Arg Cys Cys Arg Arg Arg
            20                  25                  30

Arg Arg

<210> SEQ ID NO 23
<211> LENGTH: 35
<212> TYPE: PRT
<213> ORGANISM: Artificial Sequence
<220> FEATURE:
<221> NAME/KEY: SOURCE
<222> LOCATION: 1..35
<223> OTHER INFORMATION: /mol_type="protein"
      /note="synthesized HSP2_erypa"
      /organism="Artificial Sequence"

<400> SEQUENCE: 23

Arg Arg Arg His Arg Ser Cys Arg Arg Arg Arg Arg Ser Cys Arg
1               5                   10                  15

His Arg Arg Arg His Arg Arg Gly Cys Arg Thr Arg Arg Arg Cys
            20                  25                  30

Arg Arg Tyr
        35

<210> SEQ ID NO 24
<211> LENGTH: 34
<212> TYPE: PRT
<213> ORGANISM: Artificial Sequence
<220> FEATURE:
<221> NAME/KEY: SOURCE
<222> LOCATION: 1..34
<223> OTHER INFORMATION: /mol_type="protein"
      /note="synthesized hsp1_cavpo"
      /organism="Artificial Sequence"

<400> SEQUENCE: 24

Ala Arg Tyr Arg Cys Cys Arg Ser Pro Ser Arg Ser Arg Cys Arg Arg
1               5                   10                  15

Arg Arg Arg Arg Phe Tyr Arg Arg Arg Arg Arg Cys His Arg Arg Arg
            20                  25                  30

Arg Arg

<210> SEQ ID NO 25
<211> LENGTH: 104
<212> TYPE: PRT
<213> ORGANISM: Artificial Sequence
<220> FEATURE:
<221> NAME/KEY: SOURCE
<222> LOCATION: 1..104
<223> OTHER INFORMATION: /mol_type="protein"
      /note="synthesized gbDhDi33.3"
      /organism="Artificial Sequence"

<400> SEQUENCE: 25

Ser Thr His Glu Leu Pro Asp Pro Asp Arg His Pro Arg Met Leu Gln
1               5                   10                  15

Val Ser Asp Pro Thr Lys Leu Gly Pro Lys Thr Ala Phe His Lys Trp
            20                  25                  30

Asp Trp Arg Arg Gly Met Leu Ser Lys Arg Ser Ile Lys Arg Val Gln
        35                  40                  45

Glu Asp Ser Thr Asp Asp Glu Tyr Val Ala Gly Pro Leu Pro Arg Lys
    50                  55                  60

-continued

Arg Asn Lys Phe Asp Thr Arg Val Gln Gly Pro Pro Thr Pro Glu Lys
65                  70                  75                  80

Glu Ser Tyr Thr Leu Leu Gln Ala Leu Gln Glu Ser Gly Gln Glu Ser
                85                  90                  95

Ser Ser Glu Asp Gln Glu Gln Ala
            100

<210> SEQ ID NO 26
<211> LENGTH: 104
<212> TYPE: PRT
<213> ORGANISM: Artificial Sequence
<220> FEATURE:
<221> NAME/KEY: SOURCE
<222> LOCATION: 1..104
<223> OTHER INFORMATION: /mol_type="protein"
      /note="synthesized gbDhDi33.4"
      /organism="Artificial Sequence"

<400> SEQUENCE: 26

Ser Thr His Glu Leu Pro Asp Pro Asp Arg His Pro Arg Met Leu Gln
1               5                   10                  15

Val Ser Asp Pro Thr Lys Leu Gly Pro Lys Thr Val Phe His Lys Trp
                20                  25                  30

Asp Trp Arg Arg Gly Met Leu Ser Lys Arg Ser Ile Lys Arg Val Gln
            35                  40                  45

Glu Asp Ser Thr Asp Asp Glu Tyr Val Ala Gly Pro Leu Pro Arg Lys
        50                  55                  60

Arg Asn Lys Phe Asp Thr Arg Val Gln Gly Pro Pro Thr Pro Glu Lys
65                  70                  75                  80

Glu Ser Tyr Thr Leu Leu Gln Ala Leu Gln Glu Ser Gly Gln Glu Ser
                85                  90                  95

Ser Ser Glu Asp Gln Glu Gln Ala
            100

<210> SEQ ID NO 27
<211> LENGTH: 104
<212> TYPE: PRT
<213> ORGANISM: Artificial Sequence
<220> FEATURE:
<221> NAME/KEY: SOURCE
<222> LOCATION: 1..104
<223> OTHER INFORMATION: /mol_type="protein"
      /note="synthesized gbDhDi33.3"
      /organism="Artificial Sequence"

<400> SEQUENCE: 27

Ser Thr His Glu Leu Pro Asp Pro Asp Arg His Pro Arg Met Leu Gln
1               5                   10                  15

Val Ser Asp Pro Thr Lys Leu Gly Pro Lys Thr Val Phe His Lys Trp
                20                  25                  30

Asp Trp Arg Arg Gly Met Leu Ser Lys Arg Ser Ile Lys Arg Val Gln
            35                  40                  45

Gly Asp Ser Thr Asp Gly Glu Tyr Val Ala Gly Pro Leu Pro Arg Lys
        50                  55                  60

Arg Asn Lys Phe Asp Thr Arg Val Gln Gly Pro Pro Thr Pro Glu Lys
65                  70                  75                  80

Glu Ser Tyr Thr Leu Leu Gln Ala Leu Gln Glu Ser Gly Gln Glu Ser
                85                  90                  95

Ser Ser Glu Asp Gln Glu Gln Ala
            100

```
<210> SEQ ID NO 28
<211> LENGTH: 104
<212> TYPE: PRT
<213> ORGANISM: Artificial Sequence
<220> FEATURE:
<221> NAME/KEY: SOURCE
<222> LOCATION: 1..104
<223> OTHER INFORMATION: /mol_type="protein"
      /note="synthesized gbDfDg33.4"
      /organism="Artificial Sequence"

<400> SEQUENCE: 28

Ser Thr His Glu Leu Pro Asp Pro Asp Arg His Pro Arg Met Leu Gln
1               5                   10                  15

Val Ser Asp Pro Thr Lys Leu Gly Pro Lys Thr Val Phe His Lys Trp
            20                  25                  30

Asp Trp Gly Arg Gly Met Leu Ser Lys Arg Ser Ile Lys Arg Val Gln
        35                  40                  45

Glu Asp Ser Thr Asp Asp Glu Tyr Val Ala Gly Pro Leu Pro Arg Lys
    50                  55                  60

Arg Asn Lys Phe Asp Thr Arg Val Gln Gly Pro Pro Thr Pro Glu Lys
65                  70                  75                  80

Glu Ser Tyr Thr Leu Leu Gln Ala Leu Gln Glu Ser Gly Gln Glu Ser
                85                  90                  95

Ser Ser Glu Asp Gln Glu Gln Ala
            100

<210> SEQ ID NO 29
<211> LENGTH: 54
<212> TYPE: PRT
<213> ORGANISM: Artificial Sequence
<220> FEATURE:
<221> NAME/KEY: SOURCE
<222> LOCATION: 1..54
<223> OTHER INFORMATION: /mol_type="protein"
      /note="synthesized gbDhDi33.3"
      /organism="Artificial Sequence"

<400> SEQUENCE: 29

Trp Cys Ser Glu Lys Ser Ser Lys Leu Asp Thr Thr Lys Ser Lys Cys
1               5                   10                  15

Ile Leu Arg Asp Phe Pro Leu Trp Ala Met Ala Tyr Gly Tyr Cys Asp
            20                  25                  30

Trp Val Val Lys Cys Thr Gly Val Ser Ser Ala Trp Thr Asp Met Arg
        35                  40                  45

Ile Ala Ile Ile Cys Pro
    50

<210> SEQ ID NO 30
<211> LENGTH: 38
<212> TYPE: PRT
<213> ORGANISM: Artificial Sequence
<220> FEATURE:
<221> NAME/KEY: SOURCE
<222> LOCATION: 1..38
<223> OTHER INFORMATION: /mol_type="protein"
      /note="syntehsized gbDhDi33.3"
      /organism="Artificial Sequence"

<400> SEQUENCE: 30

Trp Cys Ser Glu Lys Ser Ser Lys Leu Asp Thr Thr Lys Ser Lys Cys
1               5                   10                  15

Ile Leu Arg Asp Phe Pro Leu Trp Ala Met Ala Tyr Gly His Cys Asp
```

```
                    20                  25                  30

Trp Val Val Lys Cys Thr
             35

<210> SEQ ID NO 31
<211> LENGTH: 104
<212> TYPE: PRT
<213> ORGANISM: Artificial Sequence
<220> FEATURE:
<221> NAME/KEY: SOURCE
<222> LOCATION: 1..104
<223> OTHER INFORMATION: /mol_type="protein"
      /note="synthesized galanin"
      /organism="Artificial Sequence"

<400> SEQUENCE: 31

Ala Thr Leu Gly Leu Gly Ser Pro Val Lys Glu Lys Arg Gly Trp Thr
1               5                   10                  15

Leu Asn Ser Ala Gly Tyr Leu Leu Gly Pro His Ala Ile Asp Asn His
            20                  25                  30

Arg Ser Phe Ser Asp Lys His Gly Leu Thr Gly Lys Arg Glu Leu Glu
        35                  40                  45

Pro Glu Asp Glu Ala Arg Pro Gly Ser Phe Asp Arg Pro Leu Ser Glu
    50                  55                  60

Ser Asn Ile Val Arg Thr Ile Ile Glu Phe Leu Ser Phe Leu His Leu
65                  70                  75                  80

Lys Glu Ala Gly Ala Leu Asp Arg Leu Pro Gly Leu Pro Ala Ala Ala
                85                  90                  95

Ser Ser Glu Asp Leu Glu Arg Ser
            100

<210> SEQ ID NO 32
<211> LENGTH: 12
<212> TYPE: PRT
<213> ORGANISM: Artificial Sequence
<220> FEATURE:
<221> NAME/KEY: SOURCE
<222> LOCATION: 1..12
<223> OTHER INFORMATION: /mol_type="protein"
      /note="synthesized opsinrhrrh4_3"
      /organism="Artificial Sequence"

<400> SEQUENCE: 32

Ile Tyr Asn Ser Phe His Arg Gly Phe Ala Leu Gly
1               5                   10

<210> SEQ ID NO 33
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized opsinrhrrh4_7"
      /organism="Artificial Sequence"

<400> SEQUENCE: 33

Arg Leu Glu Leu Gln Lys Arg Leu Pro Trp Leu Glu Leu Asn Glu Lys
1               5                   10                  15

Ala Val Glu

<210> SEQ ID NO 34
<211> LENGTH: 56
```

```
<212> TYPE: PRT
<213> ORGANISM: Artificial Sequence
<220> FEATURE:
<221> NAME/KEY: SOURCE
<222> LOCATION: 1..56
<223> OTHER INFORMATION: /mol_type="protein"
      /note="synthesized psinew7"
      /organism="Artificial Sequence"

<400> SEQUENCE: 34

Arg Cys Ser Gln Tyr Gly Val Thr Ser Cys Ser Glu Cys Leu Leu Ala
1               5                   10                  15

Arg Asp Pro Tyr Gly Cys Gly Trp Cys Ser Ser Glu Gly Arg Cys Thr
            20                  25                  30

Arg Gly Glu Arg Cys Asp Glu Arg Arg Gly Ser Arg Gln Asn Trp Ser
        35                  40                  45

Ser Gly Pro Ser Ser Gln Cys Pro
    50                  55

<210> SEQ ID NO 35
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="subject: 14"
      /organism="Artificial Sequence"

<400> SEQUENCE: 35

Arg Val Pro Lys Val Ser Leu His Thr Glu Val Lys Gly Gln Phe Gly
1               5                   10                  15

Leu Gly Thr Gly Arg Ala Met
            20

<210> SEQ ID NO 36
<211> LENGTH: 11
<212> TYPE: PRT
<213> ORGANISM: Artificial Sequence
<220> FEATURE:
<221> NAME/KEY: SOURCE
<222> LOCATION: 1..11
<223> OTHER INFORMATION: /mol_type="protein"
      /note="gbCsCt38.4"
      /organism="Artificial Sequence"

<400> SEQUENCE: 36

Tyr Glu Ser Phe His Arg Gly His Ala Ala Phe
1               5                   10

<210> SEQ ID NO 37
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized gastrin_8"
      /organism="Artificial Sequence"

<400> SEQUENCE: 37

Val Ala Gly Glu Asp Ser Asp Gly Cys Tyr Val Gln Leu Pro Arg Ser
1               5                   10                  15

Arg
```

```
<210> SEQ ID NO 38
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized gbDhDi33.3"
      /organism="Artificial Sequence"

<400> SEQUENCE: 38

Val Gln Gly Asp Ser Thr Asp Gly Glu Tyr Val Ala Gly Pro Leu Pro
1               5                   10                  15

Arg Lys Arg

<210> SEQ ID NO 39
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized gasr_rabit"
      /organism="Artificial Sequence"

<400> SEQUENCE: 39

Leu Ala Gly Glu Asp Gly Asp Gly Cys Tyr Val Gln Leu Pro Arg Ser
1               5                   10                  15

Arg

<210> SEQ ID NO 40
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized gasr_prana"
      /organism="Artificial Sequence"

<400> SEQUENCE: 40

Val Ala Gly Glu Asp Asn Asp Gly Cys Tyr Val Gln Leu Pro Arg Ser
1               5                   10                  15

Arg

<210> SEQ ID NO 41
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /note="gasr_human"
      /organism="homo sapiens"

<400> SEQUENCE: 41

Ala Val Gly Glu Asp Ser Asp Gly Cys Tyr Val Gln Leu Pro Arg Ser
1               5                   10                  15

Arg

<210> SEQ ID NO 42
<211> LENGTH: 17
```

```
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /note="gasr_mouse"
      /organism="mus musculus"

<400> SEQUENCE: 42

Leu Thr Gly Glu Asp Ser Asp Gly Cys Tyr Val Gln Leu Pro Arg Ser
1               5                  10                  15

Arg

<210> SEQ ID NO 43
<211> LENGTH: 17
<212> TYPE: PRT
<213> ORGANISM: Rattus
<220> FEATURE:
<221> NAME/KEY: SOURCE
<222> LOCATION: 1..17
<223> OTHER INFORMATION: /mol_type="protein"
      /note="gasr_rat"
      /organism="rattus rattus"

<400> SEQUENCE: 43

Val Ala Gly Glu Asp Ser Asp Gly Cys Cys Val Gln Leu Pro Arg Ser
1               5                  10                  15

Arg

<210> SEQ ID NO 44
<211> LENGTH: 288
<212> TYPE: PRT
<213> ORGANISM: Artificial Sequence
<220> FEATURE:
<221> NAME/KEY: SOURCE
<222> LOCATION: 1..288
<223> OTHER INFORMATION: /mol_type="protein"
      /note="synthesized rheu.ef.24"
      /organism="Artificial Sequence"

<400> SEQUENCE: 44

Thr Leu Arg Ile Leu Tyr Asp Glu Phe Thr Arg Phe Met Asn Phe Trp
1               5                  10                  15

Thr Val Ser Asn Glu Asp Leu Asp Leu Cys Arg Tyr Val Gly Cys Lys
                20                  25                  30

Leu Ile Phe Phe Lys His Pro Thr Val Asp Phe Ile Val Gln Ile Asn
            35                  40                  45

Thr Gln Pro Pro Phe Leu Asp Thr His Leu Thr Ala Ala Ser Ile His
        50                  55                  60

Pro Gly Ile Met Met Leu Ser Lys Arg Arg Ile Leu Ile Pro Ser Leu
65                  70                  75                  80

Lys Thr Arg Pro Ser Arg Lys His Arg Val Val Val Arg Val Gly Ala
                85                  90                  95

Pro Arg Leu Phe Gln Asp Lys Trp Tyr Pro Gln Ser Asp Leu Cys Asp
            100                 105                 110

Thr Val Leu Leu Ser Ile Phe Ala Thr Ala Cys Asp Leu Gln Tyr Pro
        115                 120                 125

Phe Gly Ser Pro Leu Thr Glu Asn Pro Cys Val Asn Phe Gln Ile Leu
    130                 135                 140

Gly Pro His Tyr Lys Lys His Leu Ser Ile Ser Ser Thr Asn Asp Glu
145                 150                 155                 160
```

```
Thr Asn Lys Thr His Tyr Glu Ser Asn Leu Phe Asn Lys Thr Glu Leu
            165                 170                 175

Tyr Asn Thr Phe Gln Thr Ile Ala Gln Leu Lys Glu Thr Gly Arg Thr
            180                 185                 190

Ser Gly Val Asn Pro Asn Trp Thr Ser Val Gln Asn Thr Thr Pro Leu
            195                 200                 205

Asn Gln Ala Gly Asn Asn Ala Gln Asn Ser Arg Asp Thr Trp Tyr Lys
210                 215                 220

Gly Asn Thr Tyr Asn Asp Asn Ile Ser Lys Leu Ala Glu Ile Thr Arg
225                 230                 235                 240

Gln Arg Phe Lys Ser Ala Thr Ile Ser Ala Leu Pro Asn Tyr Pro Thr
                245                 250                 255

Ile Met Ser Thr Asp Leu Tyr Glu Tyr His Ser Gly Ile Tyr Ser Ser
            260                 265                 270

Ile Phe Leu Ser Ala Gly Arg Ser Tyr Phe Glu Thr Thr Gly Ala Tyr
            275                 280                 285
```

<210> SEQ ID NO 45
<211> LENGTH: 318
<212> TYPE: PRT
<213> ORGANISM: Artificial Sequence
<220> FEATURE:
<221> NAME/KEY: SOURCE
<222> LOCATION: 1..318
<223> OTHER INFORMATION: /mol_type="protein"
    /note="synthesized peptidase_m9"
    /organism="Artificial Sequence"

<400> SEQUENCE: 45

```
Met Ser Arg Leu Ala Glu Leu Tyr Leu Leu Gly Asp Ser Ile Lys Gly
1               5                   10                  15

Arg His Asp Asn Leu Trp Leu Ala Ala Glu Met Leu Ser Tyr Tyr
                20                  25                  30

Ala Pro Glu Gly Lys Ser Glu Leu Gly Ile Asp Ile Cys Gln Ala Lys
            35                  40                  45

Leu Glu Leu Ala Ala Lys Val Leu Pro Tyr Leu Tyr Glu Cys Ser Gly
50                  55                  60

Pro Ala Ala Ile Arg Ser Gln Asp Leu Thr Asp Gly Gln Ala Ala Ser
65                  70                  75                  80

Ala Cys Asp Ile Leu Arg Asn Lys Glu Lys Asp Phe His Gln Val Lys
                85                  90                  95

Tyr Thr Gly Lys Thr Pro Val Ala Asp Asp Gly Asn Thr Arg Val Glu
            100                 105                 110

Val Gly Val Phe Val Ser Glu Glu Asp Tyr Lys Arg Tyr Ser Ala Phe
        115                 120                 125

Ala Ser Lys Glu Val Lys Ala Gln Phe Gly Arg Val Thr Asp Asn Gly
    130                 135                 140

Gly Met Tyr Leu Glu Gly Asn Pro Ser Asp Ala Gly Asn Gln Val Arg
145                 150                 155                 160

Phe Ile Ala Tyr Glu Glu Ala Lys Leu Asn Ala Asp Leu Ser Ile Gly
                165                 170                 175

Asn Leu Glu His Glu Tyr Thr His Tyr Leu Asp Gly Arg Phe Asp Thr
            180                 185                 190

Tyr Gly Thr Phe Ser Arg Asn Leu Glu Glu Ser His Ile Val Trp Trp
        195                 200                 205

Glu Glu Gly Phe Ala Glu Tyr Val His Tyr Lys Gln Gly Gly Val Pro
    210                 215                 220
```

```
Tyr Gln Ala Ala Pro Glu Leu Ile Gly Gln Gly Ser Lys Leu Tyr Leu
225                 230                 235                 240

Ser Asp Val Phe Thr Thr Thr Glu Glu Gly Tyr Ala Glu Leu Phe Ala
                245                 250                 255

Gly Ser His Asp Thr Asp Arg Ile Tyr Arg Trp Gly Tyr Leu Ala Val
            260                 265                 270

Arg Phe Met Leu Glu Thr Asn His Asn Arg Asp Val Glu Ser Leu Leu
        275                 280                 285

Val His Ser Arg Tyr Gly Asn Ser Phe Ala Phe Tyr Ala Tyr Leu Val
    290                 295                 300

Lys Leu Leu Gly Tyr Met Tyr Asn Asn Glu Phe Gly Ile Trp
305                 310                 315

<210> SEQ ID NO 46
<211> LENGTH: 43
<212> TYPE: PRT
<213> ORGANISM: Artificial Sequence
<220> FEATURE:
<221> NAME/KEY: SOURCE
<222> LOCATION: 1..43
<223> OTHER INFORMATION: /mol_type="protein"
      /note="synthesized caeel143"
      /organism="Artificial Sequence"

<400> SEQUENCE: 46

Gly Ala Pro Gly Pro Pro Gly Leu Pro Gly Lys Gly Pro Arg Gly
1               5                   10                  15

Pro Ala Gly Ile Glu Gly Lys Pro Gly Arg Leu Gly Glu Asp Asn Arg
                20                  25                  30

Pro Gly Pro Pro Gly Pro Pro Gly Val Arg Gly
        35                  40

<210> SEQ ID NO 47
<211> LENGTH: 43
<212> TYPE: PRT
<213> ORGANISM: Artificial Sequence
<220> FEATURE:
<221> NAME/KEY: SOURCE
<222> LOCATION: 1..43
<223> OTHER INFORMATION: /mol_type="protein"
      /note="synthesized gbdhdi33.55ikn.2.1"
      /organism="Artificial Sequence"

<400> SEQUENCE: 47

Gly Pro Pro Arg Pro Pro Gly Leu Asp Gln Leu Asn Pro Glu Gly
1               5                   10                  15

Pro Ala Gly Pro Gly Gly Pro Pro Ala Ile Leu Pro Ala Leu Pro Ala
                20                  25                  30

Pro Ala Asp Pro Glu Pro Ala Pro Arg Arg Gly
        35                  40

<210> SEQ ID NO 48
<211> LENGTH: 43
<212> TYPE: PRT
<213> ORGANISM: Artificial Sequence
<220> FEATURE:
<221> NAME/KEY: SOURCE
<222> LOCATION: 1..43
<223> OTHER INFORMATION: /mol_type="protein"
      /note="synthesized steap"
      /organism="Artificial Sequence"

<400> SEQUENCE: 48
```

-continued

Gly Lys Pro Ala Glu Pro Gly Lys Pro Ala Glu Pro Gly Lys Pro Ala
1               5                   10                  15

Glu Pro Gly Thr Pro Ala Glu Pro Gly Lys Pro Ala Glu Pro Gly Thr
            20                  25                  30

Pro Ala Glu Pro Gly Lys Pro Ala Glu Pro Gly
        35                  40

<210> SEQ ID NO 49
<211> LENGTH: 43
<212> TYPE: PRT
<213> ORGANISM: Artificial Sequence
<220> FEATURE:
<221> NAME/KEY: SOURCE
<222> LOCATION: 1..43
<223> OTHER INFORMATION: /mol_type="protein"
      /note="synthesized rheu.ef.241.148"
      /organism="Artificial Sequence"

<400> SEQUENCE: 49

His Leu Ala Thr Thr Leu Gly Arg Pro Pro Arg Pro Gly Pro Pro Gly
1               5                   10                  15

Gly Pro Arg Thr Pro Gln Ile Arg Asn Leu Pro Ala Leu Pro Ala Pro
            20                  25                  30

Gln Gly Glu Pro Gly Asp Arg Ala Thr Trp Arg
        35                  40

<210> SEQ ID NO 50
<211> LENGTH: 43
<212> TYPE: PRT
<213> ORGANISM: Artificial Sequence
<220> FEATURE:
<221> NAME/KEY: SOURCE
<222> LOCATION: 1..43
<223> OTHER INFORMATION: /mol_type="protein"
      /note="synthesized rheu.ef.238rev.148"
      /organism="Artificial Sequence"

<400> SEQUENCE: 50

His Leu Ala Thr Thr Leu Gly Arg Pro Pro Arg Pro Gly Pro Pro Gly
1               5                   10                  15

Gly Pro Arg Thr Pro Gln Ile Arg Asn Leu Pro Ala Leu Pro Ala Pro
            20                  25                  30

Gln Gly Glu Pro Gly Asp Arg Ala Thr Trp Arg
        35                  40

<210> SEQ ID NO 51
<211> LENGTH: 60
<212> TYPE: PRT
<213> ORGANISM: Artificial Sequence
<220> FEATURE:
<221> NAME/KEY: SOURCE
<222> LOCATION: 1..60
<223> OTHER INFORMATION: /mol_type="protein"
      /note="synthesized collagen"
      /organism="Artificial Sequence"

<400> SEQUENCE: 51

Gly Pro Pro Gly Pro Pro Gly Pro Pro Gly Pro Pro Gly Pro Pro Gly
1               5                   10                  15

Pro Pro Gly Pro Pro Gly Pro Ala Gly Ala Pro Gly Pro Pro Gly Pro
            20                  25                  30

Pro Gly Glu Pro Gly Pro Pro Gly Pro Pro Gly Pro Pro Gly Pro Pro
        35                  40                  45

Gly Pro Pro Gly Ala Pro Gly Ala Pro Gly Pro Pro

```
               50                  55                  60

<210> SEQ ID NO 52
<211> LENGTH: 61
<212> TYPE: PRT
<213> ORGANISM: Artificial Sequence
<220> FEATURE:
<221> NAME/KEY: SOURCE
<222> LOCATION: 1..61
<223> OTHER INFORMATION: /mol_type="protein"
      /note="synthesized rheu.ef.24"
      /organism="Artificial Sequence"

<400> SEQUENCE: 52

Gly Arg Pro Pro Arg Pro Gly Pro Pro Gly Gly Pro Arg Thr Pro Gln
1               5                   10                  15

Ile Arg Asn Leu Pro Ala Leu Pro Ala Pro Gln Gly Glu Pro Gly Asp
            20                  25                  30

Arg Ala Thr Trp Arg Gly Ala Ser Gly Ala Asp Ala Ala Gly Gly Asp
        35                  40                  45

Gly Gly Glu Arg Gly Ala Asp Gly Gly Asp Pro Gly Asp
    50                  55                  60

<210> SEQ ID NO 53
<211> LENGTH: 62
<212> TYPE: PRT
<213> ORGANISM: Artificial Sequence
<220> FEATURE:
<221> NAME/KEY: SOURCE
<222> LOCATION: 1..62
<223> OTHER INFORMATION: /mol_type="protein"
      /note="synthesized mssp"
      /organism="Artificial Sequence"

<400> SEQUENCE: 53

Val Gly Gly Pro Cys Gly Pro Cys Gly Pro Cys Gly Pro Cys Cys
1               5                   10                  15

Gly Ser Cys Cys Ser Pro Cys Gly Gly Pro Cys Gly Pro Cys Gly Pro
            20                  25                  30

Cys Gly Pro Cys Gly Pro Cys Cys Gly Cys Gly Pro Cys Gly Pro
        35                  40                  45

Cys Gly Pro Cys Cys Gly Thr Thr Glu Lys Tyr Cys Gly Leu
    50                  55                  60

<210> SEQ ID NO 54
<211> LENGTH: 58
<212> TYPE: PRT
<213> ORGANISM: Artificial Sequence
<220> FEATURE:
<221> NAME/KEY: SOURCE
<222> LOCATION: 1..58
<223> OTHER INFORMATION: /mol_type="protein"
      /note="synthesized gbDhdi33.3"
      /organism="Artificial Sequence"

<400> SEQUENCE: 54

Gln Leu Asn Pro Glu Gly Pro Ala Gly Pro Gly Gly Pro Ala Ile
1               5                   10                  15

Leu Pro Ala Leu Pro Ala Pro Ala Asp Pro Glu Pro Ala Pro Arg Cys
            20                  25                  30

Gly Gly Arg Ala Asp Gly Gly Ala Ala Ala Gly Ala Ala Ala Asp Ala
        35                  40                  45

Asp His Thr Gly Tyr Glu Glu Gly Asp Leu
    50                  55
```

```
<210> SEQ ID NO 55
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized micollptase_1"
      /organism="Artificial Sequence"

<400> SEQUENCE: 55

Gly Leu Glu Thr Leu Val Glu Phe Leu Arg Ala Gly Tyr Tyr Val Arg
1               5                   10                  15

Phe Tyr Asn

<210> SEQ ID NO 56
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized gbDhDi43.4"
      /organism="Artificial Sequence"

<400> SEQUENCE: 56

Thr Leu Glu Asn Ile Leu Tyr Thr Arg Ala Ser Tyr Trp Asn Ser Phe
1               5                   10                  15

His Ala

<210> SEQ ID NO 57
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized cola_clope"
      /organism="Artificial Sequence"

<400> SEQUENCE: 57

Gly Ile Pro Thr Leu Val Glu Phe Leu Arg Ala Gly Tyr Tyr Leu Gly
1               5                   10                  15

Phe Tyr Asn

<210> SEQ ID NO 58
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized cola_vibal"
      /organism="Artificial Sequence"

<400> SEQUENCE: 58

Glu Leu Glu Thr Leu Phe Leu Tyr Leu Arg Ala Gly Tyr Tyr Ala Glu
1               5                   10                  15

Phe Tyr Asn

<210> SEQ ID NO 59
```

-continued

```
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized cola_vibpa"
      /organism="Artificial Sequence"

<400> SEQUENCE: 59

Val Leu Glu Asn Leu Gly Glu Phe Val Arg Ala Ala Tyr Tyr Val Arg
1               5                   10                  15

Tyr Asn Ala

<210> SEQ ID NO 60
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized af080248"
      /organism="Artificial Sequence"

<400> SEQUENCE: 60

Arg Leu Glu Asn Tyr Gly Glu Phe Ile Arg Ala Ala Tyr Tyr Val Arg
1               5                   10                  15

Tyr Asn Ala

<210> SEQ ID NO 61
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
      /note="synthesized mic1micrneme_5"
      /organism="Artificial Sequence"

<400> SEQUENCE: 61

Thr Tyr Ile Ser Thr Lys Leu Asp Val Ala Val Gly Ser Cys His Lys
1               5                   10                  15

<210> SEQ ID NO 62
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
      /note="synthesized rheu.ef.24"
      /organism="Artificial Sequence"

<400> SEQUENCE: 62

Thr Lys Ala Asp Thr Gln Leu Ile Val Ala Gly Gly Ser Cys Lys Ala
1               5                   10                  15

<210> SEQ ID NO 63
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
```

```
            /note="synthesized o00834"
            /organism="Artificial Sequence"

<400> SEQUENCE: 63

Thr Phe Ile Ser Thr Lys Leu Asp Val Ala Val Gly Ser Cys His Ser
1               5                   10                  15

<210> SEQ ID NO 64
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
            /note="synthesized q8wrs0"
            /organism="Artificial Sequence"

<400> SEQUENCE: 64

Thr Tyr Ser Ser Pro Gln Leu His Val Ser Val Gly Ser Cys His Lys
1               5                   10                  15

<210> SEQ ID NO 65
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
            /note="synthesized airegulator_4"
            /organism="Artificial Sequence"

<400> SEQUENCE: 65

Asp Phe Trp Arg Val Leu Phe Lys Asp Tyr Asn Leu Glu Arg Tyr
1               5                   10                  15

<210> SEQ ID NO 66
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
            /note="synthesized rheu.ef.24"
            /organism="Artificial Sequence"

<400> SEQUENCE: 66

Asn Phe Trp Thr Val Ser Asn Glu Asp Leu Asp Leu Cys Arg Tyr
1               5                   10                  15

<210> SEQ ID NO 67
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
            /note="synthesized rheu.ef.23"
            /organism="Artificial Sequence"

<400> SEQUENCE: 67

Asn Phe Trp Thr Val Ser Asn Glu Asp Leu Asp Leu Cys Arg Tyr
1               5                   10                  15

<210> SEQ ID NO 68
<211> LENGTH: 15
```

```
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized rheu.cd.21"
      /organism="Artificial Sequence"

<400> SEQUENCE: 68

Asn Phe Trp Thr Val Ser Asn Glu Asp Leu Asp Leu Cys Arg Tyr
1               5                   10                  15

<210> SEQ ID NO 69
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized q9jlw0"
      /organism="Artificial Sequence"

<400> SEQUENCE: 69

Asp Phe Trp Arg Ile Leu Phe Lys Asp Tyr Asn Leu Glu Arg Tyr
1               5                   10                  15

<210> SEQ ID NO 70
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized aire_human"
      /organism="Artificial Sequence"

<400> SEQUENCE: 70

Asp Phe Trp Arg Val Leu Phe Lys Asp Tyr Asn Leu Glu Arg Tyr
1               5                   10                  15

<210> SEQ ID NO 71
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized gliadin_7"
      /organism="Artificial Sequence"

<400> SEQUENCE: 71

Pro Gln Ala Gln Gly Ser Val Gln Pro Gln Gln Leu Pro Gln Phe Glu
1               5                   10                  15

Glu Ile Arg Asn Leu
            20

<210> SEQ ID NO 72
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized rheu.ef.24"
      /organism="Artificial Sequence"
```

<400> SEQUENCE: 72

Thr Gln Ala Gln Gly Ser Val Gln Glu Gln Leu Leu Leu Gln Leu Arg
1               5                   10                  15

Glu Gln Arg Val Leu
            20

<210> SEQ ID NO 73
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized rheu.cd.21"
      /organism="Artificial Sequence"

<400> SEQUENCE: 73

Thr Gln Ala Gln Gly Ser Val Gln Asp Gln Leu Leu Leu Gln Leu Arg
1               5                   10                  15

Glu Gln Arg Val Leu
            20

<210> SEQ ID NO 74
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized gda9_wheat"
      /organism="Artificial Sequence"

<400> SEQUENCE: 74

Pro Gln Ala Gln Gly Ser Val Gln Pro Gln Gln Leu Pro Gln Phe Glu
1               5                   10                  15

Glu Ile Arg Asn Leu
            20

<210> SEQ ID NO 75
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized gda7_wheat"
      /organism="Artificial Sequence"

<400> SEQUENCE: 75

Pro Gln Ala Gln Gly Ser Val Gln Pro Gln Gln Leu Pro Gln Phe Ala
1               5                   10                  15

Glu Ile Arg Asn Leu
            20

<210> SEQ ID NO 76
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized gda2_wheat"

/organism="Artificial Sequence"

<400> SEQUENCE: 76

Pro Gln Ala Gln Gly Ser Phe Gln Pro Gln Gln Leu Pro Gln Phe Glu
1               5                   10                  15

Glu Ile Arg Asn Leu
            20

<210> SEQ ID NO 77
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized gda3_wheat"
      /organism="Artificial Sequence"

<400> SEQUENCE: 77

Pro Gln Ala Gln Gly Ser Val Gln Pro Gln Gln Leu Pro Gln Phe Gln
1               5                   10                  15

Glu Ile Arg Asn Leu
            20

<210> SEQ ID NO 78
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nrpeptidey2r_9"
      /organism="Artificial Sequence"

<400> SEQUENCE: 78

Ala Phe Leu Ser Ala Phe Arg Cys Glu Gln Arg Leu Asp Ala Ile His
1               5                   10                  15

Ser

<210> SEQ ID NO 79
<211> LENGTH: 14
<212> TYPE: PRT
<213> ORGANISM: Artificial Sequence
<220> FEATURE:
<221> NAME/KEY: SOURCE
<222> LOCATION: 1..14
<223> OTHER INFORMATION: /mol_type="protein"
      /note="synthesized rheu.ef.24"
      /organism="Artificial Sequence"

<400> SEQUENCE: 79

Ser Ala Phe Arg Val Gln Gln Arg Val Pro Trp Val His Ser
1               5                   10

<210> SEQ ID NO 80
<211> LENGTH: 14
<212> TYPE: PRT
<213> ORGANISM: Artificial Sequence
<220> FEATURE:
<221> NAME/KEY: SOURCE
<222> LOCATION: 1..14
<223> OTHER INFORMATION: /mol_type="protein"
      /note="synthesized zc3r11.B4"
      /organism="Artificial Sequence"

<400> SEQUENCE: 80

```
Ser Arg Phe Arg Val Gln Gln Arg Leu Pro Trp Val His Ser
1               5                   10
```

<210> SEQ ID NO 81
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized ny2r"
      /organism="Artificial Sequence"

<400> SEQUENCE: 81

```
Ala Phe Leu Ser Ala Phe Arg Cys Glu Gln Arg Leu Asp Ala Ile His
1               5                   10                  15
Ser
```

<210> SEQ ID NO 82
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized aerolysin_7"
      /organism="Artificial Sequence"

<400> SEQUENCE: 82

```
Trp Asp Lys Arg Tyr Ile Pro Gly Glu Val Lys Trp Trp Asp Trp Asn
1               5                   10                  15
Trp Thr Ile Gln
                20
```

<210> SEQ ID NO 83
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized rheu.ef.24"
      /organism="Artificial Sequence"

<400> SEQUENCE: 83

```
Val Asp Pro Lys Tyr Val Thr Pro Glu Val Thr Trp His Ser Trp Asp
1               5                   10                  15
Ile Arg Arg Gly
                20
```

<210> SEQ ID NO 84
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized uro742rev"
      /organism="Artificial Sequence"

<400> SEQUENCE: 84

```
Phe Ala Trp Val Leu Ala Ser Gly Thr Ala Lys Cys Trp Ser Trp Asn
1               5                   10                  15
```

Trp Ser Ala Arg
        20

<210> SEQ ID NO 85
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized aera_aerhy"
      /organism="Artificial Sequence"

<400> SEQUENCE: 85

Trp Asp Lys Arg Tyr Ile Pro Gly Glu Val Lys Trp Trp Asp Trp Asn
1               5                   10                  15

Trp Thr Ile Gln
        20

<210> SEQ ID NO 86
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized aera_aertr"
      /organism="Artificial Sequence"

<400> SEQUENCE: 86

Trp Asp Lys Arg Tyr Leu Pro Gly Glu Met Lys Trp Trp Asp Trp Asn
1               5                   10                  15

Trp Ala Ile Gln
        20

<210> SEQ ID NO 87
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized aera_aersa"
      /organism="Artificial Sequence"

<400> SEQUENCE: 87

Val Asp Lys Arg Tyr Ile Pro Gly Glu Val Lys Trp Trp Asp Trp Asn
1               5                   10                  15

Trp Thr Ile Ser
        20

<210> SEQ ID NO 88
<211> LENGTH: 131
<212> TYPE: PRT
<213> ORGANISM: Artificial Sequence
<220> FEATURE:
<221> NAME/KEY: SOURCE
<222> LOCATION: 1..131
<223> OTHER INFORMATION: /mol_type="protein"
      /note="synthesized orexin"
      /organism="Artificial Sequence"

<400> SEQUENCE: 88

Met Asn Leu Pro Ser Ala Lys Val Ser Trp Ala Ala Val Thr Leu Leu

```
                1               5                   10                  15
            Leu Leu Leu Leu Leu Leu Pro Pro Ala Leu Leu Ser Leu Gly Val Asp
                            20                  25                  30

Ala Gln Pro Leu Pro Asp Cys Cys Arg Gln Lys Thr Cys Ser Cys Arg
                        35                  40                  45

Leu Tyr Glu Leu Leu His Gly Ala Gly Asn His Ala Ala Gly Ile Leu
                    50                  55                  60

Thr Leu Gly Lys Arg Arg Pro Gly Pro Pro Gly Leu Gln Gly Arg Leu
            65                  70                  75                  80

Gln Arg Leu Leu Gln Ala Ser Gly Asn His Ala Ala Gly Ile Leu Thr
                                85                  90                  95

Met Gly Arg Arg Ala Gly Ala Glu Leu Glu Pro Arg Leu Cys Pro Gly
                            100                 105                 110

Arg Arg Cys Leu Ala Ala Ala Ser Ala Leu Ala Pro Arg Gly Arg
                        115                 120                 125

Ser Arg Val
                    130

<210> SEQ ID NO 89
<211> LENGTH: 113
<212> TYPE: PRT
<213> ORGANISM: Artificial Sequence
<220> FEATURE:
<221> NAME/KEY: SOURCE
<222> LOCATION: 1..113
<223> OTHER INFORMATION: /mol_type="protein"
      /note="synthesized rheu.ef.24"
      /organism="Artificial Sequence"

<400> SEQUENCE: 89

Arg Lys Val Leu Leu Gln Thr Val Arg Ala Ala Lys Lys Ala Arg Arg
            1               5                   10                  15

Leu Leu Gly Met Trp Gln Pro Pro Val His Asn Val Pro Gly Ile Glu
                            20                  25                  30

Arg Asn Trp Tyr Glu Ser Cys Phe Arg Ser His Ala Ala Val Cys Gly
                        35                  40                  45

Cys Gly Asp Phe Val Gly His Ile Asn His Leu Ala Thr Thr Leu Gly
                    50                  55                  60

Arg Pro Pro Arg Pro Gly Pro Gly Gly Pro Arg Thr Pro Gln Ile
            65                  70                  75                  80

Arg Asn Leu Pro Ala Leu Pro Ala Pro Gln Gly Glu Pro Gly Asp Arg
                            85                  90                  95

Ala Thr Trp Arg Gly Ala Ser Gly Ala Asp Ala Ala Gly Gly Asp Gly
                        100                 105                 110

Gly

<210> SEQ ID NO 90
<211> LENGTH: 131
<212> TYPE: PRT
<213> ORGANISM: Homo sapiens
<220> FEATURE:
<221> NAME/KEY: SOURCE
<222> LOCATION: 1..131
<223> OTHER INFORMATION: /mol_type="protein"
      /note="orex"
      /organism="Homo sapiens"

<400> SEQUENCE: 90

Met Asn Leu Pro Ser Thr Lys Val Ser Trp Ala Ala Val Thr Leu Leu
            1               5                   10                  15
```

Leu Leu Leu Leu Leu Leu Pro Pro Ala Leu Ser Ser Gly Ala Ala
            20                  25                  30

Ala Gln Pro Leu Pro Asp Cys Cys Arg Gln Lys Thr Cys Ser Cys Arg
            35                  40                  45

Leu Tyr Glu Leu Leu His Gly Ala Gly Asn His Ala Ala Gly Ile Leu
        50                  55                  60

Thr Leu Gly Lys Arg Arg Ser Gly Pro Pro Gly Leu Gln Gly Arg Leu
65                  70                  75                  80

Gln Arg Leu Leu Gln Ala Ser Gly Asn His Ala Ala Gly Ile Leu Thr
                85                  90                  95

Met Gly Arg Arg Ala Gly Ala Glu Pro Ala Pro Arg Pro Cys Leu Gly
            100                 105                 110

Arg Arg Cys Ser Ala Pro Ala Ala Ala Ser Val Ala Pro Gly Gly Gln
        115                 120                 125

Ser Gly Ile
    130

<210> SEQ ID NO 91
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized gipreceptor_7"
      /organism="Artificial Sequence"

<400> SEQUENCE: 91

Pro Arg Leu Gly Pro Tyr Leu Gly Asp Gln Thr Leu Thr Leu Trp Asn
1               5                   10                  15

Gln Ala Leu Ala Ala
            20

<210> SEQ ID NO 92
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized rheu.ef.24"
      /organism="Artificial Sequence"

<400> SEQUENCE: 92

Pro Arg Pro Gly Pro Pro Gly Gly Pro Arg Thr Pro Gln Ile Arg Asn
1               5                   10                  15

Leu Pro Ala Leu Pro Ala
            20

<210> SEQ ID NO 93
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="synthesized gipr_mesau"
      /organism="Artificial Sequence"

<400> SEQUENCE: 93

```
Pro Thr Leu Gly Pro Tyr Pro Gly Asp Arg Thr Leu Thr Leu Arg Asn
1               5                   10                  15

Gln Ala Leu Ala Ala
            20

<210> SEQ ID NO 94
<211> LENGTH: 21
<212> TYPE: PRT
<213> ORGANISM: Rattus
<220> FEATURE:
<221> NAME/KEY: SOURCE
<222> LOCATION: 1..21
<223> OTHER INFORMATION: /mol_type="protein"
      /note="gipr_rat"
      /organism="Rattus rattus"

<400> SEQUENCE: 94

Pro Pro Leu Gly Pro Tyr Thr Gly Asn Gln Thr Pro Thr Leu Trp Asn
1               5                   10                  15

Gln Ala Leu Ala Ala
            20

<210> SEQ ID NO 95
<211> LENGTH: 21
<212> TYPE: PRT
<213> ORGANISM: Homo sapiens
<220> FEATURE:
<221> NAME/KEY: SOURCE
<222> LOCATION: 1..21
<223> OTHER INFORMATION: /mol_type="protein"
      /note="gipr_hu"
      /organism="Homo sapiens"

<400> SEQUENCE: 95

Pro Arg Pro Gly Pro Tyr Leu Gly Asp Gln Ala Leu Ala Leu Trp Asn
1               5                   10                  15

Gln Ala Leu Ala Ala
            20

<210> SEQ ID NO 96
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized prion_2"
      /organism="Artificial Sequence"

<400> SEQUENCE: 96

Ser Asn Gly Gly Gly Ser Arg Tyr Pro Gly Gln Gly Ser Pro Gly Gly
1               5                   10                  15

Asn Arg Tyr Pro Pro Gln
            20

<210> SEQ ID NO 97
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized rheu.ef.24"
      /organism="Artificial Sequence"

<400> SEQUENCE: 97
```

```
Leu Ala Thr Thr Leu Gly Arg Pro Pro Arg Pro Gly Pro Pro Gly Gly
1               5                   10                  15

Pro Arg Thr Pro Gln Ile
            20

<210> SEQ ID NO 98
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized prio_colgu"
      /organism="Artificial Sequence"

<400> SEQUENCE: 98

Trp Asn Thr Gly Gly Ser Arg Tyr Pro Gly Gln Gly Ser Pro Gly Gly
1               5                   10                  15

Asn Arg Tyr Pro Pro Gln
            20

<210> SEQ ID NO 99
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized prio_cebap"
      /organism="Artificial Sequence"

<400> SEQUENCE: 99

Trp Asn Thr Gly Gly Ser Arg Tyr Pro Gly Gln Gly Ser Pro Gly Gly
1               5                   10                  15

Asn Leu Tyr Pro Pro Gln
            20

<210> SEQ ID NO 100
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized prp1_trast"
      /organism="Artificial Sequence"

<400> SEQUENCE: 100

Trp Asn Thr Gly Gly Ser Arg Tyr Pro Gly Gln Gly Ser Pro Gly Gly
1               5                   10                  15

Asn Arg Tyr Pro Ser Gln
            20

<210> SEQ ID NO 101
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized prio_rabit"
      /organism="Artificial Sequence"
```

```
<400> SEQUENCE: 101

Trp Asn Thr Gly Gly Ser Arg Tyr Pro Gly Gln Ser Ser Pro Gly Gly
1               5                   10                  15

Asn Arg Tyr Pro Pro Gln
            20

<210> SEQ ID NO 102
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized o46593"
      /organism="Artificial Sequence"

<400> SEQUENCE: 102

Asn Thr Gly Gly Gly Ser Arg Tyr Pro Gly Gln Gly Ser Pro Gly Gly
1               5                   10                  15

Asn Arg Tyr Pro Pro Gln
            20

<210> SEQ ID NO 103
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized trivu"
      /organism="Artificial Sequence"

<400> SEQUENCE: 103

Ser Gly Gly Ser Asn Arg Tyr Pro Gly Gln Pro Gly Ser Pro Gly Gly
1               5                   10                  15

Asn Arg Tyr Pro Gly Trp
            20

<210> SEQ ID NO 104
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized neurotensn2r_1"
      /organism="Artificial Sequence"

<400> SEQUENCE: 104

Met Glu Thr Ser Ser Pro Trp Pro Pro Arg Pro Ser Pro
1               5                   10

<210> SEQ ID NO 105
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized rheu.ef.24"
      /organism="Artificial Sequence"

<400> SEQUENCE: 105
```

```
Leu Ala Thr Thr Leu Gly Arg Pro Pro Arg Pro Gly Pro
1               5                   10
```

<210> SEQ ID NO 106
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ntr2 motif"
      /organism="Artificial Sequence"

<400> SEQUENCE: 106

```
Met Glu Thr Ser Ser Pro Trp Pro Pro Arg Pro Ser Pro
1               5                   10
```

<210> SEQ ID NO 107
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ntr2 motif"
      /organism="Artificial Sequence"

<400> SEQUENCE: 107

```
Met Glu Thr Ser Ser Leu Trp Pro Pro Arg Pro Ser Pro
1               5                   10
```

<210> SEQ ID NO 108
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ntr2 motif"
      /organism="Artificial Sequence"

<400> SEQUENCE: 108

```
Met Glu Thr Ser Ser Pro Arg Pro Pro Arg Pro Ser Ser
1               5                   10
```

<210> SEQ ID NO 109
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nuclearecptr_5"
      /organism="Artificial Sequence"

<400> SEQUENCE: 109

```
Pro Val Asn Leu Leu Asn Ala Leu Val Arg Ala His Val Asp Ser Thr
1               5                   10                  15

Pro
```

<210> SEQ ID NO 110
<211> LENGTH: 16
<212> TYPE: PRT
<213> ORGANISM: Artificial Sequence
<220> FEATURE:

```
<221> NAME/KEY: SOURCE
<222> LOCATION: 1..16
<223> OTHER INFORMATION: /mol_type="protein"
      /note="synthesized ur742rev"
      /organism="Artificial Sequence"

<400> SEQUENCE: 110

Thr Phe Ile Thr Asn Ser Met Val Arg Ala His Ile Asp Ala Asp Lys
1               5                   10                  15

<210> SEQ ID NO 111
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nr41 motif"
      /organism="Artificial Sequence"

<400> SEQUENCE: 111

Pro Ala Asn Leu Leu Thr Ser Leu Val Arg Ala His Leu Asp Ser Gly
1               5                   10                  15

Pro

<210> SEQ ID NO 112
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nr42 motif"
      /organism="Artificial Sequence"

<400> SEQUENCE: 112

Pro Val Ser Leu Ile Ser Ala Leu Val Arg Ala His Val Asp Ser Asn
1               5                   10                  15

Pro

<210> SEQ ID NO 113
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nr41 motif"
      /organism="Artificial Sequence"

<400> SEQUENCE: 113

Pro Thr Asn Leu Leu Thr Ser Leu Ile Arg Ala His Leu Asp Ser Gly
1               5                   10                  15

Pro

<210> SEQ ID NO 114
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nr42 motif"
      /organism="Artificial Sequence"
```

<400> SEQUENCE: 114

Pro Val Asp Leu Ile Asn Ser Leu Val Arg Ala His Ile Asp Ser Ile
1               5                   10                  15
Pro

<210> SEQ ID NO 115
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized o97726"
      /organism="Artificial Sequence"

<400> SEQUENCE: 115

Pro Val Cys Met Met Asn Ala Leu Val Arg Ala Leu Thr Asp Ser Thr
1               5                   10                  15
Pro

<210> SEQ ID NO 116
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nr43 motif"
      /organism="Artificial Sequence"

<400> SEQUENCE: 116

Pro Ile Cys Met Met Asn Ala Leu Val Arg Ala Leu Thr Asp Ser Thr
1               5                   10                  15
Pro

<210> SEQ ID NO 117
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized nr43 motif"
      /organism="Artificial Sequence"

<400> SEQUENCE: 117

Pro Ile Cys Met Met Asn Ala Leu Val Arg Ala Leu Thr Asp Ala Thr
1               5                   10                  15
Pro

<210> SEQ ID NO 118
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized bdnfactor_3"
      /organism="Artificial Sequence"

<400> SEQUENCE: 118

```
Pro Leu Leu Phe Leu Leu Glu Glu Tyr Lys Asn Tyr Leu Asp Ala Ala
1               5                   10                  15

Asn

<210> SEQ ID NO 119
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized uro742rev"
      /organism="Artificial Sequence"

<400> SEQUENCE: 119

Pro Leu Trp Ala Leu Leu Asn Gly Tyr Val Asp Tyr Leu Glu Thr Gln
1               5                   10                  15

Ile

<210> SEQ ID NO 120
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized uro742rev"
      /organism="Artificial Sequence"

<400> SEQUENCE: 120

Pro Leu Leu Phe Leu Pro Ser Glu Tyr Gln Arg Glu Asp Gly Ala Ala
1               5                   10                  15

Glu

<210> SEQ ID NO 121
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized calcitonin"
      /organism="Artificial Sequence"

<400> SEQUENCE: 121

Lys Cys Tyr Asp Arg Met Gln Gln Leu Pro Pro Tyr Glu Gly Glu Gly
1               5                   10                  15

Pro Tyr

<210> SEQ ID NO 122
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized uro742rev"
      /organism="Artificial Sequence"

<400> SEQUENCE: 122

Thr Pro Val Arg Arg Leu Leu Pro Leu Pro Ser Tyr Pro Gly Glu Gly
1               5                   10                  15
```

Pro Gln

<210> SEQ ID NO 123
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized calr motif"
      /organism="Artificial Sequence"

<400> SEQUENCE: 123

Lys Cys Tyr Asp Arg Ile Gln Gln Leu Pro Pro Tyr Glu Gly Glu Gly
1               5                   10                  15

Pro Tyr

<210> SEQ ID NO 124
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized calr motif"
      /organism="Artificial Sequence"

<400> SEQUENCE: 124

Lys Cys Tyr Asp Arg Met Glu Gln Leu Pro Pro Tyr Gln Gly Glu Gly
1               5                   10                  15

Pro Tyr

<210> SEQ ID NO 125
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized calr motif"
      /organism="Artificial Sequence"

<400> SEQUENCE: 125

Lys Cys Tyr Asp Arg Met Gln Gln Leu Pro Ala Tyr Gln Gly Glu Gly
1               5                   10                  15

Pro Tyr

<210> SEQ ID NO 126
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized calr motif"
      /organism="Artificial Sequence"

<400> SEQUENCE: 126

Lys Cys Tyr Asp Arg Ile His Gln Leu Pro Ser Tyr Glu Gly Glu Gly
1               5                   10                  15

Leu Tyr

```
<210> SEQ ID NO 127
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized calr motif"
      /organism="Artificial Sequence"

<400> SEQUENCE: 127

Arg Cys Tyr Asp Arg Met Gln Gln Leu Pro Pro Tyr Glu Gly Glu Gly
1               5                   10                  15

Pro Tyr

<210> SEQ ID NO 128
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized calr_motif"
      /organism="Artificial Sequence"

<400> SEQUENCE: 128

Arg Cys Tyr Asp Arg Met Gln Lys Leu Pro Pro Tyr Gln Gly Glu Gly
1               5                   10                  15

Leu Tyr

<210> SEQ ID NO 129
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized cavpo207"
      /organism="Artificial Sequence"

<400> SEQUENCE: 129

Ser Arg Arg Leu Arg Val Arg Arg Phe His Arg Arg Arg Arg Thr Gly
1               5                   10                  15

Arg

<210> SEQ ID NO 130
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized uro705rev"
      /organism="Artificial Sequence"

<400> SEQUENCE: 130

Leu Arg Arg Arg Arg Pro Arg Arg Pro Leu Arg Arg Arg Arg Arg Gly
1               5                   10                  15

Arg

<210> SEQ ID NO 131
<211> LENGTH: 17
<212> TYPE: PRT
```

```
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized lt4r1"
      /organism="Artificial Sequence"

<400> SEQUENCE: 131

Gly Arg Arg Leu Gln Ala Arg Arg Phe Arg Arg Ser Arg Arg Thr Gly
1               5                   10                  15

Arg

<210> SEQ ID NO 132
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized rheu.cd.215rev.1.7"
      /organism="Artificial Sequence"

<400> SEQUENCE: 132

Arg Arg Arg Arg Pro Ala Arg Arg Phe Arg Ala Arg Arg Arg Val Arg
1               5                   10                  15

Arg

<210> SEQ ID NO 133
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized zpr5.b4.12dk.209_2"
      /organism="Artificial Sequence"

<400> SEQUENCE: 133

Arg Arg Arg Pro Arg Arg Arg Arg Val Arg Arg Arg Arg Arg Trp Arg
1               5                   10                  15

Arg

<210> SEQ ID NO 134
<211> LENGTH: 42
<212> TYPE: PRT
<213> ORGANISM: Artificial Sequence
<220> FEATURE:
<221> NAME/KEY: SOURCE
<222> LOCATION: 1..42
<223> OTHER INFORMATION: /mol_type="protein"
      /note="synthesized auto_anti-p27"
      /organism="Artificial Sequence"

<400> SEQUENCE: 134

Glu Ile Ser Lys Lys Met Ala Glu Leu Leu Lys Gly Ala Thr Met
1               5                   10                  15

Leu Asp Glu His Cys Pro Lys Cys Gly Thr Pro Leu Phe Arg Leu Lys
            20                  25                  30

Asp Gly Lys Val Phe Cys Pro Ile Cys Glu
            35                  40

<210> SEQ ID NO 135
<211> LENGTH: 40
```

```
<212> TYPE: PRT
<213> ORGANISM: Artificial Sequence
<220> FEATURE:
<221> NAME/KEY: SOURCE
<222> LOCATION: 1..40
<223> OTHER INFORMATION: /mol_type="protein"
      /note="synthesized rheu.cd.21"
      /organism="Artificial Sequence"

<400> SEQUENCE: 135
```

His Thr Ala Val Lys Gly Gln Phe Gly Leu Gly Thr Gly Arg Ala Leu
1               5                   10                  15

Gly Lys Ala Leu Lys Lys Cys Ala Phe Ala Gly Leu Arg Arg Lys Gly
                20                  25                  30

Lys Cys Phe Cys Lys Val Cys Glu
            35                  40

```
<210> SEQ ID NO 136
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized vasoprsnv2r_6"
      /organism="Artificial Sequence"

<400> SEQUENCE: 136
```

Arg Ala Gly Gly Arg Arg Gly Arg Arg Thr Gly Ser Pro Ser Glu
1               5                   10                  15

Gly Ala Arg Val
            20

```
<210> SEQ ID NO 137
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized uro742rp.1"
      /organism="Artificial Sequence"

<400> SEQUENCE: 137
```

Arg Asn Ala Ser Arg Arg Arg Gly Ser Ser Thr Ala Ser Thr Ser Glu
1               5                   10                  15

Glu Ala Ser Leu
            20

```
<210> SEQ ID NO 138
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized vasoprsnvibr_4"
      /organism="Artificial Sequence"

<400> SEQUENCE: 138
```

Thr Gln Ala Gly Arg Val Glu Arg Arg Gly Trp Arg Thr Trp Asp Lys
1               5                   10                  15

Ser Ser Ser Ser
            20

```
<210> SEQ ID NO 139
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized zc35s.b2.9"
      /organism="Artificial Sequence"

<400> SEQUENCE: 139

Ala Gln Asp Trp Ala Glu Glu Tyr Thr Ala Cys Arg Tyr Trp Asp Arg
1               5                   10                  15

Pro Pro Arg Thr
            20

<210> SEQ ID NO 140
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v2 motif"
      /organism="Artificial Sequence"

<400> SEQUENCE: 140

Arg Ala Gly Arg Arg Arg Arg Gly His Arg Thr Gly Ser Pro Ser Glu
1               5                   10                  15

Gly Ala His Val
            20

<210> SEQ ID NO 141
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v2 motif"
      /organism="Artificial Sequence"

<400> SEQUENCE: 141

Arg Ala Gly Arg Arg Arg Arg Gly Arg Arg Thr Gly Ser Pro Ser Glu
1               5                   10                  15

Gly Ala His Val
            20

<210> SEQ ID NO 142
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v2 motif"
      /organism="Artificial Sequence"

<400> SEQUENCE: 142

Arg Ala Gly Gly His Arg Gly Gly Arg Arg Ala Gly Ser Pro Arg Glu
1               5                   10                  15

Gly Ala Arg Val
```

20

<210> SEQ ID NO 143
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v2 motif"
      /organism="Artificial Sequence"

<400> SEQUENCE: 143

Arg Pro Gly Gly Arg Arg Gly Arg Arg Thr Gly Ser Pro Gly Glu
1               5                   10                  15

Gly Ala His Val
            20

<210> SEQ ID NO 144
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v2 motif"
      /organism="Artificial Sequence"

<400> SEQUENCE: 144

Arg Ala Gly Gly Cys Arg Gly Gly His Arg Thr Gly Ser Pro Ser Glu
1               5                   10                  15

Gly Ala Arg Val
            20

<210> SEQ ID NO 145
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v2 motif"
      /organism="Artificial Sequence"

<400> SEQUENCE: 145

Arg Ala Gly Gly Pro Arg Arg Gly Cys Arg Pro Gly Ser Pro Ala Glu
1               5                   10                  15

Gly Ala Arg Val
            20

<210> SEQ ID NO 146
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v1b motif"
      /organism="Artificial Sequence"

<400> SEQUENCE: 146

Thr Gln Ala Trp Arg Val Gly Gly Gly Gly Trp Arg Thr Trp Asp Arg
1               5                   10                  15

```
Pro Ser Pro Ser
         20

<210> SEQ ID NO 147
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized v1b motif"
      /organism="Artificial Sequence"

<400> SEQUENCE: 147

Thr Gln Ala Gly Arg Glu Glu Arg Arg Gly Trp Arg Thr Trp Asp Lys
1               5                   10                  15

Ser Ser Ser Ser
         20

<210> SEQ ID NO 148
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized mch2receptor_5"
      /organism="Artificial Sequence"

<400> SEQUENCE: 148

Leu Val Gln Pro Phe Arg Leu Thr Arg Trp Arg Thr Arg Tyr Lys Thr
1               5                   10                  15

Ile Arg Ile Asn
         20

<210> SEQ ID NO 149
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized uro742rp.1"
      /organism="Artificial Sequence"

<400> SEQUENCE: 149

Arg Pro Phe Cys Ile Thr Lys Trp Arg Thr Ser Phe Leu Phe Phe Lys
1               5                   10                  15

Asn Asn

<210> SEQ ID NO 150
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized receptor motif"
      /organism="Artificial Sequence"

<400> SEQUENCE: 150

Leu Val Gln Pro Phe Arg Leu Thr Ser Trp Arg Thr Arg Tyr Lys Thr
1               5                   10                  15
```

Ile Arg Ile Asn
            20

<210> SEQ ID NO 151
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized prstnoidep1r_4"
      /organism="Artificial Sequence"

<400> SEQUENCE: 151

Ile Ser Leu Gly Pro Pro Gly Gly Trp Arg Gln Ala Leu Leu Ala Gly
1               5                   10                  15

Leu

<210> SEQ ID NO 152
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized uro742rev"
      /organism="Artificial Sequence"

<400> SEQUENCE: 152

Met Gly Leu Gly Pro Ser Gly Gly Asn Arg Lys Thr Leu Phe Ile Ala
1               5                   10                  15

Gly Lys

<210> SEQ ID NO 153
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized receptor motif"
      /organism="Artificial Sequence"

<400> SEQUENCE: 153

Ile Ser Leu Gly Pro Arg Gly Gly Trp Arg Gln Ala Leu Leu Ala Gly
1               5                   10                  15

Leu

<210> SEQ ID NO 154
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized receptor motif"
      /organism="Artificial Sequence"

<400> SEQUENCE: 154

Ile Gly Leu Gly Pro Pro Gly Gly Trp Arg Gln Ala Leu Leu Ala Gly
1               5                   10                  15

Leu

```
<210> SEQ ID NO 155
<211> LENGTH: 21
<212> TYPE: PRT
<213> ORGANISM: Artificial Sequence
<220> FEATURE:
<221> NAME/KEY: SOURCE
<222> LOCATION: 1..21
<223> OTHER INFORMATION: /mol_type="protein"
      /note="Q41528"
      /organism="Artificial Sequence"

<400> SEQUENCE: 155

Pro Gln Thr Gln Gly Ser Val Gln Pro Gln Gln Leu Pro Gln Phe Glu
1               5                   10                  15

Glu Ile Arg Asn Leu
            20

<210> SEQ ID NO 156
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="zc35s.B3.3"
      /organism="Artificial Sequence"

<400> SEQUENCE: 156

Ser Pro Leu Gly Arg Gly Ala Gly Glu Pro Arg Arg Thr Ser Thr Pro
1               5                   10                  15

Val Ala Ala

<210> SEQ ID NO 157
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cyclinkinase_3"
      /organism="Artificial Sequence"

<400> SEQUENCE: 157

Glu Trp Arg Ser Leu Gly Val Gln Gln Ser Leu Gly Trp Val His
1               5                   10                  15

<210> SEQ ID NO 158
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized rheu.cd.21"
      /organism="Artificial Sequence"

<400> SEQUENCE: 158

Glu Ser Ser Arg Phe Gly Val Gln Gln Arg Leu Pro Trp Val His
1               5                   10                  15

<210> SEQ ID NO 159
<211> LENGTH: 15
<212> TYPE: PRT
<213> ORGANISM: Artificial Sequence
<220> FEATURE:
```

```
<221> NAME/KEY: SOURCE
<222> LOCATION: 1..15
<223> OTHER INFORMATION: /mol_type="protein"
      /note="synthesized cks2 motif"
      /organism="Artificial Sequence"

<400> SEQUENCE: 159

Glu Trp Arg Arg Leu Gly Val Gln Gln Ser Leu Gly Trp Val His
1               5                   10                  15

<210> SEQ ID NO 160
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"

<400> SEQUENCE: 160

Glu Trp Arg Asn Leu Gly Val Gln Gln Ser Gln Gly Trp Val His
1               5                   10                  15

<210> SEQ ID NO 161
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"

<400> SEQUENCE: 161

Glu Trp Arg Ser Ile Gly Val Gln Gln Ser His Gly Trp Ile His
1               5                   10                  15

<210> SEQ ID NO 162
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"

<400> SEQUENCE: 162

Glu Trp Arg Ser Ile Gly Val Gln Gln Ser Arg Gly Trp Ile His
1               5                   10                  15

<210> SEQ ID NO 163
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"

<400> SEQUENCE: 163

Glu Trp Arg Gly Leu Gly Val Gln Gln Ser Gln Gly Trp Val His
1               5                   10                  15
```

```
<210> SEQ ID NO 164
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"

<400> SEQUENCE: 164

Glu Trp Arg Gln Leu Gly Val Gln Gln Ser Gln Gly Trp Val His
1               5                   10                  15

<210> SEQ ID NO 165
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized o23249"
      /organism="Artificial Sequence"

<400> SEQUENCE: 165

Glu Trp Arg Ala Ile Gly Val Gln Gln Ser Arg Gly Trp Val His
1               5                   10                  15

<210> SEQ ID NO 166
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized o60191"
      /organism="Artificial Sequence"

<400> SEQUENCE: 166

Glu Trp Arg Gly Leu Gly Ile Thr Gln Ser Leu Gly Trp Gln His
1               5                   10                  15

<210> SEQ ID NO 167
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"

<400> SEQUENCE: 167

Glu Trp Arg Gly Leu Gly Ile Thr Gln Ser Leu Gly Trp Glu Met
1               5                   10                  15

<210> SEQ ID NO 168
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"
```

```
<400> SEQUENCE: 168

Glu Trp Arg Gly Leu Gly Ile Thr Gln Ser Leu Gly Trp Glu His
1               5                   10                  15

<210> SEQ ID NO 169
<211> LENGTH: 15
<212> TYPE: PRT
<213> ORGANISM: Artificial Sequence
<220> FEATURE:
<221> NAME/KEY: SOURCE
<222> LOCATION: 1..15
<223> OTHER INFORMATION: /mol_type="protein"
      /note="synthesized cks1 motif"
      /organism="Artificial Sequence"

<400> SEQUENCE: 169

Glu Trp Arg Ser Leu Gly Ile Gln Gln Ser Pro Gly Trp Met His
1               5                   10                  15

<210> SEQ ID NO 170
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized peroxisomepar_7"
      /organism="Artificial Sequence"

<400> SEQUENCE: 170

Lys Thr Glu Thr Asp Ala Ser Leu His Pro Leu Leu Gln
1               5                   10

<210> SEQ ID NO 171
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized rheu.cd.21"
      /organism="Artificial Sequence"

<400> SEQUENCE: 171

Lys Val Gln Ala Gly His Ser Leu His Pro Leu Leu Ser
1               5                   10

<210> SEQ ID NO 172
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ppat motif"
      /organism="Artificial Sequence"

<400> SEQUENCE: 172

Lys Thr Glu Thr Asp Met Ser Leu His Pro Leu Leu Gln
1               5                   10

<210> SEQ ID NO 173
<211> LENGTH: 13
<212> TYPE: PRT
<213> ORGANISM: Artificial Sequence
```

```
<220> FEATURE:
<221> NAME/KEY: SOURCE
<222> LOCATION: 1..13
<223> OTHER INFORMATION: /mol_type="protein"
      /note="synthesized ppat motif"
      /organism="Artificial Sequence"

<400> SEQUENCE: 173

Lys Thr Glu Ala Asp Met Cys Leu His Pro Leu Leu Gln
1               5                   10

<210> SEQ ID NO 174
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ppar motif"
      /organism="Artificial Sequence"

<400> SEQUENCE: 174

Lys Thr Glu Thr Asp Ala Ala Leu His Pro Leu Leu Gln
1               5                   10

<210> SEQ ID NO 175
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ppar motif"
      /organism="Artificial Sequence"

<400> SEQUENCE: 175

Lys Thr Glu Ser Asp Ala Ala Leu His Pro Leu Leu Gln
1               5                   10

<210> SEQ ID NO 176
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ppas motif"
      /organism="Artificial Sequence"

<400> SEQUENCE: 176

Lys Thr Glu Thr Glu Thr Ser Leu His Pro Leu Leu Gln
1               5                   10

<210> SEQ ID NO 177
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ppar motif"
      /organism="Artificial Sequence"

<400> SEQUENCE: 177

Lys Thr Glu Ser Asp Ala Ala Leu His Pro Leu Leu Gln
1               5                   10
```

<210> SEQ ID NO 178
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized ppas motif"
      /organism="Artificial Sequence"

<400> SEQUENCE: 178

Lys Thr Glu Ser Glu Thr Leu Leu His Pro Leu Leu Gln
1               5                   10

<210> SEQ ID NO 179
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized muscrinicm1r_4"
      /organism="Artificial Sequence"

<400> SEQUENCE: 179

Lys Met Pro Met Val Asp Pro Glu Ala Gln Ala Pro Thr Lys Gln Pro
1               5                   10                  15

Pro Lys

<210> SEQ ID NO 180
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="synthesized rheu.cd.21"
      /organism="Artificial Sequence"

<400> SEQUENCE: 180

Lys His Pro Thr Val Asp Phe Met Val Gln Ile Asn Thr Gln Pro Pro
1               5                   10                  15

Phe

<210> SEQ ID NO 181
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized acm1 motif"
      /organism="Artificial Sequence"

<400> SEQUENCE: 181

Lys Met Pro Met Val Asp Pro Glu Ala Gln Ala Pro Thr Lys Gln Pro
1               5                   10                  15

Pro Arg

<210> SEQ ID NO 182
<211> LENGTH: 18
<212> TYPE: PRT

```
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized acm1 motif"
      /organism="Artificial Sequence"

<400> SEQUENCE: 182

Lys Met Pro Met Val Asp Pro Glu Ala Gln Ala Pro Thr Lys Gln Pro
1               5                   10                  15

Pro Lys

<210> SEQ ID NO 183
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized acm1 motif"
      /organism="Artificial Sequence"

<400> SEQUENCE: 183

Lys Met Pro Met Val Asp Ser Glu Ala Gln Ala Pro Thr Lys Gln Pro
1               5                   10                  15

Pro Lys

<210> SEQ ID NO 184
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="synthesized acm1 motif"
      /organism="Artificial Sequence"

<400> SEQUENCE: 184

Lys Met Pro Met Val Asp Pro Glu Ala Gln Ala Pro Ala Lys Gln Pro
1               5                   10                  15

Pro Arg

<210> SEQ ID NO 185
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized gabab2receptr_1"
      /organism="Artificial Sequence"

<400> SEQUENCE: 185

Leu Ala Pro Gly Ala Trp Gly Trp Ala Arg Gly Ala Pro Arg Pro Pro
1               5                   10                  15

Pro Ser Ser

<210> SEQ ID NO 186
<211> LENGTH: 19
<212> TYPE: PRT
<213> ORGANISM: Artificial Sequence
<220> FEATURE:
<221> NAME/KEY: SOURCE
```

```
<222> LOCATION: 1..19
<223> OTHER INFORMATION: /mol_type="protein"
      /note="synthesized zc35s.B3.3"
      /organism="Artificial Sequence"

<400> SEQUENCE: 186

Val Gly Pro Glu Gln Trp Leu Phe Pro Glu Arg Lys Pro Lys Pro Pro
1               5                   10                  15

Pro Ser Ala

<210> SEQ ID NO 187
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized gabab2 motif"
      /organism="Artificial Sequence"

<400> SEQUENCE: 187

Leu Ala Pro Gly Ala Trp Gly Trp Ala Arg Gly Ala Pro Arg Pro Pro
1               5                   10                  15

Pro Ser Ser

<210> SEQ ID NO 188
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized gabab2receptr1"
      /organism="Artificial Sequence"

<400> SEQUENCE: 188

Leu Ala Pro Gly Ala Trp Gly Trp Thr Arg Gly Ala Pro Arg Pro Pro
1               5                   10                  15

Pro Ser Ser

<210> SEQ ID NO 189
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized zc35s.b3.3"
      /organism="Artificial Sequence"

<400> SEQUENCE: 189

Ser Glu Leu Ser Arg Gly Arg Gly Gly Pro Arg Cys Met Ser Met Pro
1               5                   10                  15

Leu Val Arg

<210> SEQ ID NO 190
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized o51896"
```

/organism="Artificial Sequence"

<400> SEQUENCE: 190

Ser Glu Leu Ser Arg Gly Arg Gly Gly Pro Arg Cys Met Ser Met Pro
1               5                   10                  15

Leu Ile Arg

<210> SEQ ID NO 191
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized sagp"
      /organism="Artificial Sequence"

<400> SEQUENCE: 191

Ser Glu Leu Val Arg Gly Arg Gly Gly Pro Arg Cys Met Ser Met Pro
1               5                   10                  15

Phe Glu Arg

<210> SEQ ID NO 192
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized o51781"
      /organism="Artificial Sequence"

<400> SEQUENCE: 192

Ser Glu Leu Ser Arg Gly Arg Gly Gly Pro Arg Cys Met Ser Met Ser
1               5                   10                  15

Leu Val Arg

<210> SEQ ID NO 193
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized o86131"
      /organism="Artificial Sequence"

<400> SEQUENCE: 193

Gly Glu Leu Ser Arg Gly Arg Gly Gly Pro Arg Cys Met Ser Met Pro
1               5                   10                  15

Leu Tyr Arg

<210> SEQ ID NO 194
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized arca"
      /organism="Artificial Sequence"

<400> SEQUENCE: 194

Ser Glu Leu Gly Arg Gly Arg Gly Gly Gly His Cys Met Thr Cys Pro
1               5                   10                  15

Ile Val Arg

<210> SEQ ID NO 195
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized arca"
      /organism="Artificial Sequence"

<400> SEQUENCE: 195

Asn Gln Leu Ser Leu Gly Met Gly Asn Ala Arg Cys Met Ser Met Pro
1               5                   10                  15

Leu Ser Arg

<210> SEQ ID NO 196
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized o31017"
      /organism="Artificial Sequence"

<400> SEQUENCE: 196

Ser Glu Leu Gly Arg Gly Arg Gly Gly Gly His Cys Met Thr Cys Pro
1               5                   10                  15

Ile Trp Arg

<210> SEQ ID NO 197
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized arca"
      /organism="Artificial Sequence"

<400> SEQUENCE: 197

Gly Glu Leu Gly Arg Gly Arg Gly Gly Gly His Cys Met Thr Cys Pro
1               5                   10                  15

Ile Val Arg

<210> SEQ ID NO 198
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized arca"
      /organism="Artificial Sequence"

<400> SEQUENCE: 198

Ser Glu Leu Gly Thr Gly Arg Gly Gly Pro Arg Cys Met Ser Cys Pro
1               5                   10                  15

Ala Ala Arg

<210> SEQ ID NO 199
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized arca"
      /organism="Artificial Sequence"

<400> SEQUENCE: 199

Ser Glu Leu Ser Arg Gly Pro Ser Gly Pro Leu Glu Met Val Cys Ser
1               5                   10                  15

Leu Trp Arg

<210> SEQ ID NO 200
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized ogfr_III"
      /organism="Artificial Sequence"

<400> SEQUENCE: 200

Ser Pro Ser Glu Thr Pro Gly Pro Arg Pro Ala Gly Pro Ala Arg Asp
1               5                   10                  15

Glu Pro Ala Glu
            20

<210> SEQ ID NO 201
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized zc37.b9.2d"
      /organism="Artificial Sequence"

<400> SEQUENCE: 201

Arg Ala Ala Ser Thr Pro Val Pro Thr Pro Ala Leu Arg Gly Pro Thr
1               5                   10                  15

Arg Gln Asp Pro Gly Glu
            20

<210> SEQ ID NO 202
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized cd3antigen_3"
      /organism="Artificial Sequence"

<400> SEQUENCE: 202

Trp Ile Phe Asp Val Gln Asn Pro Asp Glu Val Ala Lys Asn Ser Ser
1               5                   10                  15

Lys Ile Lys Val Lys Gln Arg
            20

<210> SEQ ID NO 203
<211> LENGTH: 19
<212> TYPE: PRT
<213> ORGANISM: Artificial Sequence
<220> FEATURE:
<221> NAME/KEY: SOURCE
<222> LOCATION: 1..19
<223> OTHER INFORMATION: /mol_type="protein"
      /note="synthesized zc3r11.b4"
      /organism="Artificial Sequence"

<400> SEQUENCE: 203

Asn Val Gln Asp Pro Glu Glu Gln Asn Glu Ser Ser Arg Phe Arg Val
1               5                   10                  15

Gln Gln Arg

<210> SEQ ID NO 204
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized cd3 motif"
      /organism="Artificial Sequence"

<400> SEQUENCE: 204

Trp Val Phe Asp Val Gln Asn Pro Glu Glu Val Ala Lys Asn Ser Ser
1               5                   10                  15

Lys Ile Lys Val Ile Gln Arg
            20

<210> SEQ ID NO 205
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized cd36 motif"
      /organism="Artificial Sequence"

<400> SEQUENCE: 205

Trp Ile Phe Asp Val Gln Asn Pro Asp Val Ala Lys Asn Ser Ser
1               5                   10                  15

Lys Ile Lys Val Lys Gln Arg
            20

<210> SEQ ID NO 206
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized cd36 motif"
      /organism="Artificial Sequence"

<400> SEQUENCE: 206

Trp Ile Phe Asp Val Gln Asn Pro Asp Glu Val Thr Val Asn Ser Ser
1               5                   10                  15

```
Lys Ile Lys Val Lys Gln Arg
            20

<210> SEQ ID NO 207
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized cd36 motif"
      /organism="Artificial Sequence"

<400> SEQUENCE: 207

Trp Ile Phe Asp Val Gln Asn Pro Gln Glu Val Met Met Asn Ser Ser
1               5                   10                  15

Asn Ile Gln Val Lys Gln Arg
            20

<210> SEQ ID NO 208
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized cd36 motif"
      /organism="Artificial Sequence"

<400> SEQUENCE: 208

Trp Ile Phe Asp Val Gln Asn Pro Asp Glu Val Ala Val Asn Ser Ser
1               5                   10                  15

Lys Ile Lys Val Lys Gln Arg
            20

<210> SEQ ID NO 209
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized cd36 motif"
      /organism="Artificial Sequence"

<400> SEQUENCE: 209

Trp Ile Phe Asp Val Gln Asn Pro Glu Glu Val Ala Lys Asn Ser Ser
1               5                   10                  15

Lys Ile Lys Val Lys Gln Arg
            20

<210> SEQ ID NO 210
<211> LENGTH: 25
<212> TYPE: PRT
<213> ORGANISM: Artificial Sequence
<220> FEATURE:
<221> NAME/KEY: SOURCE
<222> LOCATION: 1..25
<223> OTHER INFORMATION: /mol_type="protein"
      /note="synthesized myelinp0_5"
      /organism="Artificial Sequence"

<400> SEQUENCE: 210

Gly Val Val Leu Gly Ala Ile Leu Gly Gly Val Leu Gly Val Val Leu
1               5                   10                  15
```

Leu Leu Val Leu Leu Leu Tyr Leu Val
            20                  25

<210> SEQ ID NO 211
<211> LENGTH: 22
<212> TYPE: PRT
<213> ORGANISM: Artificial Sequence
<220> FEATURE:
<221> NAME/KEY: SOURCE
<222> LOCATION: 1..22
<223> OTHER INFORMATION: /mol_type="protein"
      /note="synthesized zc312.b11"
      /organism="Artificial Sequence"
<220> FEATURE:
<221> NAME/KEY: VARIANT
<222> LOCATION: 17..17
<223> OTHER INFORMATION: X is any amino acid

<400> SEQUENCE: 211

Met Leu Gly Arg Ile Ile Gly Gly Val Gly Cys Val Leu Leu Glu Leu
1               5                   10                  15

Xaa Gly Leu Gly Val Arg
            20

<210> SEQ ID NO 212
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized chlamidiaom3_3"
      /organism="Artificial Sequence"

<400> SEQUENCE: 212

Cys Gly Ser Tyr Val Pro Ser Cys Ser Lys Pro Cys Gly
1               5                   10

<210> SEQ ID NO 213
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="synthesized rheu.cd.21"
      /organism="Artificial Sequence"

<400> SEQUENCE: 213

Cys Thr Gly Tyr Thr Glu Phe Cys Ala Lys Tyr Thr Gly
1               5                   10

<210> SEQ ID NO 214
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="DNA"
      /note="synthesized primer"
      /organism="Artificial Sequence"

<400> SEQUENCE: 214
ggccgggcca tgggcaaggc tctta                                          25

```
<210> SEQ ID NO 215
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="synthesized primer"
      /organism="Artificial Sequence"

<400> SEQUENCE: 215
agtcaagggg caattcgggc tcgggact                                    28

<210> SEQ ID NO 216
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="synthesized primer"
      /organism="Artificial Sequence"

<400> SEQUENCE: 216
caattcgggc tcgggact                                               18

<210> SEQ ID NO 217
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="DNA"
      /note="synthesized primer"
      /organism="Artificial Sequence"

<400> SEQUENCE: 217
acacaccgca gtcaagggg                                              19

<210> SEQ ID NO 218
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="DNA"
      /note="synthesized primer"
      /organism="Artificial Sequence"

<400> SEQUENCE: 218
caattcgggc tcgggactg                                              19

<210> SEQ ID NO 219
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
      /note="synthesized primer"
      /organism="Artificial Sequence"

<400> SEQUENCE: 219
agtttacaca ccgcagtcaa gggg                                        24
```

```
<210> SEQ ID NO 220
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="synthesized primer"
      /organism="Artificial Sequence"

<400> SEQUENCE: 220
ccgcagcgag aacgccacgg agggagatcc t                              31

<210> SEQ ID NO 221
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="synthesized primer"
      /organism="Artificial Sequence"

<400> SEQUENCE: 221
acttccgaat ggctgagttt tccacgcccg t                              31

<210> SEQ ID NO 222
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="synthesized primer"
      /organism="Artificial Sequence"

<400> SEQUENCE: 222
agaggagcca cggcagggga tccgaacgtc ct                             32

<210> SEQ ID NO 223
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="synthesized primer"
      /organism="Artificial Sequence"

<400> SEQUENCE: 223
cttaccgact caaaaacgac gggcaggcgc c                              31

<210> SEQ ID NO 224
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="synthesized primer"
      /organism="Artificial Sequence"

<400> SEQUENCE: 224
cagcgagaac gccacggagg gagatcct                                  28
```

<210> SEQ ID NO 225
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
/note="synthesized primer"
/organism="Artificial Sequence"

<400> SEQUENCE: 225
gaatggctga gttttccacg cccgtccg                                28

<210> SEQ ID NO 226
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
/note="synthesized primer"
/organism="Artificial Sequence"

<400> SEQUENCE: 226
caattcgggc acgggact                                           18

<210> SEQ ID NO 227
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
/note="synthesized primer"
/organism="Artificial Sequence"

<400> SEQUENCE: 227
agtttacaca ccgaagtcaa gggg                                    24

<210> SEQ ID NO 228
<211> LENGTH: 71
<212> TYPE: DNA
<213> ORGANISM: Artificial Sequence
<220> FEATURE:
<221> NAME/KEY: source
<222> LOCATION: 1..71
<223> OTHER INFORMATION: /mol_type="DNA"
/note="synthesized zyb2"
/organism="Artificial Sequence"

<400> SEQUENCE: 228
cgggtgccga aggtgagttt acacaccgca gtcaagggc aattcgggct cgggactggc   60
cgggccatgg g                                                      71

<210> SEQ ID NO 229
<211> LENGTH: 71
<212> TYPE: DNA
<213> ORGANISM: Artificial Sequence
<220> FEATURE:
<221> NAME/KEY: source
<222> LOCATION: 1..71
<223> OTHER INFORMATION: /mol_type="DNA"
/note="synthesized zyb9"
/organism="Artificial Sequence"

<400> SEQUENCE: 229
cgggtgccga aggtgagttt acacaccgca gtcaaggggc aattcgggct cgggactggc    60
cgggctatgg g    71

<210> SEQ ID NO 230
<211> LENGTH: 71
<212> TYPE: DNA
<213> ORGANISM: Artificial Sequence
<220> FEATURE:
<221> NAME/KEY: source
<222> LOCATION: 1..71
<223> OTHER INFORMATION: /mol_type="DNA"
      /note="synthesized zkb5"
      /organism="Artificial Sequence"

<400> SEQUENCE: 230
cgggtgccgt aggtgagttt acacaccgca gtcaaggggc aattcgggct cgggactggc    60
cgggctatgg g    71

<210> SEQ ID NO 231
<211> LENGTH: 71
<212> TYPE: DNA
<213> ORGANISM: Artificial Sequence
<220> FEATURE:
<221> NAME/KEY: source
<222> LOCATION: 1..71
<223> OTHER INFORMATION: /mol_type="DNA"
      /note="synthesized zkb69"
      /organism="Artificial Sequence"

<400> SEQUENCE: 231
cgggtgccgg aggtgagttt acacaccgca gtcaaggggc aattcgggct cgggactggc    60
cgggctatgg g    71

<210> SEQ ID NO 232
<211> LENGTH: 2227
<212> TYPE: DNA
<213> ORGANISM: Artificial Sequence
<220> FEATURE:
<221> NAME/KEY: source
<222> LOCATION: 1..2227
<223> OTHER INFORMATION: /mol_type="DNA"
      /note="synthesized chimeric TTV, WV13038 clone 6"
      /organism="Artificial Sequence"

<400> SEQUENCE: 232
caattcgtgc acgggactac aaggaaaggg gttgaccccc accctccccc gccatgccca    60
ggagggtgca gacacaactg ggaaggtgct agagaccccg gggggaggct gggccagcac   120
caggcattgg ggggcaggtt cccgtctcta caccccagcc ccaggcggac agcgcgtgcc   180
cctcccgctg ccccacctgt cacccacctg ctggccccgg gctgtctctg ctcctggctc   240
ccctcccagc tgcgtcccca gctgcctctc caggaggag tgacagctgg cctgtgccac    300
accctcgagc cccccggac tacccctcc ctggggcagg accctgcct gtggcacaac     360 caagggcct gctgatgggg gctcatgtga gcagtgcccc agctgtgggt gtgggtgctg    420
ccagctgcca ccgcctttgc cctggtttcc cagatagacc ccgacccaca ctccgaagct    480
gtatcatgaa cgctgtggtg ggcggctggt ggggagcggg gttgccgtcc cactaccctc    540
tggaagcctc agccatgaag ggccctgtg gcacctttt cccggcacac ggtgctgtgt     600
ttctccactc ttgggctctg cagtgacttg aggggtcaag tctatgatcc cacgggaggc    660
tgggctaatg aggggaccag agacctcagt gctgtgcagg gagtcctgaa ccaccctggt    720

```
ggaaggccca gcccaactcc ccagtcctcc cgccagctcc ctgtggtgtc caggagacct      780
gtggtcaggc ctggaggaga agctcctcct cccctcgaca tcctccctgc agcccttgct      840
cttcaccaga gcctcctgac tccccaggac cccagagagg actgaccctc tccagccgac      900
ctctgggctc aggacagctg ggcggggcag ccacaggagc tgcctgtagg gagcagagtc      960
aggacgggga ccgagccgga cacccattct ggaagtgtct gcacttccag gcaggggaag     1020
gacggcagtg ggtagctggg agtgctgggc gaagatgggc cattgtcagg ccctcagtgg     1080
ggactgggag gtagaggtgg ggaggtctgt ggaggaagga gaagaagggc cagtgtcccg     1140
agttgggggt ggttggcagt ggacgaggcc gacaggaaca gacctgagct tggggagctc     1200
cactcagaac gaggcatcct tcagggttct gtgcatactg gtgtccctgg ctggggccg      1260 ggccccgaag tggagcctgg gactgtgagg gtggggggg tgtgctgggg tgggaggtgg      1320
atggagcccc ccctccaccg cctggccgct tgggctgaac cttggacttc ggagccggaa     1380
cagacatagg aaatggccta actgcatttg cgcaggaaca ccaaatccct cgcagctgca     1440
cggggctgag ccagggccac gggcggggtc ggccatccca gagtcctgac agctccgtgg     1500
tgtatgccaa ggggcctggg ccgctgaccg aggggcgcct ttcccaggcc agaggccccc     1560
accccacccc aggagagctg ccccccttc agttcccaga acggagcccg gctgtggaat      1620
agtgatgcgg tgaggtcatg gggaggggc ccgcatgact catatcctgg ggtaggggaa      1680
agggaggaga cggagaaggg gcccagaggc ctccacgtcc tcagctctgc tgggtcagag     1740 gccagggggct ggcggggctt ctccccagca ctgggtttta ggggagacac caggagatgc    1800
ttactctgca tccccactct gtcccccagg ccctagcca gggagagctc agtcagagtg      1860
atcctccagg ggcccagctc tgcatggatg atgttcccag agtacacacc tgggcctcgt     1920
gccagggccg gcaccgccgt tgtcagggct atggcaaggc aaacagtcaa tgtttgcctc     1980
actaaagtga ggctgcagca ccctgaaggg atccctggag ggggacgtgg tcccttgtt     2040 cccaagcttg tctgcacatg cacgtggatg tcaagggttc ccgtgtgtga gcacatgcat     2100
atttgtatgt gcatggggtg cgggcatgtg tgcctgtgtg gccggagcgt gggctcgtgg     2160
agaatgtgtg tgagttgggt gtgcacctgc atgtgcccca ggcctaggga gtcccgtgcc     2220
cgaattg                                                               2227
```

<210> SEQ ID NO 233
<211> LENGTH: 883
<212> TYPE: DNA
<213> ORGANISM: Artificial Sequence
<220> FEATURE:
<221> NAME/KEY: source
<222> LOCATION: 1..883
<223> OTHER INFORMATION: /mol_type="DNA"
    /note="synthesized chimeric TTV, gb40.27"
    /organism="Artificial Sequence"

<400> SEQUENCE: 233

```
cgggactggc cgggctatgc cccagacaca ctcacgtagg ggtgtccggc ctggcagccc       60
aggaccatgg tctgcagggt ttcctctcgg ccattcagga caaccctagt ctccagggaa      120
tagcgctggt gtcgcctatc agccgtgaag gtctcctgca ggaggaggct ctgcgggatg      180
ggcaggtgca atgggtgcct ggtgtgcaga gggaaaaaca ggccaaagcc attaaagcag      240
ctggcagtgc cagggcacaa ttgtgcccca cggtctcagc ctgggcctgt cacgagcttg      300
cagagttaag actctgccac agagaagaga acatcaggac acctggcagc cctatgcttt      360
```

| | |
|---|---|
| acaatgtggc atccagaacc cttcaccacc tcactgtgcc agagaagtgg gcatggctgg | 420 |
| ggtccccgtc gccatttgac agcaaagacc caagaggata gatgacacac agcatctggt | 480 |
| gtcacacaga ctgggattag aatccaggca cggtctttca ctagctgtgt gaccttggga | 540 |
| aaaggacttg actgttctgt gcctcagttt ccccatctgt aaaacggagg ctaaaataat | 600 |
| actgatcgga cacagtggtc agggttagag ataacataca tgaaacgacc acaagctccc | 660 |
| caagggcaaa ggtttctgac attccggttc tctgccattt tccatgtgcc cagaagagca | 720 |
| cttggtccat agtatgtgct caatgaatgt aaatgggata aaaacacgaa cgaacactct | 780 |
| gccaacgatg ctgctgttcc tttgtcatca ctgcttctgt ttaggctgta gctgacttat | 840 |
| ctaaggccat acagctgctc aatgcatagc ccggccagtc ccg | 883 |

<210> SEQ ID NO 234
<211> LENGTH: 291
<212> TYPE: DNA
<213> ORGANISM: Artificial Sequence
<220> FEATURE:
<221> NAME/KEY: source
<222> LOCATION: 1..291
<223> OTHER INFORMATION: /mol_type="DNA"
      /note="synthesized chimeric TTV, gb43.30"
      /organism="Artificial Sequence"

<400> SEQUENCE: 234

| | |
|---|---|
| cccccttgact tcggtgtgta aacttgtggt atagaacatg atgttttaag atacatgtac | 60 |
| attgtggaat ggcttgatca tgctaattaa catatgaatt acctcactta gctatctttt | 120 |
| ttatggtgaa agcacttaaa atctaccctc agcagttttc aagtacacaa tacatttcta | 180 |
| ttaactatag tcaccatgtt gtacaataaa tctcttgaat ttattcctcc tgcctaactg | 240 |
| acattttgta tcctttgact gatctctctc cccagtcccg tgcccgaatt g | 291 |

<210> SEQ ID NO 235
<211> LENGTH: 293
<212> TYPE: DNA
<213> ORGANISM: Homo sapiens
<220> FEATURE:
<221> NAME/KEY: source
<222> LOCATION: 1..293
<223> OTHER INFORMATION: /mol_type="DNA"
      /organism="Homo sapiens"

<400> SEQUENCE: 235

| | |
|---|---|
| taattgacaa aacgtgtata aacttgtggt atagaacatg atgttttaag atacatgtac | 60 |
| attgtggaat ggcttgatca tgctaattaa catatgaatt acctcactta gctatctttt | 120 |
| ttatggtgaa agcacttaaa atctaccctc agcagttttc aagtacacaa tacatttcta | 180 |
| ttaactatag tcaccatgtt gtacaataaa tctcttgaat ttattcctcc tgcctaactg | 240 |
| acattttgta tcctttgact gatctctctc cccagtcccg tgaccagtgc cct | 293 |

<210> SEQ ID NO 236
<211> LENGTH: 278
<212> TYPE: DNA
<213> ORGANISM: Artificial Sequence
<220> FEATURE:
<221> NAME/KEY: source
<222> LOCATION: 1..278
<223> OTHER INFORMATION: /mol_type="DNA"
      /note="synthesized gbDhDi43.30.sequence"
      /organism="Artificial Sequence"

<400> SEQUENCE: 236

```
gtgtgtaaac ttgtggtata gaacatgatg ttttaagata catgtacatt gtggaatggc      60
ttgatcatgc taattaacat atgaattacc tcacttagct atctttttta tggtgaaagc     120
acttaaaatc taccctcagc agttttcaag tacacaatac atttctatta actatagtca     180
ccatgttgta caataaatct cttgaattta ttcctcctgc ctaactgaca ttttgtatcc     240
tttgactgat ctctctcccc agtcccgtgc ccgaattg                             278
```

<210> SEQ ID NO 237
<211> LENGTH: 20
<212> TYPE: PRT
<213> ORGANISM: Artificial Sequence
<220> FEATURE:
<221> NAME/KEY: SOURCE
<222> LOCATION: 1..20
<223> OTHER INFORMATION: /mol_type="protein"
      /note="synthesized receptor motif"
      /organism="Artificial Sequence"

<400> SEQUENCE: 237

```
Leu Val Gln Pro Phe Arg Leu Thr Arg Trp Arg Thr Arg Tyr Lys Thr
1               5                   10                  15

Ile Arg Ile Asn
            20
```

<210> SEQ ID NO 238
<211> LENGTH: 272
<212> TYPE: DNA
<213> ORGANISM: Homo sapiens
<220> FEATURE:
<221> NAME/KEY: source
<222> LOCATION: 1..272
<223> OTHER INFORMATION: /mol_type="DNA"
      /organism="Homo sapiens"

<400> SEQUENCE: 238

```
gtgtataaac ttgtggtata gaacatgatg ttttaagata catgtacatt gtggaatggc      60
ttgatcatgc taattaacat atgaattacc tcacttagct atctttttta tggtgaaagc     120
acttaaaatc taccctcagc agttttcaag tacacaatac atttctatta actatagtca     180
ccatgttgta caataaatct cttgaattta ttcctcctcc tgcctaactg acattttgta     240
tcctttgact gatctctctc cccagtcccg tg                                   272
```

<210> SEQ ID NO 239
<211> LENGTH: 49
<212> TYPE: PRT
<213> ORGANISM: Artificial Sequence
<220> FEATURE:
<221> NAME/KEY: SOURCE
<222> LOCATION: 1..49
<223> OTHER INFORMATION: /mol_type="protein"
      /note="synthesized FASTA of gbDhDi43.30"
      /organism="Artificial Sequence"

<400> SEQUENCE: 239

```
Met Phe Tyr Thr Thr Ser Leu His Thr Glu Val Lys Gly Gln Phe Gly
1               5                   10                  15

His Gly Thr Gly Glu Arg Asp Gln Ser Lys Asp Thr Lys Cys Gln Leu
            20                  25                  30

Gly Arg Arg Asn Lys Phe Lys Arg Phe Ile Val Gln His Gly Asp Tyr
        35                  40                  45

Ser
```

-continued

```
<210> SEQ ID NO 240
<211> LENGTH: 119
<212> TYPE: PRT
<213> ORGANISM: Artificial Sequence
<220> FEATURE:
<221> NAME/KEY: SOURCE
<222> LOCATION: 1..119
<223> OTHER INFORMATION: /mol_type="protein"
      /note="synthesized TT virus variant"
      /organism="Artificial Sequence"
<220> FEATURE:
<221> NAME/KEY: SITE
<222> LOCATION: 23..23
<223> OTHER INFORMATION: Xaa can be any naturally occurring amino acid

<400> SEQUENCE: 240

Ala Gln Thr Gln Arg Arg Val Ile Pro Ala Ser Arg Gly Arg Val Pro
1               5                   10                  15

Glu Val Ser Leu His Thr Xaa Val Lys Gly Gln Phe Gly Leu Gly Thr
            20                  25                  30

Gly Arg Ala Met Gly Lys Ala Leu Lys Lys Asp Met Phe Leu Gly Lys
        35                  40                  45

Leu Tyr Lys Lys Lys Arg Ala Leu Ser Leu His Gly Leu Arg Thr Pro
50                  55                  60

Glu Ala Lys Pro Pro Ala Met Ser Trp Arg Pro Val His Asn Pro
65                  70                  75                  80

Asn Arg Ile Glu Arg Asn Leu Trp Glu Ala Phe Phe Arg Ile His Ala
                85                  90                  95

Ser Ser Cys Gly Cys Gly His Leu Val Gly His Leu Thr Val Leu Ala
            100                 105                 110

Arg Arg Tyr Gly Ala Pro Pro
        115

<210> SEQ ID NO 241
<211> LENGTH: 150
<212> TYPE: PRT
<213> ORGANISM: Torque teno virus
<220> FEATURE:
<221> NAME/KEY: SITE
<222> LOCATION: 23..23
<223> OTHER INFORMATION: Xaa can be any naturally occurring amino acid
<220> FEATURE:
<221> NAME/KEY: SOURCE
<222> LOCATION: 1..150
<223> OTHER INFORMATION: /mol_type="protein"
      /organism="Torque teno virus"

<400> SEQUENCE: 241

Ala Gln Thr Gln Arg Arg Val Ile Pro Ala Ser Arg Gly Arg Val Pro
1               5                   10                  15

Glu Val Ser Leu His Thr Xaa Val Lys Gly Gln Phe Gly Leu Gly Thr
            20                  25                  30

Gly Arg Ala Met Gly Lys Ala Leu Lys Lys Asp Met Phe Leu Gly Lys
        35                  40                  45

Leu Tyr Lys Lys Lys Arg Ala Leu Ser Leu His Gly Leu Arg Thr Pro
50                  55                  60

Glu Ala Lys Pro Pro Ala Met Ser Trp Arg Pro Val His Asn Pro
65                  70                  75                  80

Asn Arg Ile Glu Arg Asn Leu Trp Glu Ala Phe Phe Arg Ile His Ala
                85                  90                  95

Ser Ser Cys Gly Cys Gly His Leu Val Gly His Leu Thr Val Leu Ala
            100                 105                 110
```

-continued

Arg Arg Tyr Gly Ala Pro Pro Arg Pro Pro Ala Pro Gly Ala Pro Arg
         115                 120                 125

Pro Ala Leu Lys Arg Gln Leu Ala Leu Pro Ala Pro Pro Ala Asp Pro
     130                 135                 140

Gln Gln Ala Asn Pro Thr
145                 150

<210> SEQ ID NO 242
<211> LENGTH: 639
<212> TYPE: DNA
<213> ORGANISM: Artificial Sequence
<220> FEATURE:
<221> NAME/KEY: source
<222> LOCATION: 1..639
<223> OTHER INFORMATION: /mol_type="DNA"
      /note="synthesized hod11"
      /organism="Artificial Sequence"

<400> SEQUENCE: 242 cccctttgact gcggtgtgta aagcgcccca gcctgtgcct gcacagtgcc tgtgtggtgt      60
gaacccatga ccaggcctct ggagggaagg aaggttaggc ttagtggaca ccagctttcc     120
taaggtgggt cttagaccaa ctcattaaaa tggcaggatg gcttttgtg ctgtatttct      180 tgggattttc aagatgcccc acacagcaga agggatgtgc attttttct ctgccctgag      240 ttgtttgata aaaatcagtg acctcgttct ccacttagaa ctcccctgaa ctgcactcgg     300
tgtctaggac tgttggggaa ggaagtgaag agccagcatg tagtctcctc tggactctta     360
caggatctgt ccacctctgg gctctttatg taggggaagg tgtgagctcc tgggagtact     420
cctgatagag gactgtttcc ctgaaaacct cagcagtgtt tgaggcccta gcaggggaa     480 cccagacccc gcctgccaaa gcccctaatc cctcagggct attatcagca gcctaagcgc      540
cttagggtgg ccagagtcca gcccagcaag cagcaaagtc agcagcctcc tcgccctatc      600
ctctccatgc cccggggcac tccagtcccg accgaattg                            639

<210> SEQ ID NO 243
<211> LENGTH: 358
<212> TYPE: DNA
<213> ORGANISM: Artificial Sequence
<220> FEATURE:
<221> NAME/KEY: source
<222> LOCATION: 1..358
<223> OTHER INFORMATION: /mol_type="DNA"
      /note="synthesized hodL.VvWw.1.sequence"
      /organism="Artificial Sequence"

<400> SEQUENCE: 243
tcccctgaac tgcactcggt gtctaggact gttggggaag gaagtgaaga gccagcatgt      60
agtctcctct ggactcttac aggatctgtc cacctctggg ctctttatgt aggggaaggt     120
gtgagctcct gggagtactc ctgatagagg actgtttccc tgaaaacctc agcagtgttt     180
gaggccctag caggggga c ccagaccccg cctgccaaag cccctaatcc ctcagggcta     240
ttatcagcag cctaagcgcc ttagggtggc cagagtccag cccagcaagc agcaaagtca     300
gcagcctcct cgccctatcc tctccatgcc ccggggcact ccagtcccga ccgaattg      358

<210> SEQ ID NO 244
<211> LENGTH: 360
<212> TYPE: DNA
<213> ORGANISM: Homo sapiens
<220> FEATURE:
<221> NAME/KEY: source
<222> LOCATION: 1..360

<223> OTHER INFORMATION: /mol_type="DNA"
      /organism="Homo sapiens"

<400> SEQUENCE: 244
tcccctgaac tgcactcggt gtctaggact gttggggaag gaagtgaaga gccagcatgt      60
agtctcctct ggactcttac aggatctgtc cacctctggg ctctttatgt aggggaaggt     120
gtgagctcct gggagtactc ctgatagagg actgtttccc tgaaaacctc agcagtgttt     180
gaggccctag caggggggaac ccagaccccg cctgccaaag cccctaatcc ctcagggcta    240
ttatcagcag cctaagcgcc ttagggtggc cagagtccag cccagcaagc agcaaagtca    300
gcagcctcct cgccctatcc tctccatgcc ccggggcact ccagtcccag ctggctgatc    360

<210> SEQ ID NO 245
<211> LENGTH: 288
<212> TYPE: DNA
<213> ORGANISM: Artificial Sequence
<220> FEATURE:
<221> NAME/KEY: source
<222> LOCATION: 1..288
<223> OTHER INFORMATION: /mol_type="DNA"
      /note="synthesized VvWw.1.sequence"
      /organism="Artificial Sequence"
<220> FEATURE:
<221> NAME/KEY: misc_feature
<222> LOCATION: 222..228
<223> OTHER INFORMATION: /note="n is a, c, g, or t"

<400> SEQUENCE: 245 cccttgact gcggtgtgta aagcgcccca gcctgtgcct gcacagtgcc tgtgtggtgt      60
gaacccatga ccaggcctct ggagggaagg aaggttaggc ttagtggaca ccagctttcc    120
taaggtgggt cttagaccaa ctcattaaaa tggcaggatg gcttttgtg ctgtatttct     180 tgggattttc aagatgcccc acacagcaga agggatgtgc annnnnnnct ctgccctgag    240
ttgtttgata aaaatcagtg acctcgttct ccacttagaa ctcccctg                 288

<210> SEQ ID NO 246
<211> LENGTH: 289
<212> TYPE: DNA
<213> ORGANISM: Homo sapiens
<220> FEATURE:
<221> NAME/KEY: source
<222> LOCATION: 1..289
<223> OTHER INFORMATION: /mol_type="DNA"
      /organism="Homo sapiens"

<400> SEQUENCE: 246
ttcagttagc tgctgtgtgt aaagcgcccc agcctgtgcc tgcacagtgc ctgtgtggtg     60
tgaacccatg accaggcctc tggagggaag gaaggttagg cttagtggac accagctttc    120
ctaaggtggg tcttagacca actcattaaa atggcaggat gggcttttgt gctgtatttc    180
ttgggatttt caagatgccc cacacagcag aagggatgtg catttttttc tctgccctga    240
gttgtttgat aaaaatcagt gacctcgttc tccacttaga actcccctg                289

<210> SEQ ID NO 247
<211> LENGTH: 3387
<212> TYPE: DNA
<213> ORGANISM: Artificial Sequence
<220> FEATURE:
<221> NAME/KEY: source
<222> LOCATION: 1..3387
<223> OTHER INFORMATION: /mol_type="DNA"
      /note="synthesized hoht33"
      /organism="Artificial Sequence"

```
<400> SEQUENCE: 247
aattcggtcg ggactggcag agtgacgctc aggtcagcct gacagcaggg tgattgaagg      60
ggccagatac cccagcaggg cctgaggcca gaacacagca taggctggct ctgatgggtg     120
gaggaggtgg ccaggcatca tctggagctt ggagttgaga acatctgtga ctcctccttc     180
aggagggtgc tctaggagtt gagagcatcc taggtaggac catacatcta cccccatcct     240
agttccctcc agcctctctt ttcagctcca ggtctacctt aagggaccta ggacacctgg     300
gctggggcat aacaggactt ggttttatgt aaaggagctg ggaagagact gagataacag     360
agggctgcaa ggagagagac agagagagaa gaacctgcca gaagaagctc ctcagcaatc     420
cactaagccc tgatctttgc ctcactgcct gtcccttccc atccgctctt ctgctctctc     480
aatctctgcc ttcaagaaat ttggtgcata ttggaatagg gaggaataga agcaccctgg     540
gtggagctct gggcttggct gtgcacgagc tttcagtggg tggtttgctg gtctccaaag     600
atgaccctcc attagtcatg cttctcggtg tttgtcctca ggtagtctca tcccatcttg     660
agtctgggct tgccctgtga ctcactttaa ccacaagaat gtggcagaaa ggatgttgtg     720
ccagttctag aactaagcct tcagaaagcc tagcaccttc tgcttttagg agcactgagc     780
ccccatgtta gaagtccact tttatactct gctctggaga ctagcagaat tagaaatgca     840
ctgctgaatg ctgctcgaga gactaatgga gaggccatgt gaataaggag gcctgaaact     900
acatggagat agagggccag ccaccccagc accacggctc agctgtgcct cccagccatc     960
tctgccagtc ctccagggct atgagtgaac catcttggat gttctagctc ggtggagccc    1020
ccaggtgatt gcagcctcag ccaccatctg actgtagctg catgagaggc ccccagtggg    1080
accagcagga ctgccaagct gagccctgcc cacccacaga actgtgagaa ataaaaaaat    1140
ggttgtttcc ttaagccatt aagttttgga atgatttgtt actcacaatt gataactgat    1200
acagtctgtc tttagggaaa acaagggata actctgggct ccaggtgtct tctataggat    1260
gaatgggact tggttgctga caagctgaca agtttgagca tgaaactctt ttttttttt     1320
ggagaaggaa ttttgctctt gttatccagg ctggaataca gtggtgcgat ctcggcccaa    1380
ggcaacctct gcctcctggg ttcaagcaat tctcctgcct cagcctcctg agtagctggg    1440
attacaggca cccaccacta cacctggctc tttttttttt ttgtattttt agtagagaca    1500
ggttttcatt atgttggcct ggtcaggttt tgaactcctg acctcaggtg atccacctgc    1560
cttggcctcc taaaatgctg ggattacagg tgtgagccac cgtgcctggc ctgagcatga    1620
aactttttatg ctcaaacatt aaagtgtaaa cactcaccag ctcagctgaa taagaacttc    1680
tgggggcaag gcccaggaat ctacagttta gtaagtgccc ccaccactgg accctgggaa    1740
agtggactgc attttgaaaa actctagatc agttgatacc caggagtcct cataacacta    1800
agttgtaata cctcagtgtg aattagtctg atgcagctct tcttagaggt cattgacaga    1860
gggcaagaca tttccaaaag gaaggaatag ccaatatgga atgacaggtg gattggatga    1920
ccctctatta tttagtttca acctgcccct tctgccttcc ctcccacaaa ttcccttca     1980
gatcctccgt cctaatcctc ttcgatagtt cattgttctt ctgcagacag agcagcgaag    2040
tgttatctgt tgtacccact atgactagtt gatggtgcat ggcttccatg gagcagtgct    2100
gtgatccatt agtcatggag cagtgctgtg atccattgtc atgtctgcca tgaacactgg    2160
aagggggcagt ggtaatgaca gcctcttaca tttgccaact ctgcccaaca ttcttcccag    2220
tgttgggaaa gcctttgctt attccattcc ttcttggaaa gctttgttcc tccatttcac    2280
```

```
attttttaatt tttctcattt ttatggtgca ccatggatac cacctgtcca tatagctggc    2340
ttctgatttt tccagatgaa agtaatcctt cctctcctaa cctcccatga cacctaacct    2400
ggcactcatt tacggtgttc agctccttct cctgtacgtt ctcattgttc tcctctcatc    2460
ttctccccag gaatggattc cccgccaagg gaggtaccag gtcagtttct tctttgtgca    2520
acagggtgtc cctgatgagc acaaacctgg aacaagtgtt tgtagggctg gtgggcatct    2580
ggttcctctg ggtgttgtgt agcctgagcc gggggggcaaa tgggtgtttg tttttctgaa    2640
gaaggcaggc gttctgtggc agatgtgggt ggagggggtt ggggagtagt atcatggaga    2700
ggctgggatc ctatctatct ccttcccctg cttgaagggc aacttgggag aagctcaaga    2760
gggaggagtt gactgcagaa gctgggatac ctgcataact ctcaggttca agcatcactg    2820
ctttagggcc ctgggggcct atgtgtgagt caagaaaggg agatagagag agaagagaga    2880
gagaggagag agagagagag agagagaaga cagaggagag agagagagaa gaaagaggag    2940
agagagagaa gagagagcag agagagagag catgctgtca gtgaggtggc cctaagccct    3000
cttggaaata acttggaggc actgtggggt ggctctgagg tgctgaggta tacctgtagt    3060
ggggctagga ccttttccaac ctgggtctga aggttgaggc aaccttgggt gtacctgctg    3120
gtgagctgag agccctgggg acctttggca gacattccca cccctgcagc ctggagggtt    3180
tgcatgcagt gaggctgtcc tgctcatcac tacgtcctct gggacagcac attgcctgtg    3240
ctgaacaggc attcagttgc gatttgtgga atcagtgttg gtgaggaggg caagtggcaa    3300
cagaaatggg ggtgtgctcc ccccagttcc tcagctacaa tctccatgac cttctacact    3360
gccctgggcc cagtcccgac cgaattg                                        3387
```

<210> SEQ ID NO 248
<211> LENGTH: 1790
<212> TYPE: DNA
<213> ORGANISM: Artificial Sequence
<220> FEATURE:
<221> NAME/KEY: source
<222> LOCATION: 1..1790
<223> OTHER INFORMATION: /mol_type="DNA"
      /note="synthesized hoht22"
      /organism="Artificial Sequence"

<400> SEQUENCE: 248

```
caattcggtc gggactgggg agctgtgaga aagagaagag aaggtcagat caggaacatt      60
acacagaagt cggcaaaact ggaacgagga gggaaagaaa tgagcgagtc tgacactcag     120
tccatcctag ttcctatcac acagggaggg acattgccat gcacatcccc acagagatgc     180
accgtgtaag gggtcgaggc agatcctgtc cactattgcc agctctgagg tgatcaaatt     240
gtgtctgccc agggtaaccc ggttgaccta aaccaaccca ctcccttgca catcttaggt     300
gttcctgagt cagcaaggct gaggaagcca ctccagccaa aatcccttgt gcgatcttca     360
agccccaatc acaggcaatg acaaggccat gtctggctgg cctcatgggg actgccctcc     420
cctcaccaga cctagaacac aggcaatgct cagcagcgtt ctgagaagag ctgaggtcaa     480
gaactccaac cccacgcaac ccagacctga tacaaacaga cacccatttg cactcctaac     540
ccttgagcct ctatttccag acctcctcac tgggtctcag ctgagaaccc acttttagcc     600
aagcatcttt agttcagagt tcctcgcagt gaggggatcc ctcccctgcc ttgctgtctg     660
tgctgcatcc attatacccct cacaccgtgc tactcagcag gggagaaatg gagccctggg     720
gagccggcac ttttctcttc tgcctcttcc ttgccttgcc tcaggaaggg gaaaaactct     780
gggttgtttt agtttgatcc cctgtcctaa gtgaccacag gaacactagg cagtgagtac     840
```

-continued

```
atatggattc ttagcagaga gctgacaagt cttcagaaac atagaaaaca tagaagcttt     900
gagtgaggag atcagaatgt aattaggagt ttctttgga gcaaacccca ccccaagaga      960
gtgagcccaa gttcttgaag gcccacctga gcagatgaca ccagcgtctt cactatggcc    1020
acagttgtgg gtgagccagc cattgtgggg gcagctccac aggtaggact cgtgtcctga    1080
gcagcgcaca tcatccagga caatgggtcc tgagccctgg ccaaactggg catttcctgg    1140
ggctgacatg gcccagccac agcccggctg cctgcagacc acattggcat cattggtgtc    1200
ccagtagtca tcacacacgg tgccccagga gcctcggtat aggacctcca ctcggcctcg    1260
acacctgtcg cctccattca ccagcctcag ggccaaactg gattcagatc ctacagggga    1320
acacaagaac ctttcatcca tccctatcat gaggtcaaga atctaaggta agttccacac    1380
tcagggtact tcctaatgaa ctaagtcacc taggcaggca gtcacctttg catatgacta    1440
cagactaggc ttcatcaccg tgaaagtagc actgataacc tactctgccc aggtctatgg    1500
gtgctcaact tttggggaag cacctgtgac cccagtggat gtgatgggaa tggatgcccc    1560
actccccagt tgggtacaca gaggatggag ctgctcagct ccagatggca ggcccagacc    1620
cctcccttat tcaggagcat ggtcctatct gggatctgac tggcagagta ccagagatgg    1680
cagggatgag gtccccatag gattagggag accccagggg cttgttctga gcccatagat    1740
aaggatcttt tctgaccact tggaacagga tcccagtccc gaccgaattg                1790
```

<210> SEQ ID NO 249
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="synthesized DhDi primer forward"
      /organism="Artificial Sequence"

<400> SEQUENCE: 249
caattcgggc acgggact                                                     18

<210> SEQ ID NO 250
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
      /note="synthesized DhDi primer reverse"
      /organism="Artificial Sequence"

<400> SEQUENCE: 250
ccccttgact tcggtgtgta aact                                              24

<210> SEQ ID NO 251
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="synthesized cd, primer forward"
      /organism="Artificial Sequence"

<400> SEQUENCE: 251

```
cagcgagaac gccacggagg gagatcct                                         28

<210> SEQ ID NO 252
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="synthesized cd; primer reverse"
      /organism="Artificial Sequence"

<400> SEQUENCE: 252
cggacgggcg tggaaaactc agccattc                                        28

<210> SEQ ID NO 253
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="synthesized DfDg primer forward"
      /organism="Artificial Sequence"

<400> SEQUENCE: 253
cgggactggc cgggctat                                                   18

<210> SEQ ID NO 254
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="DNA"
      /note="synthesized DfDg primer reverse"
      /organism="Artificial Sequence"

<400> SEQUENCE: 254
agcccgaatt gccccttga                                                  19

<210> SEQ ID NO 255
<211> LENGTH: 3725
<212> TYPE: DNA
<213> ORGANISM: Artificial Sequence
<220> FEATURE:
<221> NAME/KEY: source
<222> LOCATION: 1..3725
<223> OTHER INFORMATION: /mol_type="DNA"
      /note="synthesized ttgb33.35"
      /organism="Artificial Sequence"
<220> FEATURE:
<221> NAME/KEY: misc_feature
<222> LOCATION: 3580..3597
<223> OTHER INFORMATION: /note="n is a, c, g, or t"

<400> SEQUENCE: 255
attttgtgca gcccgccaat ttctgttcaa acagaccaat caggaccttc tacgtgcact     60
tcctggggcg tgtctacgag gtctatataa gcaacagcgg tgacgaatgg tagagttttt    120
cttcgcccgt ccgcggcgag agcgcgagcg aagcgagcga tcgagcgtcc cgtgggcggg    180
tgccgtaggt gagtttacac accgaagtca aggggcaatt cgggcacggg actggccggg    240
ctatgggcaa ggctcttaaa aaattccccc gctctgctct ccggcaggac acaaagtcat    300
gccgtggaga ccgccggtcc ataacgtgcc aggtagagag aatcaatggt ttgcagcgtt    360
```

```
ctttcacggt catgctgctt tctgcgggtg tggtgaccct gttgggcatc ttaacggcat      420
tgctcctcgc tttcctaacg ccggtccacc gagaccacct ccagggctag accagcttaa      480
tcccgagggc ccggcaggtc ccggagggcc ccccgccatc ttgccagctc tgccggcccc      540
ggcagaccct gaaccggcac cacggcgtgg tggtggggca gatggaggcg ccgccgctgg      600
ggccgccgcc gacgcagacc ataccgggta cgaagaagga gacctagaag atcttttcgc      660
cgccgcggcc gaggacgata tgtgagtagg cggaggcgcc gccgctacta caggcgcaga      720
ctgagacggg gcagacgcag agggcgacga agagacacag acagactct agtagtgagg       780
cagtggcaac ctgacgttgt taaaaagtgt aaaataacag gatggatgcc tcttataatc      840
tgtggctctg gaagcacaca gatgaacttt ataactcaca tggacgatac tccccctatg      900
ggatacacct acgggggcaa ctttgtaaat gtaactttca gtctagaggc catctatgaa      960
caattcctgt accacagaaa caggtggtcc aggtctaacc atgacttaga cctggccaga     1020
taccaaggaa ccactctaaa actttacaga caccaaaccg tggactatat agttagctac     1080
aacagaacag gcccctttac tataagtgaa atgacttaca tgagcacaca cccggctctc     1140
atgctactac aaaaacatag aatagttgta cccagcttca gaaccaagcc aaaaggcaaa     1200
agagccataa aaattagaat aagggcccca aaactaatgc tcaccaagtg gtactttaca     1260
aaagacattt gctccatggg cctctttcaa ctaatggcaa cagctgcaga acttacaaac     1320
ccatggctca gagacaccac aaaaagccca gtaattggct tcagagtctt aaaaaacagc     1380
ttatacacat gcctttccaa cttaaaagac caagcaatac aaggtgaaag aaagactgta     1440
caaaatagat tacacccaga aaacctacat ggcacaggac ctaatgctaa aggctgggaa     1500
tacacataca caaaactaat ggcatctaca tactactcag ccaacagaaa cagcacctac     1560
aactggcaaa actatcaaac taactatgca aacacatata caaaatttaa agaaaaaaga     1620
acagcaaact taaacttaat taaagcagaa tacctatatc attaccctaa caatgtcaca     1680
caatctgact ttatattaga ctacacacta acacccgact ggggcatata cagcccctac     1740
tacctaacac ccaccagaat tagcctagac tgggacacac catggacata tgtaagatac     1800
aacccactat cagacaaagg cataggtaac agaatatatg cacagtggtg ctcagaaaaa     1860
tctagtaaat tagacaccac aaaagagcaag tgcatactaa gagacttccc actgtgggcc     1920
atggcctatg gctactgtga ctgggtggtg aagtgcacag gagtgtccag tgcttggaca     1980
gacatgagaa tagccattat atgtccctac acagaaccag cacttatagg gtcaacagaa     2040
gacgtaggct tcattccagt aagtgacacc ttttgcaacg gagacatgcc gtttcttgca     2100
ccatacatac ctattacatg gtggattaag tggtacccca tgattacaca ccaaaaggaa     2160
gttcttgagg caatagttaa ctgtggaccg tttgtacccc gagaccaaac ttccccagct     2220
tgggaataac catgggttac aaaatggatt ggaaatgggg cggctctccc ctgccttcac     2280
aggcaatcga cgacccctgc cagaagtcca cccacgaact tcccgacccc gatagacacc     2340
ctcgcatgtt acaagtctct gacccgacaa agctcggacc gaagacagtt tttcacaaat     2400
gggactggag acgtgggatg cttagcaaaa gaagtattaa agagtccaa gaagactcaa      2460
cagacgatga atatgttgca ggacccttac caagaaaaag aaacaagttc gatactcgag     2520
tccaaggccc tccaacccca gaaaagaaa gttacacttt actccaagcc ctccaagagt      2580
cggggcaaga gagcagctca gaggaccaag aacaagcacc ccaagaaaaa gaggaccaga     2640
aggaagcgct catggagcag ctccagctcc agaaacacca ccagcgagtc ctcaagcgag     2700
```

```
gcctcaaact cctcctcgga gacgtgctcc gactccggag aggagtccac tgggaccccc      2760
tcctgtccta attcaaggtc ccagtatccc agacctgctt ttccctaaca cacaaaaaaa      2820
aaaacgattt tccaactacg actgggtgtg cgagtacgag ctggccaaat ggatggatcg      2880
gcccttgcgg cactacccat cagacccccc tcactacccc tggctaccaa aaaagcctcc      2940 taccctcct acatgtagag taagtttcaa attaaagctc aatgactaaa attcaaggcc       3000
gtgggtgttt cacttcatcg gtgtctacct ctaaaagtca ctaagcactc cgagcgtaag      3060
cgaggagtgc gaccccctg cccggtagca acttcctcgg ggtccggcgc tacgccttcg       3120
gctgcgccgg cgcctcgga cccccctcg acccgaatcg ctcgcgcgat tcggacctgc        3180
ggcctcgggg gggtcggggg ctttactaaa cagactctga ggtgccgttg gacactgagg      3240
gggtgaacag caacgaaagt gagtggggcc aaacttcgcc ataaggcctt taactttggg      3300
tcgcttgtca gcagcttccg ggtccgcctg gaggccgcca ttttacattc ggccgccatt      3360
ttaggccctc gcgggcctcc atagtcgcac atcagtgacg tcacggcagc catcttggct      3420
gtgacgtcaa cgtcacgtgg ggaggacggc gtgtaacccg gaagtcatcc tcatcacgcg      3480
acctgacgtc acggccgcca ttttgtgctg tccgccatct tgtgacttcc ttccgctttt      3540
tgtaaaaaaa agaggaagtg tgacgtagcg gcgggggggn nnnnnnnnn nnnnnnncgc       3600 caccagggg cgctacgcgc ccccccccgc gcatgtgcgg gtccccccc tcggggggg        3660 ctccgccccc ccggccccc cccgggctaa atacaccgcg catgcgcggc cacgccccg        3720 ccgcc                                                                  3725

<210> SEQ ID NO 256
<211> LENGTH: 719
<212> TYPE: DNA
<213> ORGANISM: Artificial Sequence
<220> FEATURE:
<221> NAME/KEY: source
<222> LOCATION: 1..719
<223> OTHER INFORMATION: /mol_type="DNA"
      /note="synthesized zpr4.20"
      /organism="Artificial Sequence"

<400> SEQUENCE: 256
caattcgggc acgggactgg ccgggctatg gcaaggctc ttaaaaaatt ccccgctct         60 gctctccggc aggacacaaa gtcatgccgt ggagaccgcc ggtccataac gtgccaggta     120
gagagaatca atggtttgca gcgttctttc acggtcatgc tgctttctgc gggtgtggtg     180
accctgttgg gcatcttaac ggcattgctc ctcgctttcc taacgccggt ccaccgagac     240
cacctccagg gctagaccag cttaatcccg agggcccggc aggtcccgga gggcccccg      300 ccatcttgcc agctctgccg gccccggcag accctgaacc ggcaccacgg cgtggtggtg     360
gggcagatgg aggcgccgcc gctggggccg ccgccgacgc agaccatacc gggtacgaag     420
aaggagacct cgggggggc tccgcccccc cggcccccc ccgggctaaa tacaccgcgc        480
atgcgcggcc acgccccgc cgccattttg tgcagcccgc caatttctgt tcaaacagac      540
caatcaggac cttctacgtg cacttcctgg ggcgtgtcta cgaggtctat ataagcaaca     600
gcggtgacga atggtagagt ttttcttcgc ccgtccgcgg cgagagcgcg agcgaagcga     660
gcgatcgagc gtcccgtggg cgggtgccgt aggtgagttt acacaccgaa gtcaagggg     719

<210> SEQ ID NO 257
<211> LENGTH: 3758
<212> TYPE: DNA
<213> ORGANISM: Artificial Sequence
```

<220> FEATURE:
<221> NAME/KEY: source
<222> LOCATION: 1..3758
<223> OTHER INFORMATION: /mol_type="DNA"
    /note="synthesized tth25"
    /organism="Artificial Sequence"

<400> SEQUENCE: 257

| | | | | | |
|---|---|---|---|---|---|
| aagtacgtca | ctaaccacgt | gactcccgca | ggccaaccag | agtctacgtc | gtgcacttcc | 60 |
| tgggcatggt | ctacatcata | atataagaac | gtgcacttcc | gaatggctga | gttttccacg | 120 |
| cccgtccgca | gcgagaacgc | cacggaggga | gatcctcgcg | tcccgagggc | gggtgccgga | 180 |
| ggtgagttta | cacaccgcag | tcaaggggca | attcgggctc | gggactggcc | gggcccccggg | 240 |
| caaggctctt | aaaaaatgcg | ttttcgcagg | gttgcccaga | aaggaaagt | gcttttgcaa | 300 |
| actgtgccag | ctgcaaagaa | ggctaggcgg | cttctaggta | tgtggcagcc | ccccacgcac | 360 |
| aatgtcccgg | gcatcgagag | aaactggtac | gagagctgtt | ttagatccca | cgctgctgtt | 420 |
| tgtggctgtg | gcgattttgt | tggccatctt | aatcatctgg | caactactct | gggtcgtcct | 480 |
| ccgcgtcctg | gcccccagg | cggaccccgc | acgccgcaaa | taagaaacct | gccagcgctc | 540 |
| ccggcgcccc | agggcgagcc | cggtgacaga | gcgccatggc | atggggcttc | tggggccgac | 600 |
| gccgccggtg | gagacgatgg | agagcgcggc | gcagacggtg | gagacccccgc | agacgtagga | 660 |
| gacgacgccc | tactcgccgc | tttcgagctc | gtcgaagagt | aaggaggcgc | gggggggaggt | 720 |
| ggcgcagacg | ctacagaaaa | tggcgacggg | gcagacgcag | acggactcat | agaaaaaaga | 780 |
| tagtcataaa | acagtggcaa | ccaaacttta | taagacgctg | ctacgtcata | gggtacttac | 840 |
| cacttatatt | ctgcggcgaa | aatacaaccg | cccagaactt | tgccactcac | tcggacgaca | 900 |
| tgataagcaa | aggaccgtac | ggggggggca | tgactaccac | caaattcact | ctgagaatac | 960 |
| tgtacgacga | gtttaccagg | tttatgaact | tttggactgt | cagtaacgaa | gacctagacc | 1020 |
| tgtgtagata | cgtgggctgc | aaactaatat | tttttaaaca | ccccacggtg | gactttatag | 1080 |
| tacagataaa | cactcagcct | cctttcttag | acacgcacct | caccgcggcc | agcatacacc | 1140 |
| cgggcatcat | gatgctcagc | aagagacaca | tactaatacc | ctctctaaag | acccggccca | 1200 |
| gcagaaaaca | cagggtggtc | gtcagggtgg | gcgcccccaag | acttttttcag | gacaagtggt | 1260 |
| acccccagtc | agacctgtgt | gacacagttc | tgctttccat | atttgcaacc | gcctgcgact | 1320 |
| tgcaatatcc | gttcggctca | ccactaactg | acaacccttg | cgtcaacttc | cagatcctgg | 1380 |
| ggccccagta | caaaaaacac | cttagtatta | gctccactat | ggatcaaact | aacgaaaacc | 1440 |
| attataaaga | aaacttattt | aacaaaactg | aactatacaa | cacctttcaa | accatagctc | 1500 |
| agcttaaaga | gacaggacac | atttcaggca | ttagtcctac | ttggaatgaa | gtccagaatt | 1560 |
| caacaacact | tactaaagga | ggtgacaatg | ccactcagag | tagagacact | tggtataaag | 1620 |
| gaaatacata | caacgagaag | atatgcgagt | tagcacaaat | aaccagaaac | agatttaaaa | 1680 |
| atgcaaccaa | aggagcacta | ccaaactacc | ccacaataat | gtccacagac | ctatatgaat | 1740 |
| accactcagg | catacactcc | agcatatatc | tatcagctgg | caggagctac | tttgaaacca | 1800 |
| ccggggccta | ctctgacatt | atatacaacc | ctttcacaga | caaaggcaca | ggcaacataa | 1860 |
| tctggataga | ctacctcaca | aaagaagaca | ccattttgt | gaaaaacaaa | agcaaatgcg | 1920 |
| agataatgga | catgcccctg | tgggcggcct | gcacaggata | cacagagttt | tgtgcaaagt | 1980 |
| atacaggcga | ctctgccatt | atctacaatg | caagaatact | cataagatgc | ccatacactg | 2040 |
| agcccatgtt | aatagaccac | tcagacccaa | acaaaagctt | cgttccctac | tcatttaact | 2100 |

```
ttggcaacgg aaagatgccc ggaggcagct ccaacgtgcc cataagaatg agagccaagt    2160
ggtacgtgaa catattccac caaaaagaag tattagagag catagtacag tccggaccgt    2220
ttgggtacaa gggcgacata agatcagctg tactagccat gaaatacaga tttcactgga    2280
agtggggcgg aaaccctata tccaaacagg tcgtcaggaa tccctgctcc aactccagct    2340
cctccgcggc ccatagagga cctcgcagcg tacaagcggt tgacccgaaa tacaataccc    2400
cagaggtcac gtggcactcg tgggacatta gacgaggact cttttggcaaa gcaggtatta   2460 aaagaatgca acaggaatca gatgctcttt acattcctcc aggaccaatc aagagacctc    2520
gcagggacac caacgcccaa gacccagaag agcaaaacga aagctcaggt ttcagagtcc    2580
agcagcgact cccgtgggtc cactccagcc aagagacgca aagctcccaa gaagagacgg    2640
aggcgcaggg gtcggtacaa gaccaactac tcctccagct ccgagagcag cgagttctcc    2700
gactccagct ccagcaactc gcaacccaag tcctcaaagt ccaagcaggg cacagcctac    2760 acccccctatt atcttcccaa gcataaacaa agcctttatg tttgagcccc agggtcctaa   2820
acccatacag gggtacaacg actggctaga agagtacact gcttgcaaat tctgggacag    2880
accccccaga aagctacaca cagacatacc cttctacccc tgggcaccaa aaccccaaca    2940
gcaagtcagg gtgtcccttta aactcaactt tcaataaaaa ttctaggccg tgggagtttc    3000
acttgtcggt gtctgcttct taaggtcgcc aagcactccg agcgccagcg aggagtgcga    3060 cccccccctcc ggtagcaacg ccttcggagc cgcgcgctac gccttcggct gcgcgcggca    3120
cctcagaccc cccctccacc cgaaacgctt gcgcgtttcg gaccttcggc gtcggggggg    3180
tcgggagctt tattaaacag actccgagtt gccattggac actggagctg tgaatcagta    3240
acgaaagtga gtggggccag acttcgccat agggccttta tcttctcgcc attggatagt    3300
gtccggggtc gccgtaggct tcggcctcgt ttttaggcct tccggactac aaaaatggcg    3360
gttttagtga cgtcacggcc gccatttttaa gtaaggcgga agcagctcca ctttctcaca    3420
aaatggcggc ggagcacttc cggcttgccc aaaatggcgg gcaagctctt ccgggtaaag    3480
ggtcagcagc tacgtcacaa gtcacctgac tggggagggg tcacaacccg gaagccctcc    3540
tcagtcacgt ggctgttcac gtggttgcta cgtcatcggc gccatcttgt gtcgcaaaat    3600
ggcggacaac ttccgctttt ttaaaaaaag gcgcgaaaaa acgcggcggc ggcgcgcgc     3660 gctgtgcgcg cgcgccgggg gggcgccagc gcccccccc ccgcgcatgc gcgggtcccc    3720 cccccgcgg ggggctccgc ccccccggccc ccccccg                              3758

<210> SEQ ID NO 258
<211> LENGTH: 621
<212> TYPE: DNA
<213> ORGANISM: Artificial Sequence
<220> FEATURE:
<221> NAME/KEY: source
<222> LOCATION: 1..621
<223> OTHER INFORMATION: /mol_type="DNA"
      /note="synthesized zpr9.6"
      /organism="Artificial Sequence"

<400> SEQUENCE: 258
ccgcagcgag aacgccacgg agggagatcc tcgcgtcccg agggcgggtg ccggaggtga     60
gtttacacac cgcagtcaag gggcaattcg ggctcgggac tggccgggcc ccgggcaagg   120
ctcttaaaaa atgcgttttc gcagggttgc ccagaaaagg aaagtgcttt tgcaaactgt   180
gccagctgca aagaaggcta gcggcttct aggtatgtgg cagccccca cgcacaatgt    240 cccgggcatc gagagaaact ggtacgagag ctgttttaga tcccacgctg ctgtttgtgg   300
```

```
ctgtggcgat tttgttggcc atcttaatca tctggcaact actctgggtc gtcctccgcg    360
tcctgggccc ccaggcggac cccgcacgcc gcaaataaga aacctgccag cgctcccggc    420
gccccagggc gagcccggtg acagagcgcc atggcatggg gcttctgggg ccgacgccgc    480
cggtggagac gatggagagc gcggcgcaga cggtggagac cccgcaggcc aaccagagtc    540
tacgtcgtgc acttcctggg catggtctac atcataatat aagaacgtgc acttccgaat    600
ggctgagttt tccacgcccg t                                              621
```

<210> SEQ ID NO 259
<211> LENGTH: 3758
<212> TYPE: DNA
<213> ORGANISM: Artificial Sequence
<220> FEATURE:
<221> NAME/KEY: source
<222> LOCATION: 1..3758
<223> OTHER INFORMATION: /mol_type="DNA"
    /note="synthesized ttrh215"
    /organism="Artificial Sequence"

<400> SEQUENCE: 259

```
aaagtacgtc actaaccacg tgactcccac aggccaacca cagtctacgt cgtgcatttc     60
ctgggcatgg tctacatcat aatataagaa ggcgcacttc cgaatggctg agttttccac    120
gcccgtccgc agcgagaacg ccacggaggg agatcctcgc gtcccgaggg cgggtgccgg    180
aggtgagttt acacaccgca gtcaaggggc aattcgggct cgggactggc cgggccctgg    240
gcaaggctct taaaaaatgc gctttcgcag ggttgcggag aaaaggaaag tgcttctgca    300
aactctgcga gctgcaaagc aggctaggcg gcttctaggt atgtggcagc ccccgcgca    360 caatgtcccc ggcatcgaga gaaactggta cgagagctgc ttcaggtctc acgctgctgt    420 tgtggctgt ggcgactttg ttggccatat taatcatttg gcaactactc tgggtcgtcc    480
tccgcgtcct gggcccccag gcggaccccg cacgccgcaa ataagaaacc tgccagcgct    540
cccggcgccc cagggcgagc ccggtgacag agcgccatgg cgtggggttt ctggggccga    600
cgccgccggt ggagacggtg gagagcgcgg cgcagacggt ggagaccccg gagacgtagg    660
agacgacgcc ctgctcgccg cttcgagct cgtcgaagag taaggagacg cggggggagg    720
tggcgcagac gctacagaaa atggcgacgg ggcagacgca gacggactca cagaaaaaag    780
ataattataa aacagtggca accaaacttt attagacgct gctacataat aggatgccta    840
cctctcgttt tctgtggcga aaatacaacc gcccagaact atgccactca ctcagacgat    900
atgataagca aaggaccgta cggggggggc atgactacca cgaaattcac tctgagaata    960
ctgtacgacg agtttaccag gtttatgaac ttttggactg tcagtaacga agacctagac   1020
ctgtgtagat acgtgggctg caaactgata ttttttaaac accccacggt ggactttatg   1080
gtacagataa acactcagcc tcctttctta gacacaagcc tcaccgcggc cagcatacac   1140
ccgggcatca tgatgctcag caagagacga atattaatac cctctctaaa gacccggccg   1200
agcagaaaac acagggtggt cgtcagggtg gcgcccccaa gactttttca ggacaagtgg   1260
tacccccagt cagacctatg tgacacagtt ctgctttcca tatttgcaac cgcccgcgac   1320
ttgcaatatc cgttcggctc accactaact gacaacccctt gcgtcaactt ccagatcctg   1380
gggccccagt acaaaaaaca ccttagtatt agctccacta tggatgatac taacaaacag   1440
cactataaca gcaacttatt taataaaact gcactataca acacctttca aaccatagcc   1500
cggcttaaag agacaggaca aactgcaaac attagtccaa gttggagtga agtacaaaac   1560
```

| | |
|---|---|
| acaaaactac tagatcacac aggtgctaat gcaactgcca gcagagacac ttggtacaag | 1620 |
| ggaaacacat acaatgacta catacaacag ttagcagaga aaacaagaga aaggtttaaa | 1680 |
| aaagcaacaa tgtcagcact accaaactac cccacaataa tgtccacaga cttatacgaa | 1740 |
| taccactcag gcatatactc cagcatattt ctatcagctg gcaggagcta ctttgaaacc | 1800 |
| actggggcct actctgacat tatatacaac cctttgacag acaaaggcac aggcaacata | 1860 |
| atctggatag actaccttac aaaagacgac acaatctttg taaaaacaa aagcaaatgt | 1920 |
| gagataatgg acatgcccct gtgggcggcc ggcacaggat acacagagtt ttgtgcaaag | 1980 |
| tacacaggag actctgccat tatttacaat gccagaatac tcataagatg cccatacact | 2040 |
| gaacccatgc taatagacca ctcagaccca acaaaggct ttgtaccgta ctcatttaac | 2100 |
| tttggcaacg gaaagatgcc gggaggcagc tccaacgtgc cataagaat gagagccaag | 2160 |
| tggtacgtaa acatattcca ccaaaaagaa gtattggaga gcatagtaca gtccggaccg | 2220 |
| ttcgggtaca ggggcgacat aaaatcagct gtactgtcca tgaaatacag atttcactgg | 2280 |
| aaatggggcg gaaaccctat atccaaacag gtcgtcagga atccctgctc caactccagc | 2340 |
| acctccgcgg cccatagagg acctcgcagc gtacaagcgg ttgacccgaa atacaatacc | 2400 |
| ccagaagtca cttggcactc gtgggacatc agacgaggac tctttggcaa agcaggtatt | 2460 |
| aaaagaatgc aacaagaatc agatgctctt tacgttcctg caggaccact caagaggcct | 2520 |
| cgcagagaca ccaacgccca agacccggaa aagcaaaacg aaagctcacg tttcggagtc | 2580 |
| cagcagcgac tcccgtgggt ccactccagc caagagacgc aaagctccga agaagagacg | 2640 |
| caggcgcagg ggtcggtaca agaccaacta ctcctccagc tccgagagca gcgagtactc | 2700 |
| cgactccagc tccaacaact cgcaccccaa gtcctcaaag ttcaagcagg acacagccta | 2760 |
| caccccctat tatcctccca agcataaaca aagcctatat gtttgaaccc cagggtccta | 2820 |
| aacccataca ggggtacaac gattggctag aggagtacac tagttgcaag ttccgggaca | 2880 |
| gaccccgag aatgctacac acagacttac cctttaccc ctgggcacca aaaccccaag | 2940 |
| accaagtcag ggtaaccttt aaactcaact ttcaataaaa attctaggcc gtgggacttt | 3000 |
| cacttgtcgg tgtctgcttc ttaaggtcgc caagcactcc gagcgtcagc gaggagtgcg | 3060 |
| accccccccc tcggtagcaa cgccttcgga gccgcgcgct acgccttcgg ctgcgcgcgg | 3120 |
| cacctcagac ccccctcca cccgaaacgc ttgcgcgttt cggaccttcg gcgtcggggg | 3180 |
| ggtcgggagc tttattaaac agactccgag ttgccattgg acactggagc tgtgaatcag | 3240 |
| taacgaaagt gagtggggcc agacttcgcc atagggcctt tatcttctcg ccattggata | 3300 |
| gtgtccgggg ttgccgtagg cttcggcctc gttttaggc cttccggact acaaaaatgg | 3360 |
| cggattttgt gacgtcacgg ccgccatttt aagtaaggcg gaagcagctc caccctctca | 3420 |
| cataatggcg gcggagcact cccggcttgc ccaaaatggc gggcaagctc ttccgggtca | 3480 |
| aaggttggca gctacgtcac aagtcacctg actggggagg agttacatcc cggaagttct | 3540 |
| cctcggtcac gtgactgtac acgtgactgc tacgtcattg acgccatctt gtgtcacaaa | 3600 |
| atggcggtgc acttccgctt ttttgaaaaa aggcgcgaaa aaacggcggc ggcggcgcgc | 3660 |
| gcgctgcgcg cgcgcgccgg gggggcgcca gcgcccccc cccgcgcat gcacgggtcc | 3720 |
| ccccccccac gggggctcc gcccccggc ccccccc | 3758 |

<210> SEQ ID NO 260
<211> LENGTH: 642
<212> TYPE: DNA
<213> ORGANISM: Artificial Sequence

```
<220> FEATURE:
<221> NAME/KEY: source
<222> LOCATION: 1..642
<223> OTHER INFORMATION: /mol_type="DNA"
      /note="synthesized zpr12.24"
      /organism="Artificial Sequence"

<400> SEQUENCE: 260
cagcgagaac gccacggagg gagatcctcg cgtcccgagg gcgggtgccg gaggtgagtt    60
tacacaccgc agtcaagggg caattcgggc tcgggactgg ccgggccccg ggcaaggctc   120
ttaaaaaatg cgctttcgca gggttgctga gaaaaggaaa gtgcttctgc aaactgtgcg   180
agctacacag aagactaggc ggcttctaag ccgcccacag gggcatgtct acatgcttcc   240
gcagcgagaa cgccacggag ggagatcctc gcgtcccgag ggcgggtgcc ggaggtgagt   300
ttacacaccg cagtcaaagg gcaattcggg ctcgggactg gccgggcccc gggcaaggct   360
cttaaaaaat gcgctttcgc ggggttgctg agaaaaggaa agtgcttctg caaactgtgc   420
gagctacaca gaagactagg cggcttctag gtatgtggca gccccccgtg cacaatgtcc   480
ccggcatctt attagtactc tggcgttgta gataatggca gagtctccag tgtactttgc   540
acagaactct gtgtatcctg tgcaggccgc ccacaggggc atgtctacat cataatataa   600
taaggcgcac ttccgaatgg ctgagttttc cacgcccgtc cg                     642

<210> SEQ ID NO 261
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized zyb2.1. peptide"
      /organism="Artificial Sequence"

<400> SEQUENCE: 261

Arg Val Pro Lys Val Ser Leu His Thr Ala Val Lys Gly Gln Phe Gly
 1               5                  10                  15

Leu Gly Thr Gly Arg Ala Met
            20

<210> SEQ ID NO 262
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized zyb9.1 peptide"
      /organism="Artificial Sequence"

<400> SEQUENCE: 262

Arg Val Pro Lys Val Ser Leu His Thr Ala Val Lys Gly Gln Phe Gly
 1               5                  10                  15

Leu Gly Thr Gly Arg Ala Met
            20

<210> SEQ ID NO 263
<211> LENGTH: 23
<212> TYPE: PRT
<213> ORGANISM: Artificial Sequence
<220> FEATURE:
<221> NAME/KEY: SOURCE
<222> LOCATION: 1..23
```

```
<223> OTHER INFORMATION: /mol_type="protein"
      /note="synthesized zyb69.1 peptide"
      /organism="Artificial Sequence"

<400> SEQUENCE: 263

Arg Val Pro Glu Val Ser Leu His Thr Ala Val Lys Gly Gln Phe Gly
1               5                   10                  15

Leu Gly Thr Gly Arg Ala Met
            20

<210> SEQ ID NO 264
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized zyb2.3. peptide"
      /organism="Artificial Sequence"

<400> SEQUENCE: 264

Gly Ala Glu Gly Glu Phe Thr His Arg Ser Gln Gly Ala Ile Arg Ala
1               5                   10                  15

Arg Asp Trp Pro Gly His Gly
            20

<210> SEQ ID NO 265
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized zyb9.3. peptide"
      /organism="Artificial Sequence"

<400> SEQUENCE: 265

Gly Ala Glu Gly Glu Phe Thr His Arg Ser Gln Gly Ala Ile Arg Ala
1               5                   10                  15

Arg Asp Trp Pro Gly Tyr Gly
            20

<210> SEQ ID NO 266
<211> LENGTH: 23
<212> TYPE: PRT
<213> ORGANISM: Artificial Sequence
<220> FEATURE:
<221> NAME/KEY: SOURCE
<222> LOCATION: 1..23
<223> OTHER INFORMATION: /mol_type="protein"
      /note="synthesized zyb5.3. peptide"
      /organism="Artificial Sequence"

<400> SEQUENCE: 266

Gly Ala Val Gly Glu Phe Thr His Arg Ser Gln Gly Ala Ile Arg Ala
1               5                   10                  15

Arg Asp Trp Pro Gly Tyr Gly
            20

<210> SEQ ID NO 267
<211> LENGTH: 23
<212> TYPE: PRT
<213> ORGANISM: Artificial Sequence
<220> FEATURE:
<221> NAME/KEY: SOURCE
```

```
<222> LOCATION: 1..23
<223> OTHER INFORMATION: /mol_type="protein"
      /note="synthesized zkb69.3 peptide"
      /organism="Artificial Sequence"

<400> SEQUENCE: 267

Gly Ala Gly Gly Glu Phe Thr His Arg Ser Gln Gly Ala Ile Arg Ala
1               5                   10                  15

Arg Asp Trp Pro Gly Tyr Gly
            20

<210> SEQ ID NO 268
<211> LENGTH: 204
<212> TYPE: PRT
<213> ORGANISM: Artificial Sequence
<220> FEATURE:
<221> NAME/KEY: SOURCE
<222> LOCATION: 1..204
<223> OTHER INFORMATION: /mol_type="protein"
      /note="synthesized torque teno virus"
      /organism="Artificial Sequence"
<220> FEATURE:
<221> NAME/KEY: SITE
<222> LOCATION: 16..16
<223> OTHER INFORMATION: Xaa can be any naturally occurring amino acid
<220> FEATURE:
<221> NAME/KEY: SITE
<222> LOCATION: 196..196
<223> OTHER INFORMATION: Xaa can be any naturally occurring amino acid

<400> SEQUENCE: 268

Cys Thr Ser Glu Trp Leu Ser Phe Pro Arg Pro Ser Ala Ala Ala Xaa
1               5                   10                  15

Pro Arg Arg Val Ile Pro Ala Ser Arg Trp Arg Val Pro Lys Val Ser
            20                  25                  30

Leu His Thr Ala Val Lys Gly Gln Phe Gly Leu Gly Thr Gly Arg Ala
        35                  40                  45

Met Gly Lys Ala Leu Lys Val Phe Ile Leu Lys Met His Phe Ser Arg
    50                  55                  60

Ile Ser Arg Ser Lys Arg Lys Val Leu Leu Pro Ala Leu Pro Ala Pro
65                  70                  75                  80

Pro Pro Pro Arg Gln Leu Leu Met Trp Gln Pro Ile Gln Asn Gly
                85                  90                  95

Thr Gln Leu Asp Arg His Trp Phe Glu Ser Val Trp Arg Ser His Ala
            100                 105                 110

Ala Tyr Cys Gly Cys Gly Asp Cys Val Gly His Leu Gln His Leu Ala
        115                 120                 125

Ala Asn Leu Gly Arg Pro Pro His Pro Gln Pro Pro Arg Glu Gln His
    130                 135                 140

Pro Pro Gln Ile Arg Gly Leu Pro Ala Leu Pro Ala Pro Pro Ser Asn
145                 150                 155                 160

Arg Asn Ser Trp Pro Gly Thr Gly Gly Asp Ala Ala Gly Glu Gln Ala
                165                 170                 175

Gly Gly Ser Arg Gly Ala Gly Asp Gly Gly Asp Gly Glu Leu Ala Asp
            180                 185                 190

Asp Asp Leu Xaa Asp Ala Ala Ala Leu Val Glu Glu
        195                 200

<210> SEQ ID NO 269
<211> LENGTH: 138
<212> TYPE: PRT
<213> ORGANISM: Artificial Sequence
```

```
<220> FEATURE:
<221> NAME/KEY: SOURCE
<222> LOCATION: 1..138
<223> OTHER INFORMATION: /mol_type="protein"
      /note="synthesized torque teno virus"
      /organism="Artificial Sequence"

<400> SEQUENCE: 269

Ala Val Lys Pro Arg Arg Glu Ile Ser Ala Ser Arg Gly Arg Val Pro
1               5                   10                  15

Lys Val Ser Leu His Thr Glu Val Lys Gly Gln Phe Gly Leu Gly Thr
            20                  25                  30

Gly Arg Ala Met Gly Lys Ala Leu Lys Lys Ser Met Phe Ile Gly Arg
        35                  40                  45

His Tyr Arg Lys Lys Arg Ala Leu Ser Leu Cys Ala Val Arg Thr Thr
    50                  55                  60

Lys Lys Ala Cys Lys Leu Leu Ile Val Met Trp Thr Pro Pro Arg Asn
65                  70                  75                  80

Asp Gln Gln Tyr Leu Asn Trp Gln Trp Tyr Ser Ser Val Leu Ser Ser
                85                  90                  95

His Ala Ala Met Cys Gly Cys Pro Asp Ala Ile Ala His Leu Ser His
            100                 105                 110

Leu Ala Phe Val Phe Arg Ala Pro Gln Asn Pro Pro Pro Gly Pro
        115                 120                 125

Gln Arg Asn Leu Pro Leu Arg Arg Leu Pro
    130                 135

<210> SEQ ID NO 270
<211> LENGTH: 204
<212> TYPE: PRT
<213> ORGANISM: Artificial Sequence
<220> FEATURE:
<221> NAME/KEY: SOURCE
<222> LOCATION: 1..204
<223> OTHER INFORMATION: /mol_type="protein"
      /note="synthesized torque teno virus"
      /organism="Artificial Sequence"
<220> FEATURE:
<221> NAME/KEY: SITE
<222> LOCATION: 16..16
<223> OTHER INFORMATION: Xaa can be any naturally occurring amino acid
<220> FEATURE:
<221> NAME/KEY: SITE
<222> LOCATION: 196..196
<223> OTHER INFORMATION: Xaa can be any naturally occurring amino acid

<400> SEQUENCE: 270

Cys Thr Ser Glu Trp Leu Ser Phe Pro Arg Pro Ser Ala Ala Ala Xaa
1               5                   10                  15

Pro Arg Arg Val Ile Pro Ala Ser Arg Trp Arg Val Pro Lys Val Ser
            20                  25                  30

Leu His Thr Ala Val Lys Gly Gln Phe Gly Leu Gly Thr Gly Arg Ala
        35                  40                  45

Met Gly Lys Ala Leu Lys Val Phe Ile Leu Lys Met His Phe Ser Arg
    50                  55                  60

Ile Ser Arg Ser Lys Arg Lys Val Leu Leu Pro Ala Leu Pro Ala Pro
65                  70                  75                  80

Pro Pro Pro Arg Gln Leu Leu Met Trp Gln Pro Pro Ile Gln Asn Gly
                85                  90                  95

Thr Gln Leu Asp Arg His Trp Phe Glu Ser Val Trp Arg Ser His Ala
            100                 105                 110
```

```
Ala Tyr Cys Gly Cys Gly Asp Cys Val Gly His Leu Gln His Leu Ala
        115                 120                 125

Ala Asn Leu Gly Arg Pro Pro His Pro Gln Pro Pro Arg Glu Gln His
    130                 135                 140

Pro Pro Gln Ile Arg Gly Leu Pro Ala Leu Pro Ala Pro Pro Ser Asn
145                 150                 155                 160

Arg Asn Ser Trp Pro Gly Thr Gly Gly Asp Ala Ala Gly Glu Gln Ala
                165                 170                 175

Gly Gly Ser Arg Gly Ala Gly Asp Gly Gly Asp Gly Glu Leu Ala Asp
            180                 185                 190

Asp Asp Leu Xaa Asp Ala Ala Ala Leu Val Glu Glu
        195                 200

<210> SEQ ID NO 271
<211> LENGTH: 138
<212> TYPE: PRT
<213> ORGANISM: Artificial Sequence
<220> FEATURE:
<221> NAME/KEY: SOURCE
<222> LOCATION: 1..138
<223> OTHER INFORMATION: /mol_type="protein"
      /note="synthesized torque teno virus"
      /organism="Artificial Sequence"

<400> SEQUENCE: 271

Ala Val Lys Pro Arg Arg Glu Ile Ser Ala Ser Arg Gly Arg Val Pro
1               5                   10                  15

Lys Val Ser Leu His Thr Glu Val Lys Gly Gln Phe Gly Leu Gly Thr
            20                  25                  30

Gly Arg Ala Met Gly Lys Ala Leu Lys Lys Ser Met Phe Ile Gly Arg
        35                  40                  45

His Tyr Arg Lys Lys Arg Ala Leu Ser Leu Cys Ala Val Arg Thr Thr
    50                  55                  60

Lys Lys Ala Cys Lys Leu Leu Ile Val Met Trp Thr Pro Pro Arg Asn
65                  70                  75                  80

Asp Gln Gln Tyr Leu Asn Trp Gln Trp Tyr Ser Ser Val Leu Ser Ser
                85                  90                  95

His Ala Ala Met Cys Gly Cys Pro Asp Ala Ile Ala His Leu Ser His
            100                 105                 110

Leu Ala Phe Val Phe Arg Ala Pro Gln Asn Pro Pro Pro Pro Gly Pro
        115                 120                 125

Gln Arg Asn Leu Pro Leu Arg Arg Leu Pro
    130                 135

<210> SEQ ID NO 272
<211> LENGTH: 138
<212> TYPE: PRT
<213> ORGANISM: Artificial Sequence
<220> FEATURE:
<221> NAME/KEY: SOURCE
<222> LOCATION: 1..138
<223> OTHER INFORMATION: /mol_type="protein"
      /note="synthesized torque teno virus"
      /organism="Artificial Sequence"

<400> SEQUENCE: 272

Ser Gly Glu Ala Thr Glu Gly Asp Leu Arg Val Pro Arg Ala Gly Ala
1               5                   10                  15

Glu Gly Glu Phe Thr His Arg Ser Gln Gly Ala Ile Arg Ala Arg Asp
            20                  25                  30
```

```
Trp Pro Gly Tyr Gly Gln Gly Ser Glu Lys Ser Met Phe Ile Gly Arg
        35                  40                  45

His Tyr Arg Lys Lys Arg Ala Leu Ser Leu Cys Ala Val Arg Thr Thr
 50                  55                  60

Lys Lys Ala Cys Lys Leu Leu Ile Val Met Trp Thr Pro Arg Asn
 65                  70                  75                  80

Asp Gln Gln Tyr Leu Asn Trp Gln Trp Tyr Ser Ser Val Leu Ser Ser
                 85                  90                  95

His Ala Ala Met Cys Gly Cys Pro Asp Ala Val Ala His Phe Asn His
                100                 105                 110

Leu Ala Ala Val Leu Arg Ala Pro Gln Asn Pro Pro Pro Gly Pro
            115                 120                 125

Gln Arg Asn Leu Pro Leu Arg Arg Leu Pro
130                 135

<210> SEQ ID NO 273
<211> LENGTH: 202
<212> TYPE: PRT
<213> ORGANISM: Artificial Sequence
<220> FEATURE:
<221> NAME/KEY: SOURCE
<222> LOCATION: 1..202
<223> OTHER INFORMATION: /mol_type="protein"
      /note="synthesized torque teno virus"
      /organism="Artificial Sequence"

<400> SEQUENCE: 273

Met Ala Glu Phe Ser Thr Pro Val Arg Ser Gly Glu Ala Thr Glu Gly
 1               5                  10                  15

Asp His Arg Val Pro Arg Ala Gly Ala Glu Gly Glu Phe Thr His Arg
                20                  25                  30

Ser Gln Gly Ala Ile Arg Ala Arg Asp Trp Pro Gly Tyr Gly Gln Gly
            35                  40                  45

Ser Glu Lys Ser Met Phe Ile Gly Arg His Tyr Arg Lys Lys Arg Ala
 50                  55                  60

Leu Ser Leu Cys Ala Val Arg Thr Thr Lys Lys Ala Cys Lys Leu Leu
 65                  70                  75                  80

Ile Val Met Trp Thr Pro Pro Arg Asn Asp Gln Gln Tyr Leu Asn Trp
                 85                  90                  95

Gln Trp Tyr Ser Ser Val Leu Ser Ser His Ala Ser Met Cys Gly Cys
                100                 105                 110

Pro Asp Ala Val Ala His Leu Ile Asn Leu Ala Ser Val Leu Arg Ala
            115                 120                 125

Pro Gln Asn Pro Pro Pro Gly Pro Gln Arg Asn Leu Pro Leu Arg
130                 135                 140

Arg Leu Pro Ala Leu Pro Ala Pro Glu Ala Pro Gly Asp Arg Ala
145                 150                 155                 160

Pro Trp Pro Met Ala Gly Gly Ala Glu Gly Glu Asn Gly Gly Ala Gly
                165                 170                 175

Gly Asp Ala Asp His Gly Gly Ala Ala Gly Gly Pro Glu Asp Ala Asn
                180                 185                 190

Leu Leu Asp Ala Val Ala Ala Ala Glu Thr
            195                 200

<210> SEQ ID NO 274
<211> LENGTH: 152
<212> TYPE: PRT
<213> ORGANISM: Artificial Sequence
```

```
<220> FEATURE:
<221> NAME/KEY: SOURCE
<222> LOCATION: 1..152
<223> OTHER INFORMATION: /mol_type="protein"
      /note="synthesized torque teno virus"
      /organism="Artificial Sequence"

<400> SEQUENCE: 274

Ala Arg Thr Pro Arg Arg Gly Val Arg Ala Ser Arg Gly Arg Val Pro
1               5                   10                  15

Glu Val Ser Leu His Thr Ala Val Lys Gly Gln Phe Gly Leu Gly Thr
            20                  25                  30

Gly Arg Ala Met Gly Lys Ala Leu Lys Lys Ala Met Phe Leu Gly Arg
        35                  40                  45

Ile Tyr Arg Lys Lys Arg Arg Leu Pro Leu Ser Pro Leu His Ser Pro
    50                  55                  60

Pro Lys Ala Arg Lys Leu Leu Arg Gly Met Trp Arg Pro Pro Thr Gln
65                  70                  75                  80

Asn Val Ser Gly Gln Glu Arg Ser Trp Tyr Asp Ser Val Phe Tyr Ser
                85                  90                  95

His Ala Ala Phe Cys Gly Cys Gly Asp Cys Val Gly His Leu Ser Tyr
            100                 105                 110

Leu Ala Thr His Leu Gly Arg Pro Pro Ser Ala Gln Pro Pro Pro Gln
        115                 120                 125

Leu Gln Pro Pro Val Ile Arg Arg Leu Pro Ala Leu Pro Ala Pro Pro
    130                 135                 140

Asn Pro Ser Gly Asp Arg Ala Ala
145                 150

<210> SEQ ID NO 275
<211> LENGTH: 49
<212> TYPE: PRT
<213> ORGANISM: Artificial Sequence
<220> FEATURE:
<221> NAME/KEY: SOURCE
<222> LOCATION: 1..49
<223> OTHER INFORMATION: /mol_type="protein"
      /note="synthesized torque teno virus"
      /organism="Artificial Sequence"

<400> SEQUENCE: 275

Met Ala Glu Phe Ser Thr Pro Val Arg Ser Glu Gly Ala Thr Glu Gly
1               5                   10                  15

Ile Pro Asn Val Pro Arg Ala Gly Ala Gly Gly Glu Phe Thr His Arg
            20                  25                  30

Ser Gln Gly Ala Ile Arg Ala Arg Asp Trp Pro Gly Tyr Gly Gln Gly
        35                  40                  45

Ser
```